United States Patent
Gottschling et al.

(10) Patent No.: US 8,629,137 B2
(45) Date of Patent: Jan. 14, 2014

(54) CGRP ANTAGONISTS

(71) Applicants: Dirk Gottschling, Mittelbiberach (DE); Georg Dahmann, Attenweiler (DE); Henri Doods, Warthausen (DE); Annekatrin Heimann, Biberach an der Riss (DE); Stephan Georg Mueller, Warthausen (DE); Klaus Rudolf, Warthausen (DE); Gerhard Schaenzle, Biberach an der Riss (DE); Dirk Stenkamp, Biberach an der Riss (DE)

(72) Inventors: Dirk Gottschling, Mittelbiberach (DE); Georg Dahmann, Attenweiler (DE); Henri Doods, Warthausen (DE); Annekatrin Heimann, Biberach an der Riss (DE); Stephan Georg Mueller, Warthausen (DE); Klaus Rudolf, Warthausen (DE); Gerhard Schaenzle, Biberach an der Riss (DE); Dirk Stenkamp, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/633,322

(22) Filed: Oct. 2, 2012

(65) Prior Publication Data

US 2013/0029975 A1 Jan. 31, 2013

Related U.S. Application Data

(63) Continuation of application No. 12/682,760, filed as application No. PCT/EP2008/063965 on Oct. 16, 2008, now abandoned.

(30) Foreign Application Priority Data

Oct. 18, 2007 (EP) .................................... 07118809

(51) Int. Cl.
   C07D 401/14 (2006.01)
   C07D 413/14 (2006.01)
   C07D 471/04 (2006.01)
   A61K 31/506 (2006.01)
   A61K 31/551 (2006.01)
   A61P 29/00 (2006.01)

(52) U.S. Cl.
   USPC ........................................ 514/221; 540/500

(58) Field of Classification Search
   USPC .......................................... 540/500; 514/221
   See application file for complete search history.

(56) References Cited

U.S. PATENT DOCUMENTS

| 8,110,575 B2 | 2/2012 | Gottschling et al. |
| 2007/0099903 A1 | 5/2007 | Mueller et al. |
| 2011/0059954 A1 | 3/2011 | Gottschling et al. |
| 2011/0172218 A1 | 7/2011 | Gottschling et al. |
| 2011/0195954 A1 | 8/2011 | Gottschling et al. |
| 2012/0149698 A1 | 6/2012 | Gottschling et al. |
| 2012/0196872 A1 | 8/2012 | Dreyer et al. |

FOREIGN PATENT DOCUMENTS

| WO | 9952896 A1 | 10/1999 |
| WO | 0055154 A1 | 9/2000 |
| WO | 0132648 A1 | 5/2001 |
| WO | 0222592 A2 | 3/2002 |
| WO | 03040128 A1 | 5/2003 |
| WO | 2004037810 A1 | 5/2004 |
| WO | 2004037811 A1 | 5/2004 |
| WO | 2005030751 A2 | 4/2005 |
| WO | 2005100343 A1 | 10/2005 |
| WO | 2005100360 A1 | 10/2005 |
| WO | 2005103037 A2 | 11/2005 |
| WO | 2006031513 A2 | 3/2006 |
| WO | 2006100009 A1 | 9/2006 |
| WO | 2006127588 A2 | 11/2006 |
| WO | 2007000340 A2 | 1/2007 |
| WO | 2007045672 A1 | 4/2007 |
| WO | 2008020902 A1 | 2/2008 |
| WO | 2008070014 A2 | 6/2008 |
| WO | 2009034029 A2 | 3/2009 |
| WO | 2009050232 A1 | 4/2009 |

OTHER PUBLICATIONS

Doods et al., CGRP antagonists: unravelling the role of CGRP in migraine, Trends in Pharmacological Sciences, 2007, vol. 28, No. 11, pp. 580-587.

*Primary Examiner* — Bruck Kifle
(74) *Attorney, Agent, or Firm* — Michael P. Morris; Alan R. Stempel

(57) ABSTRACT

The present invention relates to new CGRP-antagonists of general formula I

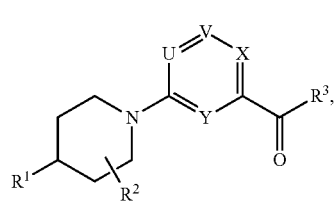

(I)

wherein U, V, X, Y, $R^1$, $R^2$ and $R^3$ are defined as stated hereinafter, the tautomers, the isomers, the diastereomers, the enantiomers, the hydrates, the mixtures thereof and the salts thereof and the hydrates of the salts, particularly the physiologically acceptable salts thereof with inorganic or organic acids or bases, pharmaceutical compositions containing these compounds, their use and processes for preparing them.

6 Claims, No Drawings

CGRP ANTAGONISTS

The present invention relates to new CGRP-antagonists of general formula I

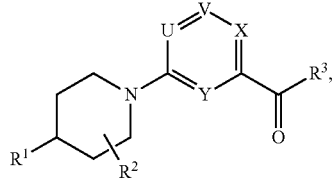

wherein U, V, X, Y, $R^1$, $R^2$ and $R^3$ are defined as mentioned hereinafter, the tautomers thereof, the isomers thereof, the diastereomers thereof, the enantiomers thereof, the hydrates thereof, the mixtures thereof and the salts thereof as well as the hydrates of the salts, particularly the physiologically acceptable salts thereof with inorganic or organic acids or bases, pharmaceutical compositions containing these compounds, the use thereof and processes for the preparation thereof.

DETAILED DESCRIPTION OF THE INVENTION

In the above general formula I in a first embodiment $R^1$ denotes a group of general formula II

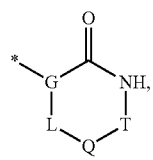

wherein
G-L denotes N,N—C($R^{4.1}$)$_2$, C=C($R^{4.1}$), C=N, C($R^{4.1}$), C($R^{4.1}$)—C($R^{4.1}$)$_2$, C($R^{4.1}$)—C($R^{4.1}$)$_2$—C($R^{4.1}$)$_2$, C=C ($R^{4.1}$)—C($R^{4.1}$)$_2$, C($R^{4.1}$)—C($R^{4.1}$)=C($R^{4.1}$), C($R^{4.1}$)—C($R^{4.1}$)$_2$—N($R^{4.2}$), C=C($R^{4.1}$)—N($R^{4.2}$), C($R^{4.1}$)—C ($R^{4.1}$)=N, C($R^{4.1}$)—N($R^{4.2}$)—C($R^{4.1}$)$_2$, C=N—C ($R^{4.1}$)$_2$, C($R^{4.1}$)—N=C($R^{4.1}$), C($R^{4.1}$)—N($R^{4.2}$)—N ($R^{4.2}$), C=N—N($R^{4.2}$), N—C($R^{4.1}$)$_2$—C($R^{4.1}$)$_2$, N—C ($R^{4.1}$)=C($R^{4.1}$), N—C($R^{4.1}$)$_2$—N($R^{4.2}$), N—C($R^{4.1}$)=N, N—N($R^{4.2}$)—C($R^{4.1}$)$_2$ or N—N=C($R^{4.1}$),
Q-T denotes C($R^5$)$_2$—C($R^5$)$_2$, C($R^5$)=C($R^5$), N=C($R^5$), C($R^5$)$_2$—C(=O), C(=O)—C($R^5$)$_2$, C($R^5$)$_2$—S(O)$_m$— or C($R^5$)$_2$—N($R^5$),
while a group C($R^5$)$_2$ contained in Q-T may also denote a cyclic group which is selected from among $C_{3-6}$-cycloalkyl, $C_{5-6}$-cycloalkenyl or heterocyclyl, or
in a group C($R^5$)$_2$—C($R^5$)$_2$, C($R^5$)=C($R^5$) or C($R^5$)$_2$—N ($R^5$) contained in Q-T in each case a group $R^5$ together with an adjacent group $R^5$ and the atoms to which these groups are attached may also denote a $C_{3-6}$-cycloalkyl, $C_{5-6}$-cycloalkenyl, heterocyclyl, aryl or heteroaryl group, which may be substituted independently of one another by 1, 2 or 3 substituents $R^{5.1}$,
$R^2$ denotes
(a) H,
(b) F, —CN, $C_{1-3}$-alkyl, —CO$_2$—$R^{2.1}$ or (c) a $C_{1-3}$-alkyl group wherein each methylene group is substituted by up to two fluorine atoms and each methyl group is substituted by up to three fluorine atoms,
$R^{2.1}$ denotes H or $C_{1-6}$-alkyl,
$R^3$ a 6 or 10-membered aryl group substituted by the groups $R^{3.1}$, $R^{3.2}$ and $R^{3.3}$ or a 6-membered heteroaryl group substituted by the groups $R^{3.1}$, $R^{3.2}$ and $R^{3.3}$ which is attached via a carbon atom,
$R^{3.1}$ denotes
(a) H,
(b) halogen, —NH$_2$, $C_{1-4}$-alkyl-NH, ($C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
(c) $C_{1-4}$-alkyl, $R^{3.1.1}$—$C_{1-3}$-alkylene, $C_{2-4}$-alkenyl, $C_{2-4}$-alkynyl, $C_{1-3}$-alkyl-O, $C_{1-3}$-alkyl-S(O)$_m$—, cyclopropyl,
(d) a $C_{1-3}$-alkyl or $C_{1-3}$-alkyl-O— group wherein each methylene group is substituted by up to two fluorine atoms and each methyl group is substituted by up to three fluorine atoms,
(e) —C(O)—$R^{3.1.2}$,
(f) —S(O)$_2$—$R^{3.1.3}$,
$R^{3.1.1}$ denotes
(a) H,
(b) $C_{3-6}$-cycloalkyl, $C_{5-6}$-cycloalkenyl,
(c) ($R^{3.1.1.1}$)$_2$N,
(d) a saturated, mono- or diunsaturated 5- or 6-membered heterocyclic group, which is substituted at a nitrogen atom by a group $R^{3.1.1.1}$ and is substituted at a carbon atom by one or two groups $R^{3.1.1.2}$, or
(e) a heteroaryl group which is substituted at a carbon atom by a group $R^{3.1.1.2}$,
$R^{3.1.1.1}$ independently of one another denote
(a) H, $C_{1-4}$-alkyl, $C_{3-6}$-cycloalkyl,
(b) heterocyclyl,
(c) aryl-$C_{0-3}$-alkylene or heteroaryl-$C_{0-3}$-alkylene,
$R^{3.1.1.2}$ independently of one another denote
(a) H, F, $C_{1-3}$-alkyl, —CN, —OH, —O—$C_{1-3}$-alkyl, —CO (O)$R^{3.1.1.2.1}$, H$_2$N, ($C_{1-4}$-alkyl)-NH, ($C_{1-4}$-alkyl)$_2$N,
(b) phenyl or phenyl-CH$_2$,
(c) a $C_{1-3}$-alkyl or —O—$C_{1-3}$-alkyl group wherein each methylene group is substituted by up to two fluorine atoms and each methyl group is substituted by up to three fluorine atoms, or
$R^{3.1.1.2.1}$ denotes H, $C_{1-6}$-alkyl, benzyl,
$R^{3.1.2}$ denotes —O—$C_{1-3}$-alkyl, —OH, —NR$^{3.1.2.1}$R$^{3.1.2.2}$,
$R^{3.1.2.1}$ denotes H, $C_{1-3}$-alkyl,
$R^{3.1.2.2}$ denotes H, $C_{1-3}$-alkyl,
$R^{3.1.2.1}$ and $R^{3.1.2.2}$ together may also form a ring which is selected from among azetidinyl, pyrrolidinyl, piperidinyl, piperazinyl and morpholinyl,
$R^{3.1.3}$ denotes —O—$C_{1-3}$-alkyl, —NR$^{3.1.3.1}$R$^{3.1.3.2}$,
$R^{3.1.3.1}$ denotes H, $C_{1-3}$-alkyl,
$R^{3.1.3.2}$ denotes H, $C_{1-3}$-alkyl,
$R^{3.1.3.1}$ and $R^{3.1.3.2}$ together may also form a ring which is selected from among azetidinyl, pyrrolidinyl, piperidinyl, piperazinyl and morpholinyl,
$R^{3.2}$ denotes
(a) H,
(b) halogen, —NH$_2$, $C_{1-4}$-alkyl-NH, ($C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl,
(c) $C_{1-4}$-alkyl, $C_{2-4}$-alkenyl, $C_{2-4}$-alkynyl, $C_{1-3}$-alkyl-O, $C_{1-3}$-alkyl-S(O)$_m$—, cyclopropyl, (d) a $C_{1-3}$-alkyl or $C_{1-3}$-alkyl-O— group wherein each methylene group is substituted by up to two fluorine atoms and each methyl group is substituted by up to three fluorine atoms, (e) —C(O)—$R^{3.2.1}$, (f) —S(O)$_2$—$R^{3.2.2}$, $R^{3.2.1}$ denotes —O—$C_{1-3}$-alkyl, —OH, —N$R^{3.2.1.1}R^{3.2.1.2}$, $R^{3.2.1.1}$ denotes H, $C_{1-3}$-alkyl, $R^{3.2.1.2}$ denotes H, $C_{1-3}$-alkyl, $R^{3.2.1.1}$ and $R^{3.2.1.2}$ together may also form a ring which is selected from among azetidinyl, pyrrolidinyl, piperidinyl, piperazinyl and morpholinyl, $R^{3.2.2}$ denotes —N$R^{3.2.2.1}R^{3.2.2.2}$, $R^{3.2.2.1}$ denotes H, $C_{1-3}$-alkyl, $R^{3.2.2.2}$ denotes H, $C_{1-3}$-alkyl, $R^{3.2.2.1}$ and $R^{3.2.2.2}$ together may also form a ring which is selected from among azetidinyl, pyrrolidinyl, piperidinyl, piperazinyl and morpholinyl, $R^{3.3}$ denotes (a) H, (b) halogen, —NH$_2$, $C_{1-4}$-alkyl-NH, ($C_{1-4}$-alkyl)$_2$N, $C_{1-3}$-alkyl-C(O)—NH, $C_{1-3}$-alkyl-S(O$_2$)—NH, —CN, —OH, —O—C(O)—NH—$C_{1-3}$-alkyl, (c) $C_{1-4}$-alkyl, $C_{2-4}$-alkenyl, $C_{2-4}$-alkynyl, $C_{1-3}$-alkyl-O, $C_{1-3}$-alkyl-S(O)$_m$—, cyclopropyl, (d) a $C_{1-3}$-alkyl or $C_{1-3}$-alkyl-O— group wherein each methylene group is substituted by up to two fluorine atoms and each methyl group is substituted by up to three fluorine atoms, (e) —C(O)—$R^{3.3.1}$, (f) —S(O)$_2$—$R^{3.3.2}$, $R^{3.3.1}$ denotes —O—$C_{1-3}$-alkyl, —OH, —N$R^{3.3.1.1}R^{3.3.1.2}$, $R^{3.3.1.1}$ denotes H, $C_{1-3}$-alkyl, $R^{3.3.1.2}$ denotes H, $C_{1-3}$-alkyl, $R^{3.3.1.1}$ and $R^{3.3.1.2}$ together may also form a ring which is selected from among azetidinyl, pyrrolidinyl, piperidinyl, piperazinyl and morpholinyl, $R^{3.3.2}$ denotes —O—$C_{1-3}$-alkyl, —N$R^{3.3.2.1}R^{3.3.2.2}$, $R^{3.3.2.1}$ denotes H, $C_{1-3}$-alkyl, $R^{3.3.2.2}$ denotes H, $C_{1-3}$-alkyl, $R^{3.3.2.1}$ and $R^{3.3.2.2}$ together may also form a ring which is selected from among azetidinyl, pyrrolidinyl, piperidinyl, piperazinyl and morpholinyl, or $R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, while the above-mentioned heterocycles may contain a carbonyl, thiocarbonyl or cyanimino group adjacent to a nitrogen atom, and may optionally additionally be substituted at one or two nitrogen atoms by a group $R^{3.3.3}$ in each case and may optionally each additionally be substituted at one or two carbon atoms by one or two groups $R^{3.3.4}$, $R^{3.3.3}$ independently of one another denote (a) $C_{1-4}$-alkyl or (b) $C_{3-6}$-cycloalkyl, $R^{3.3.4}$ independently of one another denote (a) $C_{1-4}$-alkyl or (b) $C_{3-6}$-cycloalkyl, (c) halogen, CN, —O—$C_{1-3}$-alkyl, —NH$_2$, (d) a $C_{1-3}$-alkyl- or $C_{1-3}$-alkyl-O— group wherein each methylene group is substituted by up to two and each methyl group is substituted by up to three fluorine atoms, $R^{4.1}$ independently of one another denote (a) H, (b) $C_{1-6}$-alkyl, —CN, —OH, —O—$C_{1-3}$-alkyl, (c) a $C_{1-3}$-alkyl- or $C_{1-3}$-alkyl-O— group wherein each methylene group is substituted by up to two fluorine atoms and each methyl group is substituted by up to three fluorine atoms, $R^{4.2}$ denotes H or $C_{1-6}$-alkyl, $R^5$ independently of one another denote (a) H, $C_{1-6}$-alkyl, $C_{2-6}$-alkenyl, $C_{2-6}$-alkynyl, $C_{3-6}$-cycloalkyl, (b) an aryl group optionally substituted by 1, 2 or 3 substituents $R^{5.2}$, wherein the substituents $R^{5.2}$ may be identical or different, (c) a heteroaryl group optionally substituted by 1, 2 or 3 substituents $R^{5.2}$, wherein the substituents $R^{5.2}$ may be identical or different, (d) a heterocyclic group optionally substituted by 1, 2 or 3 substituents $R^{5.2}$, wherein the substituents $R^{5.2}$ may be identical or different, $R^{5.1}$ independently of one another denote (a) H, halogen, $C_{1-6}$-alkyl, $C_{3-6}$-cycloalkyl, (b) —O—$C_{1-6}$-alkylene-N$R^7R^8$, —O—$R^6$, —O—(CH$_2$)$_s$—O—$R^6$, —CO$_2$—$R^6$, —C(O)—N$R^7R^8$, —O—C(O)—N$R^7R^8$, —N$R^6$—C(O)—N$R^7R^8$, —N$R^7$—C(O)—$R^8$, —N$R^7$—C(O)—O—$R^8$, —SO$_2$—N$R^7R^8$, —N$R^7$—SO$_2$—$R^8$, —S(O)$_m$—$R^7$, —CN, —N$R^7R^8$, —N$R^6$—C(O)—N$R^7R^8$, —O—C(O)—$R^6$, (c) a $C_{1-3}$-alkyl- or $C_{1-3}$-alkyl-O— group wherein each methylene group is substituted by up to two fluorine atoms and each methyl group is substituted by up to three fluorine atoms, (d) an aryl group substituted by 1, 2 or 3 substituents $R^6$, wherein the substituents $R^6$ may be identical or different, (e) a heteroaryl group substituted by 1, 2 or 3 substituents $R^6$, wherein the substituents $R^6$ may be identical or different, (f) a heterocyclic group substituted by 1, 2 or 3 substituents $R^6$, wherein the substituents $R^6$ may be identical or different, $R^{5.2}$ independently of one another denote (a) halogen, $C_{1-6}$-alkyl, $C_{3-6}$-cycloalkyl, (b) —O—$R^6$, —O—(CH$_2$)$_s$—O—$R^6$, —CO$_2R^6$, —C(O)—N$R^7R^8$, —O—(CO)—N$R^7R^8$, N($R^6$)—C(O)—N$R^7R^8$, —N($R^7$)—C(O)—$R^8$, —N($R^7$)—C(O)—O—$R^8$, —SO$_2$—N$R^7R^8$, —N($R^7$)—SO$_2$—$R^8$, —S(O)$_m$—$R^7$, —CN, —N$R^7R^8$, —N($R^6$)—C(O)—N$R^7R^8$, —O—C(O)—$R^6$ or (c) a $C_{1-3}$-alkyl group wherein each methylene group is substituted by up to two fluorine atoms and each methyl group is substituted by up to three fluorine atoms, $R^6$ denotes (a) H, (b) $C_{1-6}$-alkyl, $C_{3-6}$-cycloalkyl, aryl, heteroaryl, benzyl, which may be substituted by a group $R^{6.1}$, or (c) a $C_{1-3}$-alkyl group wherein each methylene group is substituted by up to two fluorine atoms and each methyl group is substituted by up to three fluorine atoms, $R^{6.1}$ denotes halogen, HO— or $C_{1-6}$-alkyl-O—, $R^7$ denotes (a) H, (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or (c) a $C_{1-3}$-alkyl group wherein each methylene group is substituted by up to two fluorine atoms and each methyl group is substituted by up to three fluorine atoms, $R^8$ denotes
- (a) H,
- (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^7$ and $R^8$ together may also form a ring which is selected from among azetidinyl, pyrrolidinyl, piperidinyl, piperazinyl and morpholinyl, wherein the ring may be unsubstituted or substituted by 1, 2 or 3 substituents $R^6$ or fluorine, wherein the substituents $R^6$ are independent of one another, m denotes one of the numbers 0, 1 or 2,
s denotes one of the numbers 1, 2 or 3,
U denotes N, N-oxide or C—$R^9$,
V denotes N, N-oxide or C—$R^{10}$,
X denotes N, N-oxide or $CR^{11}$,
Y denotes N or C—$R^{12}$
while at most three of the previously mentioned groups U, V, X or Y simultaneously denote a nitrogen atom, $R^9$ denotes
- (a) H,
- (b) a $C_{1-6}$-alkyl- or $C_{1-3}$-alkyl-O— group which may each be substituted by a group $R^{9.1}$,
- (c) $R^{9.2}R^{9.3}N$—, $R^{9.2}R^{9.3}N$—$C_{1-3}$-alkylene-,
- (d) halogen, —CN, —OH, —COOH, $C_{1-3}$-alkyl-O—$C_{1-3}$-alkylene-, $C_{3-6}$-cycloalkyl-, $C_{3-6}$-cycloalkyl-$C_{1-4}$-alkylene-, $C_{1-3}$-alkyl-C(O)—O—$C_{1-3}$-alkylene,
- (e) a $C_{1-3}$-alkyl- or $C_{1-3}$-alkyl-O— group wherein each methylene group is substituted by up to two fluorine atoms and each methyl group is substituted by up to three fluorine atoms, $R^{9.1}$ denotes H, OH or —O—$CH_3$,
$R^{9.2}$ denotes H or $C_{1-3}$-alkyl,
$R^{9.3}$ denotes H or $C_{1-3}$-alkyl, or
$R^{9.2}$ and $R^{9.3}$ together with the nitrogen atom to which they are attached denote a 3- to 6-membered heterocyclic group, $R^{10}$ denotes
- (a) H,
- (b) a $C_{1-6}$-alkyl or $C_{1-3}$-alkyl-O— group which may each be substituted by a group $R^{10.1}$,
- (c) —$NR^{10.2}R^{10.3}$, $NR^{10.2}R^{10.3}$—$C_{1-3}$-alkylene-,
- (d) halogen, —CN, —OH, $C_{1-3}$-alkyl-O—$C_{1-3}$-alkylene-, $C_{3-6}$-cycloalkyl-, $C_{3-6}$-cycloalkyl-$C_{1-4}$-alkylene-, $C_{1-3}$-alkyl-C(O)—O—$C_{1-3}$-alkylene,
- (e) an aryl-$C_{0-3}$-alkylene-O— group,
- (f) a $C_{1-3}$-alkyl or $C_{1-3}$-alkyl-O— group wherein each methylene group is substituted by up to two fluorine atoms and each methyl group is substituted by up to three fluorine atoms, $R^{10.1}$ denotes H, OH or —O—$CH_3$,
$R^{10.2}$ denotes H or $C_{1-6}$-alkyl,
$R^{10.3}$ denotes H, $C_{1-6}$-alkyl or —$SO_2$—$C_{1-3}$-alkyl, or
$R^{10.2}$ and $R^{10.3}$ together with the nitrogen atom to which they are attached denote a 3- to 6-membered heterocyclic group, $R^{11}$ denotes
- (a) H,
- (b) a $C_{1-6}$-alkyl or $C_{1-3}$-alkyl-O— group which may each be substituted by a group $R^{11.1}$,
- (c) $R^{11.2}R^{11.3}N$, $R^{11.2}R^{11.3}N$—$C_{1-3}$-alkylene,
- (d) halogen, —CN, —OH, —COOH, $C_{1-3}$-alkyl-O—$C_{1-3}$-alkylene-, $C_{3-6}$-cycloalkyl, $C_{3-6}$-cycloalkyl-$C_{1-4}$-alkylene-, $C_{1-3}$-alkyl-C(O)—O—$C_{1-3}$-alkylene,
- (e) a $C_{1-3}$-alkyl- or $C_{1-3}$-alkyl-O— group wherein each methylene group is substituted by up to two fluorine atoms and each methyl group is substituted by up to three fluorine atoms, $R^{11.1}$ denotes H, OH or —O—$CH_3$,
$R^{11.2}$ denotes H or $C_{1-3}$-alkyl,
$R^{11.3}$ denotes H or $C_{1-3}$-alkyl, or
$R^{11.2}$ and $R^{11.3}$ together with the nitrogen atom to which they are attached denote a 3- to 6-membered heterocyclic group, and
$R^{12}$ denotes H, halogen or $C_{1-3}$-alkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A second embodiment of the present invention consists in the compounds of the above general formula I, wherein U, V, X, Y, $R^2$ and $R^3$ are defined as hereinbefore in the first embodiment and $R^1$ denotes a group of general formula II

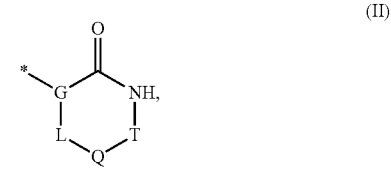

wherein
G-L denotes N,N—$C(R^{4.1})_2$, C═$C(R^{4.1})$, C═N, $C(R^{4.1})$, $C(R^{4.1})$—$C(R^{4.1})_2$, $C(R^{4.1})$—$C(R^{4.1})_2$—$C(R^{4.1})_2$, C═C $(R^{4.1})$—$C(R^{4.1})_2$, $C(R^{4.1})$—$C(R^{4.1})$═$C(R^{4.1})$, $C(R^{4.1})$—$C(R^{4.1})_2$—$N(R^{4.2})$, C═$C(R^{4.1})$—$N(R^{4.2})$, $C(R^{4.1})$—$C(R^{4.1})$═N, $C(R^{4.1})$—$N(R^{4.2})$—$C(R^{4.1})_2$, C═N—$C(R^{4.1})_2$, $C(R^{4.1})$—N═$C(R^{4.1})$, $C(R^{4.1})$—$N(R^{4.2})$—$N(R^{4.2})$, C═N—$N(R^{4.2})$, N—$C(R^{4.1})_2$—$C(R^{4.1})_2$, N—$C(R^{4.1})$═$C(R^{4.1})$, N—$C(R^{4.1})_2$—$N(R^{4.2})$, N—$C(R^{4.1})$═N, N—$N(R^{4.2})$—$C(R^{4.1})_2$ or N—N═$C(R^{4.1})$, Q-T denotes $C(R^5)_2$—$C(R^5)_2$, $C(R^5)$═$C(R^5)$, N═$C(R^5)$, $C(R^5)_2$—C(═O), C(═O)—$C(R^5)_2$, $C(R^5)_2$—S(O)$_m$ or $C(R^5)_2$—N($R^5$), while a group $C(R^5)_2$ contained in Q-T may also denote a cyclic group which is selected from among cyclobutyl, cyclopentyl, cyclohexyl, cyclopentenyl, cyclohexenyl, dioxanyl, morpholinyl, thiomorpholinyl, thiomorpholine-S-oxide, thiomorpholine-S-dioxide, azetidinyl, pyrrolidinyl, piperidinyl, tetrahydrofuranyl, tetrahydropyranyl and piperazinyl, or in a group $C(R^5)_2$—$C(R^5)_2$, $C(R^5)$═$C(R^5)$ or $C(R^5)_2$—N ($R^5$) contained in Q-T in each case a group $R^5$ together with an adjacent group $R^5$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholine-S-oxide, thiomorpholine-S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{5.1}$, $R^{4.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms, $R^{4.2}$ denotes H or $C_{1-6}$-alkyl, $R^5$ denotes
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{5.2}$, wherein the substituents $R^{5.2}$ may be identical or different,
  (c) a heteroaryl group optionally substituted by 1, 2 or 3 substituents $R^{5.2}$, wherein the substituents $R^{5.2}$ may be identical or different,
  (d) a heterocyclic group optionally substituted by 1, 2 or 3 substituents $R^{5.2}$, wherein the substituents $R^{5.2}$ may be identical or different, $R^{5.1}$ denotes
  (a) H, halogen, $C_{1-6}$-alkyl, $C_{3-6}$-cycloalkyl,
  (b) —O—$C_{1-6}$-alkylene-$NR^7R^8$, —O—$R^6$, —O—$(CH_2)_s$—O—$R^6$, —$CO_2$—$R^6$, C(O)—$NR^7R^8$, —O—C(O)—$NR^7R^8$, —$NR^7$—C(O)—$NR^7R^8$, —$NR^7$—C(O)—$R^8$, —$NR^7$—C(O)—O—$R^8$, —$SO_2$—$NR^7R^8$, —$NR^7$—$SO_2$—$R^8$, —$S(O)_m$—$R^7$, —CN, —$NR^7R^8$, —$NR^6$—C(O)—$NR^7R^8$, —O—C(O)—$R^6$,
  (c) a $C_{1-3}$-alkyl- or $C_{1-3}$-alkyl-O— group wherein each methylene group is substituted by up to two fluorine atoms and each methyl group is substituted by up to three fluorine atoms,
  (d) an aryl group substituted by 1, 2 or 3 substituents $R^6$, wherein the substituents $R^6$ may be identical or different,
  (e) a heteroaryl group substituted by 1, 2 or 3 substituents $R^6$, wherein the substituents $R^6$ may be identical or different,
  (f) a heterocyclic group substituted by 1, 2 or 3 substituents $R^6$, wherein the substituents $R^6$ may be identical or different, $R^{5.2}$ denotes
  (a) halogen, $C_{1-6}$-alkyl, $C_{3-6}$-cycloalkyl,
  (b) —O—$R^6$, —O—$(CH_2)_s$—O—$R^6$, —$CO_2R^6$, —C(O)—$NR^7R^8$, —O—(CO)—$NR^7R^8$, —$N(R^6)$—C(O)—$NR^7R^8$, —$N(R^7)$—C(O)—$R^8$, —$N(R^7)$—C(O)—O—$R^8$, —$SO_2$—$NR^7R^8$, —$N(R^7)$—$SO_2$—$R^8$, —$S(O)_m$—$R^7$, CN, $NR^7R^8$, —$N(R^6)$—C(O)—$NR^7R^8$, —O—C(O)—$R^6$ or
  (c) a $C_{1-3}$-alkyl group wherein each methylene group is substituted by up to two fluorine atoms and each methyl group is substituted by up to three fluorine atoms, $R^6$ denotes
  (a) H,
  (b) $C_{1-6}$-alkyl, $C_{3-6}$-cycloalkyl, aryl, heteroaryl, benzyl, which may be substituted by a group $R^{6.1}$, or
  (c) a $C_{1-3}$-alkyl group wherein each methylene group is substituted by up to two fluorine atoms and each methyl group is substituted by up to three fluorine atoms, $R^{6.1}$ denotes halogen, HO— or $C_{1-6}$-alkyl-O—, $R^7$ denotes
  (a) H,
  (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, $R^8$ denotes
  (a) H,
  (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or $R^7$ and $R^8$ together may also form a ring which is selected from among azetidinyl, pyrrolidinyl, piperidinyl, piperazinyl and morpholinyl, wherein the ring may be unsubstituted or substituted by 1, 2 or 3 substituents $R^6$ or fluorine, wherein the substituents $R^6$ are independent of one another, m denotes one of the numbers 0, 1 or 2 and s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A third embodiment of the present invention consists in the compounds of the above general formula I, wherein U, V, X, Y, $R^2$ and $R^3$ are defined as hereinbefore in the first embodiment and $R^1$ denotes a group of general formulae

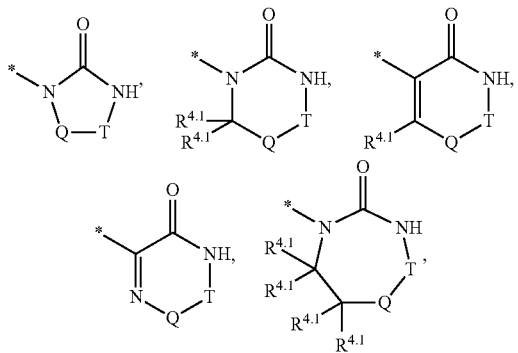

wherein

Q-T denotes $C(R^5)_2$—$C(R^5)_2$, $C(R^5)$=$C(R^5)$, N=$C(R^5)$, $C(R^5)_2$—C(=O), C(=O)—$C(R^5)_2$, $C(R^5)_2$—$S(O)_m$ or $C(R^5)_2$—$N(R^5)$, while in a group $C(R^5)_2$—$C(R^5)_2$, $C(R^5)$=$C(R^5)$ or $C(R^5)_2$—$N(R^5)$ contained in Q-T in each case a group $R^5$ together with an adjacent group $R^5$ and the atoms to which these groups are attached may also denote a group selected from cyclobutyl, cyclopentyl, cyclohexyl, cyclopentenyl, cyclohexenyl, dioxanyl, phenyl, naphthyl, thienyl, thiazolyl, thiazolinyl, oxazolyl, oxazolinyl, imidazolyl, imidazolinyl, imidazolidinyl, pyridyl, pyrimidyl, pyrazinyl, pyridazinyl, pyrrolyl, pyrrolinyl, quinolinyl, isoquinolinyl, morpholinyl, thiomorpholinyl, thiomorpholine S-oxide, thiomorpholine S-dioxide, azetidinyl, pyrrolidinyl, piperidinyl, tetrahydrofuranyl, tetrahydropyranyl, tetrahydropyridyl, furanyl, dihydrofuranyl, dihydropyranyl and piperazinyl, which may be substituted independently of one another by 1, 2 or 3 substituents $R^{5.1}$, $R^{4.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms, $R^5$ independently of one another denote
  (a) H, $C_{1-6}$-alkyl, $C_{2-6}$-alkenyl, $C_{2-6}$-alkynyl, $C_{3-6}$-cycloalkyl,
  (b) an aryl group optionally substituted by 1, 2 or 3 substituents $R^{5.2}$, wherein the substituents $R^{5.2}$ may be identical or different,
  (c) a heteroaryl group optionally substituted by 1, 2 or 3 substituents $R^{5.2}$, wherein the substituents $R^{5.2}$ may be identical or different,
  (d) a heterocyclic group optionally substituted by 1, 2 or 3 substituents $R^{5.2}$, wherein the substituents $R^{5.2}$ may be identical or different,
$R^{5.1}$ denotes
  (a) H, halogen, $C_{1-6}$-alkyl, $C_{3-6}$-cycloalkyl,
  (b) —O—$C_{1-6}$-alkylene-$NR^7R^8$, —O—$R^6$, —$CO_2R^6$, —C(O)$NR^7R^8$, —$SO_2$—$NR^7R^8$, —N($R^7$)—$SO_2$—$R^8$, —S(O)$_m$—$R^7$, —CN, —$NR^7R^8$, —O—C(O)—$R^6$ or
  (c) a $C_{1-3}$-alkyl group wherein each methylene group is substituted by up to two fluorine atoms and each methyl group is substituted by up to three fluorine atoms,
$R^{5.2}$ denotes
  (a) halogen, $C_{1-6}$-alkyl, $C_{3-6}$-cycloalkyl,
  (b) —O—$R^6$, —O—$(CH_2)_s$—O—$R^6$, —$CO_2R^6$, —S(O)$_m$—$R^7$, —CN, —O—C(O)—$R^6$ or
  (c) a $C_{1-3}$-alkyl group wherein each methylene group is substituted by up to two fluorine atoms and each methyl group is substituted by up to three fluorine atoms,
$R^6$ denotes
  (a) H,
  (b) $C_{1-6}$-alkyl, $C_{3-6}$-cycloalkyl, aryl, heteroaryl, benzyl, which may be substituted by a group $R^{6.1}$, or
  (c) a $C_{1-3}$-alkyl group wherein each methylene group is substituted by up to two fluorine atoms and each methyl group is substituted by up to three fluorine atoms,
$R^{6.1}$ denotes halogen, HO— or $C_{1-6}$-alkyl-O—,
$R^7$ denotes
  (a) H,
  (b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms,
$R^8$ denotes
  (a) H,
  (b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
  (c) a $C_{1-3}$-alkyl group wherein each methylene group is substituted by up to two fluorine atoms and each methyl group is substituted by up to three fluorine atoms, or
  $R^7$ and $R^8$ together may also form a ring which is selected from among azetidinyl, pyrrolidinyl, piperidinyl, piperazinyl and morpholinyl, wherein the ring may be unsubstituted or substituted by 1, 2 or 3 substituents $R^6$, wherein the substituents $R^6$ are independent of one another,
m denotes one of the numbers 0, 1 or 2 and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A fourth embodiment of the present invention consists in the compounds of the above general formula I, wherein U, V, X, Y, $R^2$ and $R^3$ are defined as hereinbefore in the first embodiment and $R^1$ denotes a group of general formulae

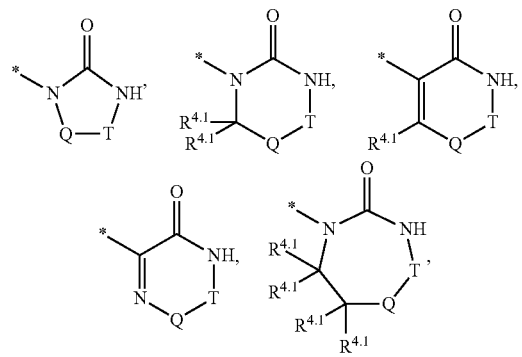

wherein
Q-T denotes $C(R^5)_2$—$C(R^5)_2$, $C(R^5)$=$C(R^5)$, N=$C(R^5)$, $C(R^5)_2$—C(=O), C(=O)—$C(R^5)_2$, $C(R^5)_2$—S(O)$_m$ or $C(R^5)_2$—N($R^5$),
  while in a group $C(R^5)_2$—$C(R^5)_2$, $C(R^5)$=$C(R^5)$ or $C(R^5)_2$—N($R^5$) contained in Q-T in each case a group $R^5$ together with an adjacent group $R^5$ and the atoms to which these groups are attached may also denote a group selected from cyclopentyl, cyclohexyl, cyclopentenyl, cyclohexenyl, dioxanyl, phenyl, naphthyl, thienyl, pyridyl, pyrazinyl, pyridazinyl, quinolinyl, isoquinolinyl, morpholinyl, pyrrolidinyl, piperidinyl, tetrahydrofuranyl, tetrahydropyranyl and piperazinyl, which may be substituted independently of one another by 1, 2 or 3 substituents $R^{5.1}$,
$R^{4.1}$ denotes
  (a) H,
  (b) $C_{1-6}$-alkyl, —CN, —OH, —O—$C_{1-3}$-alkyl,
  (c) a $C_{1-3}$-alkyl- or $C_{1-3}$-alkyl-O— group wherein each methylene group is substituted by up to two fluorine atoms and each methyl group is substituted by up to three fluorine atoms,
$R^5$ independently of one another denote
  (a) H, $C_{1-6}$-alkyl, $C_{3-6}$-cycloalkyl,
  (b) an aryl group optionally substituted by 1, 2 or 3 substituents $R^{5.2}$, wherein the substituents $R^{5.2}$ may be identical or different,
  (c) a heteroaryl group optionally substituted by 1, 2 or 3 substituents $R^{5.2}$, wherein the substituents $R^{5.2}$ may be identical or different,
  (d) a heterocyclic group optionally substituted by 1, 2 or 3 substituents $R^{5.2}$, wherein the substituents $R^{5.2}$ may be identical or different,
$R^{5.1}$ denotes
  (a) H, halogen, $C_{1-6}$-alkyl, $C_{3-6}$-cycloalkyl,
  (b) —O—$C_{1-6}$-alkylene-$NR^7R^8$, —O—$R^6$, —$CO_2R^6$, —C(O)—$NR^7R^8$, —$SO_2$—$NR^7R^8$, —$NR^7$—$SO_2$—$R^8$, —S(O)$_m$—$R^7$, —CN, —$NR^7R^8$, —O—C(O)—$R^6$ or
  (c) a $C_{1-3}$-alkyl group wherein each methylene group is substituted by up to two fluorine atoms and each methyl group is substituted by up to three fluorine atoms,
$R^{5.2}$ denotes
  (a) halogen, $C_{1-6}$-alkyl, $C_{3-6}$-cycloalkyl,
  (b) —O—$R^6$, —O—$(CH_2)_s$—$OR^6$, —$CO_2R^6$, —S(O)$_m$—$R^6$, —CN, —O—C(O)—$R^6$ or
  (c) a $C_{1-3}$-alkyl group wherein each methylene group is substituted by up to two fluorine atoms and each methyl group is substituted by up to three fluorine atoms, $R^6$ denotes
(a) H,
(b) $C_{1-6}$-alkyl, $C_{3-6}$-cycloalkyl, aryl, heteroaryl, benzyl, which may be substituted by a group $R^{6.1}$, or
(c) a $C_{1-3}$-alkyl group wherein each methylene group is substituted by up to two fluorine atoms and each methyl group is substituted by up to three fluorine atoms, $R^{6.1}$ denotes halogen, HO— or $C_{1-6}$-alkyl-O—, $R^7$ denotes
(a) H,
(b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, $R^8$ denotes
(a) H,
(b) $C_{1-6}$-alkyl, $C_{3-6}$-cycloalkyl, aryl, heteroaryl, or benzyl, while the groups are unsubstituted or may be substituted by halogen, HO— or $C_{1-6}$-alkyl-O—, or
(c) a $C_{1-3}$-alkyl group wherein each methylene group is substituted by up to two fluorine atoms and each methyl group is substituted by up to three fluorine atoms, or $R^7$ and $R^8$ together may also form a ring which is selected from among azetidinyl, pyrrolidinyl, piperidinyl, piperazinyl and morpholinyl, wherein the ring may be unsubstituted or substituted by 1, 2 or 3 substituents $R^6$, wherein the substituents $R^6$ are independent of one another, m denotes one of the numbers 0, 1 or 2 and
s denotes one of the numbers 1, 2 or 3, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifth embodiment of the present invention consists in the compounds of the above general formula I, wherein U, V, X, Y, $R^2$ and $R^3$ are defined as hereinbefore in the first embodiment and $R^1$ denotes a group of general formula

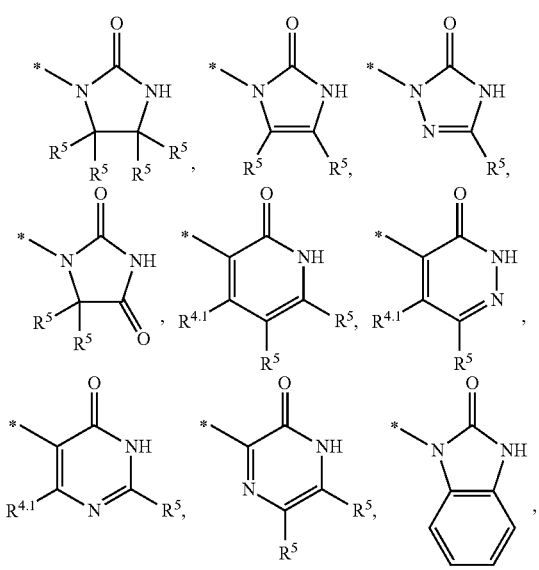

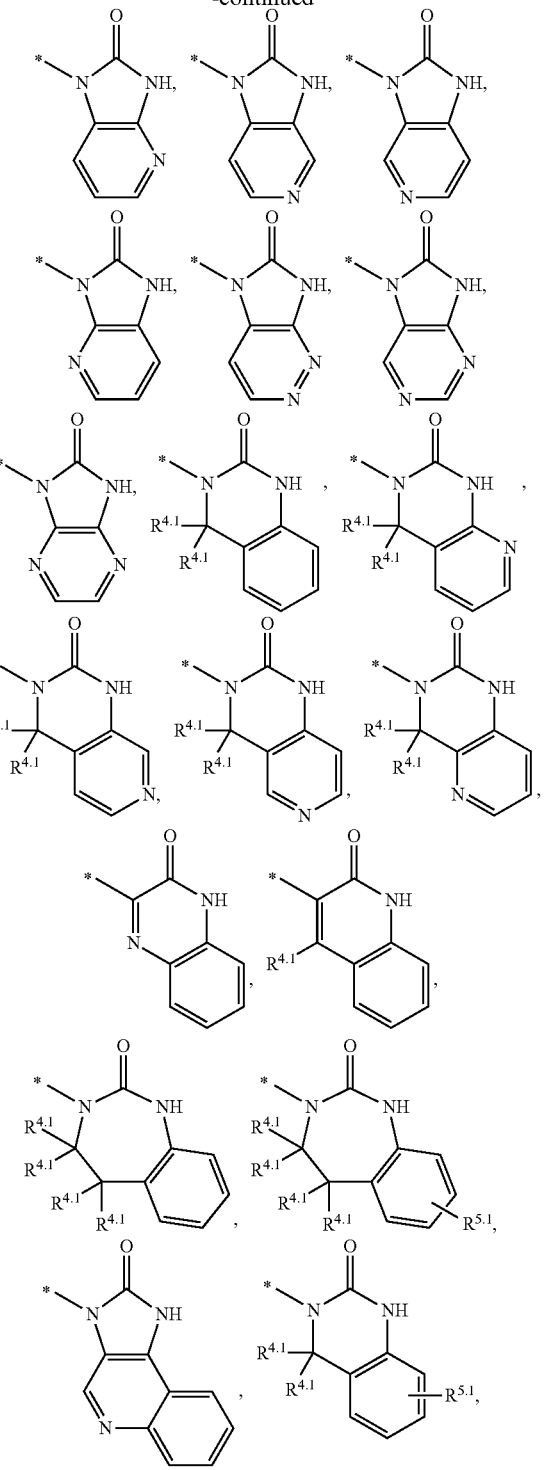

wherein
$R^{4.1}$ denotes
(a) H,
(b) $C_{1-3}$-alkyl, —OH, —O—$C_{1-3}$-alkyl,
(c) a $C_{1-3}$-alkyl- or $C_{1-3}$-alkyl-O— group wherein each methylene group is substituted by up to two fluorine atoms and each methyl group is substituted by up to three fluorine atoms, $R^5$ denotes
  (a) H, $C_{1-6}$-alkyl, $C_{3-6}$-cycloalkyl,
  (b) a phenyl group optionally substituted by 1, 2, or 3 substituents $R^{5.2}$, wherein the substituents $R^{5.2}$ may be identical or different,
  (c) a heteroaryl group optionally substituted by 1, 2 or 3 substituents $R^{5.2}$ which is selected from among benzimidazole, benzothiophene, furan, imidazole, indole, isoxazole, oxazole, pyrazine, pyrazole, pyridazine, pyridine, pyrimidine, pyrrole, thiazole, thiophene and triazole, wherein the substituents $R^{5.2}$ may be identical or different,
  (d) a heterocyclic group optionally substituted by 1, 2 or 3 substituents $R^{5.2}$, wherein the substituents $R^{5.2}$ may be identical or different,
$R^{5.1}$ denotes
  (a) H, halogen, $C_{1-6}$-alkyl, $C_{3-6}$-cycloalkyl,
  (b) —O—$C_{1-6}$-alkylene-$NR^7R^8$, —O—$R^6$, —$CO_2R^6$, —C(O)—$NR^7R^8$, —$SO_2$—$NR^7R^8$, —$NR^7$—$SO_2$—$R^8$, —$S(O)_m$—$R^7$, —CN, —$NR^7R^8$, —O—C(O)—$R^6$ or
  (c) a $C_{1-3}$-alkyl or $C_{1-3}$-alkyl-O— group wherein each methylene group is substituted by up to two fluorine atoms and each methyl group is substituted by up to three fluorine atoms,
$R^{5.2}$ denotes
  (a) halogen, $C_{1-6}$-alkyl, $C_{3-6}$-cycloalkyl,
  (b) —O—$R^6$, —O—$(CH_2)_s$—O—$R^6$, —$CO_2R^6$, —$S(O)_m$—$R^6$, —CN, —O—C(O)—$R^6$ or
  (c) a $C_{1-3}$-alkyl group wherein each methylene group is substituted by up to two fluorine atoms and each methyl group is substituted by up to three fluorine atoms,
$R^6$ denotes
  (a) H,
  (b) $C_{1-6}$-alkyl, $C_{3-6}$-cycloalkyl, aryl, heteroaryl, benzyl, which may be substituted by a group $R^{6.1}$, or
  (c) a $C_{1-3}$-alkyl group wherein each methylene group is substituted by up to two fluorine atoms and each methyl group is substituted by up to three fluorine atoms,
$R^{6.1}$ denotes HO— or $C_{1-6}$-alkyl-O—,
$R^7$ denotes
  (a) H,
  (b) $C_{1-3}$-alkyl, phenyl or benzyl, while the groups are unsubstituted or may be substituted by halogen, HO— or $H_3C$—O—,
$R^8$ denotes
  (a) H,
  (b) $C_{1-3}$-alkyl, phenyl or benzyl, while the groups are unsubstituted or may be substituted by halogen, HO— or $H_3C$—O—, or
$R^7$ and $R^8$ together may also form a ring which is selected from among azetidinyl, pyrrolidinyl, piperidinyl, piperazinyl and morpholinyl, while the ring may be unsubstituted or substituted by a substituent $R^6$,
m denotes one of the numbers 0, 1 or 2, and
s denotes one of the numbers 1, 2 or 3,
the tautomers, the diastereomers, the enantiomers, the hydrates, the mixtures thereof and the salts thereof as well as the hydrates of the salts, particularly the physiologically acceptable salts thereof with inorganic or organic acids or bases.

A sixth embodiment of the present invention consists in the compounds of the above general formula I, wherein U, V, X, Y, $R^2$ and $R^3$ are defined as hereinbefore in the first embodiment and $R^1$ denotes a group selected from

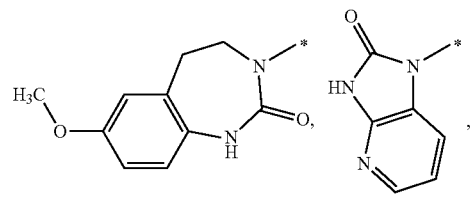

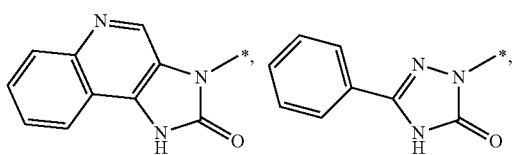

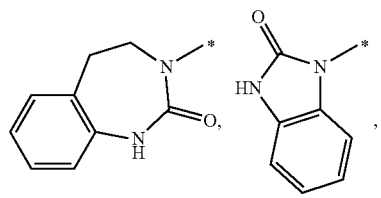

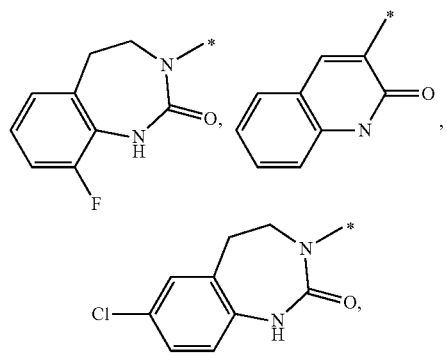

the tautomers, the diastereomers, the enantiomers, the hydrates, the mixtures thereof and the salts thereof as well as the hydrates of the salts, particularly the physiologically acceptable salts thereof with inorganic or organic acids or bases.

A seventh embodiment of the present invention consists in the compounds of the above general formula I, wherein U, V, X, Y, $R^1$ and $R^3$ are as hereinbefore defined in the first, second, third, fourth, fifth or sixth embodiment and $R^2$ denotes a hydrogen atom, the tautomers, the diastereomers, the enantiomers, the hydrates, the mixtures thereof and the salts thereof as well as the hydrates of the salts, particularly the physiologically acceptable salts thereof with inorganic or organic acids or bases.

An eighth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group of general formula III

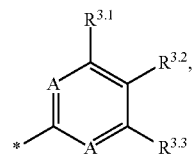
(III)

A independently of one another denote CH or N,
$R^{3.1}$ denotes
 (a) H,
 (b) halogen, —$NH_2$, $C_{1-4}$-alkyl-NH, ($C_{1-4}$-alkyl)$_2$N, $C_{1-3}$-alkyl-C(O)—NH—, $C_{1-3}$-alkyl-S(O)$_2$—NH—, —CN, —OH, —O—C(O)—NH—$C_{1-3}$-alkyl,
 (c) $C_{1-4}$-alkyl, $R^{3.1.1}$—$C_{1-3}$-alkylene, $C_{2-4}$-alkenyl, $C_{2-4}$-alkynyl, $C_{1-3}$-alkyl-O—, $C_{1-3}$-alkyl-S—,
 (d) a $C_{1-3}$-alkyl- or $C_{1-3}$-alkyl-O— group wherein each methylene group is substituted by up to two fluorine atoms and each methyl group is substituted by up to three fluorine atoms,
 (e) —C(O)—$R^{3.1.2}$,
 (f) —S(O)$_2$—$R^{3.1.3}$,
$R^{3.1.1}$ denotes
 (a) H,
 (b) $C_{3-6}$-cycloalkyl, $C_{5-6}$-cycloalkenyl,
 (c) ($R^{3.1.1.1}$)$_2$N—,
 (d) a saturated, mono- or diunsaturated 5- or 6-membered heterocyclic group, which is substituted at a nitrogen atom by a group $R^{3.1.1.1}$ and at a carbon atom by one or two groups $R^{3.1.1.2}$, or
 (e) a heteroaryl group which is substituted at a carbon atom by a group $R^{3.1.1.2}$,
$R^{3.1.1.1}$ independently of one another denote
 (a) H, $C_{1-4}$-alkyl, $C_{3-6}$-cycloalkyl,
 (b) heterocyclyl,
 (c) aryl-$C_{0-3}$-alkylene or heteroaryl-$C_{0-3}$-alkylene,
$R^{3.1.1.2}$ independently of one another denote
 (a) H, F, $C_{1-3}$-alkyl, —CN, —OH, —O—$C_{1-3}$-alkyl, —CO(O)$R^{3.1.1.2.1}$, $H_2$N, ($C_{1-4}$-alkyl)-NH—, ($C_{1-4}$-alkyl)$_2$N—,
 (b) phenyl or phenyl-$CH_2$—,
 (c) a $C_{1-3}$-alkyl or —O—$C_{1-3}$-alkyl group wherein each methylene group is substituted by up to two fluorine atoms and each methyl group is substituted by up to three fluorine atoms, or
$R^{3.1.1.2.1}$ denotes H, $C_{1-6}$-alkyl, benzyl,
$R^{3.1.2}$ denotes —O—$C_{1-3}$-alkyl, —OH, —NR$^{3.1.2.1}$R$^{3.1.2.2}$,
$R^{3.1.2.1}$ denotes H, $C_{1-3}$-alkyl,
$R^{3.1.2.2}$ denotes H, $C_{1-3}$-alkyl,
$R^{3.1.3}$ denotes —NR$^{3.1.3.1}$R$^{3.1.3.2}$,
$R^{3.1.3.1}$ denotes H, $C_{1-3}$-alkyl,
$R^{3.1.3.2}$ denotes H, $C_{1-3}$-alkyl,
$R^{3.2}$ denotes
 (a) H,
 (b) halogen, —$NH_2$, $C_{1-4}$-alkyl-NH—, ($C_{1-4}$-alkyl)$_2$N—, $C_{1-3}$-alkyl-C(O)—NH—, $C_{1-3}$-alkyl-S(O)$_2$—NH—, —CN, —OH, —O—C(O)—NH—$C_{1-3}$-alkyl,
 (c) $C_{1-4}$-alkyl, $C_{2-4}$-alkenyl, $C_{2-4}$-alkynyl, $C_{1-3}$-alkyl-O, $C_{1-3}$-alkyl-S—,
 (d) a $C_{1-3}$-alkyl- or $C_{1-3}$-alkyl-O— group wherein each methylene group is substituted by up to two fluorine atoms and each methyl group is substituted by up to three fluorine atoms,
 (e) —C(O)—$R^{3.2.1}$,
 (f) —S(O)$_2$—$R^{3.2.2}$,
$R^{3.2.1}$ denotes —O—$C_{1-3}$-alkyl, —OH, —NR$^{3.2.1.1}$R$^{3.2.1.2}$,
$R^{3.2.1.1}$ denotes H, $C_{1-3}$-alkyl,
$R^{3.2.1.2}$ denotes H, $C_{1-3}$-alkyl,
$R^{3.2.2}$ denotes —NR$^{3.2.2.1}$R$^{3.2.2.2}$,
$R^{3.2.2.1}$ denotes H, $C_{1-3}$-alkyl,
$R^{3.2.2.2}$ denotes H, $C_{1-3}$-alkyl,
$R^{3.3}$ denotes
 (a) H,
 (b) halogen, —$NH_2$, $C_{1-4}$-alkyl-NH—, ($C_{1-4}$-alkyl)$_2$N, $C_{1-3}$-alkyl-C(O)—NH—, $C_{1-3}$-alkyl-S(O)$_2$—NH, —CN, —OH, —O—C(O)—NH—$C_{1-3}$-alkyl,
 (c) $C_{1-4}$-alkyl, $C_{2-4}$-alkenyl, $C_{2-4}$-alkynyl, $C_{1-3}$-alkyl-O—, $C_{1-3}$-alkyl-S—,
 (d) a $C_{1-3}$-alkyl or $C_{1-3}$-alkyl-O— group wherein each methylene group is substituted by up to two fluorine atoms and each methyl group is substituted by up to three fluorine atoms,
 (e) —C(O)—$R^{3.3.1}$,
 (f) —S(O)$_2$—$R^{3.3.2}$,
$R^{3.3.1}$ denotes —O—$C_{1-3}$-alkyl, —OH, —NR$^{3.3.1.1}$R$^{3.3.1.2}$,
$R^{3.3.1.1}$ denotes H, $C_{1-3}$-alkyl,
$R^{3.3.1.2}$ denotes H, $C_{1-3}$-alkyl,
$R^{3.3.2}$ denotes —O—$C_{1-3}$-alkyl, —NR$^{3.3.2.1}$R$^{3.3.2.2}$,
$R^{3.3.2.1}$ denotes H, $C_{1-3}$-alkyl,
$R^{3.3.2.2}$ denotes H, $C_{1-3}$-alkyl, or $R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, while
 the heterocycles mentioned previously may contain a carbonyl, thiocarbonyl or cyanimino group adjacent to a nitrogen atom, and
 may optionally each additionally be substituted at one or two nitrogen atoms by a group $R^{3.3.3}$ and
 may optionally each additionally be substituted at one or two carbon atoms by one or two groups $R^{3.3.4}$,
$R^{3.3.3}$ independently of one another denote
 (a) $C_{1-4}$-alkyl or
 (b) $C_{3-6}$-cycloalkyl, and
$R^{3.3.4}$ independently of one another denote
 (a) $C_{1-4}$-alkyl, $C_{3-6}$-cycloalkyl,
 (b) halogen, CN, $C_{1-3}$-alkyl-O—, —$NH_2$,
 (c) a $C_{1-3}$-alkyl or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A ninth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group of general formulae III

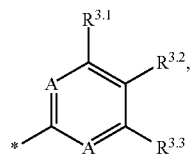
(III)

A independently of one another denotes CH or N,
$R^{3.1}$ denotes
(a) H,
(b) halogen, —NH$_2$, C$_{1-4}$-alkyl-NH—, (C$_{1-4}$-alkyl)$_2$N—, C$_{1-3}$-alkyl-C(O)—NH, —CN, —OH, —O—C(O)—NH—C$_{1-3}$-alkyl,
(c) C$_{1-4}$-alkyl, C$_{2-4}$-alkenyl, C$_{2-4}$-alkynyl, C$_{1-3}$-alkyl-O—, C$_{1-3}$-alkyl-S—,
(d) a C$_{1-3}$-alkyl or C$_{1-3}$-alkyl-O— group wherein each methylene group is substituted by up to two fluorine atoms and each methyl group is substituted by up to three fluorine atoms,
$R^{3.2}$ denotes
(a) H,
(b) halogen, —NH$_2$, C$_{1-4}$-alkyl-NH—, (C$_{1-4}$-alkyl)$_2$N—, C$_{1-3}$-alkyl-C(O)—NH—, —CN, —OH, —O—C(O)—NH—C$_{1-3}$-alkyl,
(c) C$_{1-4}$-alkyl, C$_{2-4}$-alkenyl, C$_{2-4}$-alkynyl, C$_{1-3}$-alkyl-O—, C$_{1-3}$-alkyl-S—,
(d) a C$_{1-3}$-alkyl or C$_{1-3}$-alkyl-O— group wherein each methylene group is substituted by up to two fluorine atoms and each methyl group is substituted by up to three fluorine atoms,
$R^{3.3}$ denotes
(a) H,
(b) halogen, —NH$_2$, C$_{1-4}$-alkyl-NH, (C$_{1-4}$-alkyl)$_2$N, C$_{1-3}$-alkyl-C(O)—NH, —CN, —OH, —O—C(O)—NH—C$_{1-3}$-alkyl,
(c) C$_{1-4}$-alkyl, C$_{2-4}$-alkenyl, C$_{2-4}$-alkynyl, C$_{1-3}$-alkyl-O, C$_{1-3}$-alkyl-S—,
(d) a C$_{1-3}$-alkyl- or C$_{1-3}$-alkyl-O— group wherein each methylene group is substituted by up to two fluorine atoms and each methyl group is substituted by up to three fluorine atoms,
$R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, while
the heterocycles mentioned previously may contain a carbonyl, thiocarbonyl or cyanimino group adjacent to a nitrogen atom, and
may optionally each additionally be substituted at one or two nitrogen atoms by a group $R^{3.3.3}$ and
may optionally each additionally be substituted at one or two carbon atoms by one or two groups $R^{3.3.4}$,
$R^{3.3.3}$ independently of one another denote
(a) C$_{1-4}$-alkyl or
(b) C$_{3-6}$-cycloalkyl, and
$R^{3.3.4}$ independently of one another denote
(a) C$_{1-4}$-alkyl, C$_{3-6}$-cycloalkyl,
(b) halogen, CN, C$_{1-3}$-alkyl-O—, —NH$_2$,
(c) a C$_{1-3}$-alkyl or C$_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A tenth embodiment of the present invention consists in the compounds of the above general formula I, wherein U, V, X, Y, $R^1$ and $R^2$ are as hereinbefore defined in the first, second, third, fourth, fifth, sixth or seventh embodiment and
$R^3$ denotes a group of general formulae III

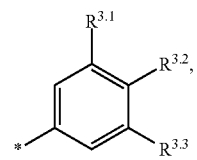
(III)

$R^{3.1}$ denotes
(a) H,
(b) F, Cl, Br, —NH$_2$, C$_{1-3}$-alkyl-NH, (C$_{1-3}$-alkyl)$_2$N, C$_{1-3}$-alkyl-C(O)—NH, —CN, —OH,
(c) C$_{1-4}$-alkyl, C$_{2-4}$-alkenyl, C$_{2-4}$-alkynyl, C$_{1-3}$-alkyl-O—, C$_{1-3}$-alkyl-S—,
(d) a C$_{1-3}$-alkyl or C$_{1-3}$-alkyl-O— group wherein each methylene group is substituted by up to two fluorine atoms and each methyl group is substituted by up to three fluorine atoms,
$R^{3.2}$ denotes
(a) H,
(b) F, Cl, Br, H$_2$N—, (C$_{1-4}$-alkyl)-NH—, (C$_{1-4}$-alkyl)$_2$N—, (C$_{1-3}$-alkyl)-C(O)—NH—, —OH,
(c) C$_{1-4}$-alkyl,
(d) a C$_{1-3}$-alkyl- or C$_{1-3}$-alkyl-O— group wherein each methylene group is substituted by up to two fluorine atoms and each methyl group is substituted by up to three fluorine atoms,
$R^{3.3}$ denotes
(a) H,
(b) F, Cl, Br, H$_2$N—, (C$_{1-4}$-alkyl)-NH—, (C$_{1-4}$-alkyl)$_2$N—, (C$_{1-3}$-alkyl)-C(O)—NH—, —OH,
(c) C$_{1-4}$-alkyl,
(d) a C$_{1-3}$-alkyl- or C$_{1-3}$-alkyl-O— group wherein each methylene group is substituted by up to two fluorine atoms and each methyl group is substituted by up to three fluorine atoms,
$R^{3.2}$ and $R^{3.3}$ together with the carbon atoms to which they are attached form a monounsaturated 5-membered or a mono- or diunsaturated 6-membered heterocyclic group or a 5- to 6-membered heteroaryl group, while the heterocycles mentioned previously may contain a carbonyl, thiocarbonyl or cyanimino group adjacent to a nitrogen atom, and
may optionally each additionally be substituted at one or two nitrogen atoms by a group $R^{3.3.3}$ and
may optionally each additionally be substituted at one or two carbon atoms by one or two groups $R^{3.3.4}$,
$R^{3.3.3}$ independently of one another denote
(a) C$_{1-4}$-alkyl or
(b) C$_{3-6}$-cycloalkyl, and
$R^{3.3.4}$ independently of one another denote
(a) C$_{1-4}$-alkyl, C$_{3-6}$-cycloalkyl,
(b) halogen, CN, C$_{1-3}$-alkyl-O—, —NH$_2$,
(c) a C$_{1-3}$-alkyl or C$_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

An eleventh embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group selected from

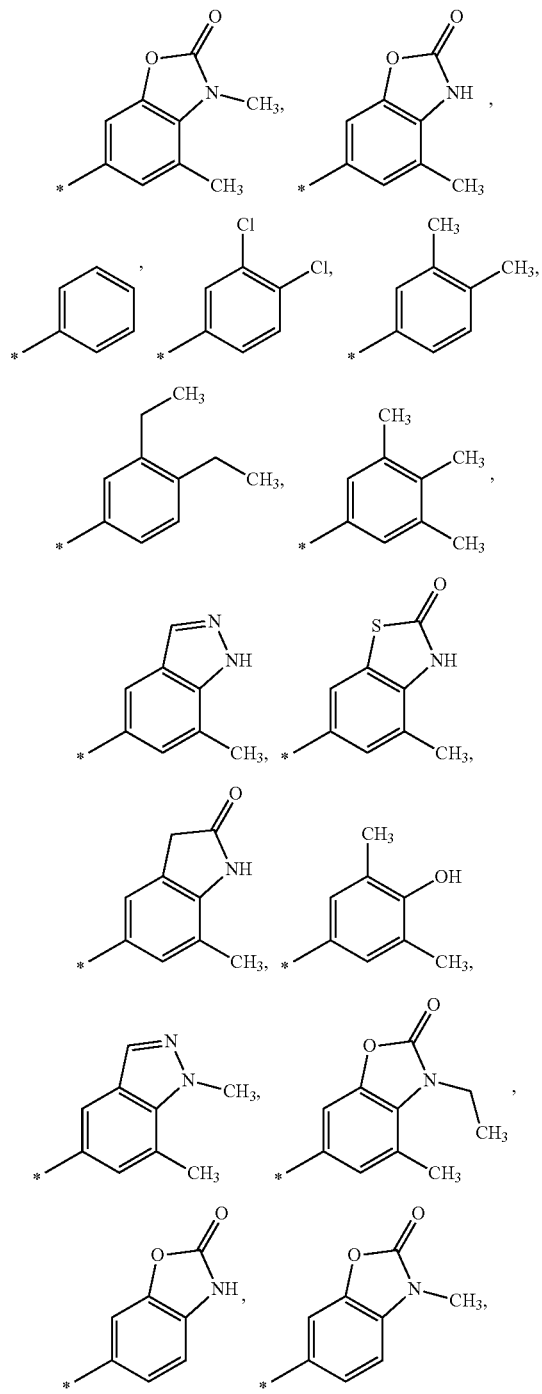

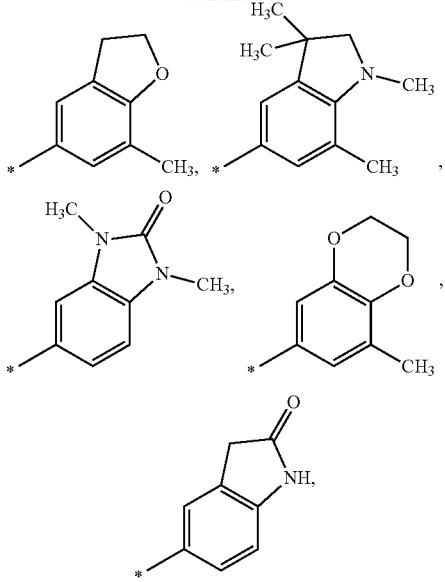

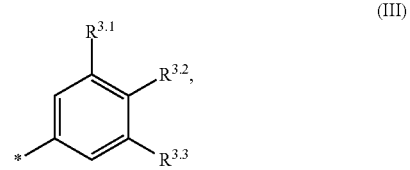

the tautomers, the diastereomers, the enantiomers, the hydrates, the mixtures thereof and the salts thereof as well as the hydrates of the salts, particularly the physiologically acceptable salts thereof with inorganic or organic acids or bases.

A twelfth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group of general formulae III $$\text{(III)}$$

$R^{3.1}$ denotes
  (a) H,
  (b) F, Cl, Br, —$NH_2$, $C_{1-3}$-alkyl-NH, ($C_{1-3}$-alkyl)$_2$N, $C_{1-3}$-alkyl-C(O)—NH, —CN, —OH,
  (c) $C_{1-4}$-alkyl, $C_{2-4}$-alkenyl, $C_{2-4}$-alkynyl, $C_{1-3}$-alkyl-O—, $C_{1-3}$-alkyl-S—,
  (d) a $C_{1-3}$-alkyl or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are attached form a monounsaturated 5-membered heterocyclic group or a mono- or diunsaturated 6-membered heterocyclic group or a 5- to 6-membered heteroaryl group, while
  the heterocycles mentioned previously may contain a carbonyl, thiocarbonyl or cyanimino group adjacent to a nitrogen atom, and
  may optionally each additionally be substituted at one or two nitrogen atoms by a group $R^{3.3.3}$ and
  may optionally each additionally be substituted at one or two carbon atoms by one or two groups $R^{3.3.4}$, $R^{3.3.3}$ independently of one another denote
- (a) $C_{1-4}$-alky-l or
- (b) $C_{3-6}$-cycloalkyl, and $R^{3.3.4}$ independently of one another denote
- (a) $C_{1-4}$-alkyl-, $C_{3-6}$-cycloalkyl-,
- (b) halogen, —CN, —O—$C_{1-3}$-alkyl, —$NH_2$,
- (c) a $C_{1-3}$-alkyl- or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A thirteenth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group of general formulae III

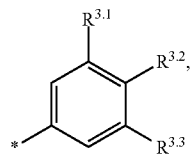

(III)

$R^{3.1}$ denotes
- (a) H,
- (b) F, Cl, Br, —$NH_2$, $C_{1-3}$-alkyl-NH—, ($C_{1-3}$-alkyl)$_2$N—, $C_{1-3}$-alkyl-C(O)—NH—, —CN, —OH,
- (c) $C_{1-4}$-alkyl, $C_{2-4}$-alkenyl, $C_{2-4}$-alkynyl, $C_{1-3}$-alkyl-O—, $C_{1-3}$-alkyl-S—,
- (d) a $C_{1-3}$-alkyl- or $C_{1-3}$-alkyl-O— group wherein each methylene group is substituted by up to two fluorine atoms and each methyl group is substituted by up to three fluorine atoms, $R^{3.2}$ and $R^{3.3}$ together with the carbon atoms to which they are attached form a monounsaturated 5-membered heterocyclic group or a 5-membered heteroaryl group, wherein
the heterocycles mentioned previously may contain a carbonyl, thiocarbonyl or cyanimino group adjacent to a nitrogen atom, and may optionally each additionally be substituted at one or two nitrogen atoms by a group $R^{3.3.3}$ and
may optionally each additionally be substituted at one or two carbon atoms by one or two groups $R^{3.3.4}$, $R^{3.3.3}$ independently of one another denote
- (a) $C_{1-4}$-alkyl or
- (b) $C_{3-6}$-cycloalkyl, and $R^{3.3.4}$ independently of one another denote
- (a) $C_{1-4}$-alkyl, $C_{3-6}$-cycloalkyl,
- (b) halogen, —CN, —O—$C_{1-3}$-alkyl, —$NH_2$,
- (c) a $C_{1-3}$-alkyl- or $C_{1-3}$-alkyl-O— group wherein each methylene group is substituted by up to two fluorine atoms and each methyl group is substituted by up to three fluorine atoms, the tautomers, the diastereomers, the enantiomers, the hydrates, the mixtures thereof and the salts thereof as well as the hydrates of the salts, particularly the physiologically acceptable salts thereof with inorganic or organic acids or bases.

A fourteenth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group of general formula IIa

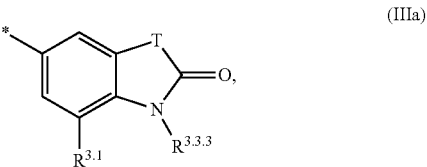

(IIIa)

T denotes O, S, $CH_2$, NH or N—$R^{3.3.3}$, $R^{3.1}$ denotes
- (a) H,
- (b) F, Cl, Br, —$NH_2$, $C_{1-3}$-alkyl-NH—, ($C_{1-3}$-alkyl)$_2$N—, $C_{1-3}$-alkyl-C(O)—NH—, —CN, —OH,
- (c) $C_{1-4}$-alkyl, $C_{2-4}$-alkenyl, $C_{2-4}$-alkynyl, $C_{1-3}$-alkyl-O—, $C_{1-3}$-alkyl-S—,
- (d) a $C_{1-3}$-alkyl- or $C_{1-3}$-alkyl-O— group wherein each methylene group is substituted by up to two fluorine atoms and each methyl group is substituted by up to three fluorine atoms, and $R^{3.3.3}$ independently of one another denote
- (a) $C_{1-4}$-alkyl or
- (b) $C_{3-6}$-cycloalkyl, the tautomers, the diastereomers, the enantiomers, the hydrates, the mixtures thereof and the salts thereof as well as the hydrates of the salts, particularly the physiologically acceptable salts thereof with inorganic or organic acids or bases.

A fifteenth embodiment of the present invention consists in the compounds of the above general formula I, wherein U, V, X, Y, $R^1$ and $R^2$ are as hereinbefore defined in the first, second, third, fourth, fifth, sixth or seventh embodiment and $R^3$ denotes a group selected from

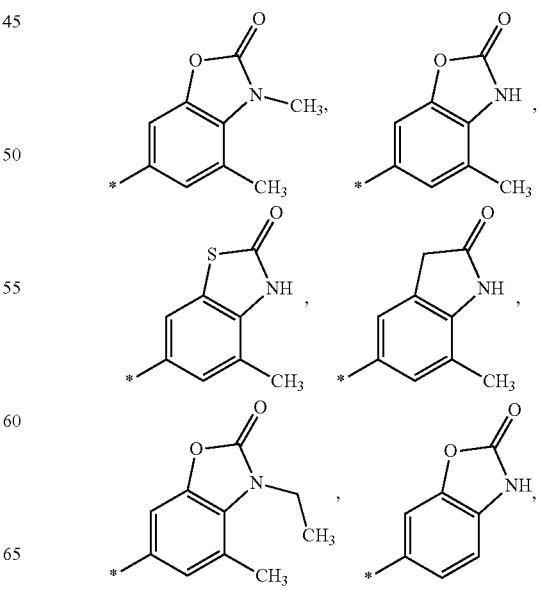

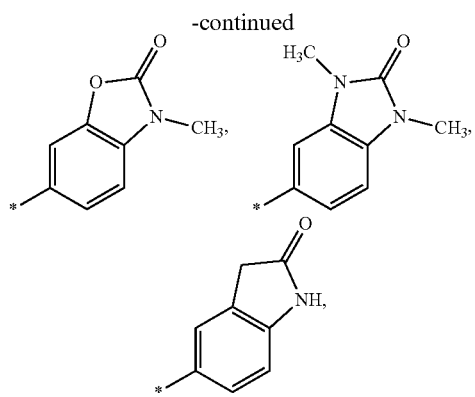

the tautomers, the diastereomers, the enantiomers, the hydrates, the mixtures thereof and the salts thereof as well as the hydrates of the salts, particularly the physiologically acceptable salts thereof with inorganic or organic acids or bases.

A sixteenth embodiment of the present invention consists in the compounds of the above general formula I, wherein Y, $R^1$, $R^2$ and $R^3$ are as hereinbefore defined in the first, second, third, fourth, fifth, sixth, seventh, eighth, ninth, tenth, eleventh, twelfth, thirteenth, fourteenth or fifteenth embodiment and U—V—X denotes a group selected from
—N=N—(C—$R^{11}$)=, —N=(C—$R^{10}$)—N=, —N=(C—$R^{10}$)—(C—$R^{11}$)=, —(N-oxide)=(C—$R^{10}$)—(C—$R^{11}$)=, —(C$R^9$)=N—N=, —(C$R^9$)=N—(C$R^{11}$)=, —(C—$R^9$)=N(oxide)-(C—$R^{11}$)=, —(C$R^9$)=(C—$R^{10}$)—N=, —(C$R^9$)=(C—$R^{10}$)—(N-oxide)=, —(C$R^9$)=(C—$R^{10}$)—(C$R^{11}$)=, and $R^9$ denotes
(a) H,
(b) a $C_{1-6}$-alkyl- or $C_{1-3}$-alkyl-O— group which may each be substituted by a group $R^{9.1}$,
(c) $R^{9.2}R^{9.3}$N, $R^{9.2}R^{9.3}$N—$C_{1-3}$-alkylene-,
(d) halogen, —CN, —OH, —COOH, $C_{1-3}$-alkyl-O—$C_{1-3}$-alkylene-, $C_{3-6}$-cycloalkyl, $C_{3-6}$-cycloalkyl-$C_{1-4}$-alkylene-, $C_{1-3}$-alkyl-C(O)—O—$C_{1-3}$-alkylene,
(e) a $C_{1-3}$-alkyl or $C_{1-3}$-alkyl-O— group wherein each methylene group is substituted by up to two fluorine atoms and each methyl group is substituted by up to three fluorine atoms, $R^{9.1}$ denotes H, OH or —O—$CH_3$,
$R^{9.2}$ denotes H or $C_{1-3}$-alkyl,
$R^{9.3}$ denotes H or $C_{1-3}$-alkyl, or
$R^{9.2}$ and $R^{9.3}$ together with the nitrogen atom to which they are attached denote a 3- to 6-membered heterocyclic group, $R^{10}$ denotes
(a) H,
(b) a $C_{1-6}$-alkyl or $C_{1-3}$-alkyl-CO— group which may each be substituted by a group $R^{10.1}$,
(c) —$NR^{10.1}R^{10.2}$, $NR^{10.1}R^{10.2}$—$C_{1-3}$-alkylene-,
(d) halogen, —CN, —OH, $C_{1-3}$-alkyl-O—$C_{1-3}$-alkylene-, $C_{3-6}$-cycloalkyl-, $C_{3-6}$-cycloalkyl-$C_{1-4}$-alkylene-, $C_{1-3}$-alkyl-C(O)—O—$C_{1-3}$-alkylene,
(e) aryl-$C_{0-3}$-alkylene-O—,
(f) a $C_{1-3}$-alkyl- or $C_{1-3}$-alkyl-O— group wherein each methylene group is substituted by up to two fluorine atoms and each methyl group is substituted by up to three fluorine atoms, $R^{10.1}$ denotes H, OH or —O—$CH_3$,
$R^{10.2}$ denotes H or $C_{1-6}$-alkyl,
$R^{10.3}$ denotes H, $C_{1-6}$-alkyl or —$SO_2$—$C_{1-3}$-alkyl, $R^{11}$ denotes
(a) H,
(b) a $C_{1-6}$-alkyl or $C_{1-3}$-alkyl-O— group which may each be substituted by a group $R^{11.1}$,
(c) $R^{11.2}R^{11.3}$N, $R^{11.2}R^{11.3}$N—$C_{1-3}$-alkylene-,
(d) halogen, —CN, —OH, —COOH, $C_{1-3}$-alkyl-O—$C_{1-3}$-alkylene-, $C_{3-6}$-cycloalkyl, $C_{3-6}$-cycloalkyl-$C_{1-4}$-alkylene-, $C_{1-3}$-alkyl-C(O)—O—$C_{1-3}$-alkylene,
(e) a $C_{1-3}$-alkyl- or $C_{1-3}$-alkyl-O— group wherein each methylene group is substituted by up to two fluorine atoms and each methyl group is substituted by up to three fluorine atoms, $R^{11.1}$ denotes H, OH or —O—$CH_3$,
$R^{11.2}$ denotes H or $C_{1-3}$-alkyl,
$R^{11.3}$ denotes H or $C_{1-3}$-alkyl, or
$R^{11.2}$ and $R^{11.3}$ together with the nitrogen atom to which they are attached denote a 3- to 6-membered heterocyclic group, the tautomers, the diastereomers, the enantiomers, the hydrates, the mixtures thereof and the salts thereof as well as the hydrates of the salts, particularly the physiologically acceptable salts thereof with inorganic or organic acids or bases.

A seventeenth embodiment of the present invention consists in the compounds of the above general formula I, wherein Y, $R^1$, $R^2$ and $R^3$ are as hereinbefore defined in the first, second, third, fourth, fifth, sixth, seventh, eighth, ninth, tenth, eleventh, twelfth, thirteenth, fourteenth or fifteenth embodiment and the ring

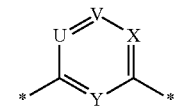

denotes a group selected from

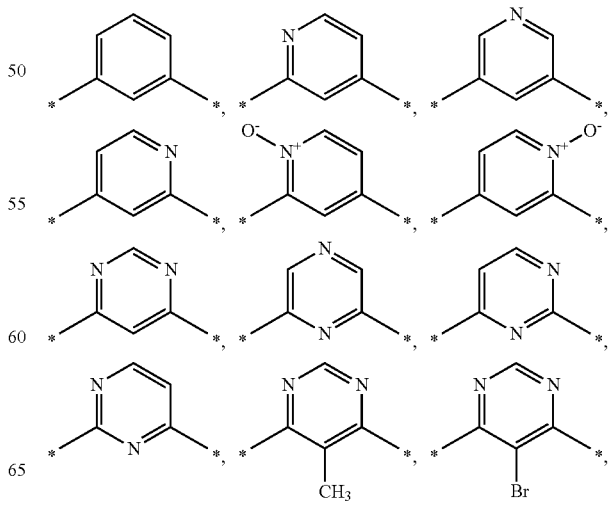

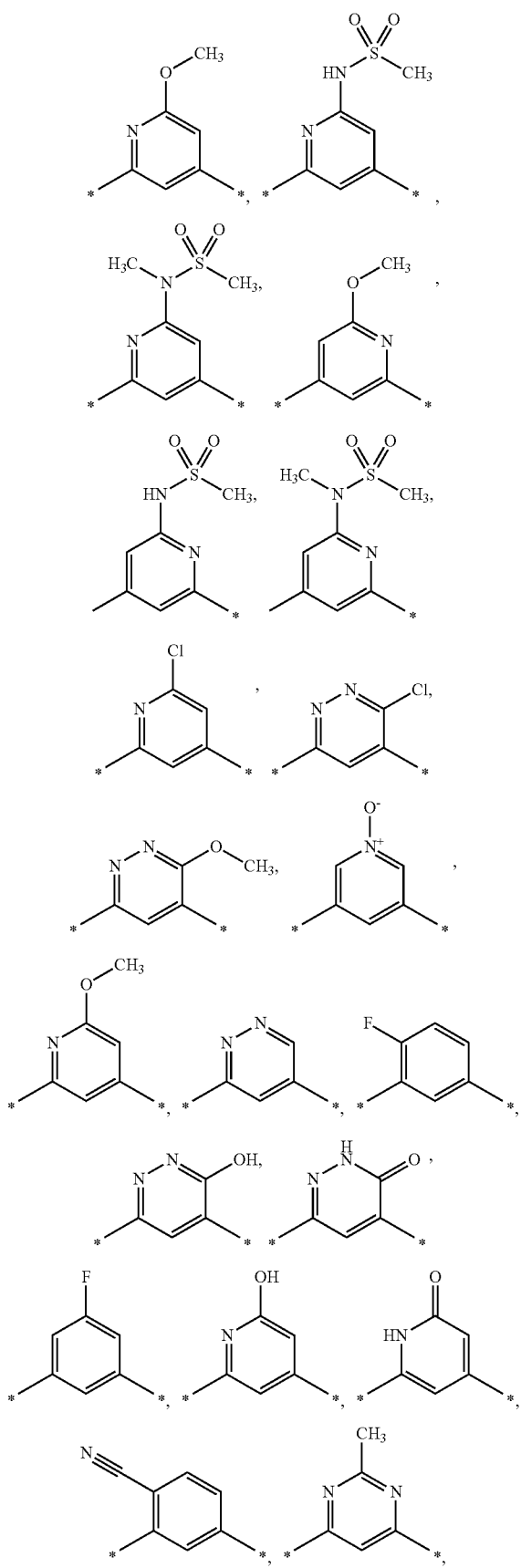
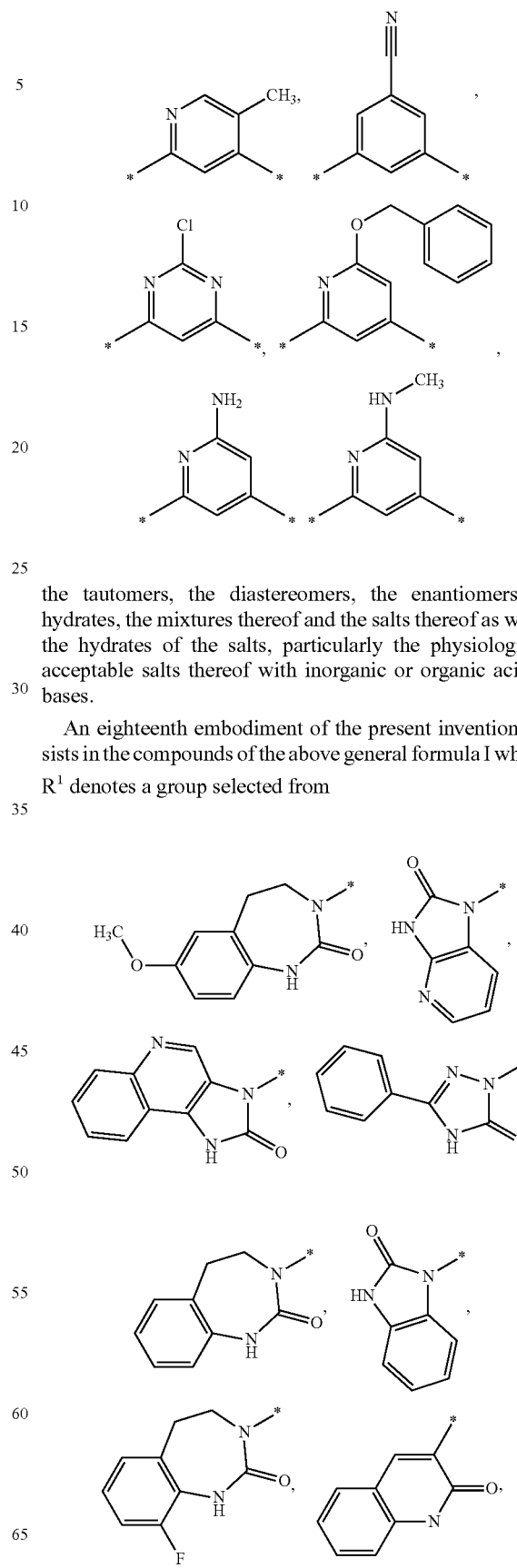

the tautomers, the diastereomers, the enantiomers, the hydrates, the mixtures thereof and the salts thereof as well as the hydrates of the salts, particularly the physiologically acceptable salts thereof with inorganic or organic acids or bases.

An eighteenth embodiment of the present invention consists in the compounds of the above general formula I wherein $R^1$ denotes a group selected from

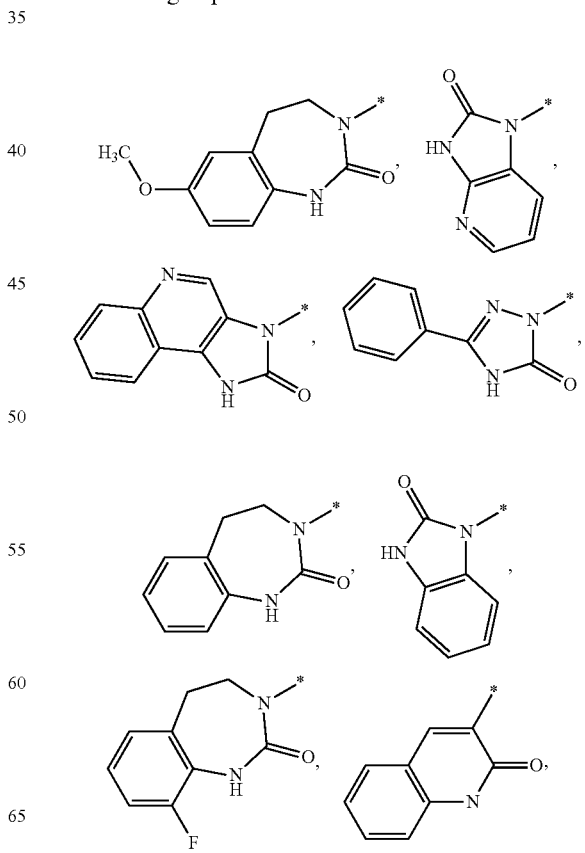

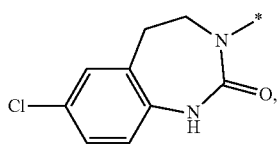

$R^2$ denotes H and
$R^3$ denotes a group selected from

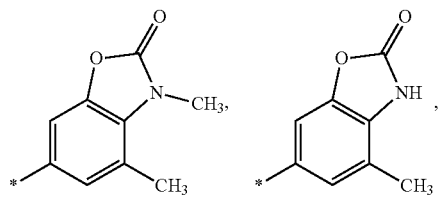

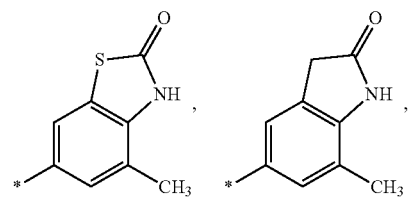

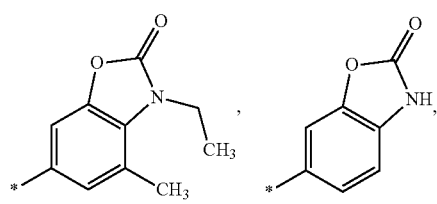

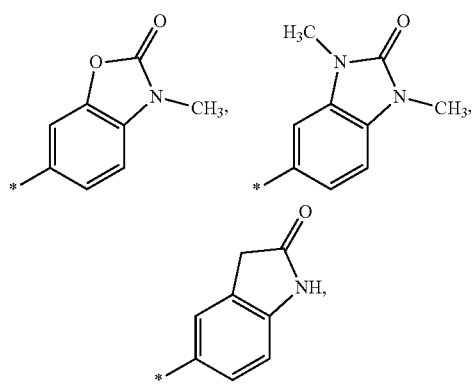

and the ring

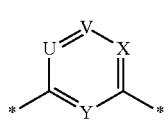

denotes a group selected from

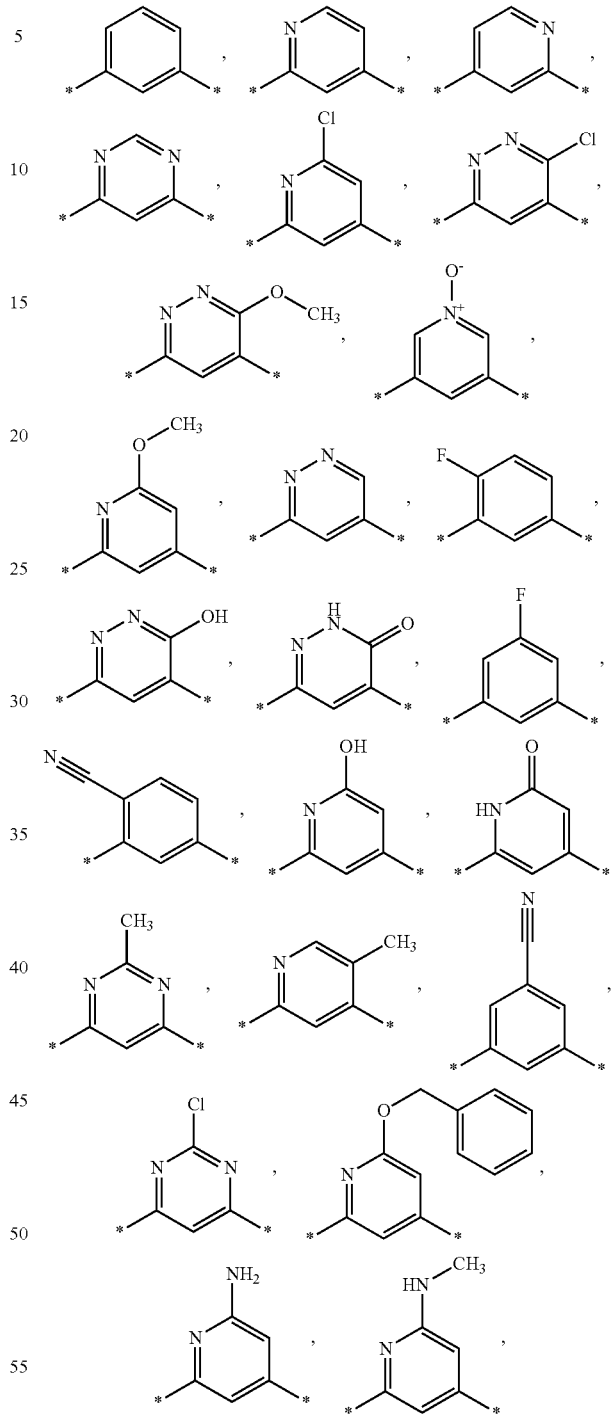

the tautomers, the diastereomers, the enantiomers, the hydrates, the mixtures thereof and the salts thereof as well as the hydrates of the salts, particularly the physiologically acceptable salts thereof with inorganic or organic acids or bases.

The following compounds are mentioned as examples of most particularly preferred compounds of the above general formula I:

| No. | Structure |
|---|---|
| (1) | 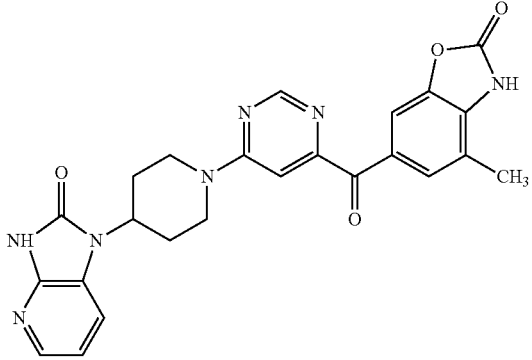 [SMILES: Cc1cc(C(=O)c2cc(N3CCC(n4c(=O)[nH]c5ncccc54)CC3)ncn2)cc2oc(=O)[nH]c12] |
| (2) | 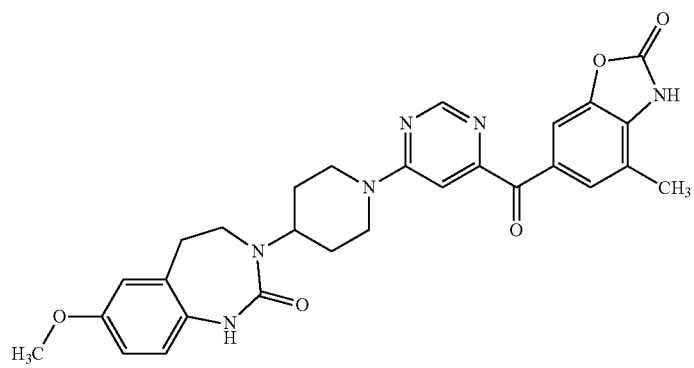 |
| (3) | 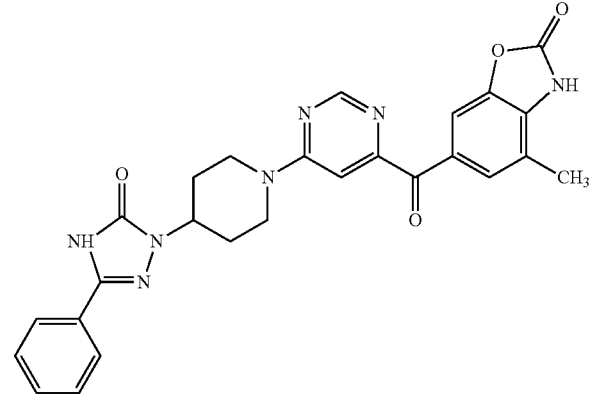 [SMILES: Cc1cc(C(=O)c2cc(N3CCC(n4nc(-c5ccccc5)[nH]c4=O)CC3)ncn2)cc2oc(=O)[nH]c12] |
| (4) | 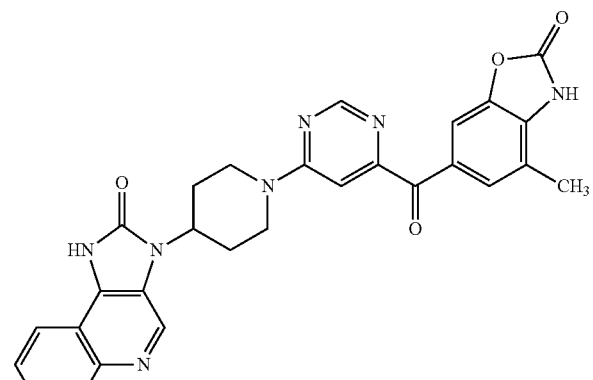 |

-continued
| No. | Structure |
|---|---|
| (5) | 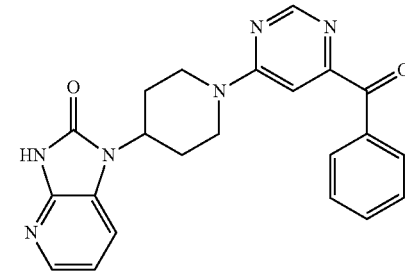 |
| (6) | 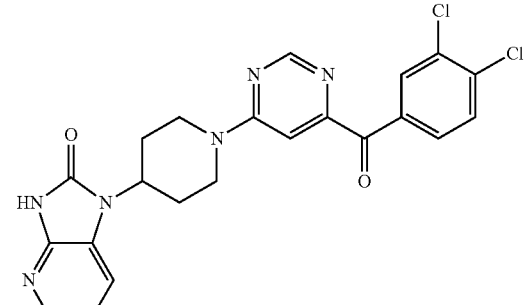 |
| (7) | 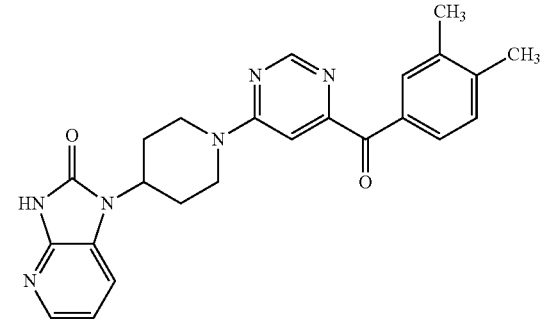 [SMILES: Cc1ccc(C(=O)c2cc(N3CCC(n4c(=O)[nH]c5ncccc54)CC3)ncn2)cc1C] |
| (8) | 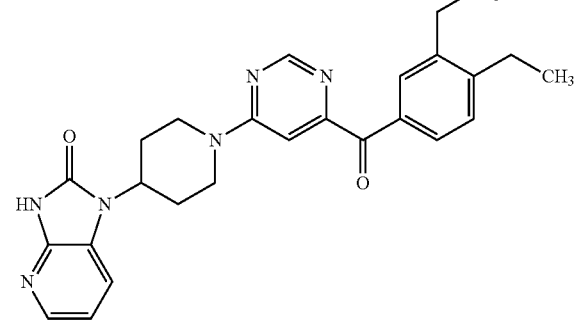 |
| (9) | 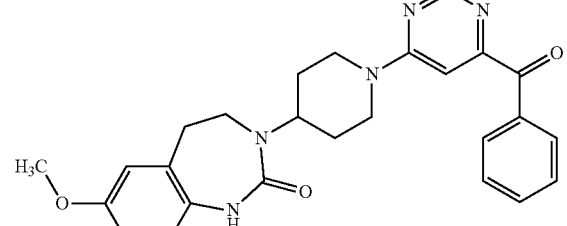 |

| No. | Structure |
|---|---|
| (10) | 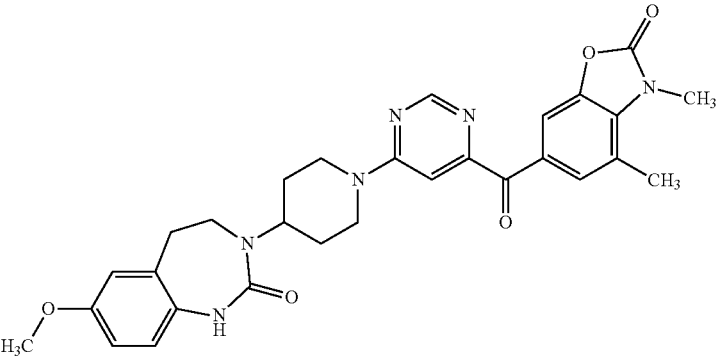 |
| (11) | 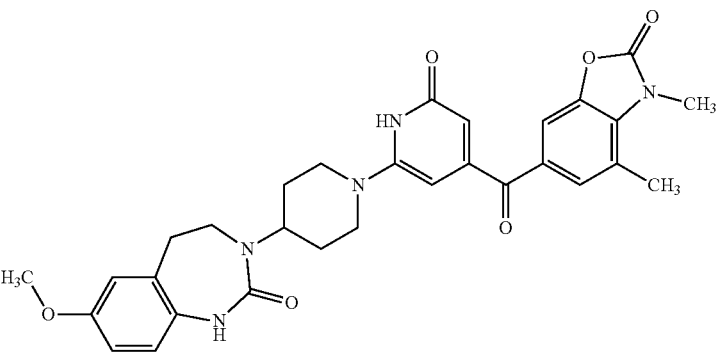 |
| (12) | 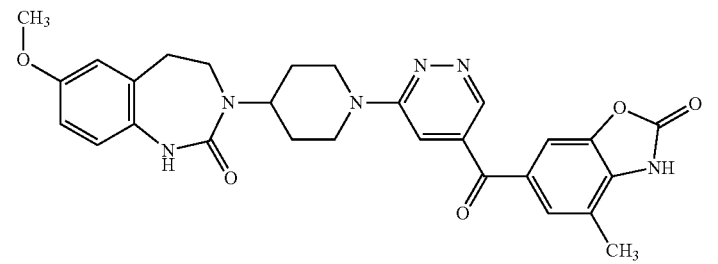 [SMILES: COc1ccc2c(c1)CCN(C1CCN(c3cc(C(=O)c4cc(C)c5[nH]c(=O)oc5c4)cnn3)CC1)C(=O)N2] |
| (13) | 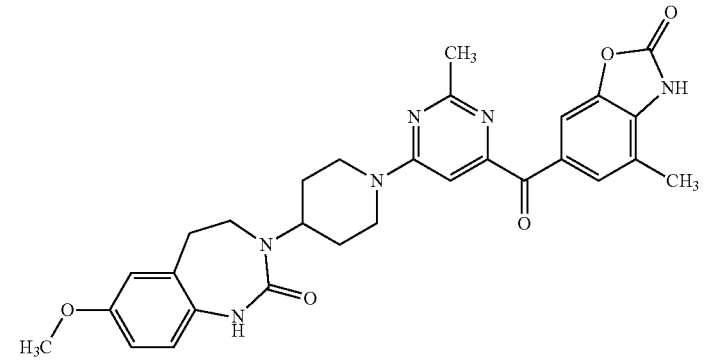 |

-continued

| No. | Structure |
|---|---|
| (14) | 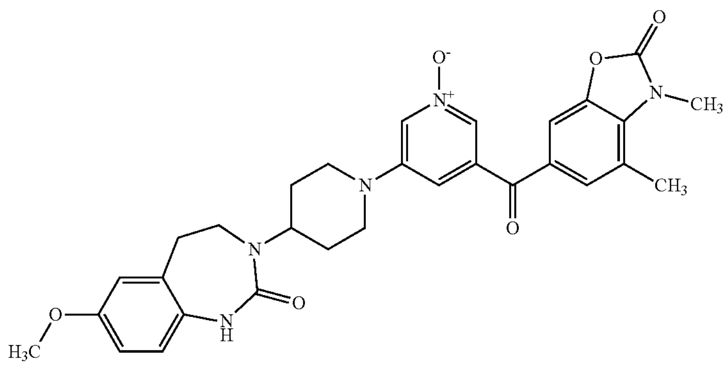 |
| (15) | 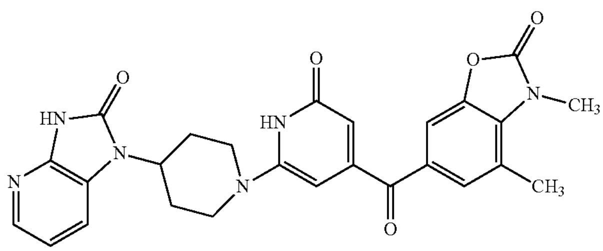 [SMILES: Cc1cc(C(=O)c2cc(N3CCC(n4c(=O)[nH]c5ncccc54)CC3)[nH]c(=O)c2)cc2oc(=O)n(C)c12] |
| (16) | 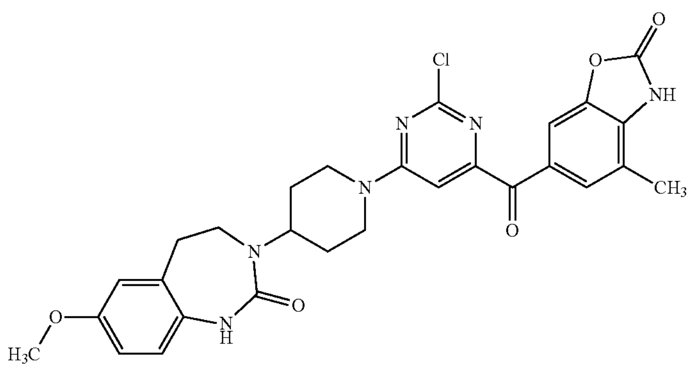 |
| (17) | 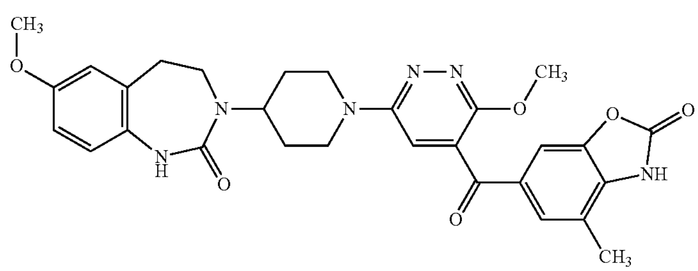 [SMILES: COc1ccc2c(c1)CCN(C1CCN(c3cc(C(=O)c4cc(C)c5[nH]c(=O)oc5c4)c(OC)nn3)CC1)C(=O)N2] |
| (18) | 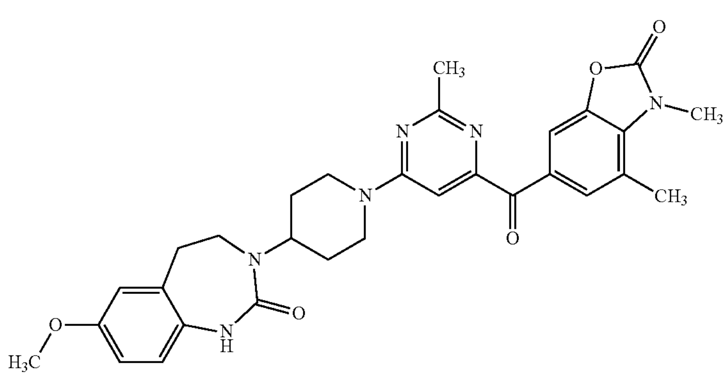 |

-continued

| No. | Structure |
|---|---|
| (19) | 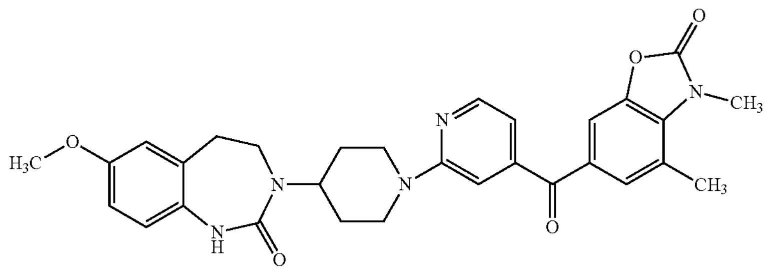 |
| (20) | 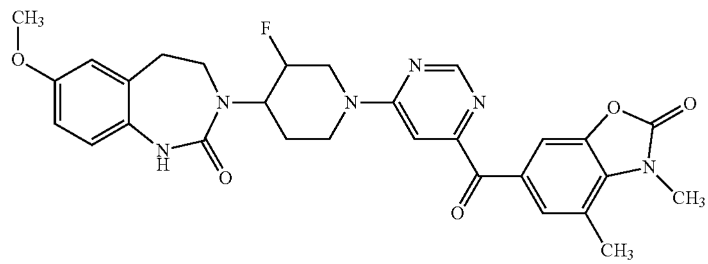 |
| (21) | 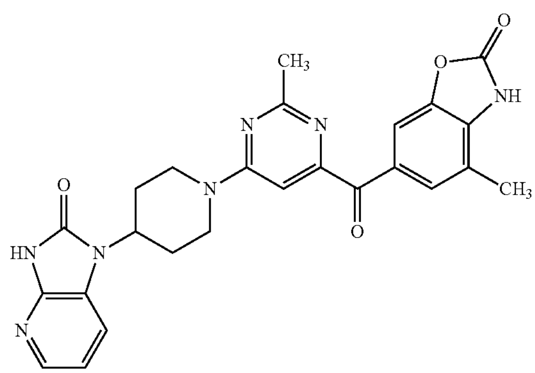 [SMILES: Cc1nc(C(=O)c2cc(C)c3[nH]c(=O)oc3c2)cc(N2CCC(n3c(=O)[nH]c4ncccc43)CC2)n1] |
| (22) | 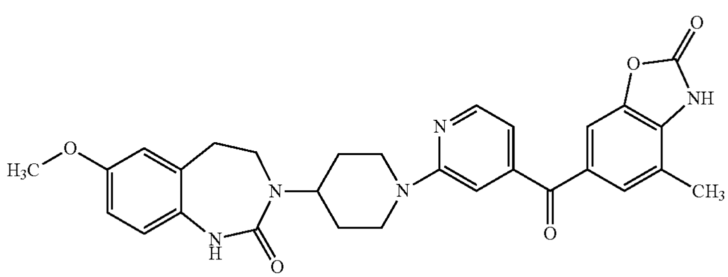 |
| (23) | 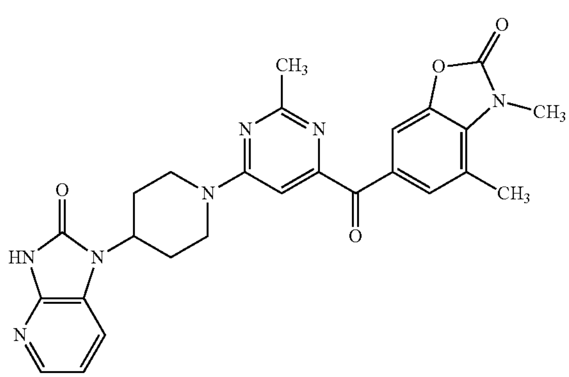 [SMILES: Cc1nc(C(=O)c2cc(C)c3c(c2)oc(=O)n3C)cc(N2CCC(n3c(=O)[nH]c4ncccc43)CC2)n1] |

-continued

| No. | Structure |
|---|---|
| (24) | 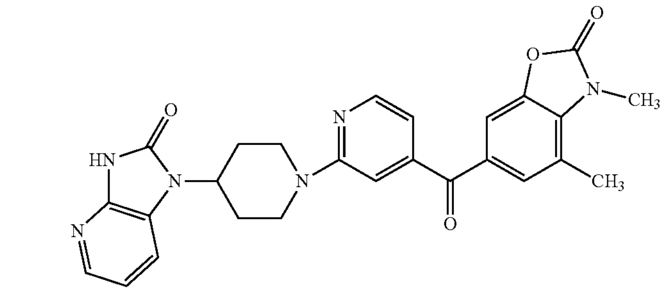 [SMILES: Cc1cc(C(=O)c2ccnc(N3CCC(n4c(=O)[nH]c5ncccc54)CC3)c2)cc2oc(=O)n(C)c12] |
| (25) | 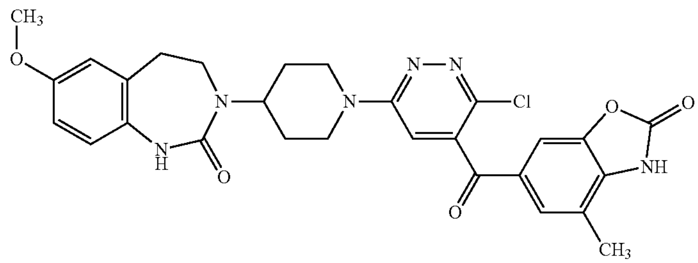 [SMILES: COc1ccc2c(c1)CCN(C1CCN(c3cc(C(=O)c4cc(C)c5[nH]c(=O)oc5c4)c(Cl)nn3)CC1)C(=O)N2] |
| (26) | 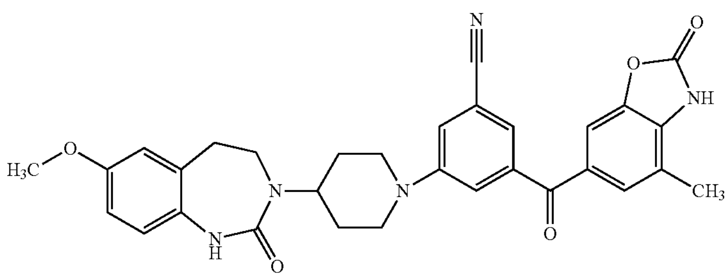 |
| (27) | 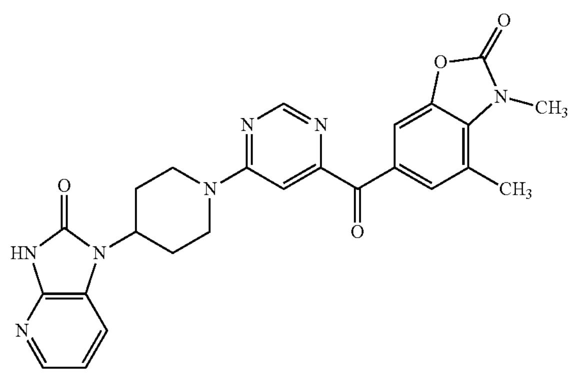 [SMILES: Cc1cc(C(=O)c2cc(N3CCC(n4c(=O)[nH]c5ncccc54)CC3)ncn2)cc2oc(=O)n(C)c12] |
| (28) | 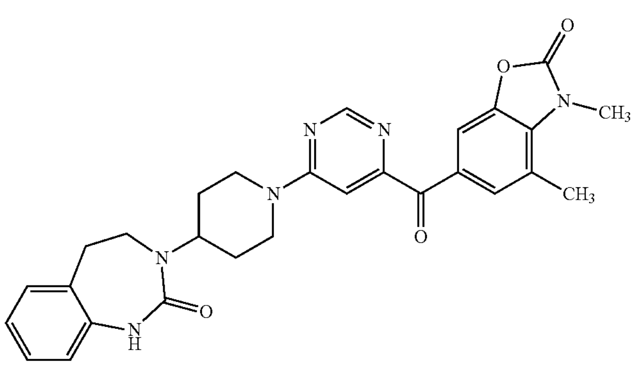 [SMILES: Cc1cc(C(=O)c2cc(N3CCC(N4CCc5ccccc5NC4=O)CC3)ncn2)cc2oc(=O)n(C)c12] |

-continued
| No. | Structure |
|---|---|
| (29) | 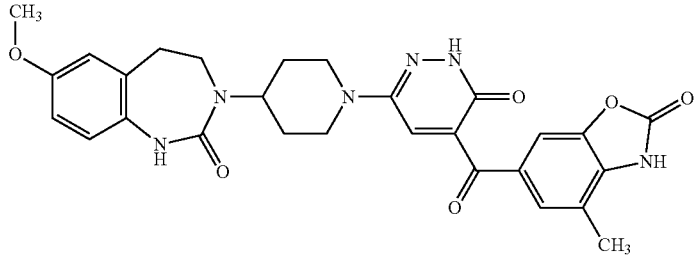 |
| (30) | 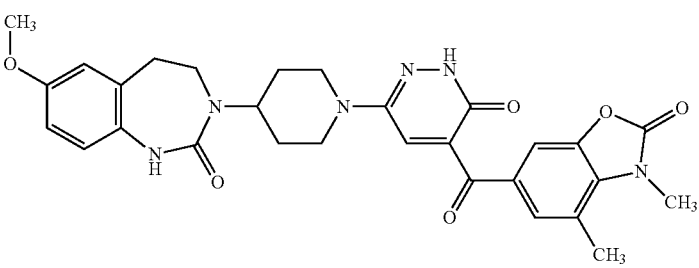 |
| (31) | 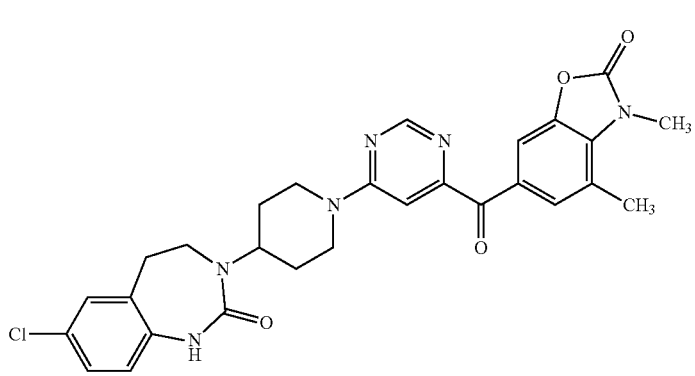 [SMILES: Cc1cc(C(=O)c2cc(N3CCC(N4CCc5cc(Cl)ccc5NC4=O)CC3)ncn2)cc2oc(=O)n(C)c12] |
| (32) | 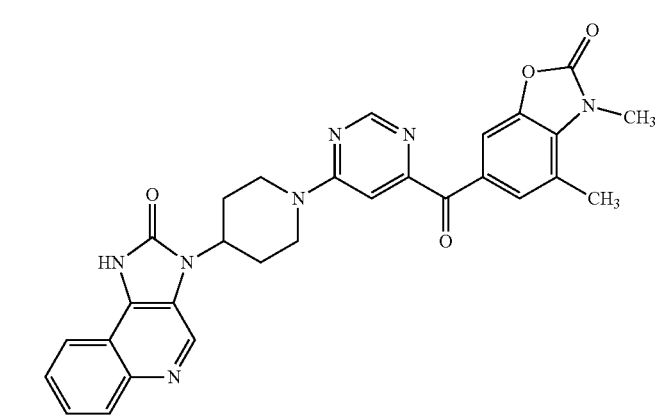 [SMILES: Cc1cc(C(=O)c2cc(N3CCC(n4c(=O)[nH]c5c6ccccc6ncc54)CC3)ncn2)cc2oc(=O)n(C)c12] |

| No. | Structure |
|---|---|
| (33) | 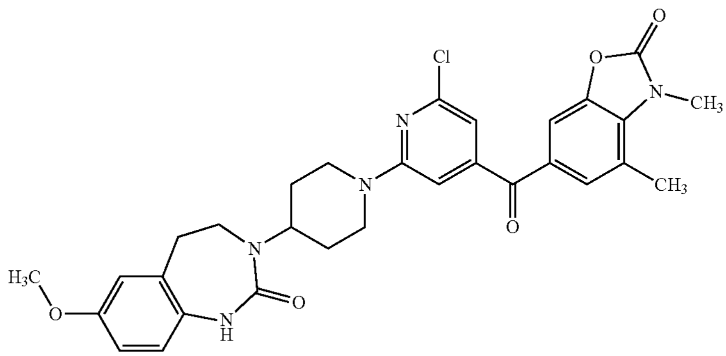 |
| (34) | 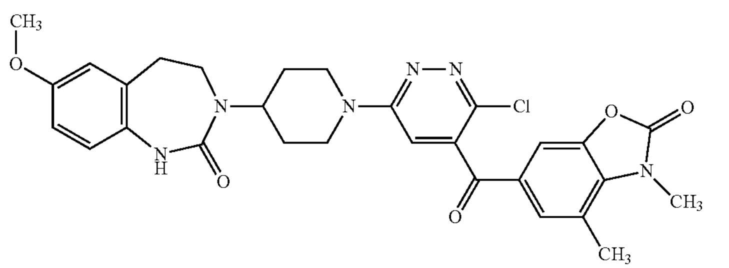 |
| (35) | 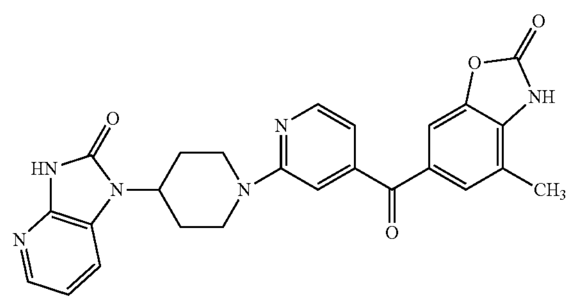 [SMILES: Cc1cc(C(=O)c2ccnc(N3CCC(n4c(=O)[nH]c5ncccc54)CC3)c2)cc2oc(=O)[nH]c12] |
| (36) | 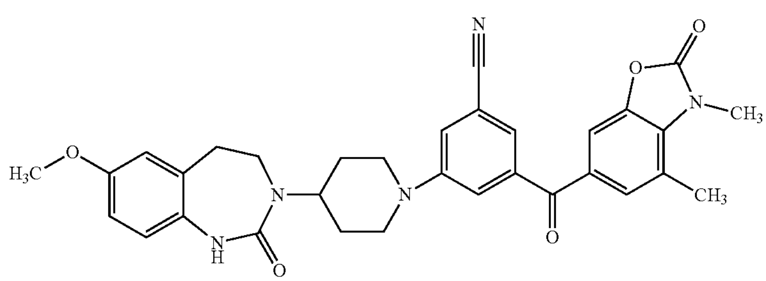 |
| (37) | 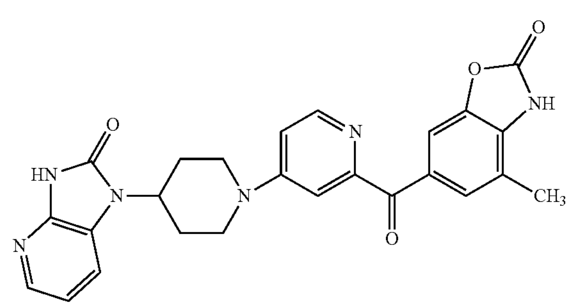 [SMILES: Cc1cc(C(=O)c2cc(N3CCC(n4c(=O)[nH]c5ncccc54)CC3)ccn2)cc2oc(=O)[nH]c12] |

| No. | Structure |
|---|---|
| (38) | 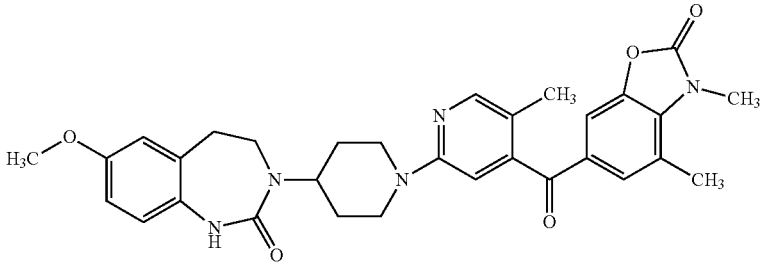 |
| (39) | 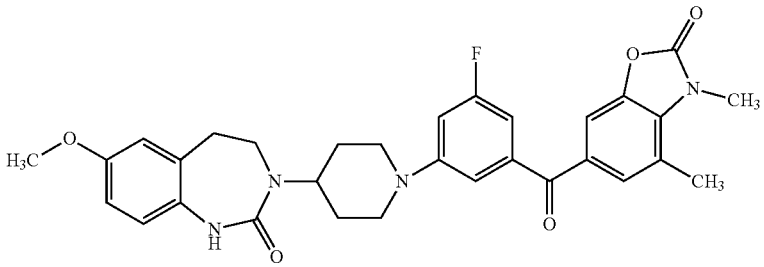 |
| (40) | 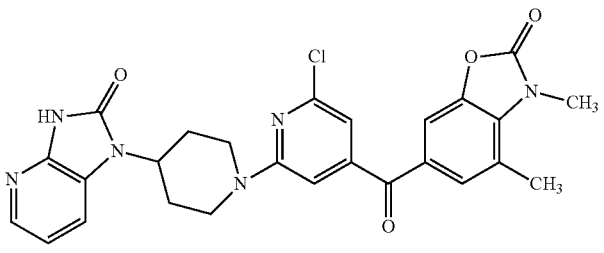 [SMILES: Cc1cc(C(=O)c2cc(Cl)nc(N3CCC(n4c(=O)[nH]c5ncccc54)CC3)c2)cc2oc(=O)n(C)c12] |
| (41) | 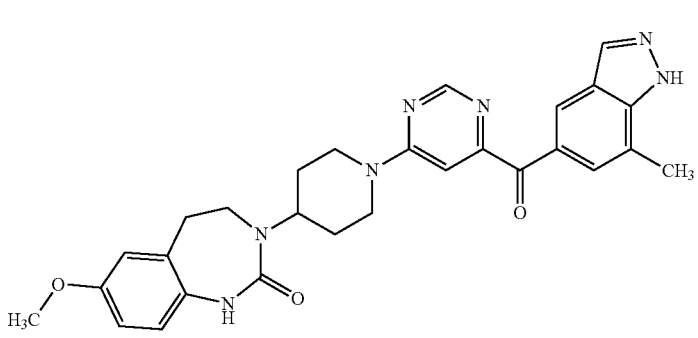 |
| (42) | 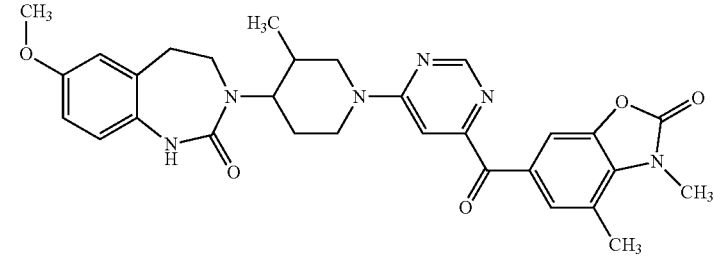 |

| No. | Structure |
|---|---|
| (43) | 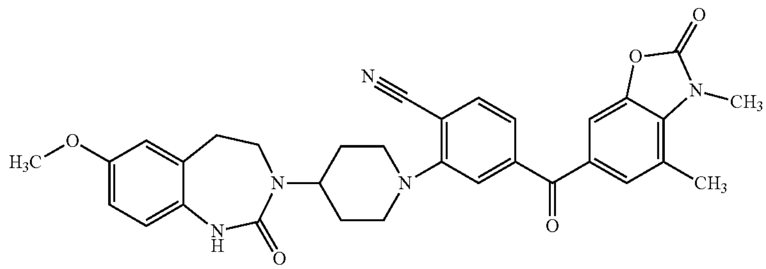 |
| (44) | 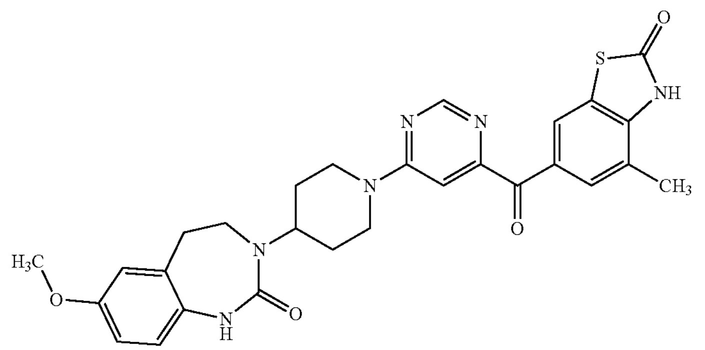 |
| (45) | 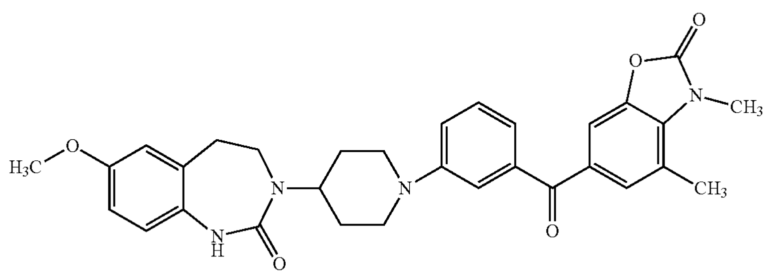 |
| (46) | 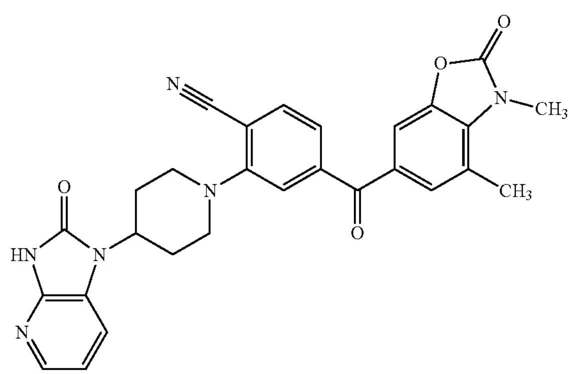 [SMILES: Cc1cc(C(=O)c2ccc(C#N)c(N3CCC(n4c(=O)[nH]c5ncccc54)CC3)c2)cc2oc(=O)n(C)c12] |
| (47) | 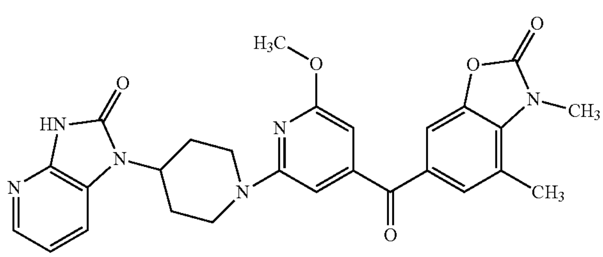 [SMILES: COc1cc(C(=O)c2cc(C)c3c(c2)oc(=O)n3C)cc(N2CCC(n3c(=O)[nH]c4ncccc43)CC2)n1] |

| No. | Structure |
|---|---|
| (48) | 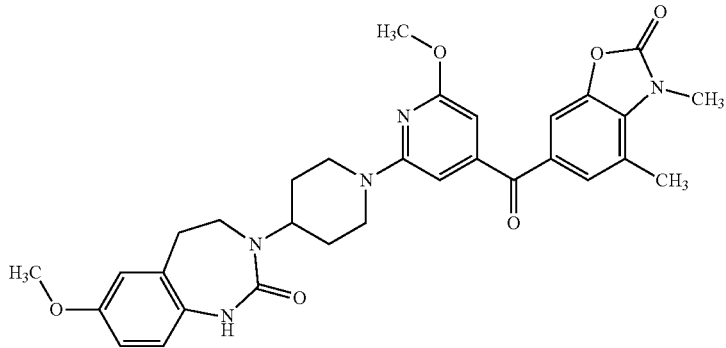 |
| (49) | 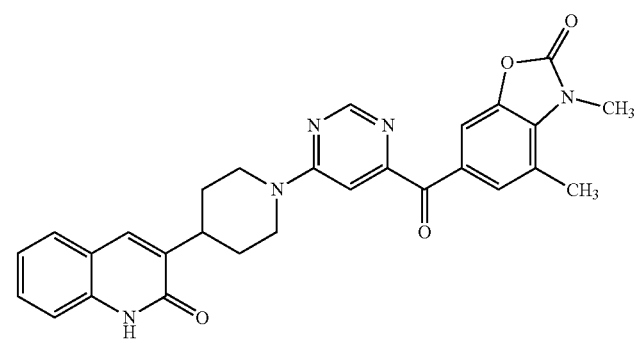 [SMILES: Cc1cc(C(=O)c2cc(N3CCC(c4cc5ccccc5[nH]c4=O)CC3)ncn2)cc2oc(=O)n(C)c12] |
| (50) | 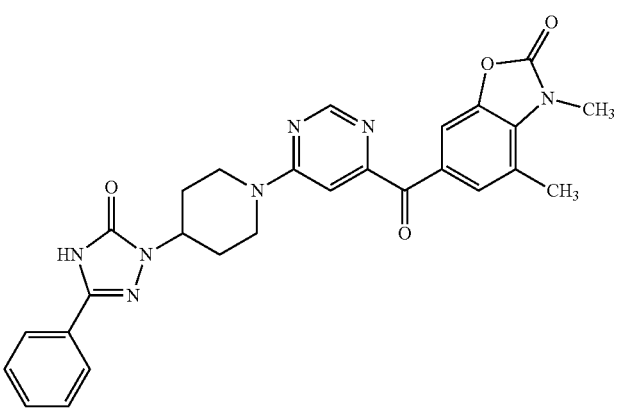 [SMILES: Cc1cc(C(=O)c2cc(N3CCC(n4nc(-c5ccccc5)[nH]c4=O)CC3)ncn2)cc2oc(=O)n(C)c12] |
| (51) | 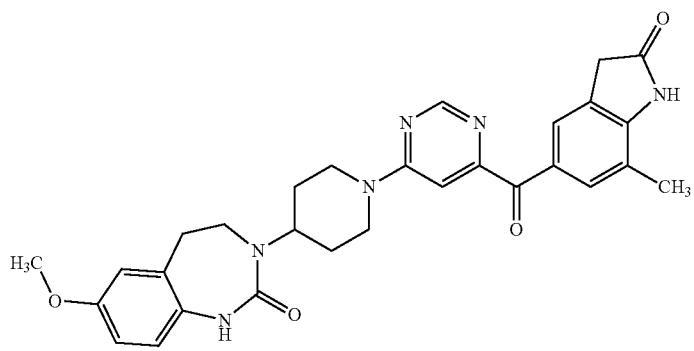 |

| No. | Structure |
|---|---|
| (52) | 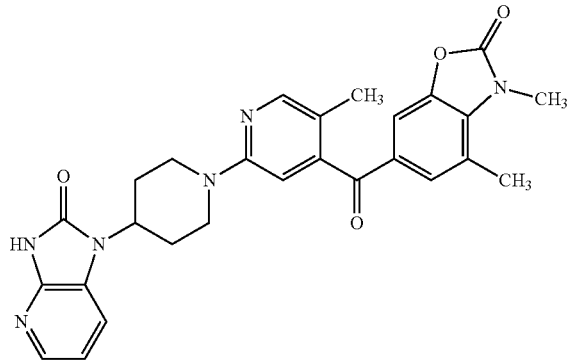 [SMILES: Cc1cnc(N2CCC(n3c(=O)[nH]c4ncccc43)CC2)cc1C(=O)c1cc(C)c2c(c1)oc(=O)n2C] |
| (53) | 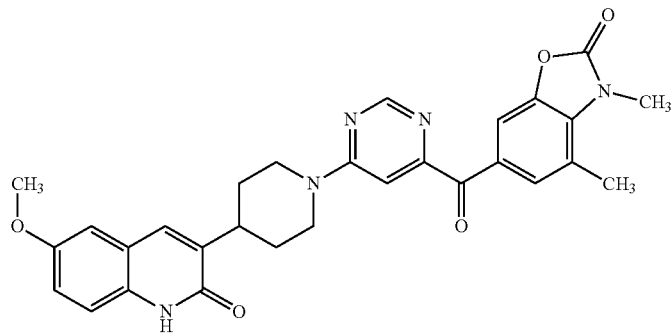 [SMILES: COc1ccc2[nH]c(=O)c(C3CCN(c4cc(C(=O)c5cc(C)c6c(c5)oc(=O)n6C)ncn4)CC3)cc2c1] |
| (54) | 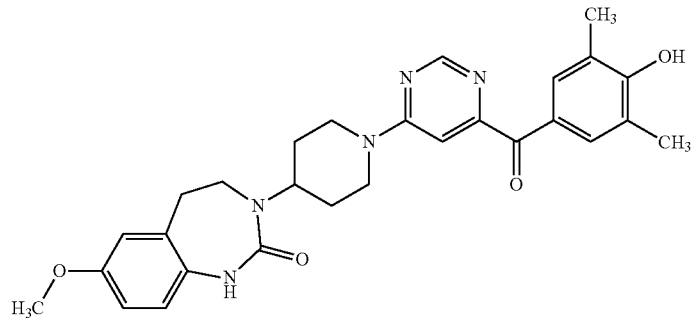 [SMILES: COc1ccc2c(c1)CCN(C1CCN(c3cc(C(=O)c4cc(C)c(O)c(C)c4)ncn3)CC1)C(=O)N2] |
| (55) | 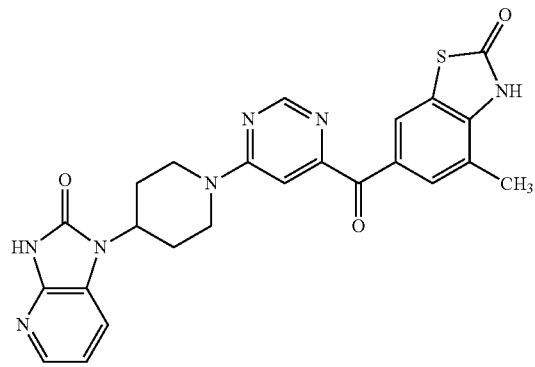 |

| No. | Structure |
|---|---|
| (56) | 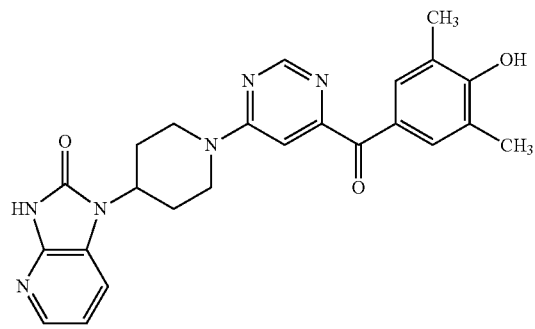 [SMILES: Cc1cc(C(=O)c2cc(N3CCC(n4c(=O)[nH]c5ncccc54)CC3)ncn2)cc(C)c1O] |
| (57) | 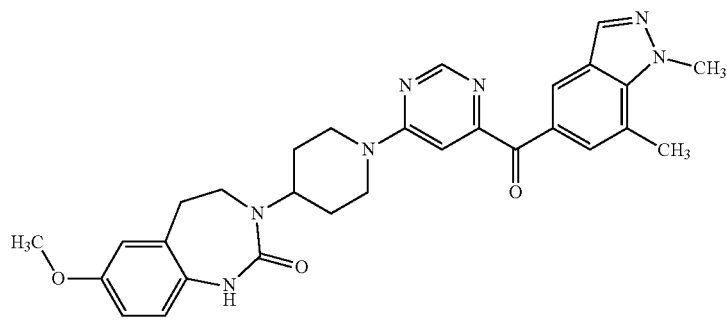 |
| (58) | 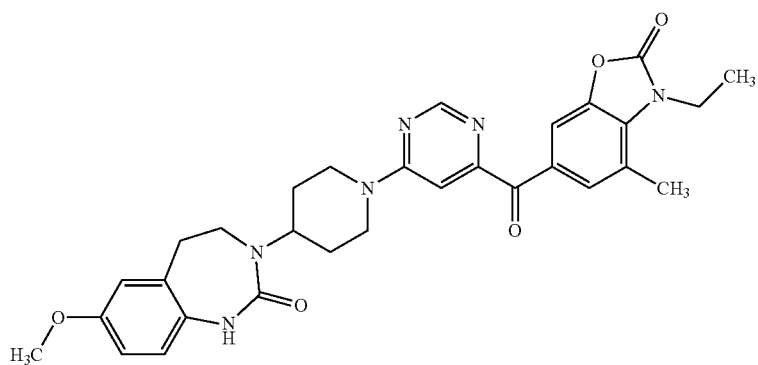 [SMILES: CCn1c(=O)oc2cc(C(=O)c3cc(N4CCC(N5CCc6cc(OC)ccc6NC5=O)CC4)ncn3)cc(C)c21] |
| (59) | 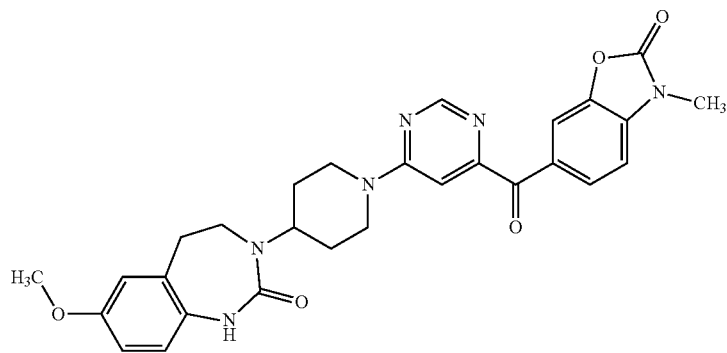 |

-continued

| No. | Structure |
|---|---|
| (60) | 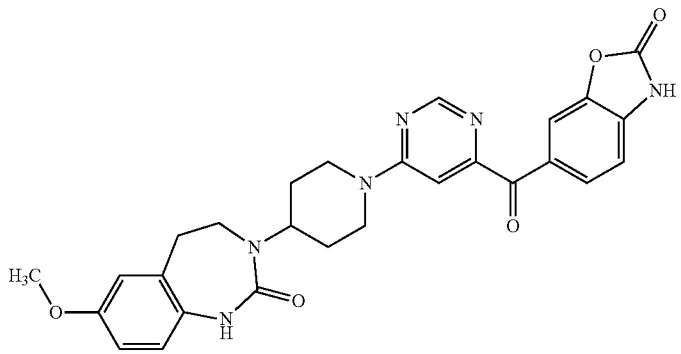 [SMILES: COc1ccc2c(c1)CCN(C1CCN(c3cc(C(=O)c4ccc5[nH]c(=O)oc5c4)ncn3)CC1)C(=O)N2] |
| (61) | 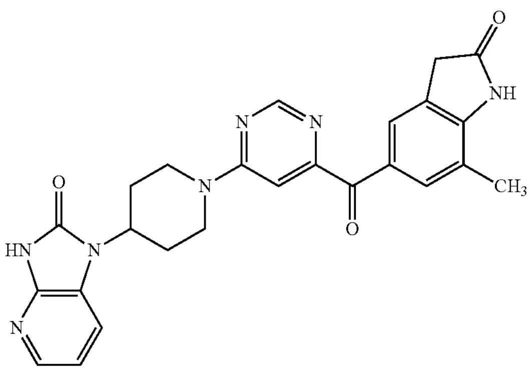 [SMILES: Cc1cc(C(=O)c2cc(N3CCC(n4c(=O)[nH]c5ncccc54)CC3)ncn2)cc2c1NC(=O)C2] |
| (62) | 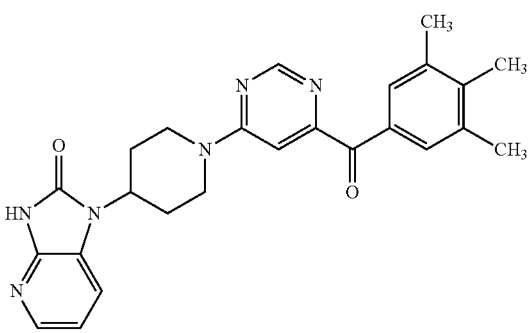 [SMILES: Cc1cc(C(=O)c2cc(N3CCC(n4c(=O)[nH]c5ncccc54)CC3)ncn2)cc(C)c1C] |
| (63) | 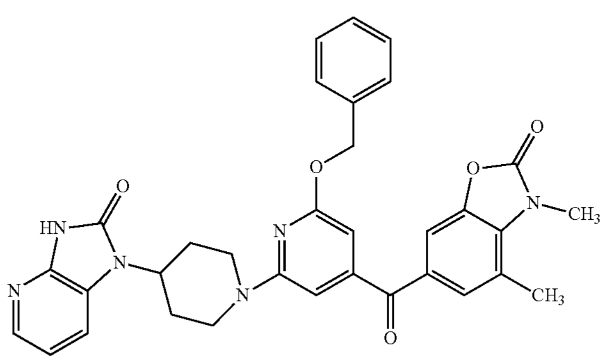 [SMILES: Cc1cc(C(=O)c2cc(OCc3ccccc3)nc(N3CCC(n4c(=O)[nH]c5ncccc54)CC3)c2)cc2oc(=O)n(C)c12] |

-continued
| No. | Structure |
|---|---|
| (64) | 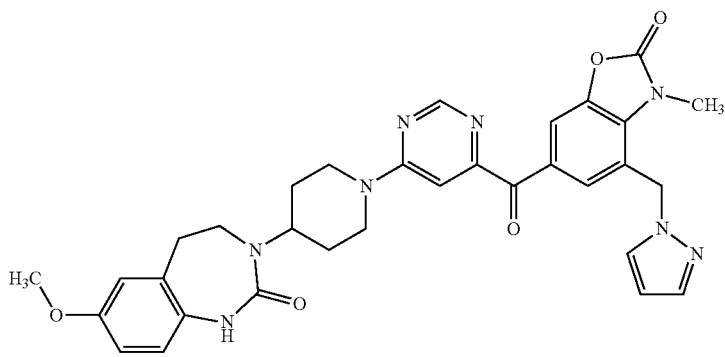 |
| (65) | 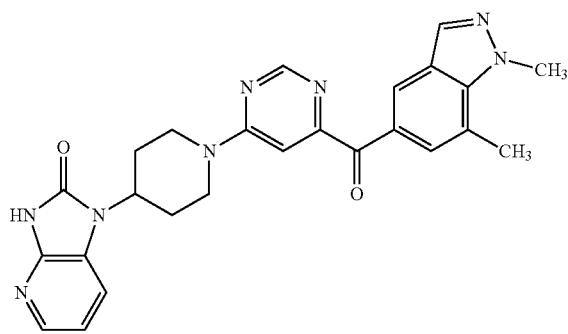 [SMILES: Cc1cc(C(=O)c2cc(N3CCC(n4c(=O)[nH]c5ncccc54)CC3)ncn2)cc2cnn(C)c12] |
| (66) | 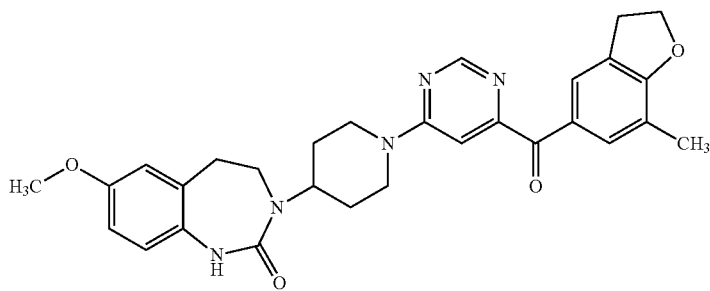 |
| (67) | 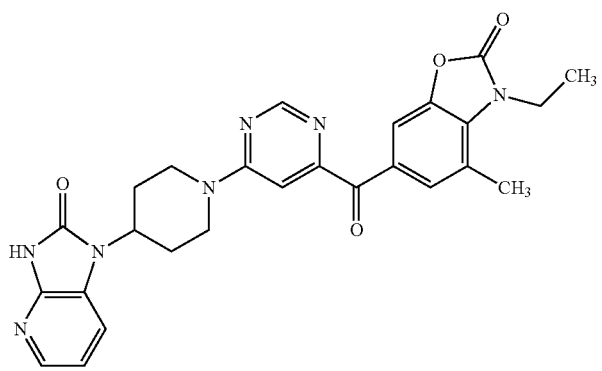 [SMILES: CCn1c(=O)oc2cc(C(=O)c3cc(N4CCC(n5c(=O)[nH]c6ncccc65)CC4)ncn3)cc(C)c21] |

-continued
| No. | Structure |
|---|---|
| (68) | 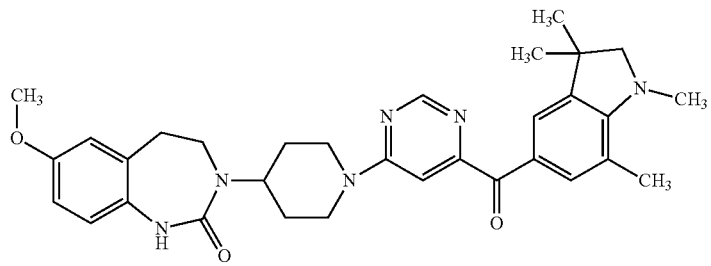 [SMILES: COc1ccc2c(c1)CCN(C1CCN(c3cc(C(=O)c4cc(C)c5c(c4)C(C)(C)CN5C)ncn3)CC1)C(=O)N2] |
| (69) | 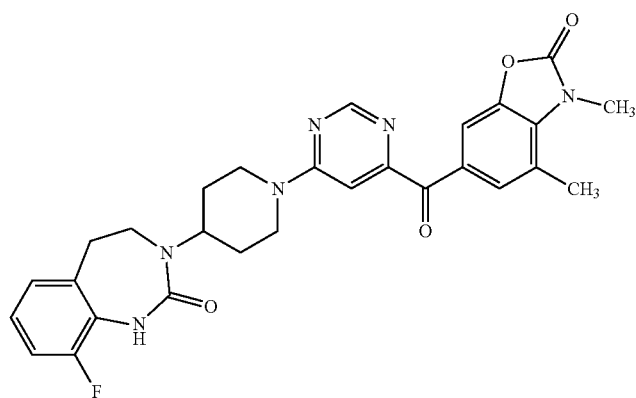 [SMILES: Cc1cc(C(=O)c2cc(N3CCC(N4CCc5cccc(F)c5NC4=O)CC3)ncn2)cc2oc(=O)n(C)c12] |
| (70) | 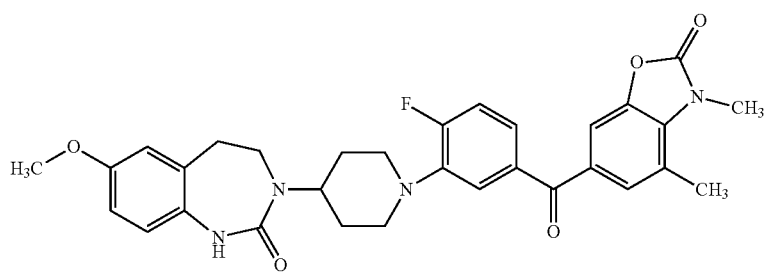 |
| (71) | 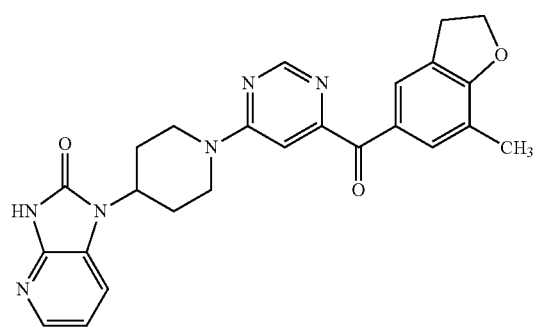 [SMILES: Cc1cc(C(=O)c2cc(N3CCC(n4c(=O)[nH]c5ncccc54)CC3)ncn2)cc2c1OCC2] |

-continued
| No. | Structure |
|---|---|
| (72) | 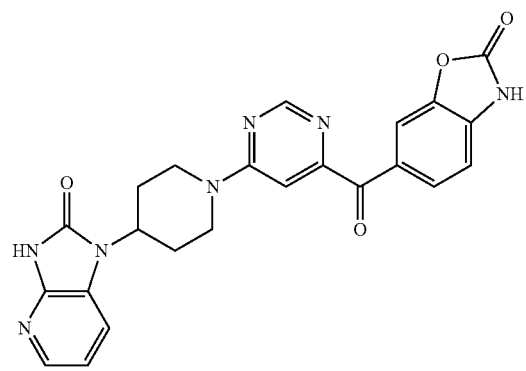 [SMILES: O=C(c1ccc2[nH]c(=O)oc2c1)c1cc(N2CCC(n3c(=O)[nH]c4ncccc43)CC2)ncn1] |
| (73) | 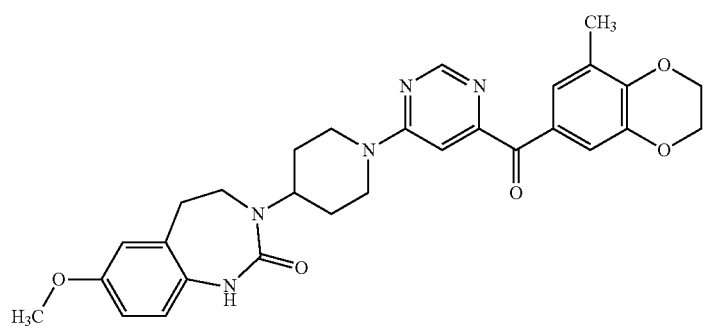 [SMILES: COc1ccc2c(c1)CCN(C1CCN(c3cc(C(=O)c4cc(C)c5c(c4)OCCO5)ncn3)CC1)C(=O)N2] |
| (74) | 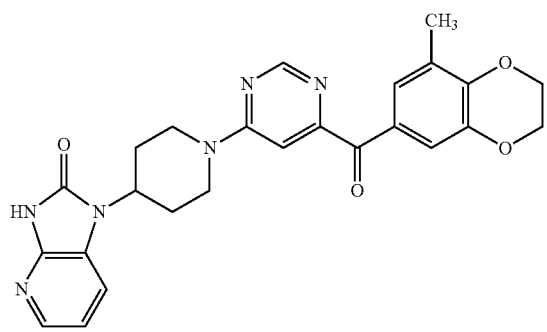 [SMILES: Cc1cc(C(=O)c2cc(N3CCC(n4c(=O)[nH]c5ncccc54)CC3)ncn2)cc2c1OCCO2] |
| (75) | 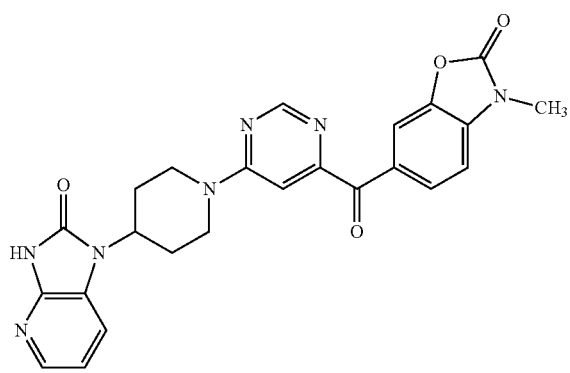 [SMILES: Cn1c(=O)oc2cc(C(=O)c3cc(N4CCC(n5c(=O)[nH]c6ncccc65)CC4)ncn3)ccc21] |

| No. | Structure |
|---|---|
| (76) | 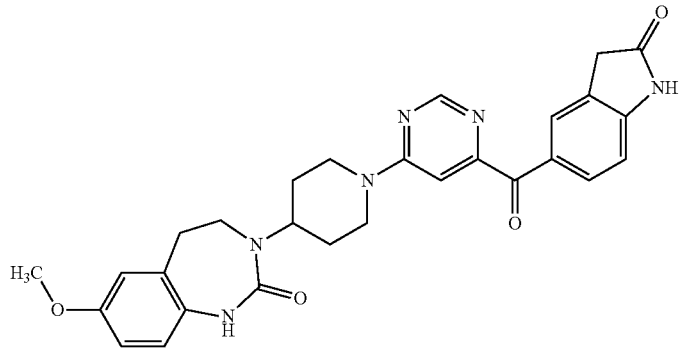 |
| (77) | 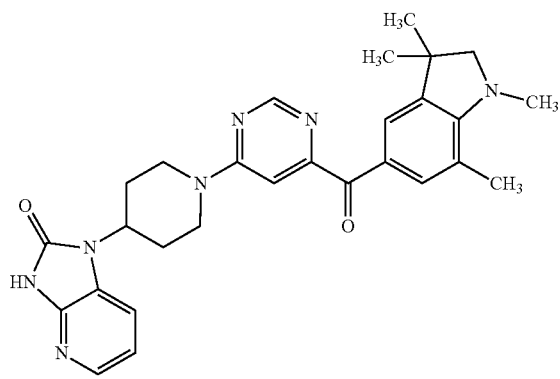 [SMILES: Cc1cc(C(=O)c2cc(N3CCC(n4c(=O)[nH]c5ncccc54)CC3)ncn2)cc2c1N(C)CC2(C)C] |
| (78) | 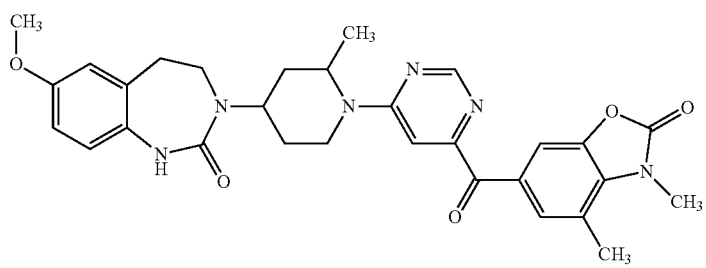 [SMILES: COc1ccc2c(c1)CCN(C1CCN(c3cc(C(=O)c4cc(C)c5c(c4)oc(=O)n5C)ncn3)C(C)C1)C(=O)N2] |
| (79) | 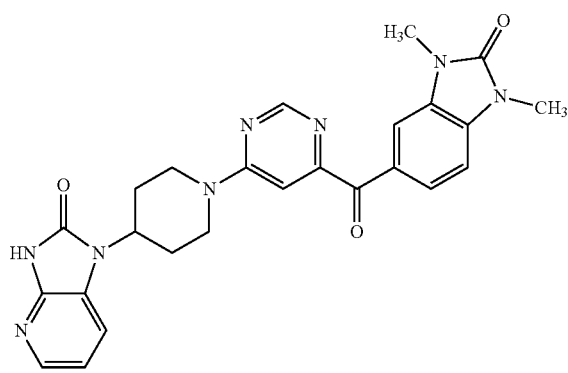 [SMILES: Cn1c(=O)n(C)c2cc(C(=O)c3cc(N4CCC(n5c(=O)[nH]c6ncccc65)CC4)ncn3)ccc21] |

| No. | Structure |
|---|---|
| (80) | 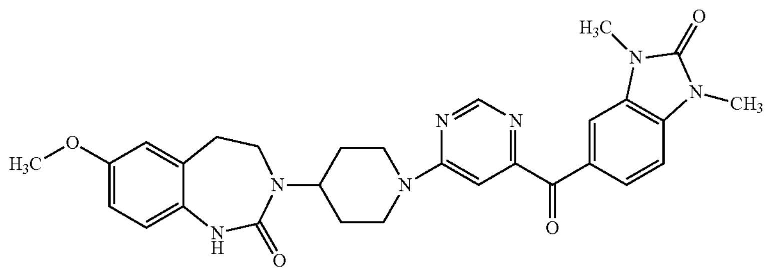 |
| (81) | 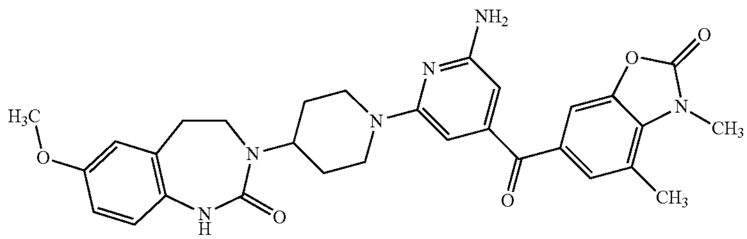 |
| (82) | 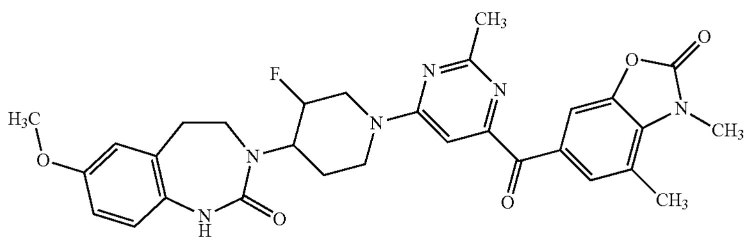 |
| (83) | 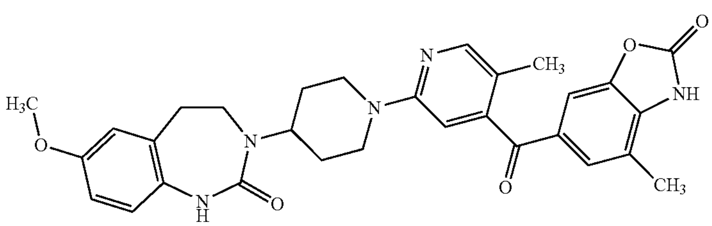 [SMILES: COc1ccc2c(c1)CCN(C1CCN(c3cc(C(=O)c4cc(C)c5[nH]c(=O)oc5c4)c(C)cn3)CC1)C(=O)N2] |
| (84) | 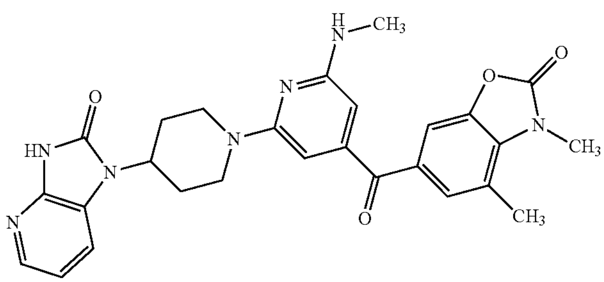 [SMILES: CNc1cc(C(=O)c2cc(C)c3c(c2)oc(=O)n3C)cc(N2CCC(n3c(=O)[nH]c4ncccc43)CC2)n1] |
| (85) | | the enantiomers, the diastereomers, the hydrates, the mixtures thereof and the salts thereof as well as the hydrates of the salts, particularly the physiologically acceptable salts thereof with inorganic or organic acids or bases.

The following compounds are mentioned as examples of more preferred compounds of the above general formula I:

| No. | Structure |
| --- | --- |
| (1) | 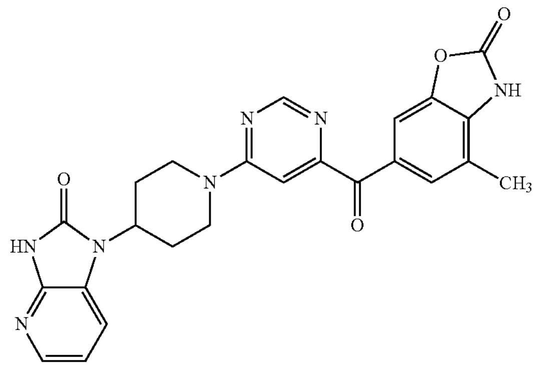 [SMILES: Cc1cc(C(=O)c2cc(N3CCC(n4c(=O)[nH]c5ncccc54)CC3)ncn2)cc2oc(=O)[nH]c12] |
| (2) | 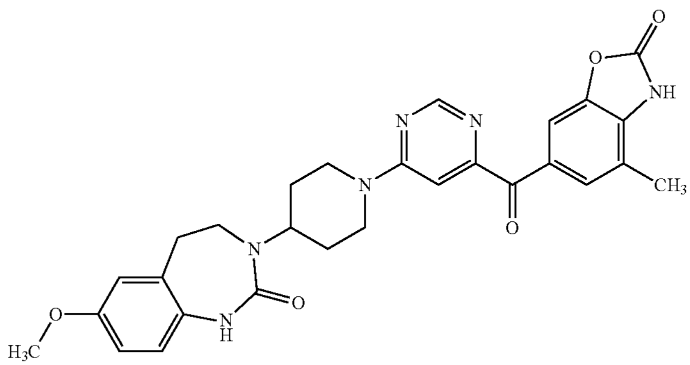 |
| (3) | 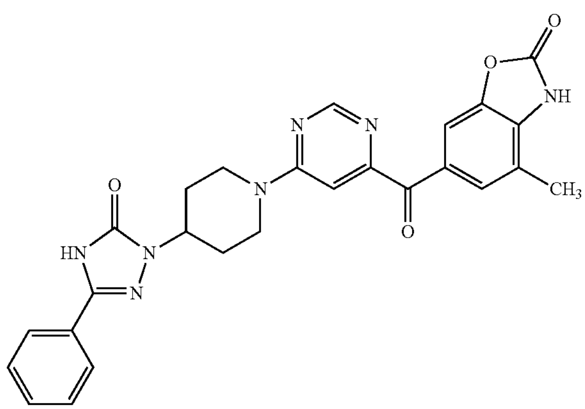 [SMILES: Cc1cc(C(=O)c2cc(N3CCC(n4nc(-c5ccccc5)[nH]c4=O)CC3)ncn2)cc2oc(=O)[nH]c12] |
| (4) | 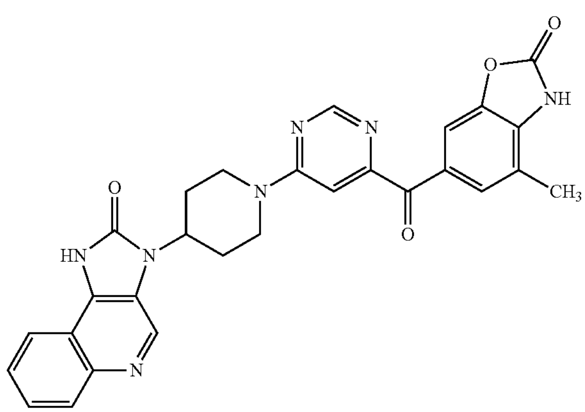 [SMILES: Cc1cc(C(=O)c2cc(N3CCC(n4c(=O)[nH]c5c6ccccc6ncc54)CC3)ncn2)cc2oc(=O)[nH]c12] |

-continued

| No. | Structure |
|---|---|
| (10) | 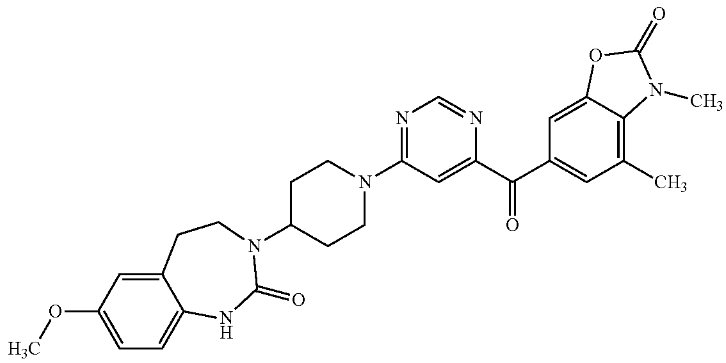 |
| (11) | 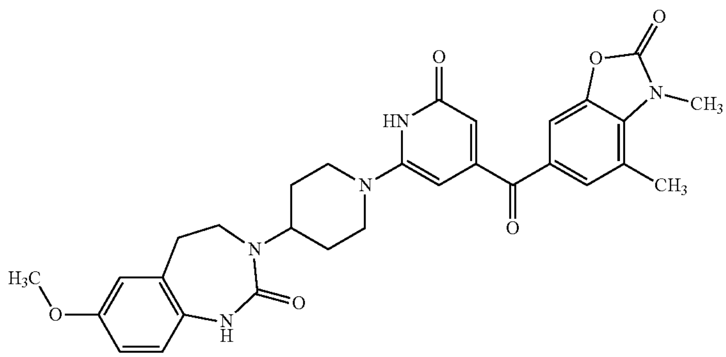 |
| (12) | 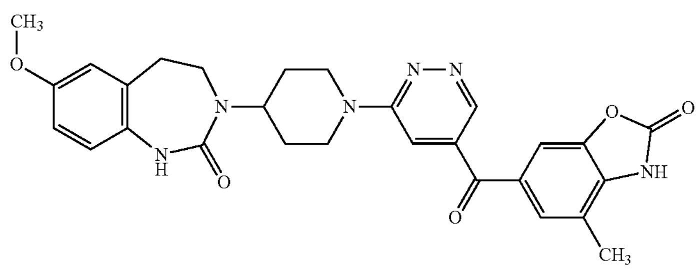 |
| (13) | 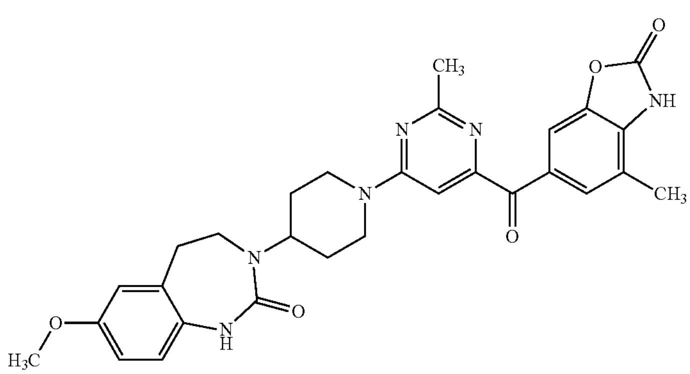 |

-continued
| No. | Structure |
|---|---|
| (14) | 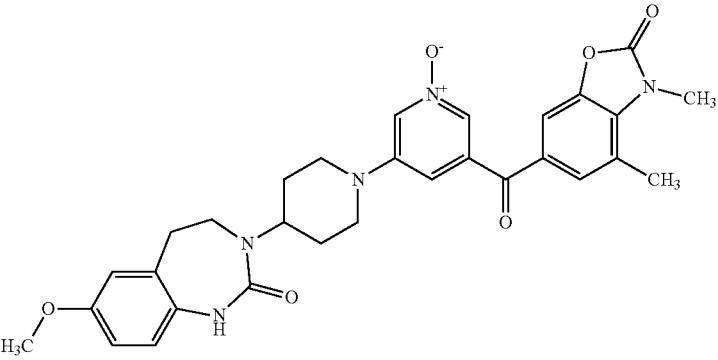 |
| (15) | 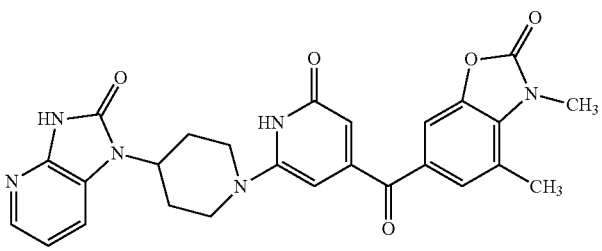 [SMILES: Cc1cc(C(=O)c2cc(N3CCC(n4c(=O)[nH]c5ncccc54)CC3)[nH]c(=O)c2)cc2oc(=O)n(C)c12] |
| (16) | 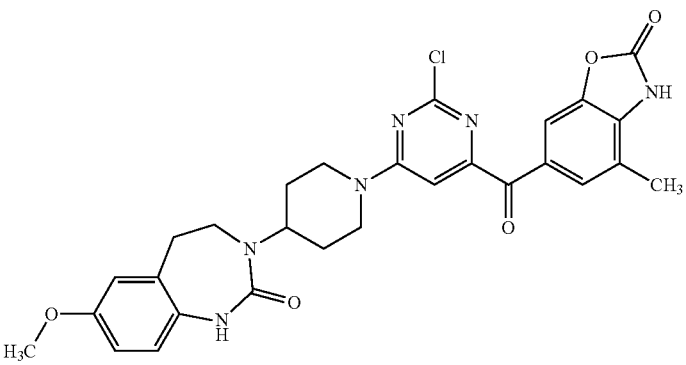 |
| (17) | 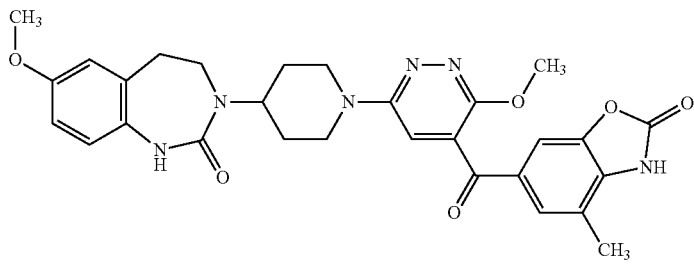 [SMILES: COc1ccc2c(c1)CCN(C1CCN(c3cc(C(=O)c4cc(C)c5[nH]c(=O)oc5c4)c(OC)nn3)CC1)C(=O)N2] |
| (18) | 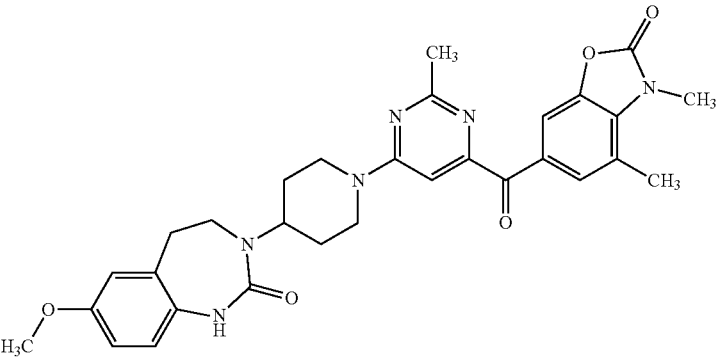 |

| No. | Structure |
|---|---|
| (19) | 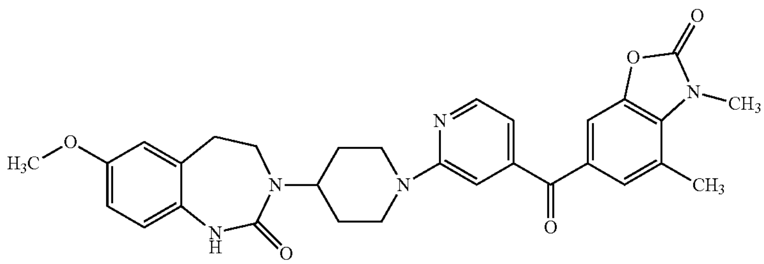 |
| (20) | 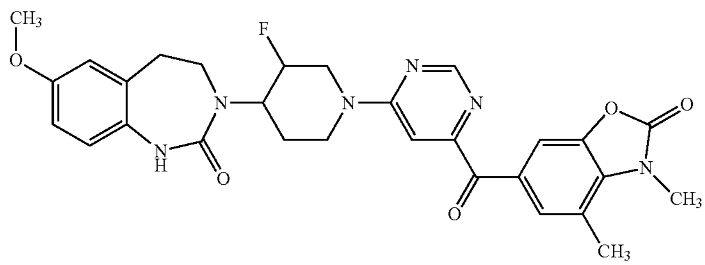 [SMILES: COc1ccc2c(c1)CCN(C1CCN(c3cc(C(=O)c4cc(C)c5c(c4)oc(=O)n5C)ncn3)CC1F)C(=O)N2] |
| (21) | 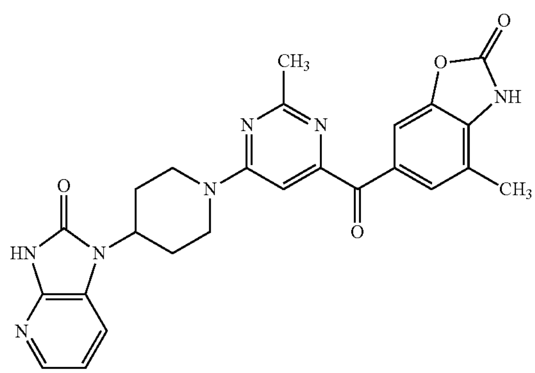 [SMILES: Cc1nc(C(=O)c2cc(C)c3[nH]c(=O)oc3c2)cc(N2CCC(n3c(=O)[nH]c4ncccc43)CC2)n1] |
| (22) | 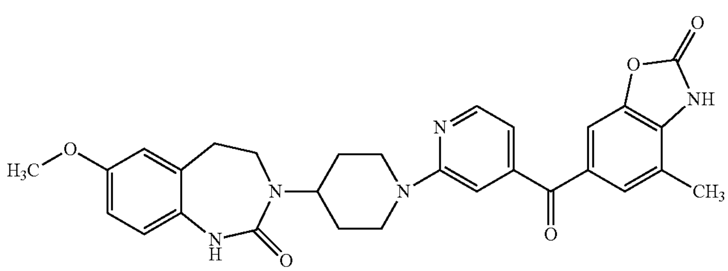 |
| (23) | 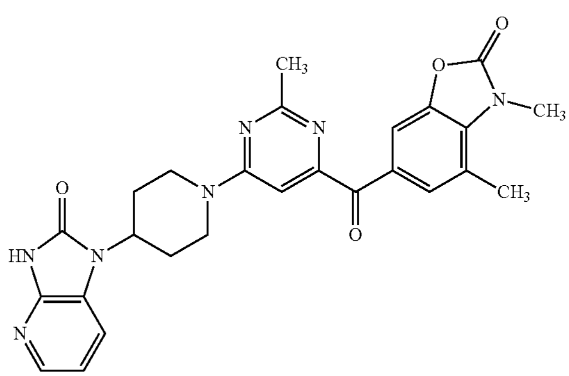 [SMILES: Cc1nc(C(=O)c2cc(C)c3c(c2)oc(=O)n3C)cc(N2CCC(n3c(=O)[nH]c4ncccc43)CC2)n1] |

-continued

| No. | Structure |
|---|---|
| (24) | 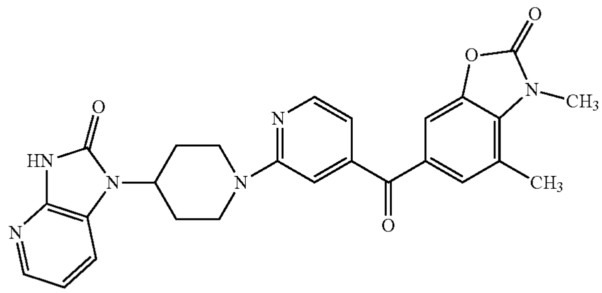 [SMILES: Cc1cc(C(=O)c2ccnc(N3CCC(n4c(=O)[nH]c5ncccc54)CC3)c2)cc2oc(=O)n(C)c12] |
| (25) | 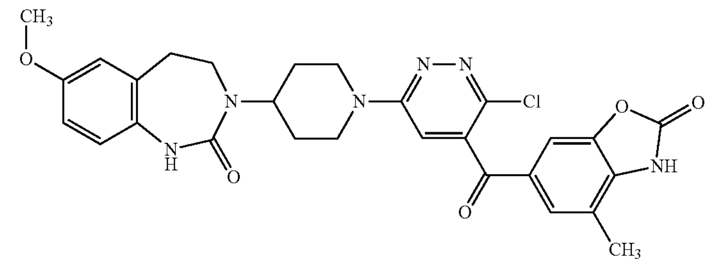 [SMILES: COc1ccc2c(c1)CCN(C1CCN(c3cc(C(=O)c4cc(C)c5[nH]c(=O)oc5c4)c(Cl)nn3)CC1)C(=O)N2] |
| (26) | 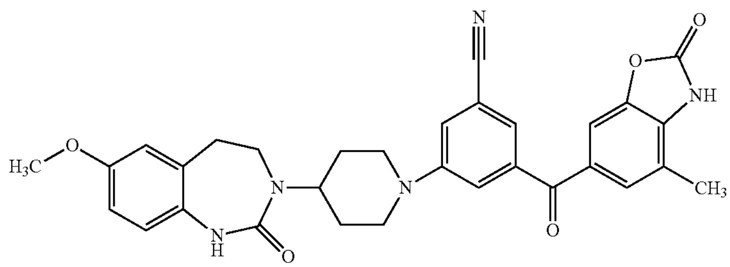 |
| (27) | 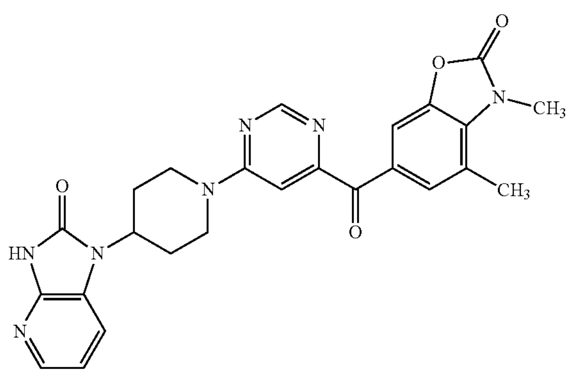 [SMILES: Cc1cc(C(=O)c2cc(N3CCC(n4c(=O)[nH]c5ncccc54)CC3)ncn2)cc2oc(=O)n(C)c12] |
| (28) | 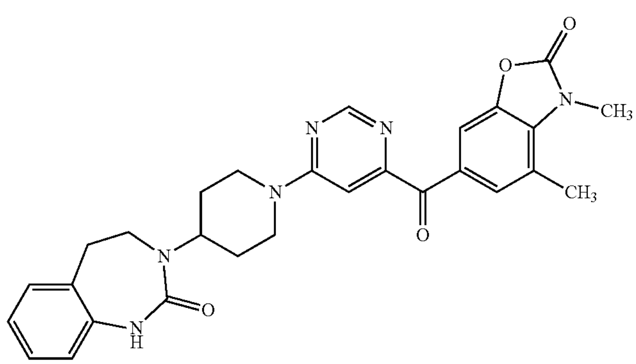 [SMILES: Cc1cc(C(=O)c2cc(N3CCC(N4CCc5ccccc5NC4=O)CC3)ncn2)cc2oc(=O)n(C)c12] |

| No. | Structure |
|---|---|
| (29) | 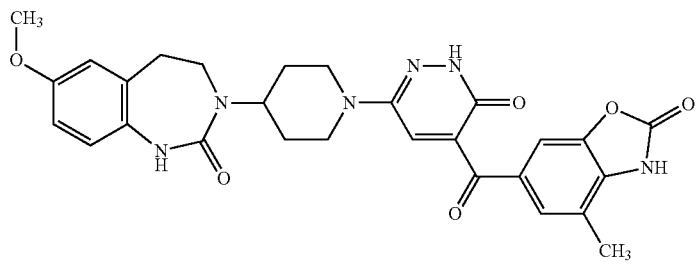 [SMILES: COc1ccc2c(c1)CCN(C1CCN(c3cc(C(=O)c4cc(C)c5[nH]c(=O)oc5c4)c(=O)[nH]n3)CC1)C(=O)N2] |
| (30) | 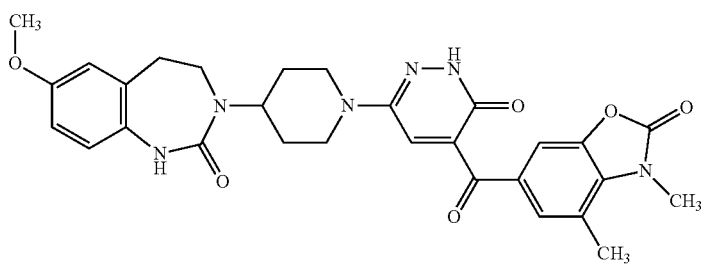 [SMILES: COc1ccc2c(c1)CCN(C1CCN(c3cc(C(=O)c4cc(C)c5c(c4)oc(=O)n5C)c(=O)[nH]n3)CC1)C(=O)N2] |
| (31) | 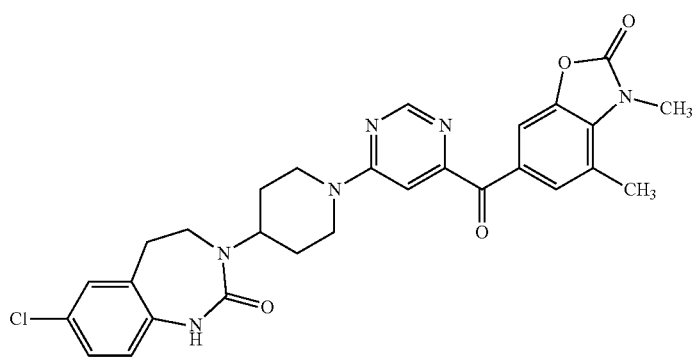 [SMILES: Cc1cc(C(=O)c2cc(N3CCC(N4CCc5cc(Cl)ccc5NC4=O)CC3)ncn2)cc2oc(=O)n(C)c12] |
| (32) | 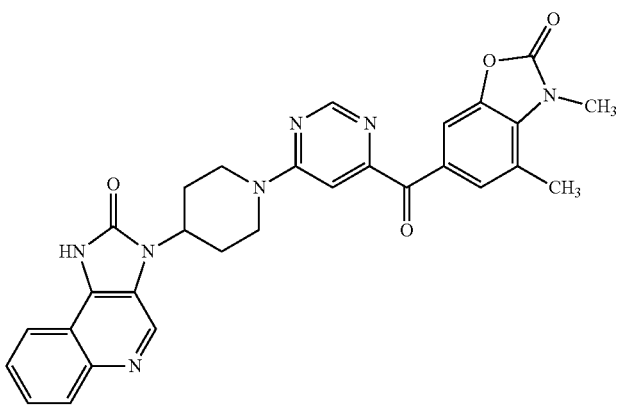 [SMILES: Cc1cc(C(=O)c2cc(N3CCC(n4c(=O)[nH]c5c6ccccc6ncc54)CC3)ncn2)cc2oc(=O)n(C)c12] |

| No. | Structure |
|---|---|
| (33) | 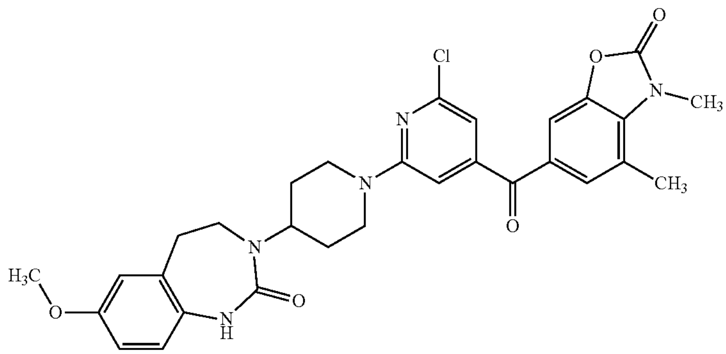 |
| (34) | 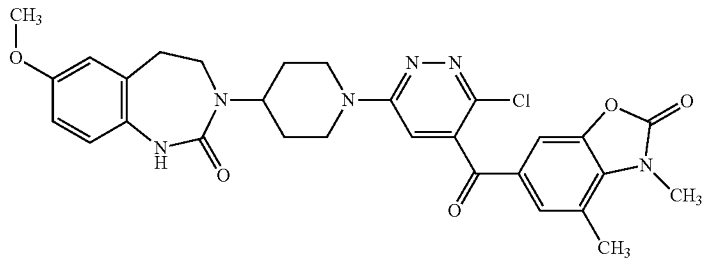 [SMILES: COc1ccc2c(c1)CCN(C1CCN(c3cc(C(=O)c4cc(C)c5c(c4)oc(=O)n5C)c(Cl)nn3)CC1)C(=O)N2] |
| (35) | 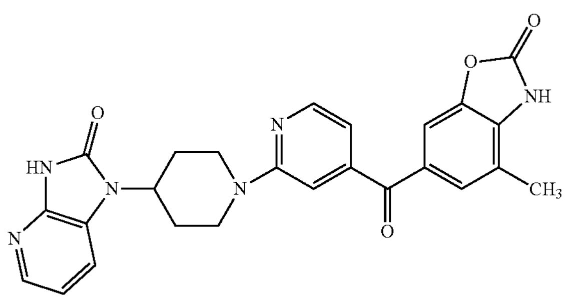 [SMILES: Cc1cc(C(=O)c2ccnc(N3CCC(n4c(=O)[nH]c5ncccc54)CC3)c2)cc2oc(=O)[nH]c12] |
| (36) | 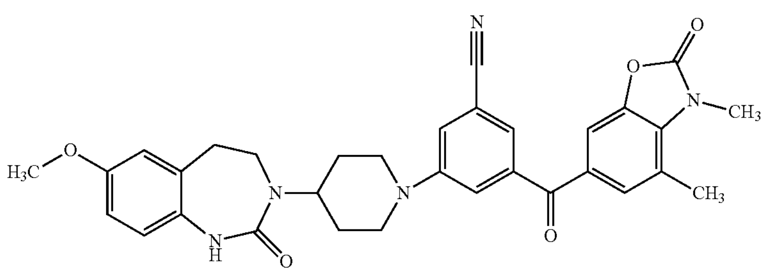 |
| (37) | 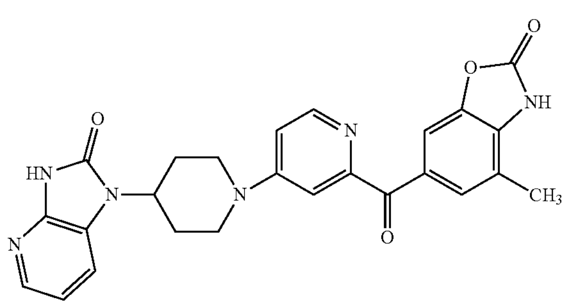 [SMILES: Cc1cc(C(=O)c2cc(N3CCC(n4c(=O)[nH]c5ncccc54)CC3)ccn2)cc2oc(=O)[nH]c12] |

| No. | Structure |
|---|---|
| (38) | 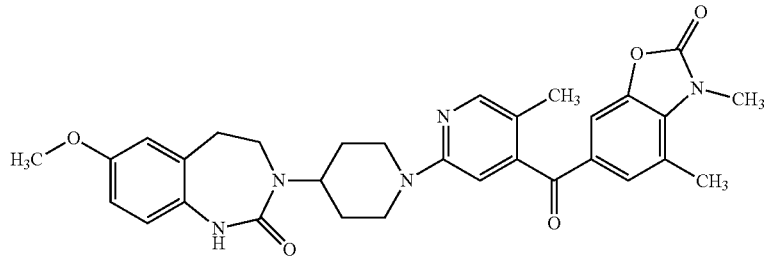 |
| (39) | 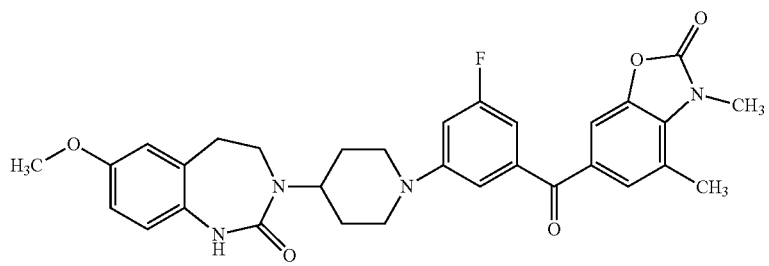 |
| (40) | 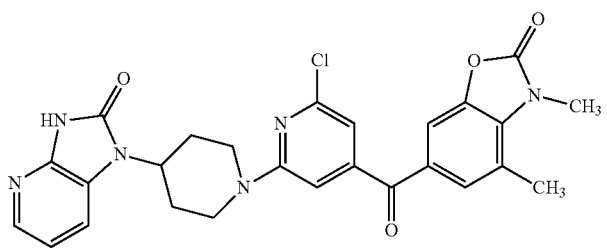 [SMILES: Cc1cc(C(=O)c2cc(Cl)nc(N3CCC(n4c(=O)[nH]c5ncccc54)CC3)c2)cc2oc(=O)n(C)c12] |
| (42) | 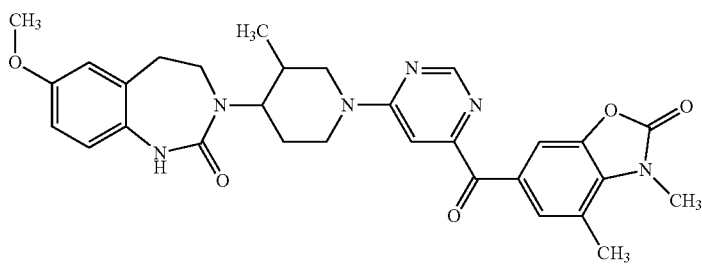 |
| (43) | 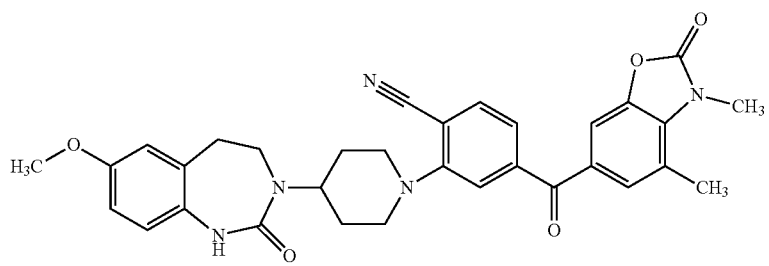 |

-continued

| No. | Structure |
|---|---|
| (44) | 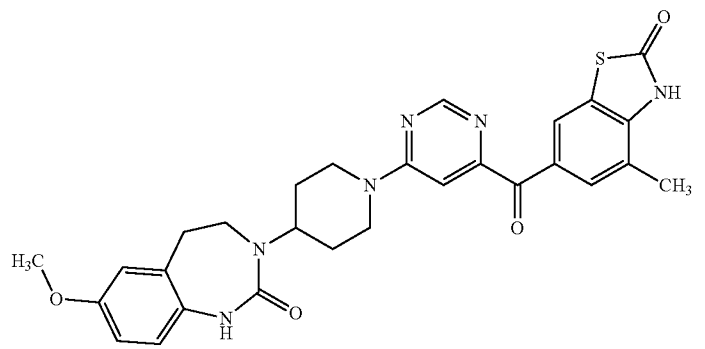 |
| (45) | 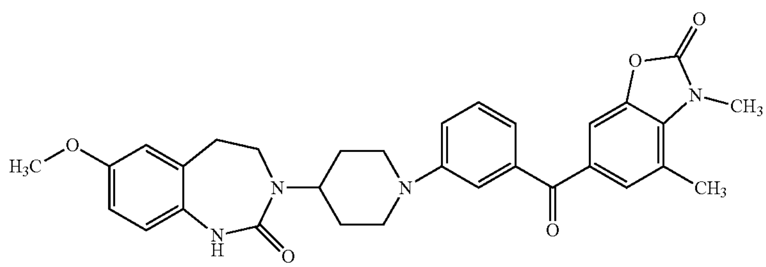 |
| (46) | 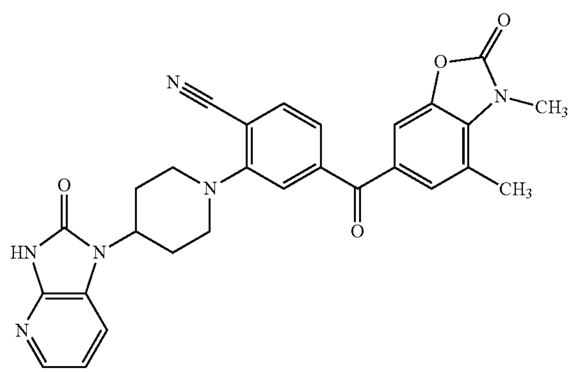 [SMILES: Cc1cc(C(=O)c2ccc(C#N)c(N3CCC(n4c(=O)[nH]c5ncccc54)CC3)c2)cc2oc(=O)n(C)c12] |
| (47) | 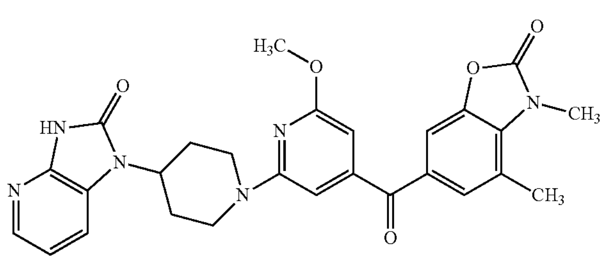 [SMILES: COc1cc(C(=O)c2cc(C)c3c(c2)oc(=O)n3C)cc(N2CCC(n3c(=O)[nH]c4ncccc43)CC2)n1] |
| (48) | 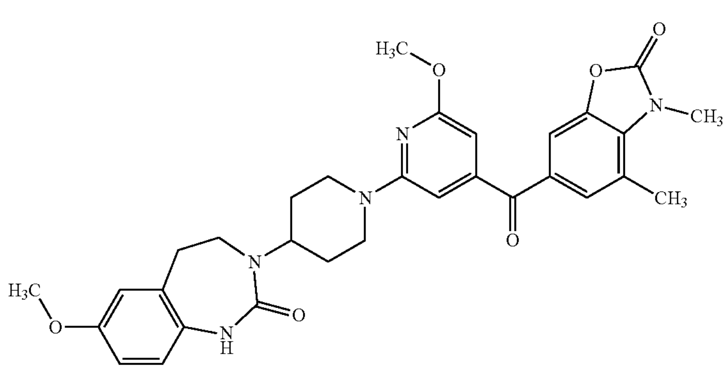 |

-continued

| No. | Structure |
|---|---|
| (49) | 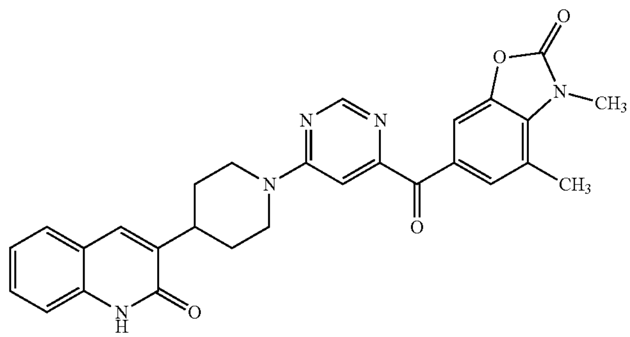 [SMILES: Cc1cc(C(=O)c2cc(N3CCC(c4cc5ccccc5[nH]c4=O)CC3)ncn2)cc2oc(=O)n(C)c12] |
| (50) | 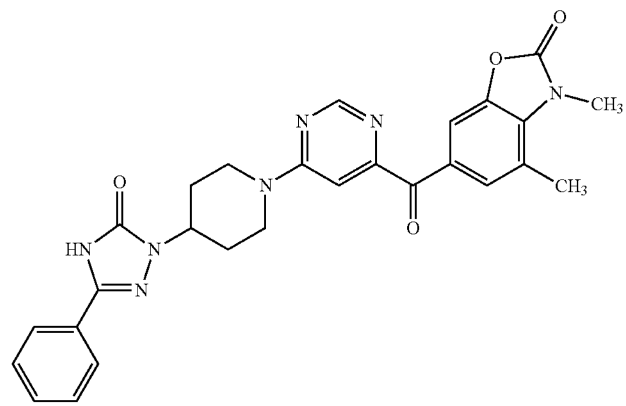 [SMILES: Cc1cc(C(=O)c2cc(N3CCC(n4nc(-c5ccccc5)[nH]c4=O)CC3)ncn2)cc2oc(=O)n(C)c12] |
| (51) | 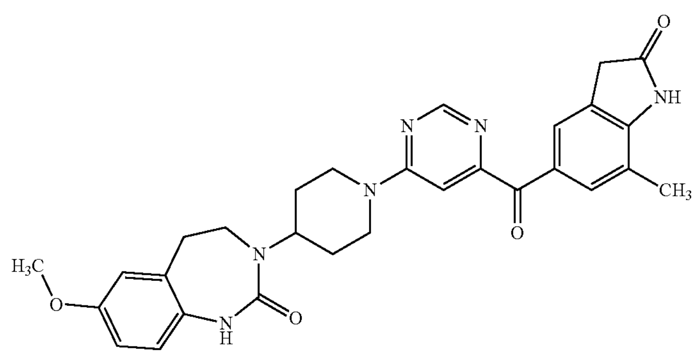 |
| (52) | 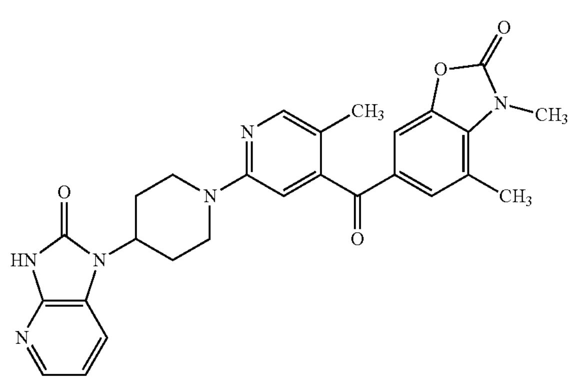 [SMILES: Cc1cnc(N2CCC(n3c(=O)[nH]c4ncccc43)CC2)cc1C(=O)c1cc(C)c2c(c1)oc(=O)n2C] |

| No. | Structure |
|---|---|
| (53) | 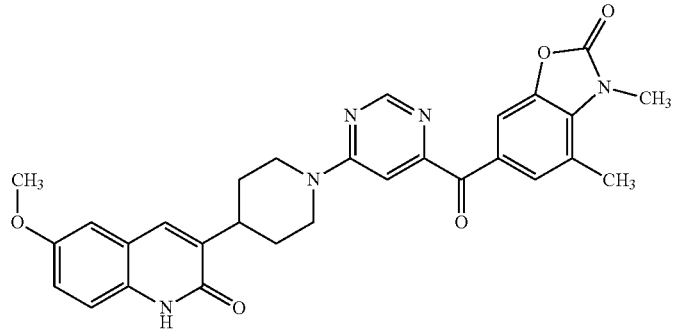 [SMILES: COc1ccc2[nH]c(=O)c(C3CCN(c4cc(C(=O)c5cc(C)c6c(c5)oc(=O)n6C)ncn4)CC3)cc2c1] |
| (55) | 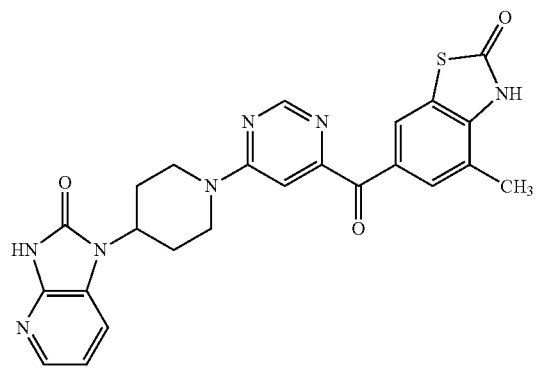 [SMILES: Cc1cc(C(=O)c2cc(N3CCC(n4c(=O)[nH]c5ncccc54)CC3)ncn2)cc2sc(=O)[nH]c12] |
| (58) | 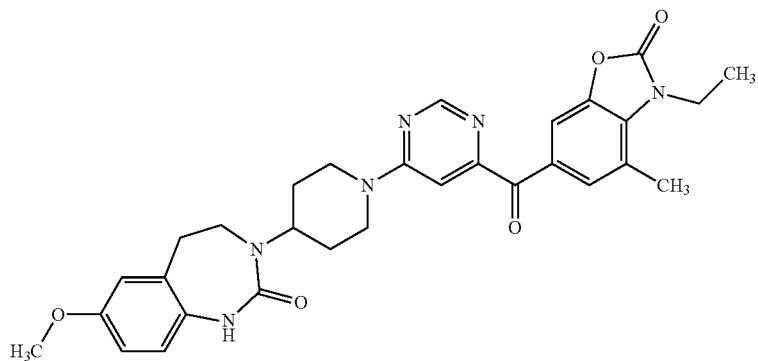 [SMILES: CCn1c(=O)oc2cc(C(=O)c3cc(N4CCC(N5CCc6cc(OC)ccc6NC5=O)CC4)ncn3)cc(C)c21] |
| (59) | 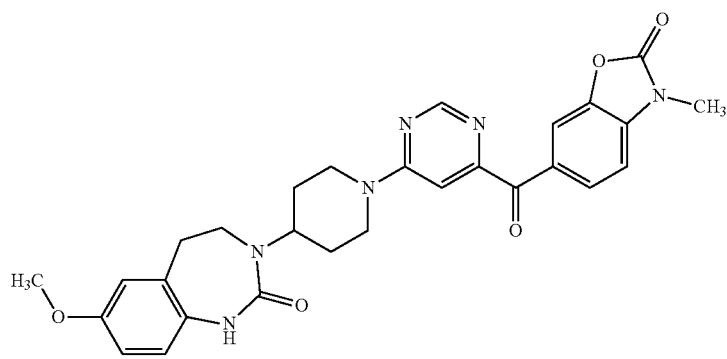 |

| No. | Structure |
|---|---|
| (60) | 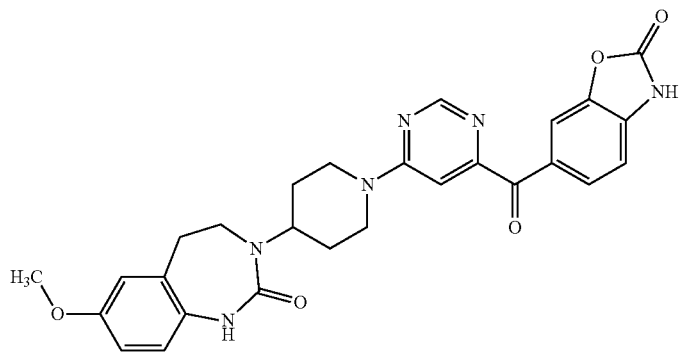 |
| (61) | 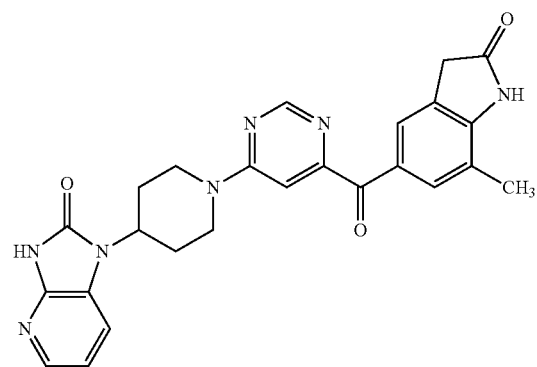 |
| (63) | 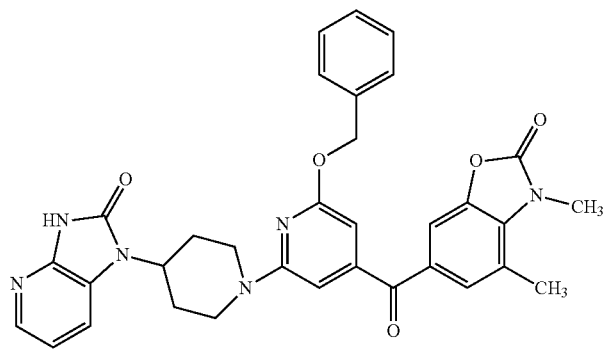 [SMILES: Cc1cc(C(=O)c2cc(OCc3ccccc3)nc(N3CCC(n4c(=O)[nH]c5ncccc54)CC3)c2)cc2oc(=O)n(C)c12] |
| (64) | 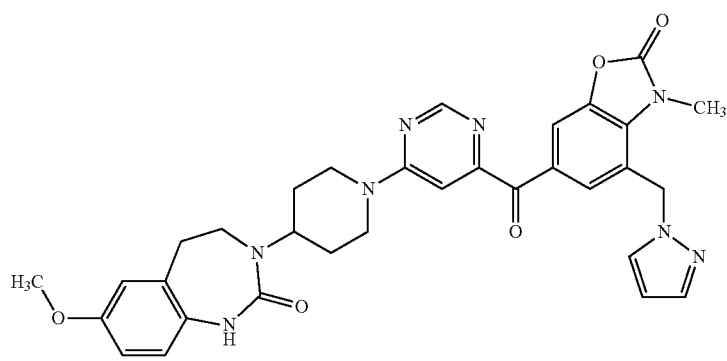 |

-continued
| No. | Structure |
|---|---|
| (67) | 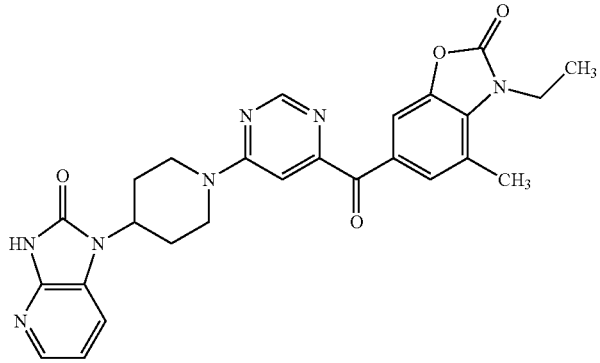 [SMILES: CCn1c(=O)oc2cc(C(=O)c3cc(N4CCC(n5c(=O)[nH]c6ncccc65)CC4)ncn3)cc(C)c21] |
| (69) | 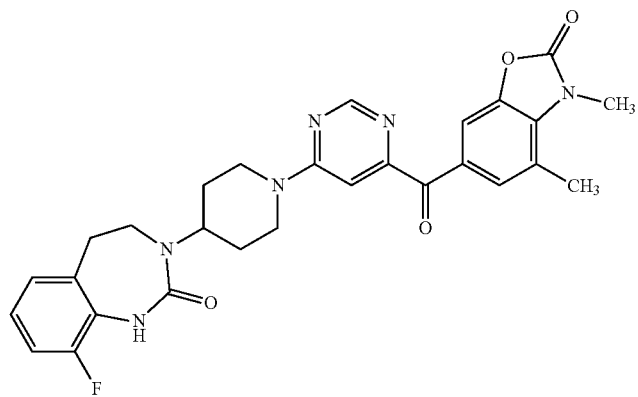 [SMILES: Cc1cc(C(=O)c2cc(N3CCC(N4CCc5cccc(F)c5NC4=O)CC3)ncn2)cc2oc(=O)n(C)c12] |
| (70) | 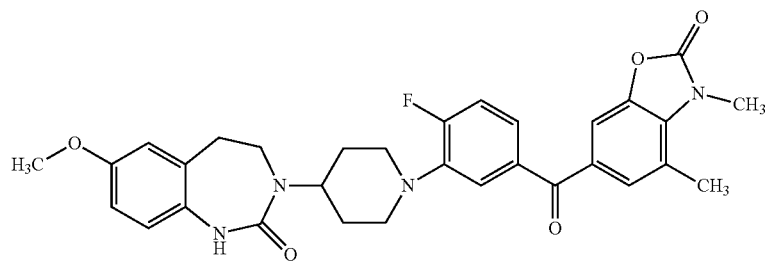 |
| (72) | 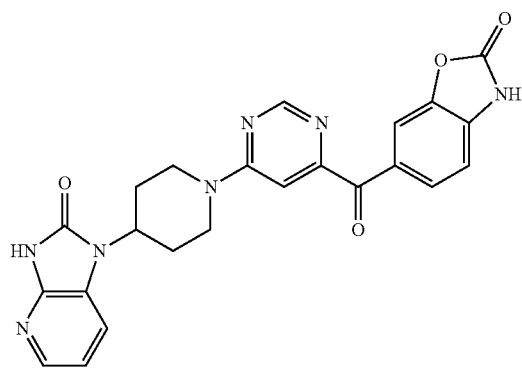 [SMILES: O=C(c1ccc2[nH]c(=O)oc2c1)c1cc(N2CCC(n3c(=O)[nH]c4ncccc43)CC2)ncn1] |

| No. | Structure |
|---|---|
| (75) | 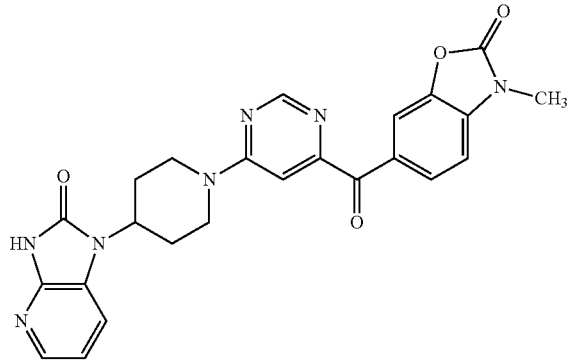 [SMILES: Cn1c(=O)oc2cc(C(=O)c3cc(N4CCC(n5c(=O)[nH]c6ncccc65)CC4)ncn3)ccc21] |
| (76) | 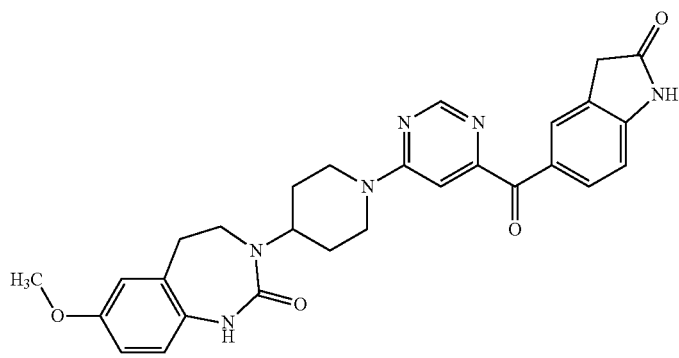 |
| (78) | 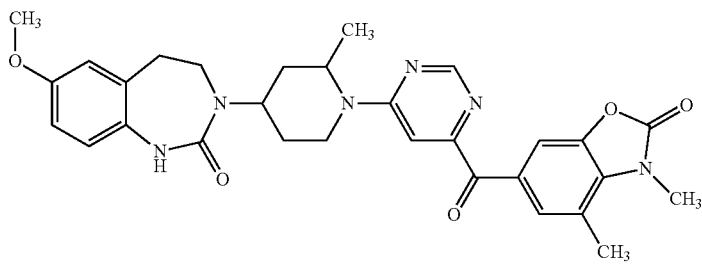 [SMILES: COc1ccc2c(c1)CCN(C1CCN(c3cc(C(=O)c4cc(C)c5c(c4)oc(=O)n5C)ncn3)C(C)C1)C(=O)N2] |

-continued
| No. | Structure |
|---|---|
| (79) | 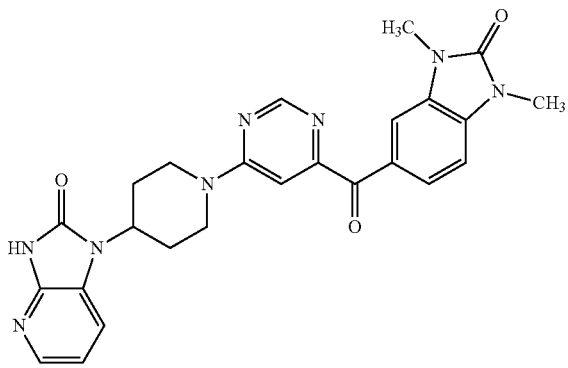 [SMILES: Cn1c(=O)n(C)c2cc(C(=O)c3cc(N4CCC(n5c(=O)[nH]c6ncccc65)CC4)ncn3)ccc21] |
| (80) | 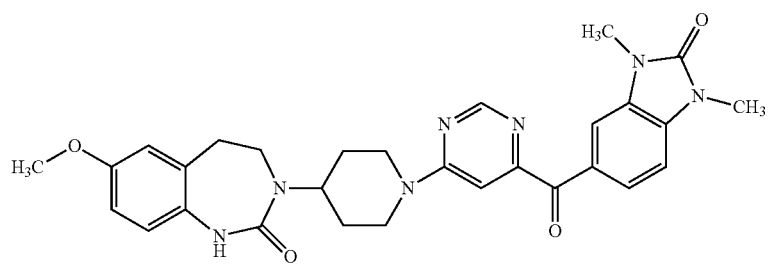 |
| (81) | 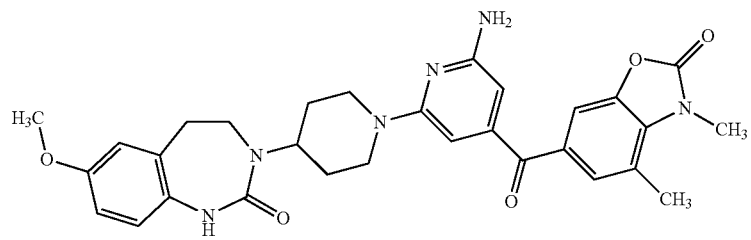 |
| (82) | 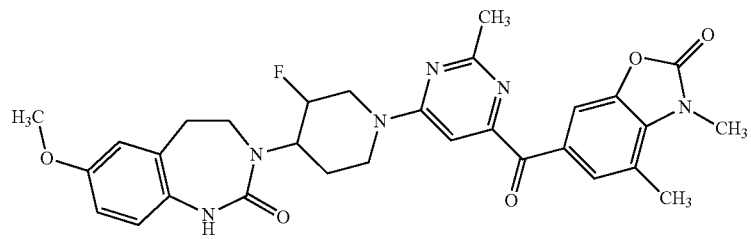 |
| (83) | 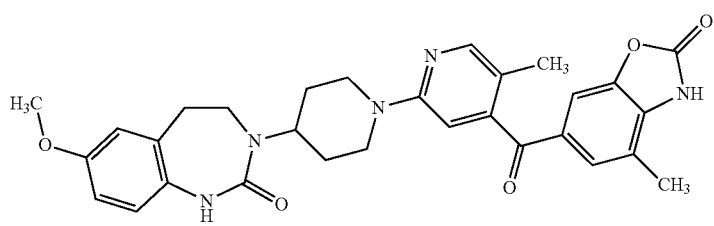 [SMILES: COc1ccc2c(c1)CCN(C1CCN(c3cc(C(=O)c4cc(C)c5[nH]c(=O)oc5c4)c(C)cn3)CC1)C(=O)N2] |

| No. | Structure |
|---|---|
| (84) | 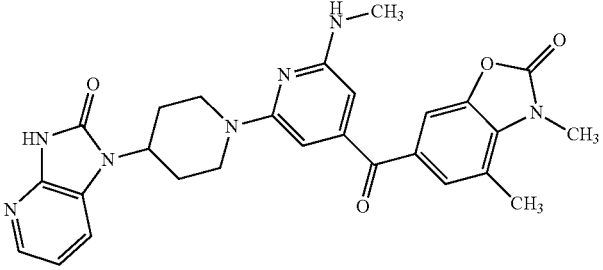 [SMILES: CNc1cc(C(=O)c2cc(C)c3c(c2)oc(=O)n3C)cc(N2CCC(n3c(=O)[nH]c4ncccc43)CC2)n1] |
| (85) | 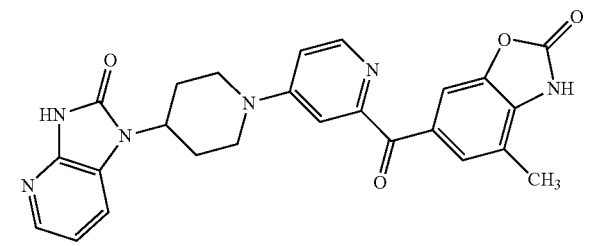 [SMILES: Cc1cc(C(=O)c2cc(N3CCC(n4c(=O)[nH]c5ncccc54)CC3)ccn2)cc2oc(=O)[nH]c12] | the enantiomers, the diastereomers, the hydrates, the mixtures thereof and the salts thereof as well as the hydrates of the salts, particularly the physiologically acceptable salts thereof with inorganic or organic acids or bases.

TERMS AND DEFINITIONS USED

The present specification of the invention is to be interpreted in accordance with the conventions and rules of chemical bonds.

The compounds included in this invention are those that are also chemically stable.

Unless otherwise stated, all the substituents are independent of one another. If for example there are a plurality of $C_{1-4}$-alkyl groups as substituents in one group, in the case of three $C_{1-4}$-alkyl substituents, independently of one another, one may represent methyl, one ethyl and one n-propyl.

Within the scope of this application, in the definition of possible substituents, these may also be represented in the form of a structural formula. If present, an asterisk (*) in the structural formula of the substituent is to be understood as being the linking point to the rest of the molecule. For example a phenyl group is shown as follows:

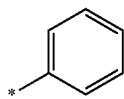

Moreover, the atom of the substituent that follows the linking point is understood as being the atom at position number 1.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant branched and unbranched alkyl groups with 1 to 3 carbon atoms, by the term "$C_{1-4}$-alkyl" are meant branched and unbranched alkyl groups with 1 to 4 carbon atoms and by the term "$C_{1-6}$-alkyl" are meant branched and unbranched alkyl groups with 1 to 6 carbon atoms. Examples include: methyl, ethyl, n-propyl, iso-propyl, n-butyl, iso-butyl, sec-butyl, tert-butyl, pentyl, neopentyl or n-hexyl. The abbreviations may optionally also be used for the above-mentioned groups Me, Et, n-Pr, i-Pr, n-Bu, i-Bu, t-Bu, etc. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are a part of other groups) are meant branched and unbranched alkylene groups with 1 to 6 carbon atoms and by the term "$C_{1-3}$-alkylene" are meant branched and unbranched alkylene groups with 1 to 3 carbon atoms. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definition propylene includes all the possible isomeric forms of the groups in question with the same number of carbons. Thus, for example, propyl also includes 1-methylethylene and butylene includes 1-methylpropylene, 1,1-dimethylethylene, 1,2-dimethylethylene.

The definition for $C_0$-alkylene denotes a bond.

By the term "$C_{2-6}$-alkenyl" (including those which are a part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they comprise at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are a part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they comprise at least one triple bond. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus, for example propynyl includes 1-propynyl and 2-propynyl, butynyl includes 1-, 2- and 3-butynyl, 1-methyl-1-propynyl, 1-methyl-2-propynyl etc.

By the term "$C_{3-6}$-cycloalkyl" (including those which are a part of other groups) are meant cyclic alkyl groups with 3 to 6 carbon atoms and by the term "$C_{5-6}$-cycloalkyl" are meant cyclic alkyl groups with 5 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{5-6}$-cycloalkenyl" (including those which are a part of other groups) are meant cyclic alkenyl groups with 5 or 6 carbon atoms, which contain an unsaturated bond. Examples include: cyclopentenyl or cyclohexenyl. Unless otherwise stated, the cyclic alkenyl groups may be substituted by one or more groups selected from among methyl, ethyl, iso-propyl, tert-butyl, hydroxy, fluorine, chlorine, bromine and iodine.

By the term "heterocyclyl" or "heterocyclic group" are meant, unless otherwise described in the definitions, stable 5-, 6- or 7-membered monocyclic or 8-, 9-, 10- or 11-membered bicyclic heterocyclic ring systems, which do not form an aromatic ring system in at least one ring and in addition to carbon atoms may carry one to four heteroatoms selected from among nitrogen, oxygen and sulphur. The two nitrogen atoms and also sulphur atoms may optionally be oxidised and nitrogen atoms may be quaternised. The heterocyclic ring may contain one or two carbonyl, thiocarbonyl or cyanimino groups adjacent to a nitrogen atom. The heterocycles mentioned previously may be linked to the rest of the molecule via a carbon atom or a nitrogen atom.

Unless otherwise stated, the heterocycles may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, COO—$C_{1-3}$-alkyl, preferably CO—O-methyl or CO—O-ethyl,
while the groups may be identical or different.

The following compounds are mentioned by way of example, but the invention is not restricted to them: azetidine, oxetane, thietane, thietane dioxide, tetrahydrofuran, dihydrofuran, dioxolane, imidazolidine, imidazoline, imidazolidinone, dihydroimidazolone, oxazoline, oxazolidine, oxazolidinone, pyrrolidinone, dihydropyrazole, pyrrolidine, pyrroline, morpholine, tetrahydropyridine, dihydropyran, tetrahydropyran, dioxane, piperazine, piperidine, piperazinone, piperidinone, pyran, thiomorpholine-S-oxide, thiomorpholine-S-dioxide, thiomorpholine, dihydroxazine, morpholinedione, morpholinethione, perhydrothiazinedioxide, ε-caprolactam, oxazepanone, diazepanone, thiazepanone, perhydroazepine, dihydroquinazolinone, dihydroindole, dihydroisoindole, benzoxazolone, benzimidazolone, chromanone, tetrahydroquinoline, tetrahydrobenzoxazole, tetrahydrobenzisoxazole, tetrahydrobenzothiophene, tetrahydrothieno-pyridine, tetrahydrobenzofuran, tetrahydro-oxazolopyridine, tetrahydro-isoxazolopyridine.

The following heterocycles are preferred according to the invention:

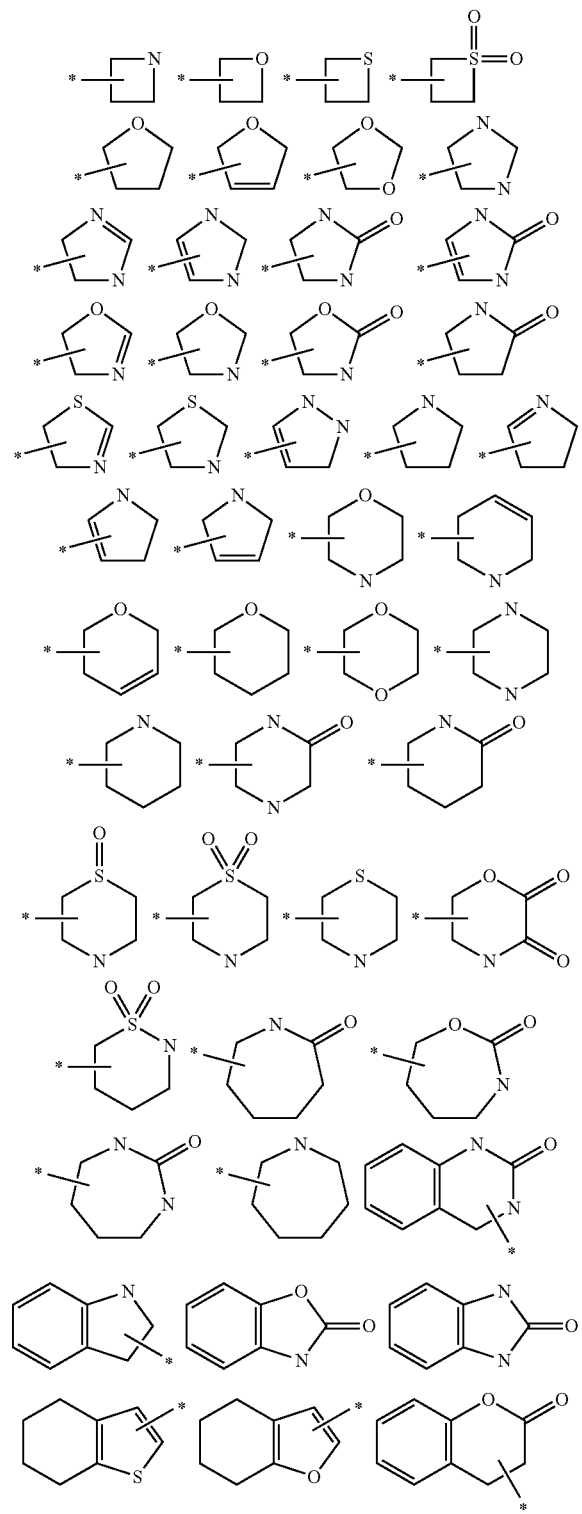

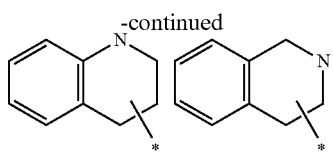

By the term "aryl" (including those which are a part of other groups) are meant monocyclic aromatic ring systems with 6 carbon atoms or bicyclic aromatic ring systems with 10 carbon atoms. Examples include phenyl, 1-naphthyl or 2-naphthyl; the preferred aryl group is phenyl.

Unless otherwise stated, the aromatic groups may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, CO—O—$C_{1-3}$-alkyl, preferably CO—O-methyl or CO—O-ethyl,
while the groups may be identical or different.

By the term "heteroaryl" are meant stable five- or six-membered heterocyclic aromatic groups or 8- to 10-membered bicyclic heteroaryl rings that may contain in each ring one, two or three heteroatoms, selected from among oxygen, sulphur and nitrogen, and additionally sufficient conjugated double bonds to form an aromatic system. Examples of five- or six-membered heterocyclic aromatic groups are as follows, but the invention is not restricted to these:
furan, pyrrole, thiophene, pyrazole, imidazole, oxazole, thiazole, isothiazole, isoxazole, oxadiazole, triazole, tetrazole, furazan, thiadiazole, pyridine, pyrimidine, pyrazine, pyridazine, triazine.

The following five-membered heterocyclic aromatic groups are preferred according to the invention:

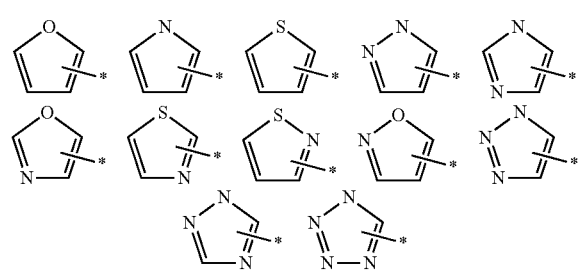

The following six-membered heterocyclic aromatic groups are preferred according to the invention:

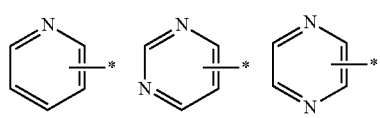

Examples of 9- or 10-membered bicyclic heteroaryl rings are as follows, but the invention is not restricted to these:
indole, isoindole, indazole, indolizine, benzofuran, benzthiophene, benzimidazole, benzoxazole, benzothiazole, benzotriazole, benzisoxazole, benzisothiazole, quinoline, isoquinoline, cinnoline, phthalazine, quinoxaline, quinazoline, pyridopyrimidine, pyridopyrazine, pyridopyridazine, pyrimidopyrimidine, pteridine, purine, quinolizine, benzoxazolecarbonitrile, quinoline, isoquinoline, quinolizine, pteridine, purine, quinolizine, benzoxazole-carbonitrile.

The following bicyclic heteroaryl rings are preferred according to this invention:

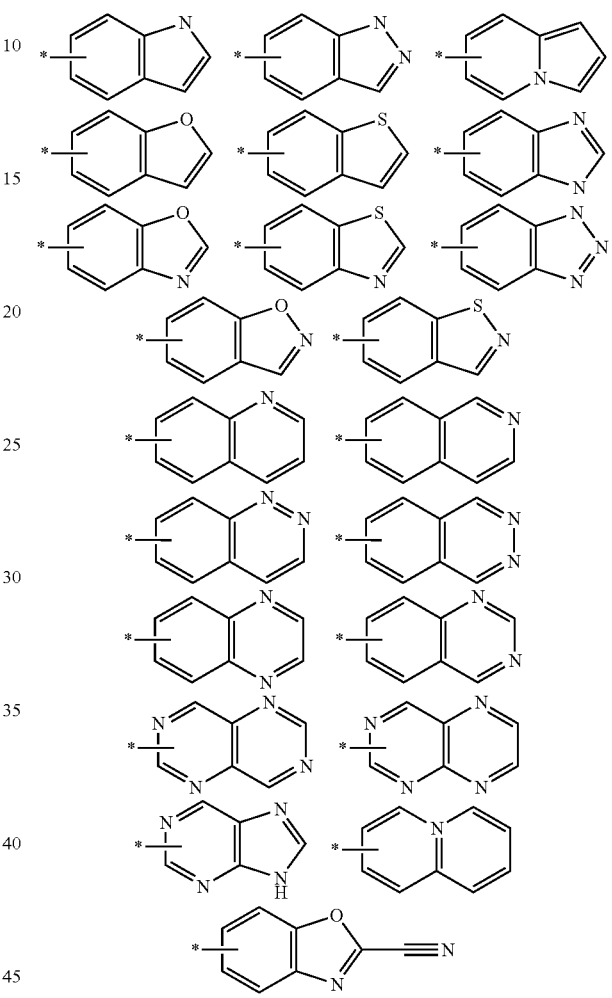

Unless otherwise stated, the heteroaryls previously mentioned may be substituted by one or more groups selected from among:
(a) OH, $NO_2$, CN, $OCF_3$, $OCHF_2$, $OCH_2F$, $NH_2$,
(b) halogen, preferably fluorine or chlorine,
(c) $C_{1-6}$-alkyl, preferably $C_{1-3}$-alkyl, particularly preferably ethyl, methyl, iso-propyl or tert-butyl,
(d) —$SO_2$—O—$C_{1-3}$-alkyl, preferably —O-methyl,
(e) —O—$C_{1-3}$-alkyl, preferably —O-methyl or —O-ethyl,
(f) COOH, CO—O—$C_{1-3}$-alkyl, preferably CO—O-methyl or CO—O-ethyl,
while the groups may be identical or different.

Bicyclic heteroaryl rings may preferably be substituted in the phenyl group.

By the term "halogen" are meant fluorine, chlorine, bromine or iodine atoms.

Compounds of general formula I may have acid groups, mainly carboxyl groups, and/or basic groups such as e.g. amino functions. Compounds of general formula I may therefore be present as internal salts, as salts with pharmaceutically useable inorganic acids such as for example hydrobromic acid, phosphoric acid, nitric acid, hydrochloric acid, sulphuric acid, methanesulphonic acid, ethanesulphonic acid, benzenesulphonic acid, p-toluenesulphonic acid or organic acids such as for example malic acid, succinic acid, acetic acid, fumaric acid, maleic acid, mandelic acid, lactic acid, tartaric acid, citric acid or as salts with pharmaceutically useable bases such as alkali or alkaline earth metal hydroxides, e.g. sodium hydroxide or potassium hydroxide, or carbonates, ammonia, zinc or ammonium hydroxides or organic amines such as e.g. diethylamine, triethylamine, ethanolamine, diethanolamine, triethanolamine, cyclohexylamine, dicyclohexylamine, inter alia.

The compounds according to the invention may be present as racemates, provided that they have only one chiral element, but may also be obtained as pure enantiomers, i.e. in the (R) or (S) form.

Compounds with a carbon double bond may be present in both the E- and the Z-form.

The following nitrogen-containing heteroaryls may be present in different tautomeric forms:

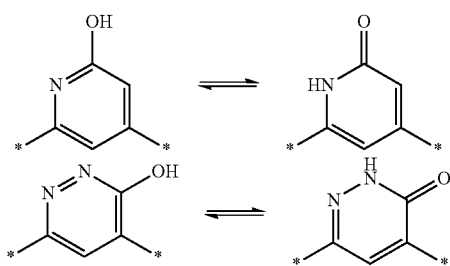

This means that the compound prepared in each case is not restricted to one tautomeric form, but encompasses all the tautomeric forms.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable.

So-called prodrugs of compounds of general formula I are also encompassed by this invention. The term prodrug is used to denote any molecule that releases the active principle of general formula I in-vivo after administration to mammals. The prodrug may have little or no pharmacological activity per se, but releases the active principle of general formula I in-vivo after administration and this has the activity described. Prodrugs for compounds of general formula I may be prepared by modifying suitable functional groups in the compound of general formula I, as known to the skilled man in this field. (H. Bundgaard (Editor), Design of Prodrugs. (1986), Elsevier)

This invention also includes those metabolites that are derived from the compounds of general formula I. By metabolites are meant, in this context, compounds that are formed in-vivo from the compound of general formula I after administration. Examples of metabolites include:

methyl groups of the compound of general formula I may be converted into the corresponding hydroxymethyl groups. (—$CH_3$→—$CH_2OH$)

alkoxy groups of the compound of general formula I may be converted into the corresponding hydroxyl groups. (—OR→—OH)

secondary amines of the compound of general formula I may be converted into the corresponding primary amines. (—$NR_1R_2$→—$NHR_1$ or —$NHR_2$)

nitrogen atoms of the compound of general formula I may be converted into the corresponding nitrogen oxides. (=N—→=$N^+$—($O^-$)—)

Methods of Preparation

The invention also relates to a process for preparing the compounds of general formula I, wherein the substituents have the meanings stated earlier.

Some methods of preparing the compounds of general formula I according to the invention

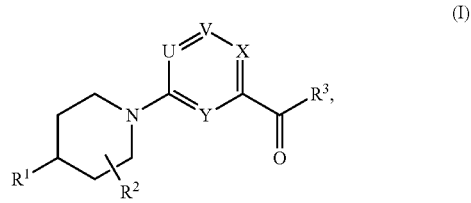

(I)

wherein U, V, X, Y, $R^1$, $R^2$ and $R^3$ are as hereinbefore defined, are illustrated in the following synthesis schemes and Examples.

In some cases the order of carrying out the reaction schemes may be varied in order to simplify the reactions or prevent unwanted by-products. The Examples that follow are provided to make the invention fully comprehensible. The Examples are intended to illustrate the invention and should in no way restrict it.

In some cases the end product may be further derivatised, e.g. by manipulation of the substituents. These manipulations may be generally known to the skilled man, such as oxidation, reduction, alkylation, acylation and hydrolysis, but need not be restricted to the above.

The compounds according to the invention may be prepared according to the schemes and specific examples provided or corresponding modifications thereof. Modifications to these reactions which are known to the skilled man but not described in detail here may also be implemented. The general methods of preparing the compounds according to the invention will become apparent to the skilled man from a study of the following schemes.

Starting compounds are commercially available or are prepared by processes which are described in the literature, known in the art or as described herein. Before the reaction is carried out corresponding functional groups in the compounds may be protected by conventional protective groups. These protective groups may be cleaved again at a suitable stage within the reaction sequence using methods familiar to the skilled man.

In the reactions described below, any reactive groups present such as hydroxy, carboxy, amino, alkylamino, amide or imino groups may be protected during the reaction by conventional protective groups that are cleaved again after the reaction.

For Example
   a suitable protective group for a hydroxy group may be the methoxy, benzyloxy, trimethylsilyl, acetyl, benzoyl, tert.-butyl, trityl, benzyl or tetrahydropyranyl group,
   suitable protective groups for a carboxyl group may be the trimethylsilyl, methyl, ethyl, tert.-butyl, benzyl or tetrahydropyranyl group, and
   suitable protective groups for an amide group may be the N-methoxymethyl-(MOM), N-benzyloxymethyl (BOM), N-(trimethylsilyl)ethoxymethyl (SEM), N-tert-butyldimethylsiloxymethyl, N-tert-butyldimethylsilyl (TBDMS), N-triisopropylsilyl-(TIPS), N-benzyl, N-4-methoxybenzyl (PMB), N-triphenylmethyl (Trt), N-tert-butoxycarbonyl (BOC), N-benzyloxycarbonyl (Cbz) or N-trimethylsilylethylsulphonyl (SES)
   a suitable protective group for an amino, alkylamino or imino group may be the acetyl, trifluoroacetyl, benzoyl, ethoxycarbonyl, tert.-butoxycarbonyl, benzyloxycarbonyl, benzyl, methoxybenzyl or 2,4-dimethoxybenzyl group and additionally, for the amino group, the phthalyl group.

Other protective groups and their cleavage are described in T. W. Greene, P. G. M. Wuts, "Protective Groups in Organic Synthesis", Wiley, 2006.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide, or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is conveniently cleaved in the presence of boron tribromide in a solvent such as methylene chloride at temperatures between −35 and −25° C.

A 2,4-dimethoxybenzyl group is preferably cleaved in trifluoroacetic acid in the presence of anisole.

A tert. butyl or tert. butyloxycarbonyl group is preferably cleaved by treating with an acid such as trifluoroacetic acid or hydrochloric acid, optionally using a solvent such as methylene chloride, dioxan or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

A methoxymethyl group may be cleaved in the presence of an acid such as concentrated hydrochloric acid in a solvent such as dimethoxyethane. Alternatively an acid such as trifluoroacetic acid may also be used without a solvent.

An N-(trimethylsilyl)ethoxymethyl group may be cleaved in the presence of TBAF and 1,3-dimethyl-3,4,5,6-tetrahydro-2(1H)-pyrimidone. Alternatively the SEM protective group may also be cleaved with an acid such as hydrogen chloride in an organic solvent such as dioxane or ethanol.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine at temperatures between 0 and 100° C., preferably at ambient temperature and under an inert gas, or by treating with a catalytic amount of tris-(triphenylphosphine)-rhodium (I)chloride in a solvent such as aqueous ethanol and optionally in the presence of a base such as 1,4-diazabicyclo[2,2,2] octane at temperatures between 20 and 70° C.

The following methods of preparing the compounds of general formula I according to the invention and their precursors have proved particularly suitable:

An end compound of general formula I wherein U, V, X, Y, $R^1$, $R^2$ and $R^3$ are as hereinbefore defined may be obtained by reacting a compound of general formula (1-1) with an electron-poor compound of general formula (1-2) that has a leaving group LG. Halides, preferably chlorides and bromides, —$SO_2CH_3$, —$OSO_2CH_3$, —$OSO_2C_6H_4$—$CH_3$ or —S—$CH_3$ (—S—$CH_3$ requires further reaction with an organic peroxide in order to be converted into the actual leaving group) etc. may act as the leaving group LG, but it is not restricted to this list. The use of chlorides is most particularly preferred.

Scheme 1:

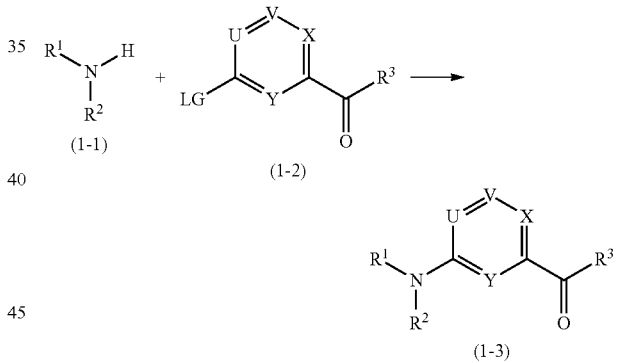

The reaction may be carried out by nucleophilic aromatic substitution in an inert solvent using an auxiliary base in a temperature range of from 0° C. to the reflux temperature of the solvent. The reaction is carried out in a suitable inert solvent, such as tetrahydrofuran, toluene, xylene, dialkylformamide (particularly preferably dimethylformamide), cyclic amide (particularly preferably N-methyl-pyrrolidone), 1,4-dioxane, acetonitrile or in inert solvent mixtures. Suitable auxiliary bases include tertiary amines such as triethylamine or ethyldiisopropylamine, alkali metal carbonates such as potassium carbonate or sodium carbonate, sodium hydride (NaH) or lithium diisopropylamide (LDA). The inert solvent used must be compatible with the base used. The reaction is preferably carried out in dimethylformamide, at temperatures between ambient temperature and the reflux temperature of the solvent, in the presence of a tertiary amine base.

Alternatively the structures of general formula (1-3) shown in Scheme 1 wherein U, V, X, Y, $R^1$, $R^2$ and $R^3$ are as hereinbefore defined may be synthesised by transition metal-catalysed reactions. A compound of general formula (1-1) may react with a compound of general formula (1-2) that has a leaving group LG in an inert solvent in the presence of a catalyst and an auxiliary base. In addition, a suitable ligand may be used for the catalyst. Chlorides, bromides, iodides, trifluoroacetates, trifluoromethanesulphonates, methanesulphonates and toluenesulphonates, but this list is not restrictive. Xylene, tetrahydrofuran, dimethylformamide, dimethoxyethane, toluene, benzene, 1,4-dioxane, acetonitrile or solvent mixtures may be used as inert solvents. The preferred solvent is xylene. Suitable bases are particularly amine bases such as e.g. triethylamine or diisopropylethylamine or also inorganic bases such as caesium carbonate, caesium acetate, potassium carbonate, sodium carbonate or potassium phosphate. Preferred reaction temperatures are from RT to the reflux temperature of the solvent at normal pressure. Typical catalysts are e.g. transition metal catalysts, such as e.g. palladium catalysts of the tris(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2Cl_2$, Pd(dppf) $C_2$ or palladium(II)-chloride type. Typical ligands are e.g. triphenylphosphine, triphenylarsene, 2,2'-bis(diphenylphosphino)-1,1'-binaphthyl (BINAP), 2-di-tert-butylphosphino-2',4',6'-triisopropylbiphenyl (XPhos), 4,5-bis-diphenylphosphanyl-9,9-dimethyl-9H-xanthene (XantPhos) or 2-(di-tert-butylphosphino)biphenyl.

Compounds of general formula (2-4), wherein U, V, X, Y, $R^1$, $R^2$ and $R^3$ are as hereinbefore defined, may be prepared as shown in Scheme 2.

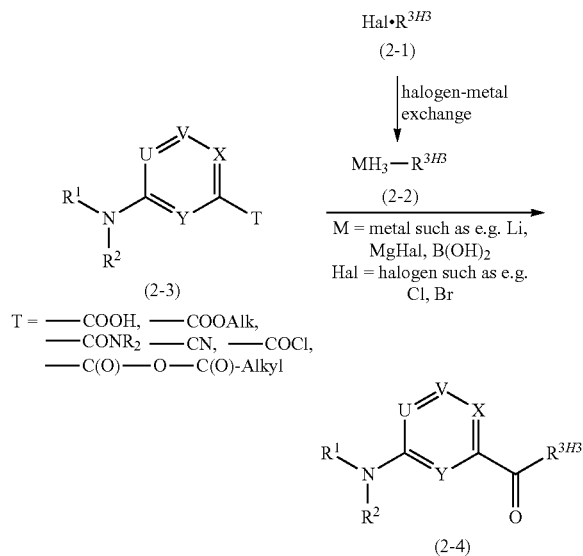

The reaction starts from a compound of general formula (2-1) wherein Hal denotes a halogen atom, preferably chlorine, bromine or iodine. The Grignard or lithiated compound of general formula (2-2) may be prepared from the correspondingly halogenated compound of general formula (2-1) either by a so-called halogen-metal exchange or by inserting the metal in a halogen-carbon bond. In order to synthesise the corresponding lithiated compound of general formula (2-2) the halogen-metal exchange may be carried out for example with an organo-lithium compound such as e.g. n-, sec- or tert.-butyllithium. The corresponding magnesium compounds (Grignard compounds) may also be obtained by a halogen-metal exchange with a corresponding Grignard reagent such as e.g. isopropyl- or sec-butyl-magnesium bromide or chloride or diisopropyl- or di-sec-butylmagnesium with or in the presence of a salt such as e.g. lithium chloride (that may accelerate the metallisation process). The corresponding transmetallising organo-magnesium compound may also be synthesised in-situ from corresponding precursors (cf. e.g. Angew. Chem. 2004, 116, 3396-3399 and Angew. Chem. 2006, 118, 165-169 and references contained therein). In addition, -ate complexes of the organo-magnesium compounds may also be used, resulting from the combination of e.g. butylmagnesium chloride or bromide or isopropyl-magnesium chloride or bromide and butyllithium. (cf. Angew. Chem. 2000, 112, 2594-2596 and Tetrahedron Lett. 2001, 42, 4841-4844 and references contained therein). The halogen-metal exchange is preferably carried out between −100° C. and 40° C., most particularly preferred is a temperature range of from −80° C. to 10° C. in an inert solvent, preferably alkylether (most particularly preferably diethyl ether), cyclic ether (most particularly preferably 1,4-dioxane or tetrahydrofuran), toluene, hexane or solvent mixtures thereof. The magnesium or organolithium compounds thus obtained may optionally be transmetallised with metal salts such as e.g. cerium trichloride, zinc chloride or bromide, indium chloride or bromide, in order to synthesise alternative organometallic compounds of general formula (2-2) that are also suitable for the reaction described. Alternatively the organo-metallic compound (2-2) may also be prepared by inserting a metal into a carbon-halogen bond. Lithium or magnesium are suitable elemental metals for this transformation. The insertion reaction is preferably carried out between −80° C. and 100° C., while most particularly preferred is a temperature range from −70° C. to 40° C. in an inert solvent, preferably alkylether (most particularly preferably diethyl ether), cyclic ether (most particularly preferably 1,4-dioxane or tetrahydrofuran), toluene, hexane or solvent mixtures thereof. In cases where no spontaneous reaction takes place it may be necessary to activate the metal with e.g. 1,2-dibromo-ethane, iodine, trimethylsilyl chloride, acetic acid, hydrogen chloride or ultrasound. The reaction of the organo-metallic compound of general formula (2-2) with a compound (2-3) is preferably carried out in a temperature range from −100° C. to 100° C., while a temperature range from −80° C. to 50° C. is particularly preferred. The reaction is carried out in an inert solvent, such as e.g. preferably alkylether (most particularly preferably diethyl ether, dimethoxyethane), cyclic ether (most particularly preferably 1,4-dioxane or tetrahydrofuran), aromatic hydrocarbons (most particularly preferably toluene or benzene), hexane or solvent mixtures thereof. All the reactions may be carried out in the air, but it is preferable to carry them out in a protective gas atmosphere such as argon or nitrogen. It may prove advantageous to temporarily protect the functional group in compound (2-3).

The lithium-substituted or magnesium-substituted compound of general formula (2-2) may react with a compound of general formula (2-3) that contains a carboxyl group or derivatives thereof such as esters, nitriles, carboxylic acid chlorides or amides, such as e.g. grapevine amides. These reactions may often be carried out without any additional transition metal catalyst or transmetallisation to another metal such as e.g. cerium, indium or zinc. In some cases, however, the two modifications mentioned may also prove advantageous. Aromatic boric acids, esters derived therefrom, dialkylarylboranes or aryltrifluoroborates may be reacted with acid chlorides or carboxylic acids in the presence of a transition metal, such as e.g. palladium, as catalyst, to obtain the corresponding ketones (V. Polackova, St. Toma, I.

Augustinova, Iveta; Tetrahedron; 2006; 62; 50; 11675-11678 and references cited therein and R. Kakino, H. Narahashi, I. Shimizu, A. Yamamoto, Bull. Chem. Soc. Jpn., 2002, 75, 1333-1345).

The corresponding boron-substituted compound, such as e.g. boric acids, dialkylarylboranes or boric acid ester can be synthesised from the metallised species by reaction with a boron electrophil such as e.g. a boric acid ester or derivatives thereof. Boron-substituted compounds may also be synthesised from the halogenated or pseudohalogenated precursor molecules using a transition metal catalyst, preferably palladium, and a boron or borolan compound. (Tetrahedron Lett. 2003, 4895-4898 and references cited therein).

The metallisation and/or coupling reaction may also be carried out in microreactors and/or in the micromixer. The reactions may be carried out without any further additions or, in the case of unreactive reactants, promoters such as e.g. $BF_3*OEt_2$ may also be added (cf. M. Schlosser, Organometallics in Synthesis, John Wiley & Sons, Chichester/New York/Brisbane/Toronto/Singapore, 1994).

The halogenated compounds of general formula (2-1) are either commercially available or may be synthesised by methods known in the field of organic chemistry or described in the specialist literature (cf. e.g. J. March, Advanced Organic Reactions, Reactions Mechanism, and Structure, 4th Edition, John Wiley & Sons, Chichester/New York/Brisbane/Toronto/Singapore, 1992 and literature cited therein). The use of transition metals and organometallic compounds for the synthesis is described in detail in monographs (cf. e.g. L. Brandsma, S. F. Vasilevsky, H. D. Verkruijsse, Application of Transition Metals Catalysts in Organic Synthesis, Springer-Verlag, Berlin/Heidelberg, 1999; M. Schlosser, Organometallics in Synthesis, John Wiley & Sons, Chichester/New York/Brisbane/Toronto/Singapore, 1994, P. J. Stang, F. Diederich, Metal-Catalyzed Cross-Coupling Reactions, Wiley-VCH, Weinheim, 1997 and references contained therein.)

A method of synthesising compounds of general formula (3-4) wherein U, V, X, Y and $R^3$ are as hereinbefore defined is illustrated in Scheme 3.

Starting from a halogenated compound (particularly preferred are the chlorides, bromides and iodides) of general formula (3-1) the corresponding lithium or magnesium-substituted compound may be synthesised by a halogen-metal exchange reaction, e.g. with butyllithium, isopropylmagnesium halide or diisopropylmagnesium or by insertion of an elemental metal into the halogen-carbon bond. The corresponding boron-substituted compounds, such as e.g. boric acid, dialkylarylborane or boric acid ester, can be synthesised from the metallised species by reaction with a boron electrophile such as e.g. a boric acid ester or derivatives thereof. Boron-substituted compounds may also be synthesised from the halogenated or pseudohalogenated precursor molecules using a transition metal catalyst, preferably palladium, and a boron or borolan compound (Tetrahedron Lett. 2003, 4895-4898 and references cited therein). The lithium-substituted or magnesium-substituted compound of general formula (3-2) may be added to a compound of general formula (3-3) that contains a carboxyl group or derivatives thereof such as esters, nitriles, carboxylic acid chlorides or amides, such as e.g. grapevine amides. These reactions may often be carried out without any additional transition metal catalyst or transmetallisation to another metal such as e.g. cerium, indium or zinc. In some cases, however, the two modifications mentioned may also prove advantageous. Aromatic boric acids, esters derived therefrom, dialkylarylboranes or aryltrifluoroborates may be reacted with acid chlorides or carboxylic acids in the presence of a transition metal, such as e.g. palladium, as catalyst, to obtain the corresponding ketones (V. Polackova, St. Toma, I. Augustinova, Iveta; Tetrahedron; 2006; 62; 50; 11675-11678 and references cited therein and R. Kakino, H. Narahashi, I. Shimizu, A. Yamamoto, Bull. Chem. Soc. Jpn., 2002, 75, 1333-1345).

Compounds of general formula (4-3), wherein U, V, X, Y and $R^3$ are as hereinbefore defined, may be prepared as shown in Scheme 4.

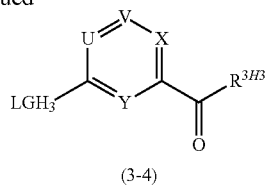

(3-4)

Scheme 3:

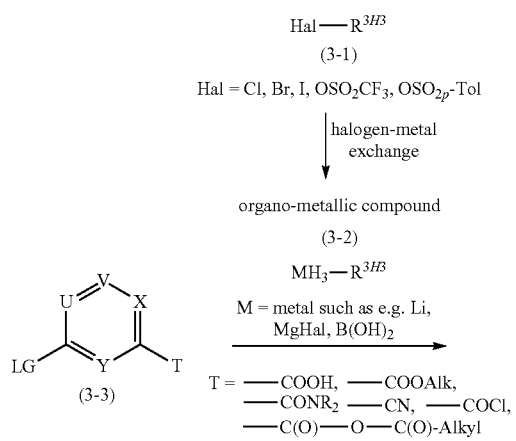

Scheme 4:

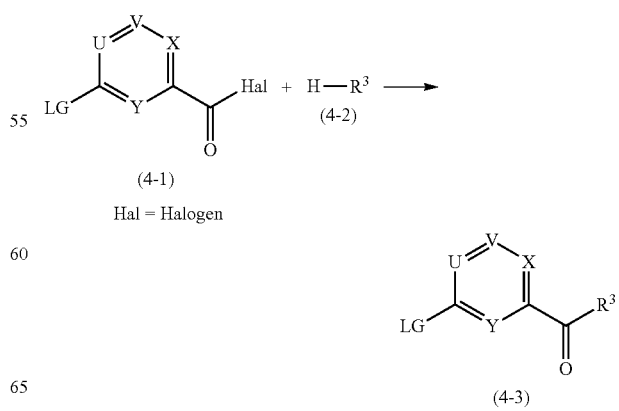

A compound of general formula (4-1) that has a leaving group LG and an acid halide group may be reacted with an aromatic compound of general formula (4-2) under Friedel-Crafts acylation conditions or variations thereof. Friedel-Crafts reactions are carried out in the presence of a catalyst which is used in either catalytic or stoichiometric amounts. Suitable catalysts are, in particular, $AlCl_3$, $FeCl_3$, iodine, iron, $ZnCl_2$, sulphuric acid or trifluoromethanesulphonic acid. Instead of the acid halide the corresponding carboxylic acid, anhydride, ester or nitrile may also be used. The reaction is preferably carried out in halogenated hydrocarbons. Dichloromethane and 1,2-dichloroethane are particularly preferred. Friedel-Crafts reactions are carried out in a temperature range of from −30° C. to 120° C., preferably from 30° C. to 100° C. However, the reactions may also be carried out without a solvent. The reactions may also be carried out in the microwave.

Compounds of general formula (5-3), wherein U, V, X, Y, $R^1$, $R^2$ and $R^3$ are as hereinbefore defined, may be prepared as shown in Scheme 5.

Scheme 5:

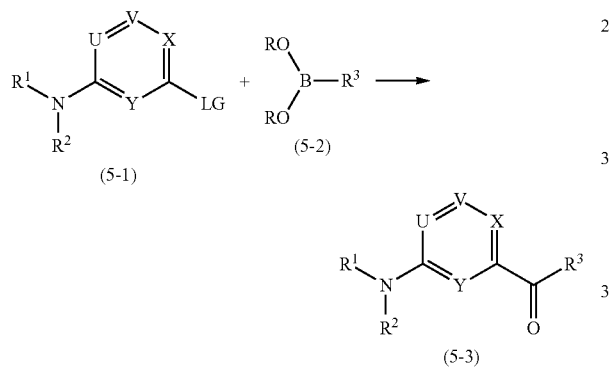

(5-1)

(5-2)

(5-3)

Analogously to a method of T. Ishiyama et al. (J. Org. Chem., 1998, 63, 4726) a compound of general formula (5-1) that has a leaving group LG may be reacted with a boron-substituted compound, such as boric acid (R=H), boric acid ester (R=alkyl) dialkylarylborane in the presence of a catalyst and a base, in an inert solvent and a carbon monoxide atmosphere, preferably in a temperature range from ambient temperature to the reflux temperature of the solvent. Preferably, elevated reaction temperatures from 80° C. to 110° C. are used, under elevated carbon monoxide pressure. A suitable ligand may additionally be used for the catalyst. Alkali metal iodides such as sodium iodide or potassium iodide may be added as additives. Bromides, iodides, trifluoroacetates, trifluoromethanesulphonates, methanesulphonates and toluenesulphonates may act as the leaving group LG, although this list is not restrictive. The inert solvents used may be xylene, tetrahydrofuran, dimethylformamide, dimethoxyethane, toluene, benzene, anisole, 1,4-dioxane, acetonitrile or solvent mixtures. The preferred solvent is anisole. Suitable bases are inorganic bases such as caesium carbonate, caesium acetate, potassium carbonate, sodium carbonate or potassium phosphate. The reactions are carried out in a carbon monoxide atmosphere, in which the carbon monoxide pressure may be 1 to 50 bar. Typical catalysts are e.g. palladium catalysts such as tris-(dibenzylideneacetone)-dipalladium(0), tetrakis-(triphenylphosphine)-palladium(0), palladium-(II)-acetate, $Pd(PPh_3)_2Cl_2$, $Pd(CH_3CN)_2C_2$, $Pd(dppf)C_2$ or palladium(II)-chloride. Typical ligands are e.g. triphenylphosphine, tricyclohexylphosphine, tri-tert-butylphosphine, triphenylarsene, BINAP, XPhos, XantPhos, or 2-(di-tert-butylphosphino)biphenyl, 1,1′-bis(diphenylphosphino)ferrocene (Dppf), 1,2-bis(diphenylphosphino)ethane (dppe), 1,3-bis(diphenylphosphino)propane(dppp) and 1,4-bis(diphenylphosphino)butane (dppb).

It is particularly preferable to use $Pd(PPh_3)_2Cl_2$ as catalyst, potassium carbonate as base, 1 bar of carbon monoxide, potassium iodide as additive and anisole as solvent. The corresponding boron-substituted compounds are either commercially obtainable or can be synthesised from metallised compounds by reaction with a boron electrophil such as e.g. a boric acid ester or a derivative thereof. Moreover, the boron-substituted compounds may be prepared from the corresponding halogenated or pseudohalogenated precursor molecules in a transition metal-catalysed reaction, e.g. with palladium and a diborolane or borolane compound. (Tetrahedron Lett. 2003, 4895-4898 and references cited therein).

A method of synthesising compounds of general formula (6-3), wherein U, V, X, Y and $R^3$ are as hereinbefore defined, is shown in Scheme 6:

Scheme 6:

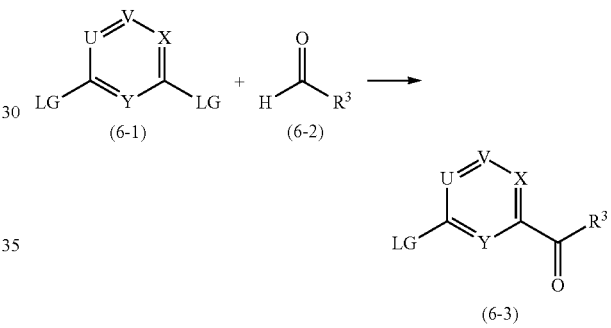

(6-1)

(6-2)

(6-3)

Analogously to a method of A. Miyashita et al. (Heterocycles, 1997, Vol. 45, No. 11, 2159-2173) compounds of general formula (6-1) that have a leaving group LG can be reacted with aromatic aldehydes in the presence of a catalyst and a base in inert solvents to obtain compounds of general formula (6-3). Fluorides, chlorides, bromides, iodides, trifluoromethanesulphonates, methanesulphonates and toluenesulphonates may act as the leaving group LG, but the list is not restrictive. Particularly preferred are chlorides and bromides. Cyclic ethers (preferably tetrahydrofuran) and dialkylformamides (preferably dimethylformamide), may be used as inert solvents. Suitable catalysts are azolium salts, such as 1,3-dimethylimidazolium iodide or 1,3-dimethylbenzimidazolium iodide. Suitable bases are metal hydrides. Sodium hydride is most particularly preferred. The reactions are carried out in a temperature range from RT to the reflux temperature of the solvent. Elevated temperatures are preferred.

The reaction may also be carried out with sodium p-tolylsulphinate instead of azolium salts and base, in the presence of an alkali metal cyanide (preferably potassium cyanide) in an inert solvent at elevated temperatures. (A. Miyashita et al., Heterocycles, 1998, Vol. 47, No. 1, 407-414).

Compounds of general formula (7-4) wherein U, V, X, Y and $R^3$ are as hereinbefore defined, as shown in Scheme 7, may be prepared analogously to A. Miyashita et al. (Heterocycles, 1997, Vol. 45, No. 11, 2159-2173) and the literature cited therein.

Scheme 7:

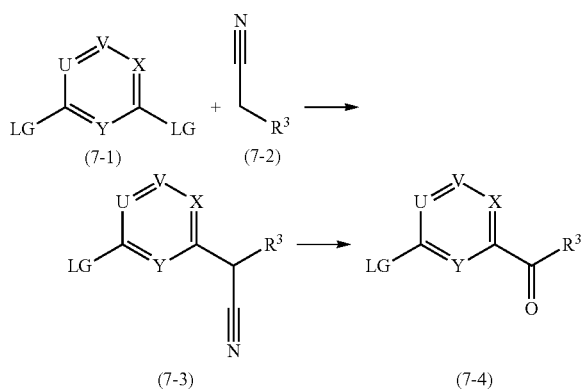

Compounds of general formula (7-1) that have a leaving group LG may be reacted with 2-arylacetonitrile or 2-heteroarylacetonitrile in the presence of a base in an inert solvent to obtain compounds of general formula (7-3). Fluorides, chlorides, bromides, iodides, trifluoromethanesulphonates, methanesulphonates and toluenesulphonates may act as the leaving group LG, but the list is not restrictive. Particularly preferred are chlorides and bromides. The inert solvent may be a dialkylformamide (preferably dimethylformamide). Metal hydrides are suitable as the base. Sodium hydride is most particularly preferred. The reactions are carried out in a temperature range from RT to the reflux temperature of the solvent. Preferably the reactions are carried out at elevated temperatures.

The compounds of general formula (7-4) are synthesised by oxidative decyanisation of compounds of general formula (7-3). Oxidative decyanisations are carried out in inert solvents through which oxygen gas is passed in the presence of a base. Cyclic ethers (preferably tetrahydrofuran) may be used as inert solvents. Suitable bases are metal hydrides. Sodium hydride is most particularly preferred. The reactions are carried out in a temperature range from −20° C. to the reflux temperature of the solvent. Reactions are preferably carried out at RT.

The new compounds of general formula I according to the invention may contain one or more chiral centres. If for example there are two chiral centres present, the compounds may occur in the form of two diastereomeric pairs of antipodes. The invention includes the individual isomers as well as the mixtures thereof. The diastereomers may be separated on the basis of their different physico-chemical properties, e.g. by fractional crystallisation from suitable solvents, by high pressure liquid or column chromatography, using chiral or preferably non-chiral stationary phases.

Racemates covered by general formula I may be separated for example by HPLC on suitable chiral stationary phases (e.g. Chiral AGP, Chiralpak AD). Racemates which contain a basic or acidic function can also be separated via the diastereomeric, optically active salts which are produced on reacting with an optically active acid, for example (+) or (−)-tartaric acid, (+) or (−)-diacetyl tartaric acid, (+) or (−)-monomethyl tartrate or (+) or (−)-camphorsulphonic acid, or an optically active base, for example with (R)-(+)-1-phenylethylamine, (S)-(−)-1-phenylethylamine or (S)-brucine.

According to a conventional method of separating isomers, the racemate of a compound of general formula I is reacted with one of the abovementioned optically active acids or bases in equimolar amounts in a solvent and the resulting crystalline, diastereomeric, optically active salts thereof are separated using their different solubilities. This reaction may be carried out in any type of solvent provided that it is sufficiently different in terms of the solubility of the salts. Preferably, methanol, ethanol or mixtures thereof, for example in a ratio by volume of 50:50, are used. Then each of the optically active salts is dissolved in water, carefully neutralised with a base such as sodium carbonate or potassium carbonate, or with a suitable acid, e.g. with dilute hydrochloric acid or aqueous methanesulphonic acid, and in this way the corresponding free compound is obtained in the (+) or (−) form.

The (R) or (S) enantiomer alone or a mixture of two optically active diastereomeric compounds covered by general formula I may also be obtained by performing the syntheses described above with a suitable reaction component in the (R) or (S) configuration.

The new compounds of general formula I and the physiologically acceptable salts thereof have valuable pharmacological properties, based on their selective CGRP-antagonistic properties. The invention further relates to pharmaceutical compositions containing these compounds, their use and the preparation thereof.

The new compounds mentioned above and the physiologically acceptable salts thereof have CGRP-antagonistic properties and exhibit good affinities in CGRP receptor binding studies. The compounds display CGRP-antagonistic properties in the pharmacological test systems described hereinafter.

The following experiments were carried out to demonstrate the affinity of the above-mentioned compounds for human CGRP-receptors and their antagonistic properties:

A. Binding Studies with SK-N-MC Cells (Expressing the Human CGRP Receptor)

SK-N-MC cells are cultivated in "Dulbecco's modified Eagle medium". The medium is removed from confluent cultures. The cells are washed twice with PBS buffer (Gibco 041-04190 M), detached by the addition of PBS buffer mixed with 0.02% EDTA, and isolated by centrifuging. After resuspension in 20 ml of "Balanced Salts Solution" [BSS (in mM): NaCl 120, KCl 5.4, NaHCO$_3$ 16.2, MgSO$_4$ 0.8, NaHPO$_4$ 1.0, CaCl$_2$ 1.8, D-glucose 5.5, HEPES 30, pH 7.40] the cells are centrifuged twice at 100×g and resuspended in BSS. After the number of cells has been determined, the cells are homogenised using an Ultra-Turrax and centrifuged for 10 minutes at 3000×g. The supernatant is discarded and the pellet is recentrifuged in Tris buffer (10 mM Tris, 50 mM NaCl, 5 mM MgCl$_2$, 1 mM EDTA, pH 7.40) enriched with 1% bovine serum albumin and 0.1% bacitracin, and resuspended (1 ml/1000000 cells). The homogenised product is frozen at −80° C. The membrane preparations are stable for more than 6 weeks under these conditions.

After thawing, the homogenised product is diluted 1:10 with assay buffer (50 mM Tris, 150 mM NaCl, 5 mM MgCl$_2$, 1 mM EDTA, pH 7.40) and homogenised for 30 seconds with an Ultra-Turrax. 230 µl of the homogenised product are incubated for 180 minutes at ambient temperature with 50 pM $^{125}$I-iodotyrosyl-Calcitonin-Gene-Related Peptide (Amersham) and increasing concentrations of the test substances in a total volume of 250 µl. The incubation is ended by rapid filtration through GF/B glass fibre filters treated with polyethyleneimine (0.1%) using a cell harvester. The protein-bound radioactivity is measured using a gamma counter. Non-specific binding is defined as the bound radioactivity after the presence of 1 µM human CGRP-alpha during incubation.

The concentration binding curves are analysed using computer-aided non-linear curve fitting.

The compounds mentioned hereinbefore show $K_i$ values ≤50 μM in the test described.

B. CGRP Antagonism in SK-N-MC Cells

SK-N-MC cells (1 million cells) are washed twice with 250 μl incubation buffer (Hanks' HEPES, 1 mM 3-isobutyl-1-methylxanthine, 1% BSA, pH 7.4) and pre-incubated at 37° C. for 15 minutes. After the addition of CGRP (10 μl) as agonist in increasing concentrations ($10^{-11}$ to $10^{-6}$ M), or additionally the substance in 3 to 4 different concentrations, the mixture is incubated for another 15 minutes.

Intracellular cAMP is then extracted by the addition of 20 μl of 1M HCl and centrifugation (2000×g, 4° C., for 15 minutes). The supernatants are frozen in liquid nitrogen and stored at −20° C.

The cAMP contents of the samples are determined by radioimmunoassay (Messrs. Amersham) and the $pA_2$ values of antagonistically acting substances are determined graphically.

The compounds according to the invention exhibit CGRP-antagonistic properties in the in vitro test model described, in a dosage range between $10^{-12}$ and $10^{-4}$ M.

To demonstrate that the compounds of general formula I exhibit good to very good CGRP-antagonistic activities with different structural elements, the following Table gives the $K_i$ values obtained according to the test procedure described above. It should be noted that the compounds were selected for their different structural elements and not in order to emphasise specific compounds:

| Example | $K_i$ [nM] |
| --- | --- |
| (1) | 0.4 |
| (3) | 4 |
| (4) | 1 |

Indications

In view of their pharmacological properties the compounds according to the invention and the salts thereof with physiologically acceptable acids are thus suitable for the acute and prophylactic treatment of headaches, particularly migraine or cluster headaches and tension headaches. Moreover, the compounds according to the invention also have a positive effect on the following diseases: non-insulin-dependent diabetes mellitus ("NIDDM"), cardiovascular diseases, morphine tolerance, diarrhoea caused by clostridium toxin, skin diseases, particularly thermal and radiation-induced skin damage including sunburn, lichen, pruritis, pruritic toxidermies and severe itching, inflammatory diseases, e.g. inflammatory diseases of the joints (osteoarthritis, rheumatoid arthritis, neurogenic arthritis), generalised soft-tissue rheumatism (fibromyalgia), neurogenic inflammation of the oral mucosa, inflammatory lung diseases, allergic rhinitis, asthma, COPD, diseases accompanied by excessive vasodilatation and resultant reduced blood supply to the tissues, e.g. shock and sepsis, chronic pain, e.g. diabetic neuropathies, neuropathies induced by chemotherapy, HIV-induced neuropathies, postherpetic neuropathies, neuropathies induced by tissue trauma, trigeminal neuralgias, temporomandibular dysfunctions, CRPS (complex regional pain syndrome), back pain, and visceral complaints, such as e.g. irritable bowel syndrome (IBS) and inflammatory bowel syndrome. In addition, the compounds according to the invention have a general pain-relieving effect. The symptoms of menopausal hot flushes caused by vasodilatation and increased blood flow in oestrogen-deficient women and hormone-treated patients with prostate carcinoma and castrated men are favourably affected by the CGRP antagonists of the present application in a preventive and acute-therapeutic capacity, this therapeutic approach being distinguished from hormone replacement by the absence of side effects. The dosage required to achieve a corresponding effect is conveniently 0.0001 to 3 mg/kg of body weight, preferably 0.01 to 1 mg/kg of body weight, when administered intravenously or subcutaneously, and 0.01 to 10 mg/kg of body weight, preferably 0.1 to mg/kg of body weight when administered orally, nasally or by inhalation, 1 to 3× a day in each case.

If the treatment with CGRP antagonists and/or CGRP release inhibitors is given as a supplement to conventional hormone replacement, it is advisable to reduce the doses specified above, in which case the dosage may be from ⅕ of the lower limits mentioned above up to 1/1 of the upper limits specified.

The invention further relates to the use of the compounds according to the invention as valuable adjuvants for the production and purification (by affinity chromatography) of antibodies as well as in RIA and ELISA assays, after suitable radioactive labelling, for example by tritiation of suitable precursors, for example by catalytic hydrogenation with tritium or replacing halogen atoms with tritium, and as a diagnostic or analytical adjuvant in neurotransmitter research.

Combinations

Categories of active substance which may be used in combination include e.g. antiemetics, prokinetics, neuroleptics, antidepressants, neurokinin antagonists, anticonvulsants, histamine-H1-receptor antagonists, β-blockers, α-agonists and α-antagonists, ergot alkaloids, mild analgesics, non-steroidal antiphlogistics, corticosteroids, calcium antagonists, $5\text{-HT}_{1B/1D}$-agonists or other anti-migraine agents which may be formulated together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, into conventional galenic preparations such as plain or coated tablets, capsules, powders, suspensions, solutions, metered dose aerosols or suppositories.

Thus other active substances which may be used for the combinations mentioned above include for example the non-steroidal antiinflammatories aceclofenac, acemetacin, acetylsalicylic acid, acetaminophen (paracetamol), azathioprine, diclofenac, diflunisal, fenbufen, fenoprofen, flurbiprofen, ibuprofen, indometacin, ketoprofen, leflunomide, lornoxicam, mefenamic acid, naproxen, phenylbutazone, piroxicam, sulphasalazine, zomepirac or the pharmaceutically acceptable salts thereof as well as meloxicam and other selective COX2-inhibitors, such as for example rofecoxib, valdecoxib, parecoxib, etoricoxib and celecoxib, as well as substances that inhibit earlier or later stages of prostaglandin synthesis or prostaglandin receptor antagonists such as e.g. EP2-receptor antagonists and IP-receptor antagonists.

It is also possible to use ergotamine, dihydroergotamine, metoclopramide, domperidone, diphenhydramine, cyclizine, promethazine, chlorpromazine, vigabatrin, timolol, isometheptene, pizotifen, botox, gabapentin, pregabalin, duloxetine, topiramate, riboflavin, montelukast, lisinopril, micardis, prochloroperazine, dexamethasone, flunarizine, dextropropoxyphene, meperidine, metoprolol, propranolol, nadolol, atenolol, clonidine, indoramin, carbamazepine, phenyloin, valproate, amitryptiline, imipramine, venlafaxine, lidocaine or diltiazem and other 5-HT$_{1B/1D}$-agonists such as, for example, almotriptan, avitriptan, eletriptan, frovatriptan, naratriptan, rizatriptan, sumatriptan and zolmitriptan.

Furthermore, CGRP antagonists with vanilloid receptor antagonists, such as e.g. VR-1 antagonists, glutamate receptor antagonists, such as e.g. MGlu5 receptor antagonists, mGlu1 receptor antagonists, iGlu5 receptor antagonists, AMPA receptor antagonists, purine receptor blockers, such as e.g. P2X3 antagonists, NO-synthase inhibitors, such as e.g. INOS inhibitors, calcium channel blockers, such as e.g. PQ-type blockers, N-type blockers, potassium channel openers, such as e.g. KCNQ channel openers, sodium channel blockers, such as e.g. PN3 channel blockers, NMDA receptor antagonists, acid-sensing ion channel antagonists, such as e.g. ASIC3 antagonists, bradykinin receptor antagonists such as e.g. B1 receptor antagonists, cannabinoid receptor agonists, such as e.g. CB2 agonists, CB1 agonists, somatostatin receptor agonists, such as e.g. Sst2 receptor agonists may be added.

The dosage of these active substances is expediently 1/5 of the lowest usually recommended dose to 1/1 of the normally recommended dose, i.e. for example 20 to 100 mg of sumatriptan.

Formulations

The compounds prepared according to the invention may be administered either on their own or optionally in combination with other active substances for the treatment of migraine by intravenous, subcutaneous, intramuscular, intraarticular, intrarectal, intranasal route, by inhalation, topically, transdermally or orally, while aerosol formulations are particularly suitable for inhalation. The combinations may be administered either simultaneously or sequentially.

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. In amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula I according to the preferred embodiments above.

It is particularly preferable if the compounds of formula I are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula I are administered by inhalation, particularly preferably if they are administered once or twice a day. For this purpose, the compounds of formula I have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Experimental Section

As a rule IR, $^1$H-NMR and/or mass spectra have been obtained for the compounds prepared. Unless stated otherwise, R$_f$ values are determined using ready-made TLC silica gel plates 60 F254 (E. Merck, Darmstadt, Item no. 1.05714) without chamber saturation. The ratios given for the eluants relate to units by volume of the particular solvents. The units by volume given for NH₃ relate to a concentrated solution of NH₃ in water.

Unless stated otherwise, the acid, base and salt solutions used in working up the reaction solutions are aqueous systems of the specified concentrations. Silica gel made by Millipore (MATREX™, 35-70 μm) is used for chromatographic purifications.

The HPLC data provided are measured under the parameters listed below and using the columns mentioned:

Columns used:

(column temperature: 30° C.; Injection volume: 5 μL; detection at 254 nm)

| | |
|---|---|
| S1 | Zorbax column (Agilent Technologies), SB (Stable Bond) C18; 3.5 μm; 4.6 × 75 mm |
| S2 | Zorbax column (Agilent Technologies), SB (Stable Bond) C18; 1.8 μm; 3.0 × 30 mm |
| S3 | Zorbax column (Agilent Technologies), SB (Stable Bond) C18; 5 μm; 4.6 × 75 mm |
| S4 | Xbridge (Waters) C18; 3.0 × 30 mm, 2.5 μm |
| S5 | Sunfire C18 (Waters); 3.5 μm; 4.6 × 75 mm |
| S6 | Symmetry C18 (Waters); 4.6 × 75 mm, 3.5 μm |

Solvents used:

solvent A: water (with 0.1% formic acid), solvent B: acetonitrile (with 0.1% formic acid), solvent C: water (with 0.1% ammonia), solvent D: acetonitrile (with 0.1% ammonia).

The percentages stated refer to the total volume

Gradients:

| gradient | time [min] | % A | % B |
|---|---|---|---|
| G1 | 0.00 | 95 | 5 |
| (1.6 mL/min) | 0.10 | 95 | 5 |
| | 1.75 | 5 | 95 |
| | 1.90 | 5 | 95 |
| | 1.95 | 95 | 5 |
| | 2.00 | 95 | 5 |
| G2 | 0.00 | 95 | 5 |
| (1.6 mL/min) | 4.50 | 10 | 90 |
| | 5.00 | 10 | 90 |
| | 5.50 | 95 | 5 |
| G3 | 0.00 | 95 | 5 |
| (1.6 mL/min) | 4.00 | 50 | 50 |
| | 4.50 | 10 | 90 |
| | 5.00 | 10 | 90 |
| | 5.50 | 95 | 5 |
| G4 | 0.00 | 95 | 5 |
| (1.6 mL/min) | 1.00 | 10 | 90 |
| | 2.50 | 50 | 50 |
| | 2.75 | 95 | 5 |
| G5 | 0.00 | 95 | 5 |
| (1.6 mL/min) | 2.00 | 10 | 90 |
| | 5.00 | 10 | 90 |
| | 5.50 | 95 | 5 |

| gradient | time [min] | % C | % D |
|---|---|---|---|
| G6 | 0.00 | 95 | 5 |
| (1.4 mL/min) | 1.80 | 10 | 90 |
| | 2.00 | 10 | 90 |
| | 2.20 | 95 | 5 |
| G7 | 0.00 | 95 | 5 |
| (1.6 mL/min) | 2.00 | 50 | 50 |
| | 2.25 | 10 | 90 |
| | 2.50 | 10 | 90 |
| | 2.75 | 95 | 5 |

| gradient | time [min] | % A | % B |
|---|---|---|---|
| G8 | 0.00 | 95 | 5 |
| (1.4 mL/min) | 2.00 | 00 | 100 |
| | 3.00 | 00 | 100 |
| | 3.40 | 95 | 5 |

| | column | gradient |
|---|---|---|
| method A | S1 | G1 |
| method B | S2 | G1 |
| method C | S1 | G2 |
| method D | S1 | G3 |
| method E | S2 | G4 |
| method F | S1 | G5 |
| method G | S4 | G6 |
| method H | S2 | G7 |
| method I | S5 | G3 |
| method K | S5 | G2 |
| method L | S6 | G3 |
| method M | S6 | G8 |

In preparative HPLC purifications as a rule the same gradients are used as were used to obtain the analytical HPLC data. The products are collected under mass control, the fractions containing product are combined and freeze-dried.

In the absence of any more information regarding the configuration, it is unclear whether there are pure enantiomers involved or whether partial or even total racemisation has taken place.

The following abbreviations are used in the test descriptions:

18-crown-6 crown ether (1,4,7,10,13,16-hexaoxacyclooctadecan)
AcOH acetic acid
AIBN 2,2'-azobis(2-methylpropionitrile)
BINAP 2,2'-bis(diphenylphosphino)-1,1'-binaphthyl
BOC tert.-butyloxycarbonyl
CAD circulating air dryer
Cyc cyclohexane
CDI 1,1'-carbonyldiimidazole
DCM dichloromethane
DIPE diisopropylether
DIPEA diisopropylethylamine
DMF N,N-dimethylformamide
of theoretical of theory
D-water deionised water
EI electron jet ionisation (at MS)
ESI electrospray ionisation (at MS)
EtOAc ethyl acetate
EtOH ethanol
el eluant
HCl hydrogen chloride
HCOOH formic acid
HPLC High Performance Liquid chromatography
HPLC-MS HPLC coupled mass spectrometry
i. vac. in vacuo (under vacuum)
conc. concentrated
MeOH methanol
MS mass spectrometry
MW molecular weight [g/mol]
NaOH sodium hydroxide NH₄OH ammonium hydroxide (aqueous ammonia solution, 30%)
NMP N-methyl-2-pyrrolidine
Pd₂dba₃ bis(dibenzylideneacetone) palladium (0)
PE petroleum ether
R_f retention index (in TLC)
RT ambient temperature
R_t retention time (in HPLC)
TEA triethylamine
TFA trifluoroacetic acid
THF tetrahydrofuran Preparation of the Starting Compounds Intermediate 1a 1-piperidin-4-yl-1,3-dihydroimidazo[4,5-b]pyridin-2-one-dihydrochloride

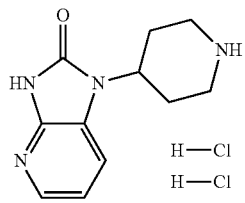

This compound and its precursors were synthesised as described in WO 2005/013894.
ESI-MS: m/z=219 (M+H)⁺
R_f: 0.11 (silica gel, DCM/MeOH/NH₄OH=80:20:2)

Intermediate 1b 1-piperidin-4-yl-1,3-dihydroimidazo[4,5-b]pyridin-2-one

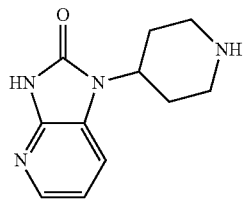 [SMILES: O=c1[nH]c2ncccc2n1C1CCNCC1]

Step 1: benzyl 4-(2-chloro-pyridin-3-yl-amino)-piperidine-1-carboxylate

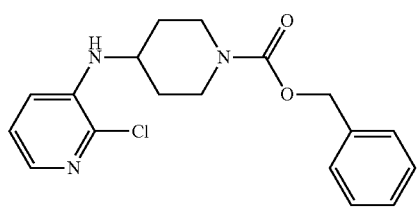 [SMILES: O=C(OCc1ccccc1)N1CCC(Nc2cccnc2Cl)CC1]

560 mL (7.25 mol) TFA were added dropwise to 930 g (3.99 mol) N-benzyloxycarbonyl-4-piperidone and 466 g (3.63 mol) 2-chloro-3-aminopyridine in 9.5 L isopropyl acetate at approx. 15° C. 922 g (4.35 mol) sodium triacetoxyborohydride were added batchwise. The mixture was stirred until the reaction was complete. At RT the reaction mixture was combined with 860 mL sodium hydroxide solution (2 mol/L). The organic phase was separated off, washed with 5 L water and evaporated down.
Yield: 1250 g (roughly 100% of theoretical)
ESI-MS: m/z=346 (M+H)⁺

Step 2: benzyl 4-[1-(2-chloro-pyridin-3-yl)-ureido]-piperidine-1-carboxylate

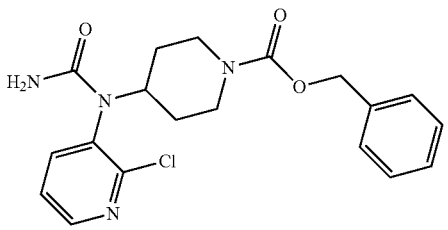 [SMILES: NC(=O)N(c1cccnc1Cl)C1CCN(C(=O)OCc2ccccc2)CC1]

530 mL (6.1 mol) chlorosulphonyl isocyanate were placed in 6 L THF and cooled to −15° C. A solution of 1.25 kg (3.63 mol) benzyl 4-(2-chloro-pyridin-3-yl-amino)-piperidine-1-carboxylate in 7 L THF was then added dropwise to this mixture within one hour such that the temperature of the reaction mixture did not exceed −7° C. The mixture was stirred for 90 minutes at approx. −8° C. and then 700 mL water were added dropwise within 30 minutes. The mixture was stirred for 30 minutes at approx. 10° C. and then slowly combined with 8.1 L sodium hydroxide solution (2 mol/L). The reaction mixture was then heated to 50° C. and the phases were separated. The organic phase was washed with 2 L water. Then 10 L solvent were distilled off from the organic phase, 15 L butyl acetate were added to the residue and another 8 L were distilled off. The product was crystallised by slow cooling to 0° C. The precipitate was suction filtered, washed with 2 L butyl acetate and dried at 40° C.
Yield: 1108 g (78.8% of theoretical)
ESI-MS: m/z=389/391 (M+H)⁺

Step 3: benzyl 4-(2-oxo-2,3-dihydro-imidazo[4,5-b]pyridin-1-yl)-piperidine-1-carboxylate

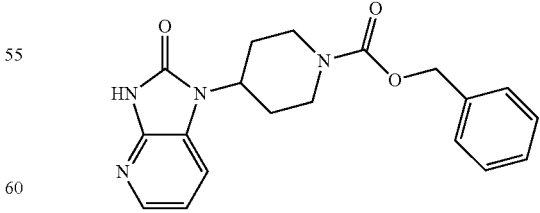

1108 g (2.85 mol) benzyl 4-[1-(2-chloro-pyridin-3-yl)-ureido]-piperidine-1-carboxylate were refluxed with 720 g (8.57 mol) sodium hydrogen carbonate in 14.5 L tert-amylalcohol. 3 L solvent were distilled off. The reaction mixture was cooled to 35° C. and combined with 11 mL water. Then 13 g (0.058 mol) palladium acetate and 49 g (0.115 mol) 1,4-bis-(diphenylphosphino)-butane (DPPB) were added and the mixture was heated to reflux temperature. It was stirred at 100° C. until the reaction was complete, cooled to RT and 7.5 L of water were added. The organic phase was separated off, washed with 5 L water and then evaporated down. The oily residue was mixed twice with 3 L isopropyl acetate and distilled off. Then the residue was dissolved hot in 7 L isopropyl acetate and slowly cooled to ambient temperature. The solid that crystallised out was suction filtered, washed with 2 L isopropyl acetate and tert.-butyl-methylether and dried at 50° C.

Yield: 690 g (69% of theoretical)
ESI-MS: m/z=353 (M+H)+

Step 4: 1-piperidin-4-yl-1,3-dihydro-imidazo[4,5-b]pyridin-2-one

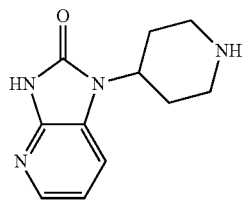 [SMILES: O=c1[nH]c2ncccc2n1C1CCNCC1]

690 g (1.96 mol) benzyl 4-(2-oxo-2,3-dihydro-imidazo[4,5-b]pyridin-1-yl)-piperidine-1-carboxylate were dissolved in 5.4 L methanol and hydrogenated with the addition of 46 g Pd/C (10%; 6.6% by weight) at 60° C. under a hydrogen pressure of 60 psi until all the hydrogen had been taken up. The catalyst was filtered off. 4 L methanol were distilled off from the filtrate. 2 L methylcyclohexane were added and a further 1.5 L solvent were distilled off. The suspension thus obtained was suction filtered, the residue was washed with methylcyclohexane and dried at 40° C.

Yield: 446 g (100% of theoretical)
ESI-MS: m/z=219 (M+H)+

Intermediate 2

3-piperidin-4-yl-1,3,4,5-tetrahydro-1,3-benzodiazepin-2-one

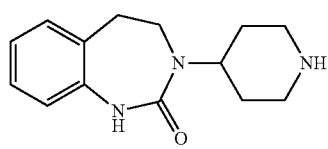 [SMILES: O=C1Nc2ccccc2CCN1C1CCNCC1]

This compound and its precursors were synthesised as described in European Patent Application No. 1 619 187.

ESI-MS: m/z=246.2 (M+H)+

Intermediate 3

7-methoxy-3-piperidin-4-yl-1,3,4,5-tetrahydro-1,3-benzodiazepin-2-one

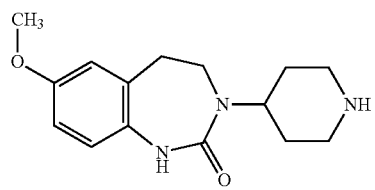 [SMILES: COc1ccc2c(c1)CCN(C1CCNCC1)C(=O)N2]

Step 1: (5-methoxy-2-nitrophenyl)-acetonitrile

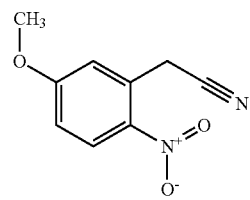

24.0 g (214 mmol) potassium-tert-butoxide in 100 mL DMF were slowly added dropwise to a solution of 13.17 g (86.0 mmol) 4-nitroanisole and 18.0 g (107 mmol) 4-chlorophenoxyacetonitrile in 50 mL DMF. The reaction mixture was stirred for 30 min at −10° C. and then poured into 300 g of a 1:1 mixture of conc. HCl and ice. After extraction with EtOAc the organic phase was washed with water, dried and concentrated to dryness by rotary evaporation in vacuo with gentle heating. The residue was treated with a 1:1 mixture of PE/EtOAc and the product that crystallised out was suction filtered. After washing with a 1:1 mixture of PE/EtOAc the crystals were dried in the air. 6.5 g of the desired product was obtained.

Yield: 6.5 g (39% of theoretical)
ESI-MS: m/z=210 (M+NH4)+
Rf: 0.45 (silica gel; PE/EtOAc=1:1)

Step 2: 2-(5-methoxy-2-nitrophenyl)-ethylamine

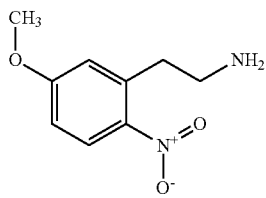

Under a nitrogen atmosphere 200 mL (200 mmol) of a 1M borane in THF solution were slowly added dropwise at RT to 12.6 g (65.7 mmol) (5-methoxy-2-nitrophenyl)-acetonitrile in 380 mL THF. The reaction mixture was refluxed for 2 h. After cooling, 30 mL methanol were added dropwise within 20 min. At the same time the temperature was maintained at 10° C. to 20° C. with an ice bath. The reaction mixture was stirred for 30 min at RT and then within 30 min 45 mL of a 2M HCl solution were added dropwise thereto. The reaction mixture was concentrated by rotary evaporation i. vac. with gentle heating. The residue was diluted to approx. 200 mL with water and extracted with 200 mL EtOAc. The aqueous phase was made alkaline with a 15% (w/v) aqueous potassium carbonate solution and continuously extracted with diethyl ether overnight using a rotary perforator according to Ludwig (Messrs Normag). The organic extract was concentrated to dryness by rotary evaporation. 9.98 g of the desired product was obtained.

Yield: 9.98 g (77% of theoretical)
ESI-MS: m/z=197 (M+H)$^+$
R$_t$(HPLC)=2.13 min (Method C)

Step 3: (1-benzylpiperidin-4-yl)-[2-(5-methoxy-2-nitrophenyl)-ethyl]-amine

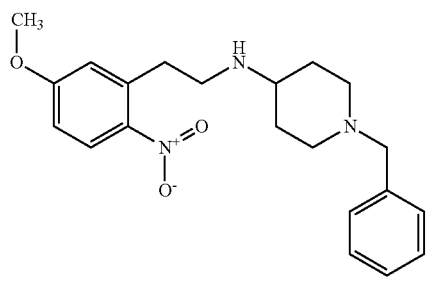 [SMILES: COc1ccc([N+](=O)[O-])c(CCNC2CCN(Cc3ccccc3)CC2)c1]

Under a nitrogen atmosphere a mixture of 9.98 g (50.9 mmol) 2-(5-methoxy-2-nitrophenyl)-ethylamine, 9.80 mL (54.9 mmol) N-benzylpiperidone and 6.30 mL (114 mmol) acetic acid in 270 mL DCM was cooled to 0° C. in an ice bath. At this temperature 14.2 g (67.0 mmol) sodium triacetoxyborohydride were added batchwise within 20 min. The reaction mixture was stirred for a further 4 h at 0° C. and left to warm up to RT overnight. Then the mixture was combined with 400 mL of a 15% (w/v) aqueous potassium carbonate solution and stirred for 1 h at RT. The organic phase was separated off, dried and concentrated by rotary evaporation. 18.8 g of the desired product were obtained.

Yield: 18.8 g (quantitative)
ESI-MS: m/z=370 (M+H)$^+$
R$_t$(HPLC)=1.93 min (Method C)

Step 4: [2-(2-amino-5-methoxyphenyl)-ethyl]-(1-benzylpiperidin-4-yl)-amine

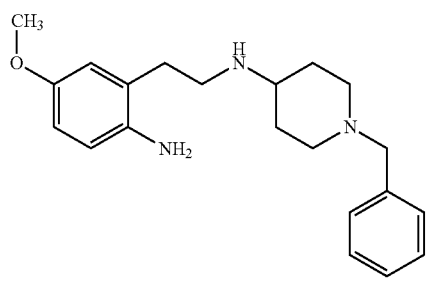 [SMILES: COc1ccc(N)c(CCNC2CCN(Cc3ccccc3)CC2)c1]

26.0 g (70.3 mmol) (1-benzylpiperidin-4-yl)-[2-(5-methoxy-2-nitrophenyl)-ethyl]-amine were hydrogenated with 5.00 g (2.45 mmol) rhodium charcoal (5%, moistened with water) in 350 mL methanol in a 3 bar hydrogen atmosphere for 3 h at RT. The catalyst was removed by suction filtering and the solution was concentrated by rotary evaporation. 23.9 g of residue was obtained, which was immediately reacted further without any further purification.

Yield: 23.9 g (quantitative)
R$_t$(HPLC)=R$_t$=0.99 min (Method D)

Step 5: 3-(1-benzylpiperidin-4-yl)-7-methoxy-1,3,4,5-tetrahydro-1,3-benzodiazepin-2-one

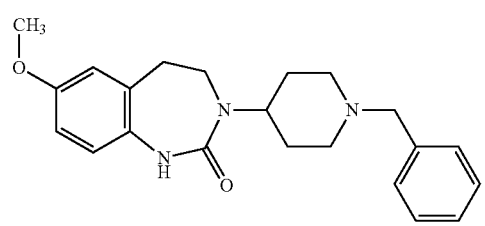 [SMILES: COc1ccc2c(c1)CCN(C1CCN(Cc3ccccc3)CC1)C(=O)N2]

35.0 g (216 mmol) N,N-carbonyldiimidazole were added to 23.9 g (70.3 mmol) [2-(2-amino-5-methoxyphenyl)-ethyl]-(1-benzylpiperidin-4-yl)-amine in 175 mL DMF and the mixture was stirred for 2 h at 100° C. The reaction mixture was poured onto approx. 1 kg of ice water and stirred overnight. The precipitated product was suction filtered, washed with 100 mL water and dried at 45° C. in the CAD. The residue was stirred with 150 mL DIPE and suction filtered. The solid product was washed with 50 mL DIPE. After drying in the CAD at 35° C., 21.6 g of the desired product were obtained.

Yield: 21.6 g (84% of theoretical)
ESI-MS: m/z=366 (M+H)$^+$
R$_t$(HPLC)=2.12 min (Method C)

Step 6: 7-methoxy-3-piperidin-4-yl-1,3,4,5-tetrahydro-1,3-benzodiazepin-2-one

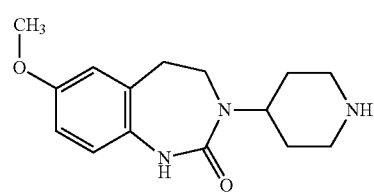 [SMILES: COc1ccc2c(c1)CCN(C1CCNCC1)C(=O)N2]

A mixture of 21.6 g (59.2 mmol) 3-(1-benzyl-piperidin-4-yl)-7-methoxy-1,3,4,5-tetrahydro-1,3-benzodiazepin-2-one and 2.5 g palladium on charcoal (10%) in 300 mL methanol was hydrogenated in a 3 bar hydrogen atmosphere at 50° C. until the reaction was complete. The catalyst was removed by suction filtering and the mother liquor was concentrated by rotary evaporation. The residue was triturated with 150 mL DIPE, suction filtered, washed with 100 mL DIPE and dried at 40° C. in the CAD. 13.2 g of the desired product was obtained.

Yield: 13.2 g (81% of theoretical)
ESI-MS: m/z=276 (M+H)$^+$
R$_t$(HPLC)=0.73 min (Method A)

Intermediate 4

3-piperidin-4-yl-1,3-dihydroimidazo[4,5-c]quinolin-2-one

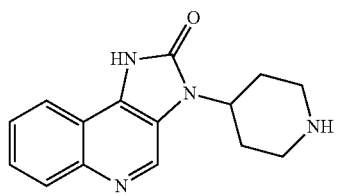 [SMILES: O=c1[nH]c2c3ccccc3ncc2n1C1CCNCC1]

Step 1: 3-bromoquinoline-1-oxide

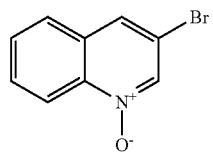 [SMILES: [O-][n+]1cc(Br)cc2ccccc21]

A solution of 72% 3-chloroperbenzoic acid (97.8 g (0.408 mol) dissolved in 1000 mL DCM, dried on sodium sulphate and filtered off) was added dropwise to a solution of 85.0 g (0.409 mol) 3-bromoquinoline in 100 mL DCM which had been cooled to 5° C. Care was taken to ensure that the temperature of the reaction mixture did not exceed 10° C. After the addition had ended the mixture was stirred for 5 h, then a solution of 72% 3-chloroperbenzoic acid (25.0 g (0.104 mol) dissolved in 200 mL DCM, dried on sodium sulphate and filtered off) was again added dropwise and the mixture was stirred overnight at RT. Saturated aqueous sodium carbonate solution was added, the phases were separated and the organic phase was dried on sodium sulphate. The solution was filtered through activated charcoal and then evaporated down i. vac.

Yield: 224 g (99% of theoretical)
ESI-MS: m/z=223/225 (Br)
$R_f$=0.15 (silica gel, PE/EtOAc=2:1)

Step 2: 3-bromo-4-nitroquinoline-1-oxide

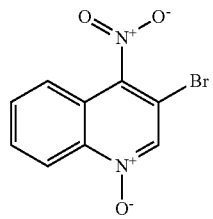 [SMILES: O=[N+]([O-])c1c(Br)c[n+]([O-])c2ccccc12]

A solution of 190 g (0.848 mol) 3-bromoquinoline-1-oxide in 500 mL concentrated sulphuric acid was heated to 90° C. Then 120 g (1.19 mol) potassium nitrate was added in small batches such that the temperature of the reaction did not exceed 95° C. The mixture was stirred for 3 h at 90° C., left to cool to RT and the mixture was poured onto ice. The precipitated product was filtered off and the filter cake was washed with water. The residue was dissolved in DCM and washed with saturated, aqueous sodium hydrogen carbonate solution until the solution reacted in alkaline manner. The phases were separated and the aqueous phase was extracted with DCM. The combined organic phases were dried on sodium sulphate and evaporated down i. vac. After comminution of the residue and exhaustive drying i. vac. The product was obtained as a yellow solid.

Yield: 104 g (46% of theoretical)
ESI-MS: m/z=268/270 (M+H)$^+$ (Br)
$R_f$=0.77 (silica gel, EtOAc)

Step 3 (1-benzylpiperidin-4-yl)-(4-nitro-1-oxyquinolin-3-yl)-amine

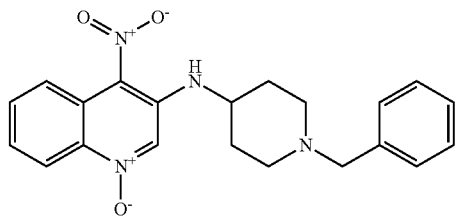 [SMILES: O=[N+]([O-])c1c(NC2CCN(Cc3ccccc3)CC2)c[n+]([O-])c2ccccc12]

104 g (0.387 mol) 3-bromo-4-nitroquinoline-1-oxide were added to 320 mL (1.54 mol) 4-amino-1-benzylpiperidine. Then 500 mL THF were added and the mixture was heated until the substances were fully dissolved. Then it was stirred for 3 h at 70° C. and the reaction mixture was then evaporated down i. vac. The residue obtained was dissolved in 2.5 L DCM and washed with saturated aqueous sodium hydrogen carbonate solution. The aqueous phase was extracted with 300 mL DCM. Then the organic phases were combined, dried on sodium sulphate and evaporated down i. vac. The residue was dissolved in 250 mL methanol. The product precipitated as a solid was suction filtered and dried i. vac.

Yield: 104 g (71% of theoretical)
ESI-MS: m/z=379 (M+H)$^+$
$R_f$=0.75 (silica gel, EtOAc)

Step 4 $N^3$-(1-benzylpiperidin-4-yl)quinoline-3,4-diamine

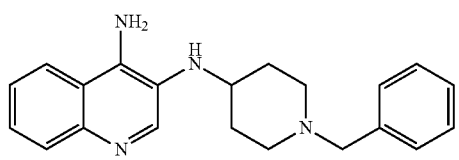 [SMILES: Nc1c(NC2CCN(Cc3ccccc3)CC2)cnc2ccccc12]

12.0 g rhodium charcoal (5%, moistened with water) were added to 76.0 g (0.20 mol) (1-benzylpiperidin-4-yl)-(4-nitro-1-oxyquinolin-3-yl)-amine in 1.0 L THF. The reaction was shaken for 4.5 h under a hydrogen atmosphere (50 psi) at RT. The catalyst was filtered off and the solvent was eliminated i. vac. Because of its proneness to oxidation the crude product was used immediately for the next step.

Yield: 66.0 g $R_f$=0.30 (silica gel, DCM/MeOH/Cyc/NH$_4$OH=70:15:15:2)

Step 5 3-(1-benzylpiperidin-4-yl)-1,3-dihydroimidazo[4,5-c]quinolin-2-one

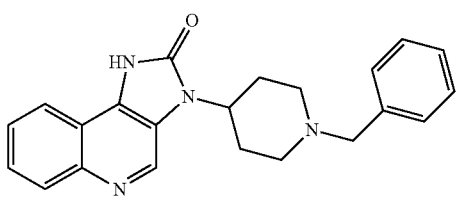 [SMILES: O=c1[nH]c2c3ccccc3ncc2n1C1CCN(Cc2ccccc2)CC1]

22.6 g (139 mmol) 1,1'-carbonyldiimidazole were added to 9.00 g (27.1 mmol) N$^3$-(1-benzylpiperidin-4-yl)-quinoline-3,4-diamine in 100 mL DMF. The mixture was heated to 100° C. and stirred for 1.5 h. After the reaction mixture had cooled it was poured onto 300 mL water. The precipitated solid was filtered off, washed with water and dried i. vac. At 30° C. The residue was triturated with diethyl ether, suction filtered and the solid product was dried i. vac.

Yield: 7.42 g (77% of theoretical)

ESI-MS: m/z=359 (M+H)$^+$

R$_t$(HPLC)=1.57 min (Method C)

Step 6 3-piperidin-4-yl-1,3-dihydroimidazo[4,5-c]quinolin-2-one

A mixture of 44.0 g (0.123 mol) 3-(1-benzylpiperidin-4-yl)-1,3-dihydroimidazo[4,5-c]quinolin-2-one and 10.0 g palladium on charcoal (Pd/C 10%) in 500 mL methanol was hydrogenated for 16 h at 50° C. in a hydrogen atmosphere of 50 psi. After filtration of the reaction mixture the solvent was eliminated in vacuo. Adding isopropanol caused the product to be precipitated out. This was filtered off and then dried in vacuo.

Yield: 31.2 g (95% of theoretical)

ESI-MS: m/z=269 (M+H)$^+$ $R_f$=0.20 (silica gel, DCM/MeOH/Cyc/NH$_4$OH=70:15:15:2)

Intermediate 5

6-chloropyrimidine-4-carboxylic Acid Chloride

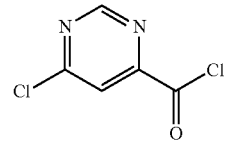

Step 1: 6-hydroxypyrimidine-4-carboxylic Acid

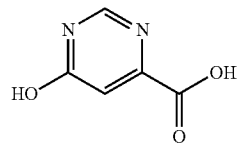

63.5 g (287 mmol) sodium diethyl-oxalacetate and 30.2 g (287 mmol) formamidine acetate were added to 24.1 g (597 mmol) NaOH in 3.6 L water. The mixture was stirred overnight at RT. Then activated charcoal was added and the mixture was refluxed for 1 h. It was filtered hot and after cooling acidified with aqueous HCl. The solution was concentrated to dryness by rotary evaporation. The residue contained the desired product and was used in the next step without further purification.

Yield: 83.0 g

Step 2: 6-chloropyrimidine-4-carboxylic Acid Chloride

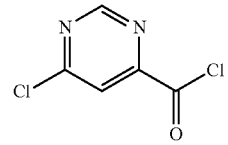

50 g (0.35 mol) 6-hydroxypyrimidine-4-carboxylic acid was taken and 500 mL phosphorus oxychloride was added. Then 150 g (0.720 mol) phosphorus pentachloride was added batchwise with stirring. The reaction mixture was refluxed for 5 h. The phosphorus oxychloride was distilled off and the residue was purified by vacuum distillation through a column.

Yield: 52 (83% of theoretical)

ESI-MS: m/z=176/178/180 (M)$^+$ (2 Cl)

Intermediate 6

4-methyl-3H-benzoxazol-2-one

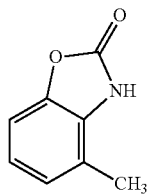

25.0 g (200 mmol) 2-amino-m-cresol and 70.4 mL (400 mmol) DIPEA were placed in 1.0 L DCM and cooled to 0° C. To this a solution of 38.0 g (227 mmol) CDI was added dropwise over 30 min. The mixture was stirred for 30 min at 0° C., then stirred overnight at RT. After evaporation of the reaction mixture i. vac. down to half the volume, the aqueous phase was washed with water (2×250 mL), 1M aqueous potassium hydrogen sulphate solution (1×250 mL) and again water (1×250 mL). The organic phase was evaporated down i. vac. The crude product left as a solid was triturated with a mixture of diethyl ether and PE, the precipitated solid was suction filtered, washed with PE and dried i. vac.

Yield: 25.0 g (86% of theoretical)

ESI-MS: m/z=150 (M+H)$^+$ $R_t$(HPLC)=2.67 min (Method C)

Intermediate 7

6-(6-chloropyrimidine-4-carbonyl)-4-methyl-3H-benzoxazol-2-one

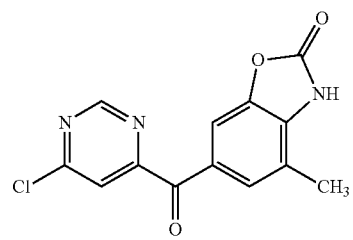 [SMILES: Cc1cc(C(=O)c2cc(Cl)ncn2)cc2oc(=O)[nH]c12]

A well stirred mixture of 2.34 g (13.2 mmol) 6-chloropyrimidine-4-carboxylic acid chloride, 8.00 g (60.0 mmol) aluminium trichloride and 1.79 g (12.0 mmol) 4-methyl-3H-benzoxazol-2-one was heated to 130° C. for 1.5 h. After cooling to RT the mixture was decomposed with ice water, then extracted with ethyl acetate, the organic phase was dried on sodium sulphate and evaporated down i. vac. The crude product left as a solid was triturated with diethyl ether, suction filtered and dried in the air.

Yield: 2.00 g (52% of theoretical)

ESI-MS: m/z=290/292 (M+H)$^+$ (Cl)

$R_t$(HPLC)=3.17 min (Method C)

Intermediate 8

6-(6-chloropyrimidine-4-carbonyl)-3,4-dimethyl-3H-benzoxazol-2-one

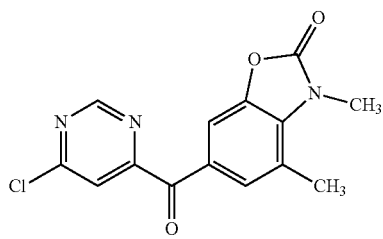 [SMILES: Cc1cc(C(=O)c2cc(Cl)ncn2)cc2oc(=O)n(C)c12]

0.35 g (8.0 mmol) sodium hydride (55%, suspension in mineral oil) were added to 2.2 g (7.6 mmol) of 6-(6-chloropyrimidine-4-carbonyl)-4-methyl-3H-benzoxazol-2-one in 10 mL N,N'-dimethylformamide. The reaction mixture was stirred for 30 min at RT. Then 0.95 mL (15.0 mmol) iodomethane were added and the mixture was stirred for 1 h at RT. The reaction mixture was combined with ice water, the aqueous phase was extracted several times with EtOAc. The combined organic phases were dried on sodium sulphate, filtered and concentrated to dryness by rotary evaporation. The residue was triturated with diethyl ether, suction filtered and dried.

Yield: 1.6 g (69% of theoretical)

ESI-MS: m/z=304/306 (Cl) (M+H)$^+$ $R_t$(HPLC) 3.55 min (Method C)

Intermediate 9

(6-chloro-pyrimidin-4-yl)-(3,4-dichloro-phenyl)-methanone

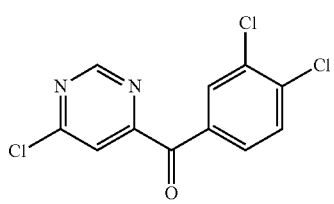 [SMILES: O=C(c1ccc(Cl)c(Cl)c1)c1cc(Cl)ncn1]

3.00 g (17.0 mmol) 6-chloro-pyrimidine-4-carboxylic acid chloride, 11.3 g (84.8 mmol) aluminium trichloride and 1.80 mL (16.0 mmol) o-dichlorobenzene were heated for 1.5 h to 130° C. After cooling to RT the mixture was mixed with ice water, then extracted with EtOAc, the organic phase was dried on magnesium sulphate and evaporated down i. vac. The residue was triturated with DIPE, suction filtered and dried.

Yield: 2.40 g (49% of theoretical)

EI-MS: m/z=286/288/290/292 (3×Cl) (M$^+$)

$R_f$: 0.76 (silica gel, PE/EtOAc=2/1)

Intermediate 10

(6-chloro-pyrimidin-4-yl)-(3,4-dimethyl-phenyl)-methanone

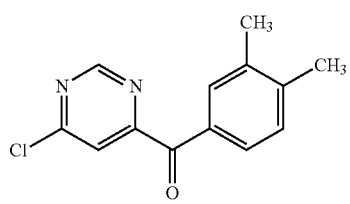 [SMILES: Cc1ccc(C(=O)c2cc(Cl)ncn2)cc1C]

1.0 g (5.7 mmol) 6-chloro-pyrimidine-4-carboxylic acid chloride were dissolved in 10 mL DCM, added to 3.7 g (28 mmol) aluminium trichloride in 10 mL DCM and the mixture was stirred for 30 min at RT. Then 0.70 mL (5.8 mmol) xylene (dissolved in 10 mL DCM) were slowly added dropwise to the reaction mixture and this was stirred for 14 h at RT. It was then combined with DCM and 15% potassium carbonate solution and the aqueous phase was extracted several times with DCM. The organic phases were combined, dried on magnesium sulphate and evaporated down i. vac.

Yield: 0.88 g (63% of theoretical)
ESI-MS: m/z=247/249 (Cl) (M+H)$^+$
$R_f$: 0.71 (silica gel, PE/EtOAc=2/1)

Intermediate 11

(6-chloro-pyrimidin-4-yl)-(3,4-diethyl-phenyl)-methanone

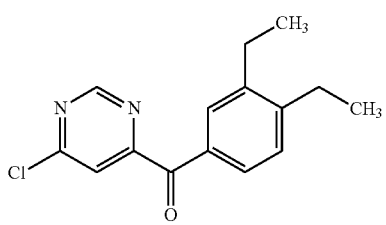 [SMILES: CCc1ccc(C(=O)c2cc(Cl)ncn2)cc1CC]

1.0 g (5.7 mmol) 6-chloro-pyrimidine-4-carboxylic acid chloride were dissolved in 10 mL DCM, added to 3.7 g (28 mmol) aluminium trichloride in 10 mL DCM and the mixture was stirred for 30 min at RT. Then 0.93 mL (5.5 mmol) 1,2-diethylbenzene (dissolved in 10 mL DCM) were slowly added dropwise to the reaction mixture and this was stirred for 14 h at RT. It was then combined with DCM and 15% potassium carbonate solution and the aqueous phase was extracted several times with DCM. The organic phases were combined, dried on magnesium sulphate and evaporated down i. vac.

Yield: 1.4 g (90% of theoretical)
ESI-MS: m/z=275 (M+H)$^+$
$R_f$: 0.77 (silica gel, PE/EtOAc=2/1)

Intermediate 12

(6-chloro-pyrimidin-4-yl)-(3,4,5-trimethyl-phenyl)-methanone

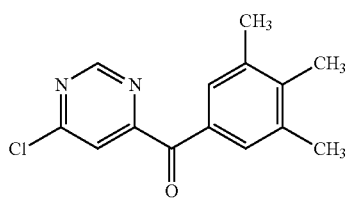 [SMILES: Cc1cc(C(=O)c2cc(Cl)ncn2)cc(C)c1C]

1.0 g (5.7 mmol) 6-chloro-pyrimidine-4-carboxylic acid chloride were dissolved in 10 mL DCM, added to 3.7 g (28 mmol) aluminium trichloride in 10 mL DCM and the mixture was stirred for 30 min at RT. Then 0.70 g (5.8 mmol) 1,2,3-trimethylbenzene (dissolved in 10 mL DCM) were slowly added dropwise to the reaction mixture and this was stirred for 14 h at RT. It was then combined with DCM and 15% potassium carbonate solution and the aqueous phase was extracted several times with DCM. The organic phases were combined, dried on magnesium sulphate and evaporated down i. vac.

Yield: 0.90 g (61% of theoretical)
ESI-MS: m/z=261/263 (Cl) (M+H)$^+$
$R_f$: 0.71 (silica gel, PE/EtOAc=2/1)

Intermediate 13

3-{1-[6-(4-benzyloxy-3,5-dimethyl-benzoyl)-pyrimidin-4-yl]-piperidin-4-yl}-7-methoxy-1,3,4,5-tetrahydro-benzo[d][1,3]diazepin-2-one

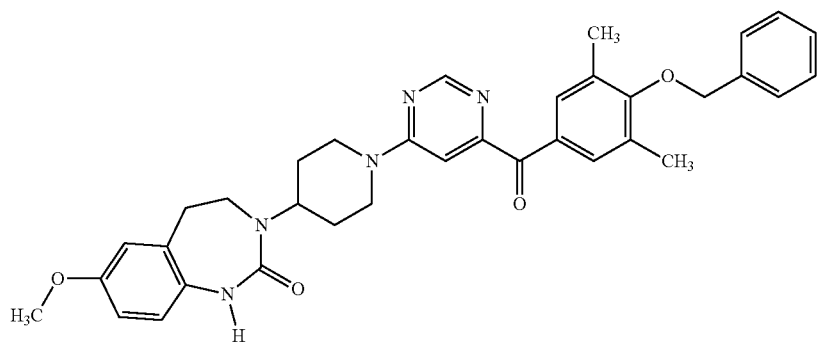 [SMILES: COc1ccc2c(c1)CCN(C1CCN(c3cc(C(=O)c4cc(C)c(OCc5ccccc5)c(C)c4)ncn3)CC1)C(=O)N2]

Step 1: (4-benzyloxy-3,5-dimethyl-phenyl)-(6-chloro-pyrimidin-4-yl)-methanone

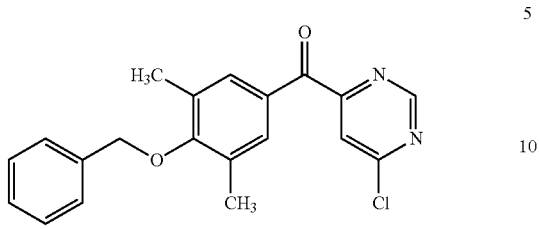

150 mg (1.00 mmol) 4,6-dichloropyrimidine, 367 mg (1.50 mmol) 4-benzyloxy-3,5-dimethylbenzaldehyde and 166 mg (0.600 mmol) 1,3-dimethyl-3H-benzimidazol-1-ium-iodide (Chem. Pharm. Bull. 1990, 1147-52) in 10.0 mL THF were stirred at RT. Then 73.0 mg (1.51 mmol) sodium hydride (50% in mineral oil) were added and the reaction mixture was refluxed for 2.5 h. The reaction mixture was added to ice water and extracted with DCM. The organic phase was dried and evaporated down.

Yield: 100 mg (28% of theoretical)
ESI-MS: m/z=353/55 (Cl) (M+H)$^+$

Step 2: 3-{1-[6-(4-benzyloxy-3,5-dimethyl-benzoyl)-pyrimidin-4-yl]-piperidin-4-yl}-7-methoxy-1,3,4,5-tetrahydro-benzo[d][1,3]diazepin-2-one

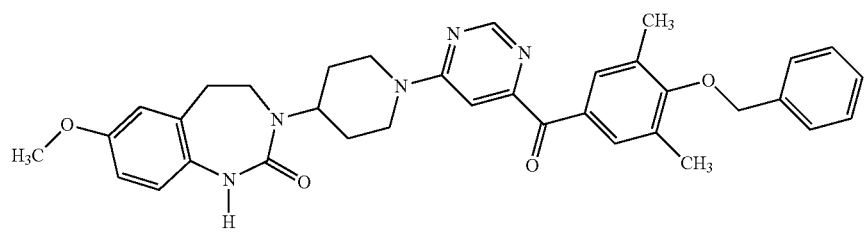 [SMILES: COc1ccc2c(c1)CCN(C1CCN(c3cc(C(=O)c4cc(C)c(OCc5ccccc5)c(C)c4)ncn3)CC1)C(=O)N2]

lk200 mg (0.730 mmol) 7-methoxy-3-piperidin-4-yl-1,3,4,5-tetrahydro-1,3-benzodiazepin-2-one, 240 mg (0.680 mmol) (4-benzyloxy-3,5-dimethyl-phenyl)-(6-chloro-pyrimidin-4-yl)-methanone and 0.400 mL (2.30 mmol) DIPEA were combined in 2.0 mL DMF and stirred for 3 h at RT. The mixture was added to ice water, the precipitate was suction filtered and dried.

Yield: 400 mg (89% of theoretical)
Purity: 90%
ESI-MS: m/z=592 (M+H)$^+$
$R_t$(HPLC): 5.0 min (method C)

Intermediate 14

6-chloro-pyrimidine-4-carboxylic Acid methoxy-methyl-amide

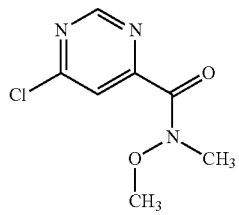

20.7 mL (0.120 mol) DIPEA were added at 0° C. to 10.7 g (54.4 mmol) 6-chloropyrimidine-4-carboxylic acid chloride and 5.50 g (56.4 mmol) N,O-dimethylhydroxylamine in 150 mL DCM and stirred for 1 h at 0° C. and 1 h at RT. The mixture was diluted with DCM and washed with water. The organic phase was dried on sodium sulphate, filtered and evaporated down.

Yield: 11.8 g (100% of theoretical)
Purity: 93%

Intermediate 15

6-(4-chloro-pyridin-2-carbonyl)-4-methyl-3H-benzoxazol-2-one

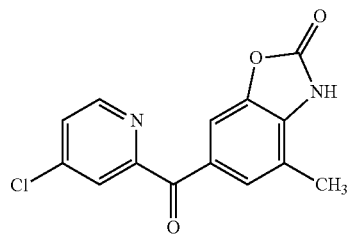 [SMILES: Cc1cc(C(=O)c2cc(Cl)ccn2)cc2oc(=O)[nH]c12]

2.80 mL (38.1 mmol) thionyl chloride and 0.50 mL DMF were added to 2.00 g (12.7 mmol) 4-chloropicolinic acid in 30 mL DCM and the mixture was refluxed for 2 h. The reaction mixture was evaporated to dryness and coevaporated twice with toluene. The residue was mixed with 8.00 g (60.0 mmol) aluminium trichloride and 1.79 g (12.0 mmol) 4-methyl-3H-benzoxazol-2-one and stirred at 130° C. The mixture was decomposed with ice water and extracted twice with EtOAc. The organic phases were combined, dried on magnesium sulphate, filtered and evaporated down i. vac. The residue was triturated with DiPE and suction filtered. For further purification the residue was purified by preparative HPLC-MS. The fractions containing the product were combined and freeze-dried.

Yield: 30 mg (1% of theoretical)
ESI-MS: m/z=289/291 (Cl) (M+H)$^+$
m/z=287/289 (Cl) (M−H)$^-$
$R_f$: 0.17 (silica gel, PE/EtOAc=2/1)

Intermediate 16

5-phenyl-2-piperidin-4-yl-2,4-dihydro-[1,2,4]triazol-3-one

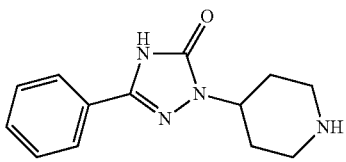 [SMILES: O=c1[nH]c(-c2ccccc2)nn1C1CCNCC1]

This compound and its precursors were synthesised analogously to US2001/36946 A1 (US2001-789391).

$R_f$: 0.28 (silica gel, DCM/Cyc/MeOH/NH$_4$OH=70/15/15/2)

Intermediate 17

1-{1-[6-(4-benzyloxy-3,5-dimethyl-benzoyl)-pyrimidin-4-yl]-piperidin-4-yl}-1,3-dihydro-imidazo[4,5-b]pyridin-2-one

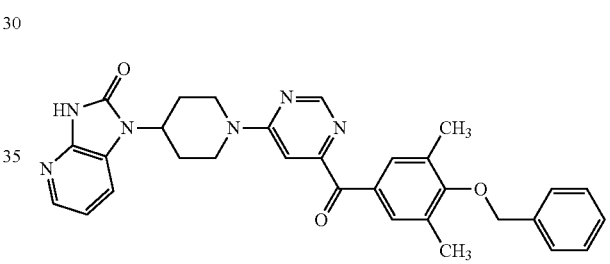

Step 1: 2-benzyloxy-5-bromo-1,3-dimethyl-benzene

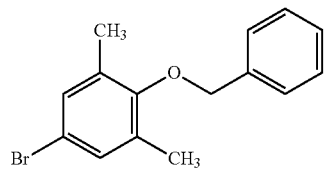 [SMILES: Cc1cc(Br)cc(C)c1OCc1ccccc1]

11.7 mL (96.5 mmol) benzylbromide were added dropwise to 20 g (96.5 mmol) 2,6-dimethyl-4-bromophenol and 16.5 g (118 mmol) potassium carbonate in 300 mL acetone and stirred overnight at RT. The precipitate formed was suction filtered, washed with acetone and the filtrate was evaporated down. The residue was dissolved in DCM, filtered through Alox and washed with DCM. The filtrate was evaporated down.

Yield: 28.5 g (99% of theoretical)
Purity: 98%
$R_t$(HPLC): 1.43 min (method E)

Step 2: (4-benzyloxy-3,5-dimethyl-phenyl)-(6-chloro-pyrimidin-4-yl)-methanone

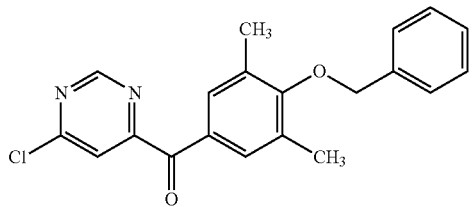 [SMILES: Cc1cc(C(=O)c2cc(Cl)ncn2)cc(C)c1OCc1ccccc1]

Under an argon atmosphere 2.8 mL (4.5 mmol) of a 1.6 M n-butyllithium solution were added to a mixture of 1.2 g (4.0 mmol) 2-benzyloxy-5-bromo-1,3-dimethyl-benzene in mL THF cooled to −75° C. and the mixture was stirred for 1 h at −75° C. Then 0.96 g (4.3 mmol) 6-chloro-pyrimidine-4-carboxylic acidmethoxy-methyl-amide, dissolved in 10 mL THF, were added dropwise. After another 30 min stirring at −75° C. the reaction mixture was slowly heated to 0° C. The mixture was combined with saturated sodium hydrogen carbonate solution and extracted with diethyl ether. The organic phase was dried and evaporated down. The residue was purified by flash chromatography.

Yield: 0.43 g (29% of theoretical)

Step 3: 1-{1-[6-(4-benzyloxy-3,5-dimethyl-benzoyl)-pyrimidin-4-yl]-piperidin-4-yl}-1,3-dihydro-imidazo[4,5-b]pyridin-2-one

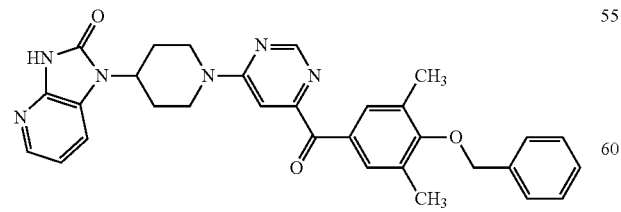

170 mg (0.779 mmol) 1-piperidin-4-yl-1,3-dihydro-imidazo[4,5-b]pyridin-2-one, 270 mg (0.727 mmol) (4-benzyloxy-3,5-dimethyl-phenyl)-(6-chloro-pyrimidin-4-yl)-methanone and 0.200 mL (1.42 mmol) TEA were combined in 2.0 mL DMF and stirred overnight at RT. The reaction mixture was stirred into ice water, the precipitate was suction filtered and dried.

Yield: 390 mg (95% of theoretical)

Intermediate 18

7-methoxy-3-(1-{6-[7-methyl-1-(2-trimethylsilanyl-ethoxymethyl)-1H-indazole-5-carbonyl]-pyrimidin-4-yl}-piperidin-4-yl)-1,3,4,5-tetrahydro-benzo[d][1,3]diazepin-2-one

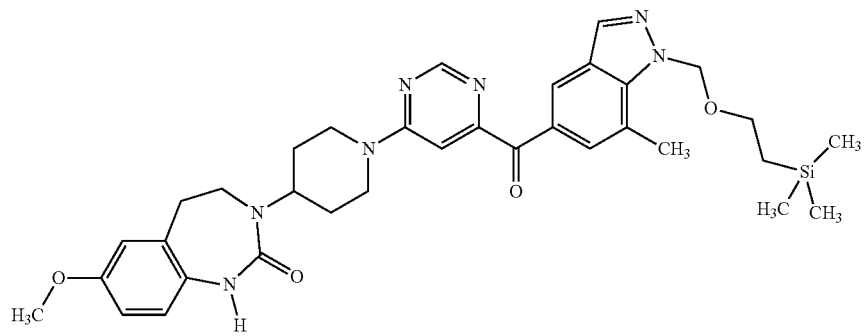

Step 1: 4-bromo-2,6-dimethylphenyldiazonium tetrafluoroborate

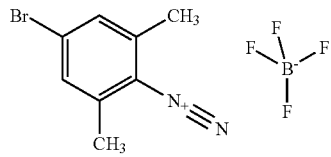

21.2 g (0.104 mol) 4-bromo-2,6-dimethylaniline in 58.0 mL (0.444 mol) tetrafluoroboric acid (48% in water) were diluted with water to form a stirrable suspension. 7.18 g (0.104 mol) sodium nitrite, dissolved in water, were slowly added dropwise to the reaction mixture which was cooled to 0° C. After the addition had ended the mixture was stirred for 1 h at RT. The product precipitated as a solid was suction filtered, washed three times with diethyl ether and dried.

Yield: 26.5 g (85% of theoretical)

Step 2: 5-bromo-7-methyl-1H-indazole

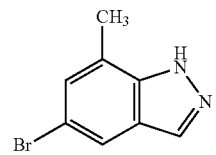

39.0 g (0.130 mol) 4-bromo-2,6-dimethylphenyldiazonium-tetrafluoroborate were added batchwise to 25.5 g (0.260 mol) potassium acetate and 1.72 g (6.50 mmol) 18-crown-6 in 700 mL chloroform with mechanical stirring, stirred for a further 3 h at RT and then left to stand overnight at RT. The precipitated product was suction filtered and washed with 100 mL chloroform. The precipitate was stirred with 500 mL water and extracted with 800 mL DCM. The organic phase was dried and evaporated down i. vac. The remaining filtrate was washed with 1 L water, dried on sodium sulphate and evaporated down. The residue was combined with DIPE, the precipitated substance was suction filtered, washed again with DIPE and dried. The solids obtained were combined.

Yield: 19.8 g (72% of theoretical)
ESI-MS: m/z=209/211 (Br) (M−H)⁻
$R_f$: 0.5 (silica gel, DCM/MeOH=90/10)

Step 3: 5-bromo-7-methyl-1-(2-trimethylsilanyl-ethoxymethyl)-1H-indazole

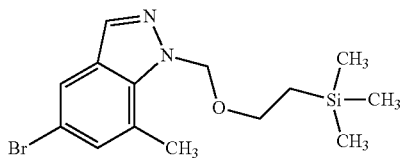

1.95 mL (11.0 mmol) (2-chloromethoxy-ethyl)-trimethylsilane were added to 2.11 g (10.0 mmol) 5-bromo-7-methyl-1H-indazole and 1.80 mL (12.3 mmol) N-methyldicyclohexylamine in 50 mL THF and stirred overnight at RT. The precipitate formed was filtered off and the filtrate was evaporated down. The residue was purified by flash chromatography.

Yield: 0.78 g (23% of theoretical)
ESI-MS: m/z=341/343 (Br) (M+H)⁺
$R_t$(HPLC): 1.6 min (method E)

Step 4: (6-chloro-pyrimidin-4-yl)-[7-methyl-1-(2-trimethylsilanyl-ethoxymethyl)-1H-indazol-5-yl]-methanone

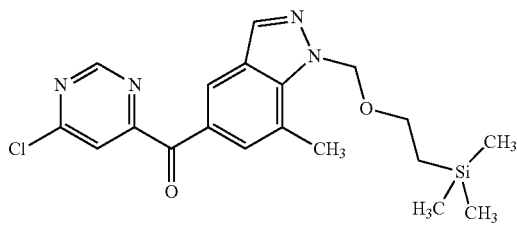 [SMILES: Cc1cc(C(=O)c2cc(Cl)ncn2)cc2cnn(COCC[Si](C)(C)C)c12]

Under an argon atmosphere 0.34 g (1.00 mmol) 5-bromo-7-methyl-1-(2-trimethylsilanyl-ethoxymethyl)-1H-indazole in 10 mL THF were cooled to −75° C., mixed with 0.70 mL (1.1 mmol) of a 1.6 molar n-butyllithium solution and stirred for 1 h at −75° C. Then 0.25 g (1.1 mmol) 6-chloro-pyrimidine-4-carboxylic acidmethoxy-methyl-amide, dissolved in a little THF, were added dropwise. The cooling bath was removed and the mixture was heated to 0° C. and stirred for a further hour in the ice bath. The mixture was stirred with saturated sodium hydrogen carbonate solution, extracted with EtOAc, the organic phase was dried and evaporated down. The residue was purified by flash chromatography.

Yield: 58 mg (14% of theoretical)
$R_t$(HPLC): 1.4 min (method E)

Step 5: 7-methoxy-3-(1-{6-[7-methyl-1-(2-trimethyl-silanyl-ethoxymethyl)-1H-indazole-5-carbonyl]-pyrimidin-4-yl}-piperidin-4-yl)-1,3,4,5-tetrahydro-benzo[d][1,3]diazepin-2-one

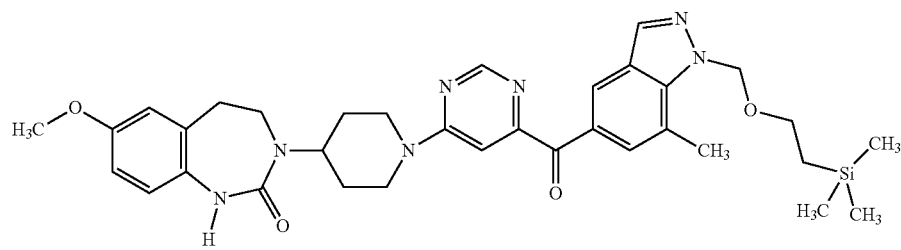

36 mg (0.13 mmol) 7-methoxy-3-piperidin-4-yl-1,3,4,5-tetrahydro-1,3-benzodiazepin-2-one, 50 mg (0.12 mmol) (6-chloro-pyrimidin-4-yl)-[7-methyl-1-(2-trimethylsilanyl-ethoxymethyl)-1 H-indazol-5-yl]-methanone and 30 µL (0.21 mmol) TEA were combined in 0.5 mL DMF and stirred overnight at RT. The reaction mixture was mixed with ice water, the product precipitated as a solid was filtered off and dried.

Yield: 71 mg (84% of theoretical)
ESI-MS: m/z=642 (M+H)⁺
$R_t$(HPLC): 1.78 min (method B)

Intermediate 19

6-(6-chloro-pyrimidine-4-carbonyl)-3-methyl-3H-benzoxazol-2-one

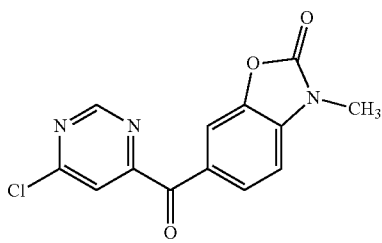 [SMILES: Cn1c(=O)oc2cc(C(=O)c3cc(Cl)ncn3)ccc21]

Step 1: 6-(6-chloro-pyrimidine-4-carbonyl)-3H-benzoxazol-2-one

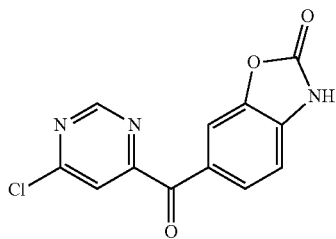 [SMILES: O=C(c1ccc2[nH]c(=O)oc2c1)c1cc(Cl)ncn1]

3.93 g (22.2 mmol) 6-chloropyrimidine-4-carboxylic acid chloride, 3.00 g (22.2 mmol) 2-benzoxazolinone and 14.8 g (111 mmol) aluminium trichloride were combined and heated for 3 h to 130° C. Then the mixture was combined with ice water and EtOAc, the solid was suction filtered and the phases were separated. The aqueous phase was extracted twice with EtOAc, the organic phases were combined, dried and evaporated down. The residue was triturated in DIPE, suction filtered and dried.

Yield: 1.4 g (23% of theoretical)
ESI-MS: m/z=274/276 (M–H)⁻
R$_t$(HPLC): 1.17 min (method B)

Step 2: 6-(6-chloro-pyrimidine-4-carbonyl)-3-methyl-3H-benzoxazol-2-one

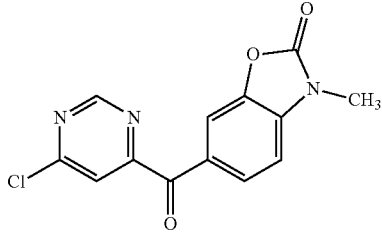 [SMILES: Cn1c(=O)oc2cc(C(=O)c3cc(Cl)ncn3)ccc21]

135 mg (3.10 mmol) sodium hydride (55%, suspension in mineral oil) were added to 800 mg (2.90 mmol) 6-(6-chloro-pyrimidine-4-carbonyl)-3H-benzoxazol-2-one in 10 mL DMF and the mixture was stirred for 30 min at RT. Then 0.368 mL (5.80 mmol) iodomethane were added and the mixture was stirred for a further hour at RT. The mixture was mixed with ice water and extracted twice with EtOAc. The organic phases were combined, washed with water, dried and evaporated down. The residue was triturated with DIPE, suction filtered and dried.

Yield: 600 mg (71% of theoretical)
ESI-MS: m/z=290/292 (M+H)⁺
R$_t$(HPLC): 1.33 min (method B)

Intermediate 20

5-(6-chloro-pyrimidine-4-carbonyl)-1,3-dihydro-indol-2-one

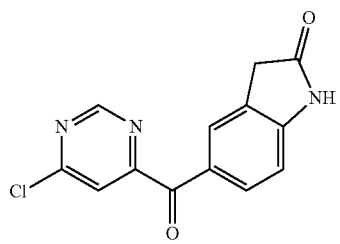 [SMILES: O=C1Cc2cc(C(=O)c3cc(Cl)ncn3)ccc2N1]

3.93 g (22.2 mmol) 6-chloropyrimidine-4-carboxylic acid chloride, 2.96 g (22.2 mmol) 2-oxoindole and 14.8 g (111 mmol) aluminium trichloride were combined and heated for 3 h to 130° C. Then the mixture was mixed with ice water and extracted twice with EtOAc. The organic phases were combined, dried and evaporated down. The residue was triturated in DIPE, suction filtered, washed and dried.

Yield: 1.4 g (23% of theoretical)
ESI-MS: m/z=272/274 (M–H)⁻
R$_t$(HPLC): 1.12 min (method B)

Intermediate 21

6-(2-bromo-pyridine-4-carbonyl)-4-methyl-3H-benzoxazol-2-one

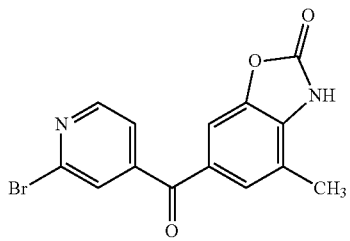

2.20 mL (30.0 mmol) thionyl chloride and 0.390 mL (4.80 mmol) DMF were added to 2.00 g (9.90 mmol) 2-bromopyridine-4-carboxylic acid in 30 mL DCM and refluxed for 2 h. The reaction mixture was evaporated to dryness and coevaporated twice with toluene. The residue was combined with 6.24 g (46.8 mmol) aluminium trichloride and 1.50 g (10.1 mmol) 4-methyl-3H-benzoxazol-2-one and the mixture obtained was stirred overnight at 110° C. and for 5 hours at 130° C. The mixture was decomposed with ice water and extracted twice with DCM. The organic phases were dried on magnesium sulphate, filtered and evaporated down i. vac. The residue was triturated with DIPE/MeOH and suction filtered. The product obtained is a mixture of the corresponding bromine and chlorine compound (40/60).

Yield: 1.0 g (~30% of theoretical)

Intermediate 22

7-chloro-3-piperidin-4-yl-1,3,4,5-tetrahydro-benzo[d][1,3]diazepin-2-one

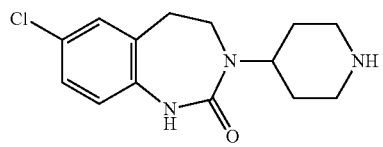 [SMILES: O=C1Nc2ccc(Cl)cc2CCN1C1CCNCC1]

801 mg (6.00 mmol) N-chlorosuccinimide were added to 1.23 g (5.00 mmol) 3-piperidin-4-yl-1,3,4,5-tetrahydro-benzo[d][1,3]diazepin-2-one in 10.0 mL carbon tetrachloride and the mixture was refluxed for 72 h. The solvent was eliminated i. vac. and the crude product was purified by flash chromatography. The fractions containing the product were concentrated by rotary evaporation and purified by preparative HPLC.

Yield: 420 mg (30% of theoretical)
ESI-MS: m/z=280/282 (Cl) (M+H)$^+$
$R_f$(HPLC): 1.96 min (method C)

Intermediate 23

6-(6-chloro-pyrimidine-4-carbonyl)-3-ethyl-4-methyl-3H-benzoxazol-2-one

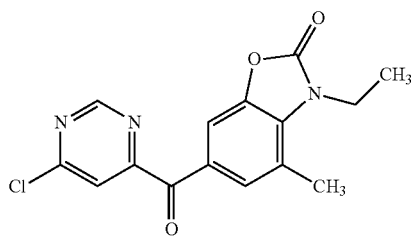 [SMILES: CCn1c(=O)oc2cc(C(=O)c3cc(Cl)ncn3)cc(C)c21]

44 mg (1.0 mmol) sodium hydride (55%, suspension in mineral oil) were added to 0.25 g (0.86 mmol) 6-(6-chloro-pyrimidine-4-carbonyl)-4-methyl-3H-benzoxazol-2-one in 2.0 mL DMF and the mixture was stirred for 30 min at RT. Then 98 µL (1.2 mmol) ethyl iodide were added and the mixture was stirred for 1 h at RT. The reaction mixture was diluted with ice water and extracted with EtOAc. The organic phase was washed with water, dried on sodium sulphate, filtered and evaporated down i. vac. The residue was purified by flash chromatography. The fractions containing the product were combined and evaporated down.

Yield: 110 mg (40% of theoretical)
$R_f$(HPLC): 3.83 min (method C)

Intermediate 24

6-(6-chloro-pyrimidine-4-carbonyl)-4-methyl-3H-benzothiazol-2-one

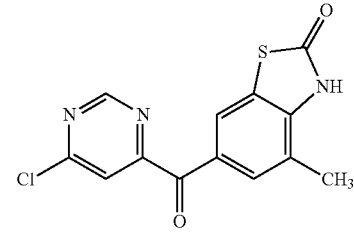

Step 1: 4-methyl-3H-benzothiazol-2-one

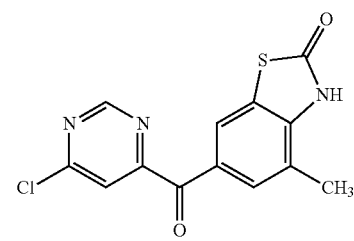

5.00 g (30.5 mmol) 2-amino-4-methylbenzothiazole in 15.0 mL formic acid, 6.10 mL glacial acetic acid and 112 mL conc. hydrochloric acid were cooled to −5° C. with stirring and slowly combined with a solution of 2.10 g (30.5 mmol) sodium nitrite in 5.0 mL water. The reaction mixture was stirred for 20 min at this temperature, then heated to RT and then refluxed overnight. The cooled mixture was then mixed with water and extracted several times with EtOAc. The combined organic phases were washed with saturated sodium chloride solution, dried on sodium sulphate, filtered and the filtrate was evaporated down.

Yield: 3.70 g (74% of theoretical)
ESI-MS: m/z=164 (M−H)$^-$
$R_f$(HPLC): 0.89 min (method B)

Step 2: 6-(6-chloro-pyrimidine-4-carbonyl)-4-methyl-3H-benzothiazol-2-one 1.93 g (10.0 mmol) 6-chloropyrimidine-4-carboxylic acid chloride, 1.80 g (10.9 mmol) 4-methyl-3H-benzothiazol-2-one and 7.33 g (55.0 mmol) aluminium trichloride were combined and heated to 130° C. for 3 h with stirring. The mixture was combined with ice water and EtOAc, the flakes formed were suction filtered and the phases were separated. The aqueous phase was extracted with EtOAc. The organic phases were combined, dried on sodium sulphate, filtered and the filtrate was evaporated down i. vac. The residue was triturated with DIPE, the precipitate was suction filtered and dried.

Yield: 1.10 g (33% of theoretical)

R$_t$(HPLC): 1.40 min (method B)

Intermediate 25

6-(2-chloro-pyridine-4-carbonyl)-3,4-dimethyl-3H-benzoxazol-2-one

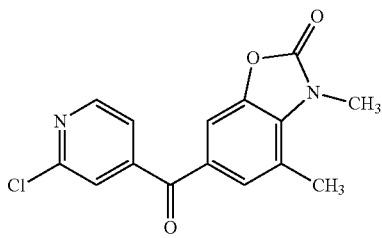 [SMILES: Cc1cc(C(=O)c2ccnc(Cl)c2)cc2oc(=O)n(C)c12]

Step 1: 6-(2-chloro-pyridine-4-carbonyl)-4-methyl-3H-benzoxazol-2-one

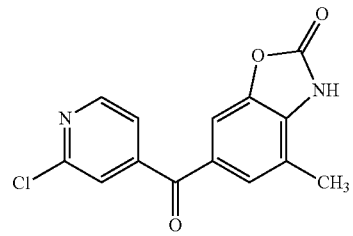 [SMILES: Cc1cc(C(=O)c2ccnc(Cl)c2)cc2oc(=O)[nH]c12]

2.80 mL (38.1 mmol) thionyl chloride and 0.50 mL DMF were added to 2.10 g (12.9 mmol) 2-chloroisonicotinic acid in 30.0 mL DCM and the mixture was refluxed for 2 h. The reaction mixture was evaporated to dryness and coevaporated twice with toluene. The residue was combined with 8.00 g (60.0 mmol) aluminium trichloride and 1.79 g (12.0 mmol) 4-methyl-3H-benzoxazol-2-one and stirred overnight at 130° C. The mixture was decomposed with ice water and extracted twice with EtOAc. The organic phases were combined, dried on magnesium sulphate, filtered and evaporated down i. vac. The residue was triturated with DIPE and isopropanol, suction filtered and dried.

Yield: 1.70 g (46% of theoretical)

ESI-MS: m/z=287/289 (Cl) (M−H)$^−$

R$_f$: 0.13 (silica gel, PE/EtOAc=2/1)

Step 2: 6-(2-chloro-pyridine-4-carbonyl)-3,4-dimethyl-3H-benzoxazol-2-one

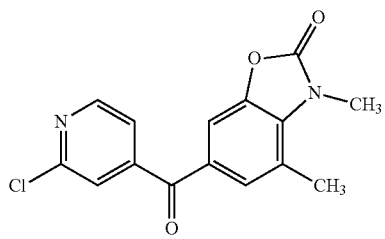

220 mg (1.94 mmol) potassium-tert-butoxide were added to 500 mg (1.73 mmol) 6-(2-chloro-pyridine-4-carbonyl)-4-methyl-3H-benzoxazol-2-one in 10.0 mL THF and the mixture was stirred for 30 min at RT. Then 0.220 mL (3.46 mmol) methyl iodide were added and the mixture was stirred overnight at RT. The reaction mixture was diluted with EtOAc and washed several times with saturated sodium chloride solution. The organic phase was dried on magnesium sulphate, filtered and evaporated down i. vac. The residue was triturated with DIPE and suction filtered.

Yield: 390 mg (74% of theoretical)

ESI-MS: m/z=303/5 (Cl) (M+H)$^+$

R$_t$(HPLC): 1.42 min (method B)

Intermediate 26

3-(3-fluoro-piperidin-4-yl)-7-methoxy-1,3,4,5-tetrahydro-benzo[d][1,3]diazepin-2-one

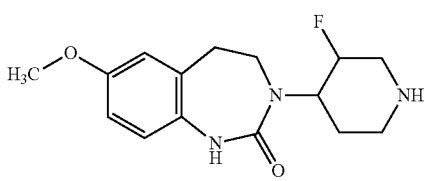 [SMILES: COc1ccc2c(c1)CCN(C1CCNCC1F)C(=O)N2]

Step 1: (5-methoxy-2-nitro-phenyl)-acetonitrile

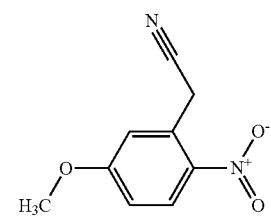

A solution of 110 g (0.653 mol) 4-(chloro-phenoxy)-acetonitrile and 100 g (0.653 mol) 1-methoxy-4-nitrobenzene in DMF were added dropwise to 161 g (1.44 mol) potassium-tert-butoxide in 1.50 L DMF within 1.5 h at −30° C. The reaction mixture was stirred for 30 min at −30° C., then poured into 2.0 L of a 2N aqueous hydrochloric acid solution and stirred for 1 h. The precipitate formed was suction filtered, washed with water and then dissolved in EtOAc. This solution was dried on sodium sulphate, filtered and the filtrate was evaporated down. The residue was added to EtOAc/PE=1/1 and cooled. The product precipitated as a solid was suction filtered, washed with DIPE and dried.

Yield: 55 g (44% of theoretical)
ESI-MS: m/z=191 (M−H)⁻
R$_f$: 0.4 (silica gel: EtOAc/PE=1/9)

Step 2: 2-(5-methoxy-2-nitro-phenyl)-ethylamine

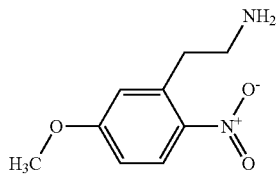

1.5 L of a 1 M borane solution in THF were slowly added dropwise at 10° C. to 110 g (0.572 mol) (5-methoxy-2-nitro-phenyl)-acetonitrile in 0.5 L THF and the mixture was stirred for 16 h at RT. The reaction mixture was combined at 0° C. with 250 ml MeOH and the mixture was stirred for 1 h at RT. Then 250 mL of a 2N aqueous hydrochloric acid solution were added and the excess THF was evaporated down. The aqueous phase was extracted with EtOAc, then made basic with saturated sodium carbonate solution and then extracted with EtOAc. The organic phase was washed with water and saturated NaCl solution, dried on sodium sulphate, filtered and the filtrate was evaporated down.

Yield: 67.0 g (60% of theoretical)
ESI-MS: m/z=197 (M+H)⁺
R$_f$: 0.3 (silica gel: MeOH/chloroform=1/9)

Step 3: tert-butyl 3-fluoro-4-[2-(5-methoxy-2-nitro-phenyl)-ethylamino]-piperidine-1-carboxylate

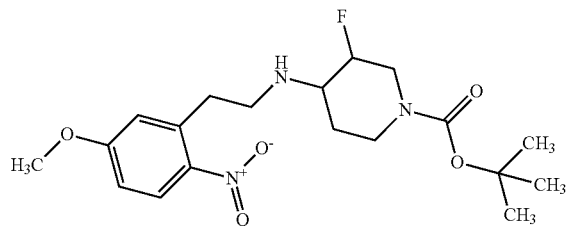 [SMILES: COc1ccc([N+](=O)[O-])c(CCNC2CCN(C(=O)OC(C)(C)C)CC2F)c1]

1.00 mL (17.7 mmol) acetic acid and 2.09 g (9.86 mmol) sodium triacetoxyborohydride were added at 0° C. to 1.50 g (7.65 mmol) 2-(5-methoxy-2-nitro-phenyl)-ethylamine and 1.80 g (8.29 mmol) tert-butyl 3-fluoro-4-oxo-piperidine-1-carboxylate in 25 mL DCM and then the mixture was stirred for 3 h at RT. The reaction mixture was combined at 0° C. with a saturated potassium carbonate solution and the aqueous phase was extracted several times with DCM. The combined organic phases were washed with water and saturated sodium chloride solution, dried on sodium sulphate, filtered and the filtrate was evaporated down. The residue was purified by flash chromatography.

Yield: 1.75 g (58% of theoretical)
R$_f$: 0.65 (silica gel: MeOH/chloroform=1/9)

Step 4: tert-butyl 4-[2-(2-amino-5-methoxy-phenyl)-ethylamino]-3-fluoro-piperidine-1-carboxylate

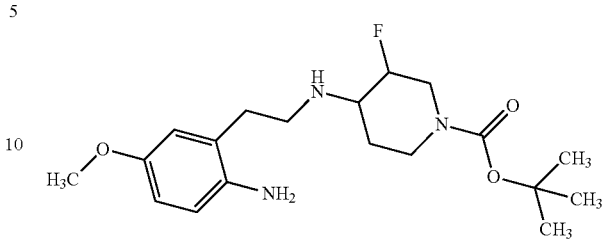

3.50 g (8.81 mmol) tert-butyl 3-fluoro-4-[2-(5-methoxy-2-nitro-phenyl)-ethylamino]-piperidine-1-carboxylate were stirred with 0.8 g palladium on charcoal (Pd/C 10%) and 17.5 mL (359 mmol) hydrazine hydrate in 50 mL EtOH for 16 h at RT. The catalyst was suction filtered through kieselguhr and the solution was concentrated by rotary evaporation.

Yield: 3 g (93% of theoretical)
R$_f$: 0.5 (silica gel: MeOH/chloroform 1/9)

Step 5: tert-butyl 3-fluoro-4-(7-methoxy-2-oxo-1,2,4,5-tetrahydro-benzo[d][1,3]diazepin-3-yl)-piperidine-1-carboxylate

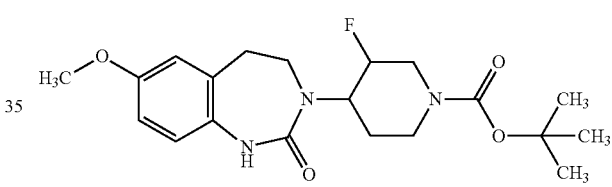

3.97 g (24.5 mmol) CDI were added to 3.00 g (8.16 mmol) tert-butyl 4-[2-(2-amino-5-methoxy-phenyl)-ethylamino]-3-fluoro-piperidine-1-carboxylate in 20 mL DMF and the mixture was refluxed for 2 h. The reaction mixture was cooled and mixed with ice water. The aqueous phase was extracted several times with EtOAc, the organic phases were combined, dried on sodium sulphate, filtered and the filtrate was evaporated down. The residue was purified by flash chromatography.

Yield: 2.10 g (65% of theoretical)
ESI-MS: m/z=394 (M+H)⁺
R$_f$: 0.65 (silica gel: MeOH/chloroform=1/9)

Step 6: 3-(3-fluoro-piperidin-4-yl)-7-methoxy-1,3,4,5-tetrahydro-benzo[d][1,3]diazepin-2-one

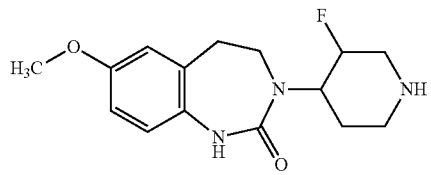 [SMILES: COc1ccc2c(c1)CCN(C1CCNCC1F)C(=O)N2]

3.20 g (8.13 mmol) tert-butyl 3-fluoro-4-(7-methoxy-2-oxo-1,2,4,5-tetrahydro-benzo[d][1,3]diazepin-3-yl)-piperidine-1-carboxylate were cooled to 0° C. and at this temperature slowly combined with 50 mL of a hydrochloric acid solution (4 M in dioxane). Then the mixture was heated to RT and stirred for 16 h at RT. The precipitate formed was suction filtered, washed with diethyl ether and dried.

Yield: 2.20 g (92% of theoretical)

ESI-MS: m/z=294 (M+H)$^+$ $R_f$: 0.2 (silica gel: MeOH/chloroform=1/9)

Intermediate 27

7-methoxy-3-(3-methyl-piperidin-4-yl)-1,3,4,5-tetrahydro-benzo[d][1,3]diazepin-2-one

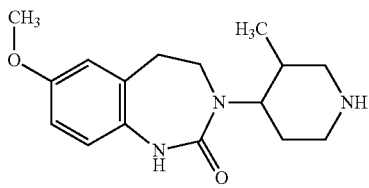 [SMILES: COc1ccc2c(c1)CCN(C1CCNCC1C)C(=O)N2]

Step 1: tert-butyl 4-[2-(5-methoxy-2-nitro-phenyl)-ethylamino]-3-methyl-piperidine-1-carboxylate

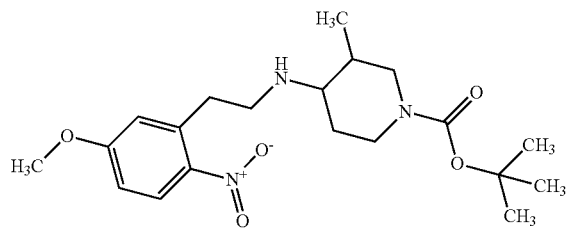 [SMILES: COc1ccc([N+](=O)[O-])c(CCNC2CCN(C(=O)OC(C)(C)C)CC2C)c1]

1.74 mL (29.0 mmol) acetic acid and 3.48 g (16.4 mmol) sodium triacetoxyborohydride were added at 0° C. to 2.50 g (12.7 mmol) 2-(5-methoxy-2-nitro-phenyl)-ethylamine and 2.93 g (13.7 mmol) tert-butyl 3-methyl-4-oxo-piperidine-1-carboxylate (WO2004/41777) in 75 mL DCM and the mixture was stirred for 3 h at RT. The reaction mixture was combined at 0° C. with a saturated potassium carbonate solution and the aqueous phase was extracted several times with DCM. The combined organic phases were washed with water and saturated sodium chloride solution, dried on sodium sulphate, filtered and the filtrate was evaporated down. The residue was purified by flash chromatography.

Yield: 4.50 g (90% of theoretical)

ESI-MS: m/z=394 (M+H)$^+$ $R_f$: 0.65 (silica gel: MeOH/chloroform=1/9)

Step 2: tert-butyl 4-[2-(2-amino-5-methoxy-phenyl)-ethylamino]-3-methyl-piperidine-1-carboxylate

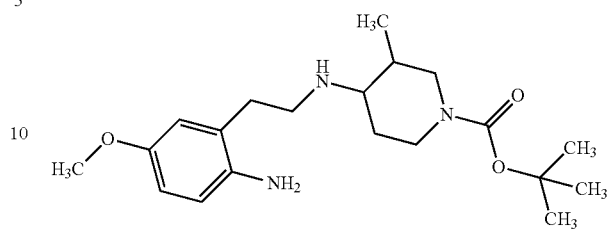

4.50 g (11.4 mmol) tert-butyl 4-[2-(5-methoxy-2-nitro-phenyl)-ethylamino]-3-methyl-piperidine-1-carboxylate were stirred with 0.6 g palladium on charcoal (Pd/C 10%) and 22.5 mL (460 mmol) hydrazine hydrate in 100 mL EtOH for 16 h at RT. The catalyst was suction filtered through kieselguhr and the filtrate was evaporated down i. vac.

Yield: 4 g (96% of theoretical)

ESI-MS: m/z=364 (M+H)$^+$ $R_f$: 0.5 (silica gel: MeOH/chloroform=1/9)

Step 3: tert-butyl 4-(7-methoxy-2-oxo-1,2,4,5-tetrahydro-benzo[d][1,3]diazepin-3-yl)-3-methyl-piperidine-1-carboxylate

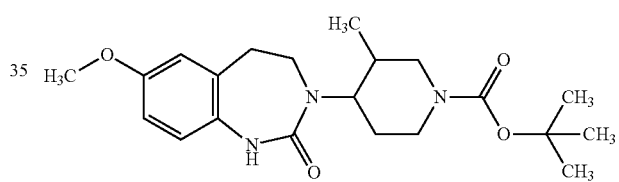

7.20 g (44.4 mmol) CDI were added to 5.40 g (14.9 mmol) tert-butyl 4-[2-(2-amino-5-methoxy-phenyl)-ethylamino]-3-methyl-piperidine-1-carboxylate in 75 mL DMF and the mixture was refluxed for 2 h. The reaction mixture was cooled to RT and stirred for 16 h. After the addition of ice water the aqueous phase was extracted several times with EtOAc. The organic phase was dried on sodium sulphate, filtered and the filtrate was evaporated down i. vac. The residue obtained was purified by flash chromatography.

Yield: 4.00 g (69% of theoretical)

$R_f$: 0.65 (silica gel: MeOH/chloroform=1/9)

Step 4: 7-methoxy-3-(3-methyl-piperidin-4-yl)-1,3,4,5-tetrahydro-benzo[d][1,3]diazepin-2-one

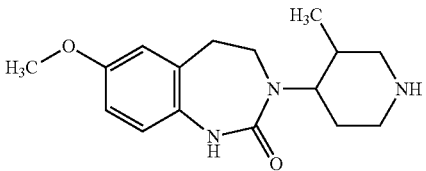 [SMILES: COc1ccc2c(c1)CCN(C1CCNCC1C)C(=O)N2]

2.50 g (6.42 mmol) tert-butyl 4-(7-methoxy-2-oxo-1,2,4,5-tetrahydro-benzo[d][1,3]diazepin-3-yl)-3-methyl-piperidine-1-carboxylate were slowly combined with 50 mL hydrochloric acid solution (4 M in dioxane) at 0° C. Then the mixture was heated to RT and stirred for 16 h. The precipitate formed was suction filtered, washed with diethyl ether and dried.

Yield: 1.50 g (81% of theoretical)

ESI-MS: m/z=290 (M+H)$^+$ $R_f$: 0.2 (silica gel: MeOH/chloroform=1/9)

Intermediate 28

7-methoxy-3-(2-methyl-piperidin-4-yl)-1,3,4,5-tetrahydro-benzo[d][1,3]diazepin-2-one Step 1: benzyl 4-[2-(5-methoxy-2-nitro-phenyl)-ethylamino]-2-methyl-piperidine-1-carboxylate

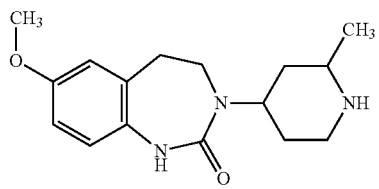 [SMILES: COc1ccc2c(c1)CCN(C1CCNC(C)C1)C(=O)N2]

At 0° C. 1.04 mL (17.3 mmol) acetic acid and 2.09 g (9.86 mmol) sodium triacetoxyborohydride were added to 1.50 g (7.65 mmol) 2-(5-methoxy-2-nitro-phenyl)-ethylamine and 2.04 g (8.25 mmol) benzyl 2-methyl-4-oxo-piperidine-1-carboxylate (WO2007/11810) in 75 mL DCM and the mixture was stirred for 3 h at RT. Then the reaction mixture was combined at 0° C. with a saturated potassium carbonate solution and the aqueous phase was extracted several times with DCM. The combined organic phases were washed with water and saturated sodium chloride solution, dried on sodium sulphate, filtered and the filtrate was evaporated down. The residue was purified by flash chromatography.

Yield: 3.00 g (92% of theoretical)

ESI-MS: m/z=428 (M+H)$^+$ $R_f$: 0.6 (silica gel: MeOH/chloroform=1/9)

Step 2: benzyl 4-[2-(2-amino-5-methoxy-phenyl)-ethylamino]-2-methyl-piperidine-1-carboxylate

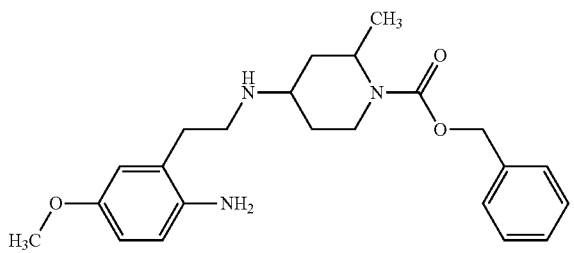 [SMILES: COc1ccc(N)c(CCNC2CCN(C(=O)OCc3ccccc3)C(C)C2)c1]

5.30 g (12.4 mmol) benzyl 4-[2-(5-methoxy-2-nitro-phenyl)-ethylamino]-2-methyl-piperidine-1-carboxylate were stirred with 1.5 g palladium on charcoal (Pd/C 10%) and 24.3 mL (499 mmol) hydrazine hydrate in 100 mL EtOH for 16 h at RT. The catalyst was suction filtered through kieselguhr and the filtrate was evaporated down i. vac.

Yield: 4.60 g (93% of theoretical)

ESI-MS: m/z=398 (M+H)$^+$ $R_f$: 0.5 (silica gel: MeOH/chloroform=1/9)

Step 3: benzyl 4-(7-methoxy-2-oxo-1,2,4,5-tetrahydro-benzo[d][1,3]diazepin-3-yl)-2-methyl-piperidine-1-carboxylate 3.17 g (19.6 mmol) CDI were added to 2.60 g (6.54 mmol) benzyl 4-[2-(2-amino-5-methoxy-phenyl)-ethylamino]-2-methyl-piperidine-1-carboxylate in 20 mL DMF and the mixture was refluxed for 2 h. The reaction mixture was cooled to RT and stirred for 16 h. Then ice water was added. The aqueous phase was extracted several times with EtOAc. The organic phases were combined, dried on sodium sulphate, filtered and the filtrate was evaporated down i. vac. The residue was purified by flash chromatography.

Yield: 2.24 g (81% of theoretical)

ESI-MS: m/z=424 (M+H)$^+$ $R_f$: 0.65 (silica gel: MeOH/chloroform=1/9)

Step 4: 7-methoxy-3-(2-methyl-piperidin-4-yl)-1,3,4,5-tetrahydrobenzo[d][1,3]diazepin-2-one

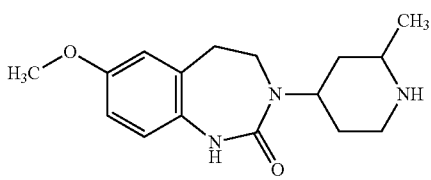

2.00 g (4.88 mmol) benzyl 4-(7-methoxy-2-oxo-1,2,4,5-tetrahydro-benzo[d][1,3]diazepin-3-yl)-2-methyl-piperidine-1-carboxylate were cooled to 0° C. and at this temperature 50 mL hydrochloric acid solution (4 M in dioxane) were slowly added. Then the mixture was heated to RT and stirred for 16 h. The precipitate formed was suction filtered, washed with diethyl ether and dried.
Yield: 1.20 g (85% of theoretical)
ESI-MS: m/z=290 (M+H)$^+$
$R_f$: 0.2 (silica gel: MeOH/chloroform=1/9)

Intermediate 29

6-(2,6-dichloro-pyridine-4-carbonyl)-3,4-dimethyl-3H-benzoxazol-2-one

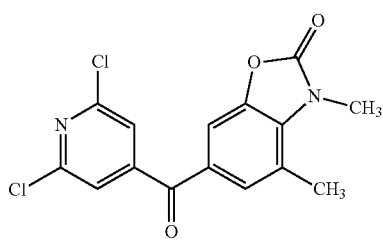 [SMILES: Cc1cc(C(=O)c2cc(Cl)nc(Cl)c2)cc2oc(=O)n(C)c12]

Step 1: 6-(2,6-dichloro-pyridine-4-carbonyl)-4-methyl-3H-benzoxazol-2-one

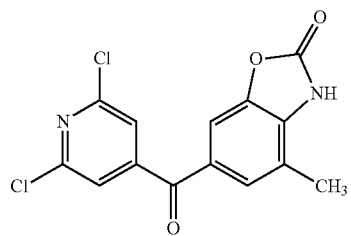 [SMILES: Cc1cc(C(=O)c2cc(Cl)nc(Cl)c2)cc2oc(=O)[nH]c12]

3.00 g (14.3 mmol) 2,6-dichloropyridine-4-carboxylic acid chloride, 1.80 g (11.0 mmol) 4-methyl-3H-benzoxazol-2-one and 9.47 g (71.0 mmol) aluminium trichloride were combined and heated for 2 h to 125° C. with stirring. Then the mixture was decomposed with ice water and EtOAc and the phases were separated. The aqueous phase was extracted several times with EtOAc. The organic phases were combined, dried on sodium sulphate, filtered and the filtrate was evaporated down i. vac. The residue was triturated with diethyl ether, the precipitate was suction filtered and dried i. vac.

Yield: 2.90 g (63% of theoretical)
ESI-MS: m/z=321/323/325 (2×Cl) (M+H)$^+$
$R_t$(HPLC): 1.49 min (method B)

Step 2: 6-(2,6-dichloro-pyridine-4-carbonyl)-3,4-dimethyl-3H-benzoxazol-2-one

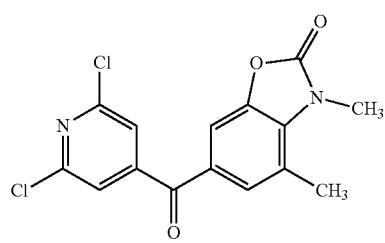 [SMILES: Cc1cc(C(=O)c2cc(Cl)nc(Cl)c2)cc2oc(=O)n(C)c12]

Under a nitrogen atmosphere 2.30 g (7.12 mmol) 6-(2,6-dichloro-pyridine-4-carbonyl)-4-methyl-3H-benzoxazol-2-one in 10 mL DMF were combined at 0° C. with 310 mg (7.10 mmol) sodium hydride (55%, suspension in mineral oil). The reaction mixture was stirred for 30 min at RT. Then 0.44 mL (7.10 mmol) iodomethane were added and the mixture was stirred overnight at RT. The reaction mixture was poured onto water and the precipitated product was suction filtered, washed with water and dried.
Yield: 2.40 g (quantitative)
ESI-MS: m/z=409/411 (2×Cl) (M+H)$^+$
$R_t$(HPLC): 1.59 min (method B)

Intermediate 30

6-(2-benzyloxy-6-chloro-pyridine-4-carbonyl)-3,4-dimethyl-3H-benzoxazol-2-one

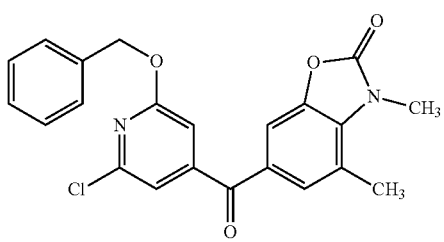 [SMILES: Cc1cc(C(=O)c2cc(Cl)nc(OCc3ccccc3)c2)cc2oc(=O)n(C)c12]

Step 1: 6-(2-benzyloxy-6-chloro-pyridine-4-carbonyl)-4-methyl-3H-benzoxazol-2-one

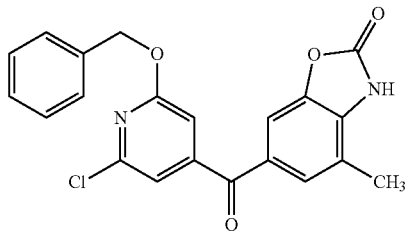 [SMILES: Cc1cc(C(=O)c2cc(Cl)nc(OCc3ccccc3)c2)cc2oc(=O)[nH]c12]

3.85 mL (3.85 mmol) sodium benzylate solution (1M in benzylalcohol) were added to 1.24 g (3.85 mmol) 6-(2,6-dichloro-pyridine-4-carbonyl)-4-methyl-3H-benzoxazol-2-one in 50 mL THF and stirred overnight at RT. The reaction mixture was combined with saturated sodium hydrogen carbonate solution and extracted with EtOAc. The combined organic phases were dried and evaporated down i. vac.

Yield: 1.10 g (72% of theoretical)

$R_t$(HPLC): 2.60 min (method F)

Step 2: 6-(2-benzyloxy-6-chloro-pyridine-4-carbonyl)-3,4-dimethyl-3H-benzoxazol-2-one

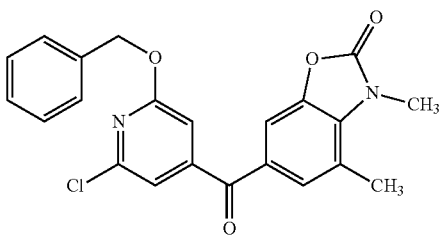 [SMILES: Cc1cc(C(=O)c2cc(Cl)nc(OCc3ccccc3)c2)cc2oc(=O)n(C)c12]

Under a nitrogen atmosphere and while cooling with ice 220 mg (5.06 mmol) sodium hydride (55%, suspension in mineral oil) were added to 2.00 g (5.07 mmol) 6-(2-benzyloxy-6-chloro-pyridine-4-carbonyl)-4-methyl-3H-benzoxazol-2-one in 10 mL DMF. The reaction mixture was stirred for 30 min at RT. Then 0.312 mL (5.06 mmol) iodomethane were added and the mixture was stirred overnight at RT. The reaction mixture was poured onto water and the precipitated product was suction filtered, washed with water and dried. The residue was stirred with diethyl ether, suction filtered and dried.

Yield: 2.00 g (97% of theoretical)

ESI-MS: m/z=409 (Cl) (M+H)+

$R_t$(HPLC): 1.80 min (method B)

Intermediate 31

6-(3-bromo-benzoyl)-3,4-dimethyl-3H-benzoxazol-2-one

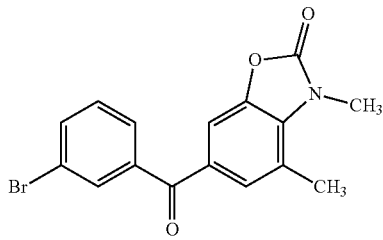 [SMILES: Cc1cc(C(=O)c2cccc(Br)c2)cc2oc(=O)n(C)c12]

Step 1: 6-(3-bromo-benzoyl)-4-methyl-3H-benzoxazol-2-one

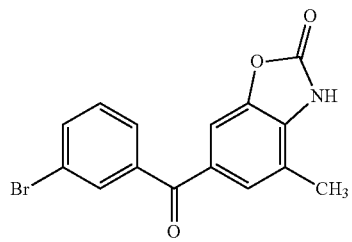 [SMILES: Cc1cc(C(=O)c2cccc(Br)c2)cc2oc(=O)[nH]c12]

2.08 g (9.48 mmol) 3-bromo-benzoic acid chloride, 1.41 g (9.48 mmol) 4-methyl-3H-benzoxazol-2-one and 5.33 g (40.0 mmol) aluminium trichloride were heated to 125° C. with stirring for 1.5 h. Then the mixture was mixed with ice water and the grease precipitated was separated from the solvent by decanting. The residue was dissolved in EtOAc, evaporated down and a little MeOH was triturated. The precipitate formed was suction filtered, washed with diethyl ether and dried i. vac.

Yield: 1.00 g (32% of theoretical)

ESI-MS: m/z=332 (M+H)+

$R_t$(HPLC): 1.53 min (method B)

Step 2: 6-(3-bromo-benzoyl)-3,4-dimethyl-3H-benzoxazol-2-one

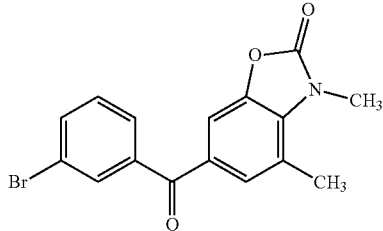 [SMILES: Cc1cc(C(=O)c2cccc(Br)c2)cc2oc(=O)n(C)c12]

144 mg (3.30 mmol) sodium hydride (55%, suspension in mineral oil) were added at RT to 1.00 g (3.01 mmol) 6-(3-bromo-benzoyl)-4-methyl-3H-benzoxazol-2-one in 4 mL DMF.

The reaction mixture was stirred for 30 min at RT. Then 0.285 mL (4.50 mmol) iodomethane were added and the mixture was stirred for 1 h at RT. The reaction mixture was poured onto ice water and the precipitate formed was suction filtered, washed with water and dried i. vac.

Yield: 0.98 g (94% of theoretical)
ESI-MS: m/z=346 (M+H)+
$R_f$(HPLC): 1.61 min (method B)

Intermediate 32

6-methoxy-3-piperidin-4-yl-1H-quinolin-2-one

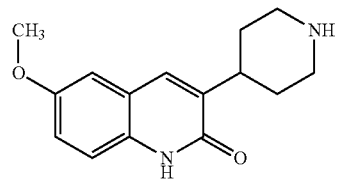

Step 1: 1-benzyl-4-(2-chloro-6-methoxy-quinoline-3-yl)-piperidin-4-ol

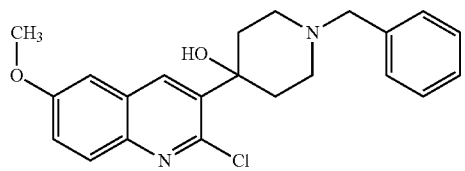 [SMILES: COc1ccc2nc(Cl)c(C3(O)CCN(Cc4ccccc4)CC3)cc2c1]

Under an argon atmosphere 14.0 mL (28.0 mmol) of a 2 M lithium diisopropylamide solution in 50 mL THF were cooled to −78° C. and combined with stirring with a solution of 5.00 g (25.1 mmol) of 2-chloro-6-methoxy-quinoline in THF. After 1 h stirring at −78° C., 4.5 mL (25.2 mmol) N-benzylpiperidone were added dropwise. After 1 h stirring at −78° C. the mixture was allowed to come up to RT and stirred overnight. The mixture was evaporated down i. vac. and purified by flash chromatography through Alox. The fractions containing the product were combined and evaporated down.

Yield: 2.10 g (13% of theoretical)
Purity: 60%
ESI-MS: m/z=383 (M+H)+
$R_f$(HPLC): 1.14 min (method B)

Step 2: 3-(1-benzyl-1.2.3.6-tetrahydro-pyridin-4-yl)-6-methoxy-quinolin-2-ol

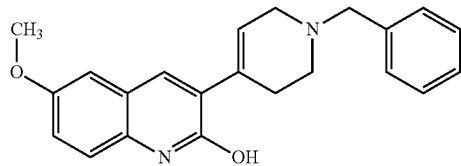 [SMILES: COc1ccc2nc(O)c(C3=CCN(Cc4ccccc4)CC3)cc2c1]

1.90 g (4.96 mmol) 1-benzyl-4-(2-chloro-6-methoxy-quinoline-3-yl)-piperidin-4-ol were added to 25 mL of a 4N aqueous hydrochloric acid solution and stirred overnight at 100° C. Then 15 ml of a concentrated aqueous hydrochloric acid solution were added dropwise and the mixture was again stirred overnight. The mixture was evaporated down by half i. vac., diluted with water and extracted with EtOAc. The organic phase was dried on sodium sulphate, filtered and evaporated down. The residue was triturated with PE/EtOAc and the product remaining as a solid was suction filtered and dried.

Yield: 165 mg (8% of theoretical)
Purity: 80%
ESI-MS: m/z=347 (M+H)+

Step 3:
6-methoxy-3-piperidin-4-yl-1H-quinolin-2-one

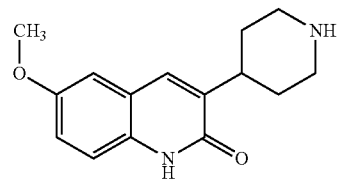 [SMILES: COc1ccc2[nH]c(=O)c(C3CCNCC3)cc2c1]

A mixture of 160 mg (0.462 mmol) 3-(1-benzyl-1.2.3.6-tetrahydro-pyridin-4-yl)-6-methoxy-quinolin-2-ol and 20 mg palladium on charcoal (Pd/C 10%) in 30 mL MeOH was first of all hydrogenated for 17.5 h at 50° C. in a hydrogen atmosphere of 50 psi. Then 10 mL THF and 20 mg palladium on charcoal (Pd/C 10%) were added and hydrogenation continued for a further 2 h under the same conditions. Another 20 mg palladium on charcoal (Pd/C 10%) were added and the mixture was hydrogenated overnight at 50° C. in a hydrogen atmosphere of 60 psi. Then the reaction mixture was filtered, washed with DMF and the filtrate was evaporated down. The residue was added to EtOAc, triturated with PE and filtered. The precipitate was washed with DIPE and dried.

Yield: 56 mg (35% of theoretical)
Purity: 75%
ESI-MS: m/z=259 (M+H)+
$R_f$(HPLC): 0.90 min (method B)

Intermediate 33

6-(3.6-dichloro-pyridazine-4-carbonyl)-4-methyl-3H-benzoxazol-2-one

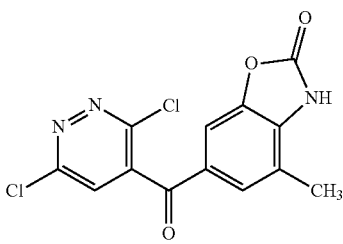 [SMILES: Cc1cc(C(=O)c2cc(Cl)nnc2Cl)cc2oc(=O)[nH]c12]

2.00 mL (27.4 mmol) thionyl chloride were added to 1.92 g (9.95 mmol) 3,6-dichloro-pyridazine-4-carboxylic acid in 10 mL 1,2-dichloroethane and the mixture was refluxed for 2 h. The reaction mixture was evaporated to dryness and coevaporated with 1,2-dichloroethane. Then 5.30 g (39.8 mmol) aluminium trichloride and 1.56 g (10.5 mmol) 4-methyl-3H-benzoxazol-2-one were added and the mixture was stirred for 1 h at 100° C. under a nitrogen atmosphere. Then it was stirred for a further 2 h at 120° C., 3 h at 130° C. and then cooled for 48 h at RT. The mixture was decomposed with ice water and extracted with DCM. The organic phases were combined, washed with water, dried on sodium sulphate, filtered and evaporated down i. vac. The residue was triturated with DIPE, suction filtered and dried.

Yield: 0.660 g (18% of theoretical)
ESI-MS: m/z=324 (M+H)$^+$
$R_t$(HPLC): 1.43 min (method B)

Intermediate 34

6-(5-bromo-1-oxy-pyridin-3-carbonyl)-3,4-dimethyl-3H-benzoxazol-2-one

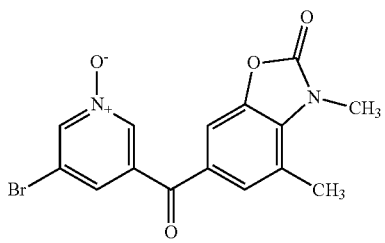 [SMILES: Cc1cc(C(=O)c2cc(Br)c[n+]([O-])c2)cc2oc(=O)n(C)c12]

Step 1: 5-bromo-nicotinic acid chloride hydrochloride

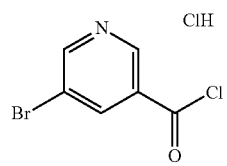

2.00 g (9.90 mmol) 5-bromonicotinic acid were mixed with 20 mL thionyl chloride and boiled for 4 h. The mixture was evaporated to dryness i. vac. and coevaporated twice with toluene. The residue was reacted further as the crude product.

Yield: 2.35 g (92% of theoretical)

Step 2: 6-(5-bromo-pyridin-3-carbonyl)-4-methyl-3H-benzoxazol-2-one

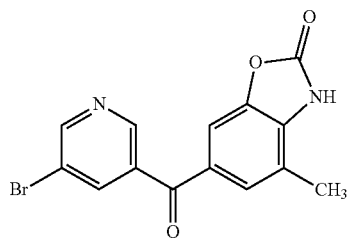 [SMILES: Cc1cc(C(=O)c2cncc(Br)c2)cc2oc(=O)[nH]c12]

2.57 g (10.0 mmol) 5-bromo-nicotinic acid chloride hydrochloride, 1.49 g (10.0 mmol) 4-methyl-3H-benzoxazol-2-one and 5.33 g (40.0 mmol) aluminium trichloride were heated to 125° C. with stirring for 1.5 h. After cooling to RT the mixture was mixed with ice water. The precipitate formed was suction filtered, washed with water and dried i. vac.

Yield: 2.30 g (69% of theoretical)
ESI-MS: m/z=333 (M+H)$^+$
$R_t$(HPLC): 1.41 min (method B)

Step 3: 6-(5-bromo-pyridin-3-carbonyl)-3,4-dimethyl-3H-benzoxazol-2-one

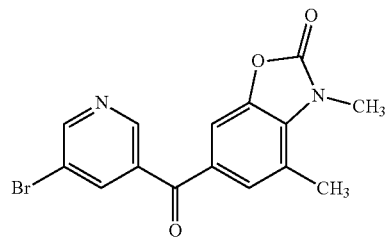 [SMILES: Cc1cc(C(=O)c2cncc(Br)c2)cc2oc(=O)n(C)c12]

0.18 g (4.00 mmol) sodium hydride (55%, suspension in mineral oil) were added at RT to 1.27 g (3.80 mmol) 6-(5-bromo-pyridin-3-carbonyl)-4-methyl-3H-benzoxazol-2-one in 5 mL DMF. The reaction mixture was stirred for 30 min at RT. Then 0.32 mL (5.00 mmol) iodomethane were added and the mixture was stirred overnight at RT. The reaction mixture was poured onto ice water and the precipitate formed was suction filtered, washed with water and dried i. vac.

Yield: 1.15 g (87% of theoretical)
ESI-MS: m/z=347 (M+H)$^+$
$R_t$(HPLC): 1.54 min (method B)

Step 4: 6-(5-bromo-1-oxy-pyridin-3-carbonyl)-3,4-dimethyl-3H-benzoxazol-2-one

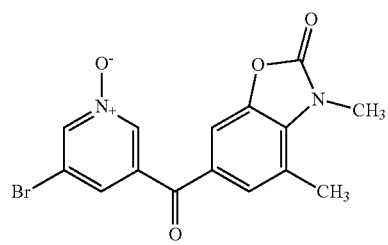 [SMILES: Cc1cc(C(=O)c2cc(Br)c[n+]([O-])c2)cc2oc(=O)n(C)c12]

0.690 g (4.00 mmol) m-chloro-perbenzoic acid were added to 1.05 g (3.03 mmol) 6-(5-bromo-pyridin-3-carbonyl)-3,4-dimethyl-3H-benzoxazol-2-one in 15 mL DCM and the mixture was stirred for 4 h at RT. After the addition of another 100 mg of m-chloro-perbenzoic acid the reaction mixture was stirred overnight at RT. Then it was diluted with DCM and extracted twice with 1N aqueous sodium hydroxide solution. The organic phase was dried on sodium sulphate, filtered and evaporated down i. vac. and the residue obtained was dried.

Yield: 1.05 g (96% of theoretical)
ESI-MS: m/z=363 (M+H)$^+$
$R_t$(HPLC): 1.27 min (method B)

Intermediate 35

6-(2-chloro-6-methoxy-pyridine-4-carbonyl)-3,4-dimethyl-3H-benzoxazol-2-one

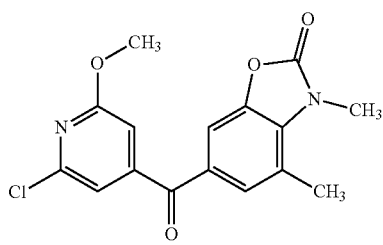 [SMILES: COc1cc(C(=O)c2cc(C)c3c(c2)oc(=O)n3C)cc(Cl)n1]

Step 1: 6-(2,6-dichloro-pyridine-4-carbonyl)-4-methyl-3H-benzoxazol-2-one

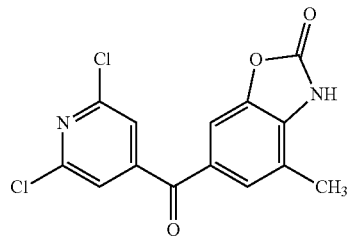 [SMILES: Cc1cc(C(=O)c2cc(Cl)nc(Cl)c2)cc2oc(=O)[nH]c12]

10.0 g (47.5 mmol) 2,6-dichloropyridine-4-carboxylic acid chloride, 7.08 g (47.5 mmol) 4-methyl-3H-benzoxazol-2-one and 32.0 g (240 mmol) aluminium trichloride were heated to 120° C. for 1 h with stirring. The mixture was mixed with ice water and extracted several times with EtOAc. The solid precipitated from EtOAc was suction filtered and washed with EtOAc. The organic phase remaining was separated off, dried on sodium sulphate, filtered and evaporated down. The residue was combined with a little EtOAc, the precipitated solid was suction filtered and washed with a little EtOAc. For further purification the mixture was recrystallised from EtOAc.
Yield: 7.00 g (46% of theoretical)
ESI-MS: m/z=323 (M+H)$^+$
R$_t$(HPLC): 1.6 min (method B)

Step 2: 6-(2-chloro-6-methoxy-pyridine-4-carbonyl)-4-methyl-3H-benzoxazol-2-one

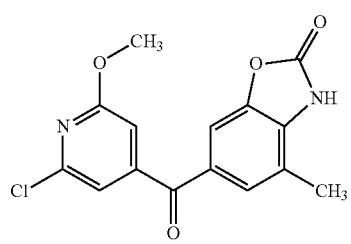 [SMILES: COc1cc(C(=O)c2cc(C)c3[nH]c(=O)oc3c2)cc(Cl)n1]

Under a nitrogen atmosphere 0.21 g (9.3 mmol) sodium were added batchwise to 50 mL MeOH. After the sodium had dissolved completely, 1.0 g (3.1 mmol) of 6-(2,6-dichloro-pyridine-4-carbonyl)-4-methyl-3H-benzoxazol-2-one were added and the mixture was refluxed for 5 h. Then the reaction mixture was evaporated down i. vac., the residue was combined with 50 mL water and the precipitated solid was suction filtered. This was washed with a little water and dried.
Yield: 0.9 g (91% of theoretical)
ESI-MS: m/z=319 (M+H)$^+$
R$_t$(HPLC): 1.45 min (method B)

Step 3: 6-(2-chloro-6-methoxy-pyridine-4-carbonyl)-3,4-dimethyl-3H-benzoxazol-2-one

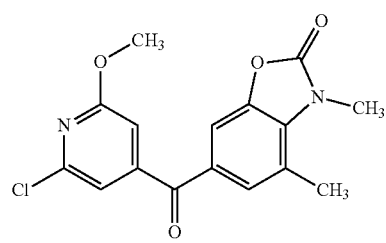 [SMILES: COc1cc(C(=O)c2cc(C)c3c(c2)oc(=O)n3C)cc(Cl)n1]

Under a nitrogen atmosphere 0.13 g (2.9 mmol) sodium hydride (55%, suspension in mineral oil) were added 0.90 g (2.8 mmol) 6-(2-chloro-6-methoxy-pyridine-4-carbonyl)-4-methyl-3H-benzoxazol-2-one in 10 mL DMF at RT. The reaction mixture was stirred for 30 min at RT. Then 0.18 mL (5.0 mmol) iodomethane in 1 mL DMF were added dropwise and the mixture was stirred overnight at RT. The reaction mixture was poured onto water and the precipitate formed was suction filtered and washed with water. The residue was extracted with diethyl ether, suction filtered and dried.
Yield: 0.84 g (89% of theoretical)
ESI-MS: m/z=333 (M+H)$^+$
R$_t$(HPLC): 1.70 min (method B)

Intermediate 36

3-(1-{5-[hydroxy-(4-methyl-2-oxo-2,3-dihydro-benzoxazol-6-yl)-methyl]-pyridazin-3-yl}-piperidin-4-yl)-7-methoxy-1,3,4,5-tetrahydro-benzo[d][1,3]diazepin-2-one

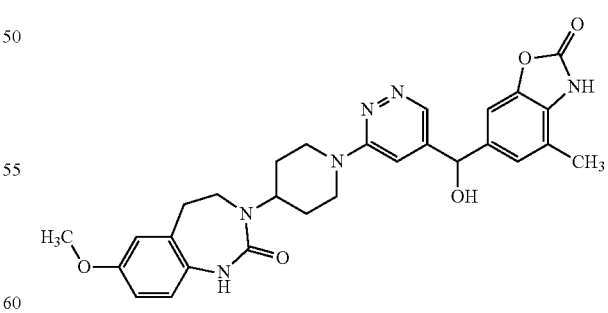

A mixture of 0.25 g (0.40 mmol) 3-{1-[6-chloro-5-(4-methyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one, 0.10 mL (0.71 mmol) TEA and 50 mg palladium on charcoal (Pd/C 10%) in MeOH was hydrogenated for 3 h at 50° C. in a hydrogen atmosphere of 50 psi. After filtration of the reaction mixture the filtrate was evaporated down to approx. 3 mL and mixed with a little ice water. The precipitate formed was suction filtered and dried. The residue contained the desired product in the mixture and was used in the next step without further purification.

Yield: 130 mg (12% of theoretical)
Purity: 20%

Intermediate 37

6-(3-bromo-4-fluoro-benzoyl)-3,4-dimethyl-3H-benzoxazol-2-one

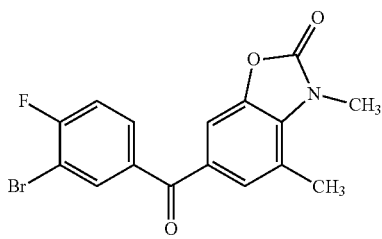 [SMILES: Cc1cc(C(=O)c2ccc(F)c(Br)c2)cc2oc(=O)n(C)c12]

Step 1: 3-bromo-4-fluoro-benzoic Acid Chloride

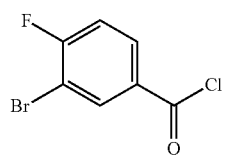 [SMILES: O=C(Cl)c1ccc(F)c(Br)c1]

2.17 g (9.41 mmol) 3-bromo-4-fluorobenzoic acid were mixed with 20 mL thionyl chloride and then boiled for 2 h. The reaction mixture was evaporated to dryness and coevaporated twice with toluene. The residue was reacted further as the crude product.

Yield: 2.23 g

Step 2: 6-(3-bromo-4-fluoro-benzoyl)-4-methyl-3H-benzoxazol-2-one

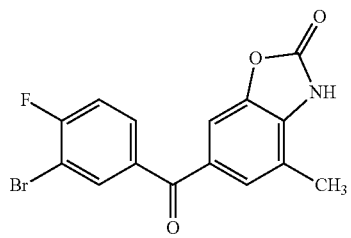 [SMILES: Cc1cc(C(=O)c2ccc(F)c(Br)c2)cc2oc(=O)[nH]c12]

2.23 g (9.40 mmol) 3-bromo-4-fluoro-benzoic acid chloride, 1.40 g (9.40 mmol) 4-methyl-3H-benzoxazol-2-one and 5.01 g (37.60 mmol) aluminium trichloride were heated to 125° C. for 1.5 h with stirring. After cooling to RT the mixture was mixed with ice water. The precipitate formed was suction filtered and washed with water. Then the precipitate was triturated with MeOH, suction filtered, washed with MeOH and dried i. vac.

Yield: 1.90 g (58% of theoretical)
ESI-MS: m/z=350 (M+H)$^+$
$R_f$(HPLC): 3.89 min (method C)

Step 3: 6-(3-bromo-4-fluoro-benzoyl)-3,4-dimethyl-3H-benzoxazol-2-one

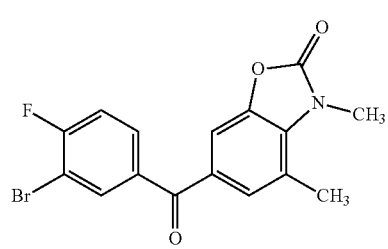 [SMILES: Cc1cc(C(=O)c2ccc(F)c(Br)c2)cc2oc(=O)n(C)c12]

0.175 g (4.00 mmol) sodium hydride (55%, suspension in mineral oil) were added at RT to 1.33 g (3.80 mmol) 6-(3-bromo-4-fluoro-benzoyl)-4-methyl-3H-benzoxazol-2-one in 5 mL DMF. The reaction mixture was stirred for 30 min at RT. Then 0.317 mL (5.00 mmol) iodomethane were added and the mixture was stirred for 1 h at RT. Then 0.100 mL (15.8 mmol) iodomethane were added and the mixture was stirred overnight at RT. After the addition of ice water the reaction mixture was extracted with EtOAc. The organic phase was washed with water, dried on sodium sulphate and evaporated down i. vac. The residue was purified by flash chromatography. The fractions containing the product were combined, evaporated down and dried i. vac.

Yield: 1.38 g (quantitative)
ESI-MS: m/z=364 (M+H)$^+$
$R_f$(HPLC): 1.32 min (method E)

Intermediate 38

3-{1-[6-chloro-5-(3,4-dimethyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one

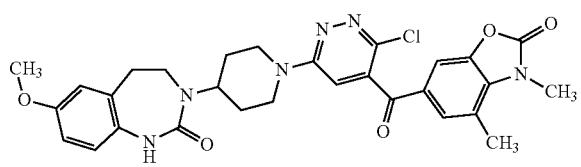 [SMILES: COc1ccc2c(c1)CCN(C1CCN(c3cc(C(=O)c4cc(C)c5c(c4)oc(=O)n5C)c(Cl)nn3)CC1)C(=O)N2]

Step 1: 6-(3.6-dichloro-pyridazine-4-carbonyl)-3,4-dimethyl-3H-benzoxazol-2-one

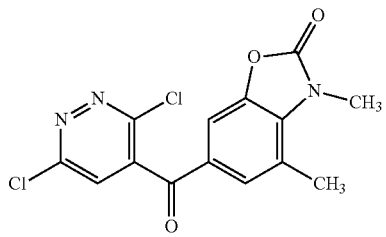 [SMILES: Cc1cc(C(=O)c2cc(Cl)nnc2Cl)cc2oc(=O)n(C)c12]

85 mg (2.1 mmol) sodium hydride (55%, suspension in mineral oil) were added to 0.65 g (2.0 mmol) 6-(3.6-dichloro-pyridazine-4-carbonyl)-4-methyl-3H-benzoxazol-2-one in 10 mL DMF while cooling with ice. The reaction mixture was stirred for 20 min. Then 0.19 mL (3.1 mmol) iodomethane were added while cooling with ice and the mixture was stirred for 2 h at RT. The reaction mixture was mixed with ice water, the precipitate formed was suction filtered and dried.

Yield: 0.62 g (82% of theoretical)

Step 2: 3-{1-[6-chloro-5-(3,4-dimethyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one

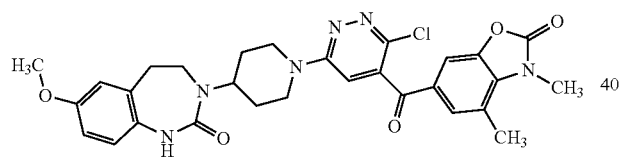

550 mg (2.00 mmol) 7-methoxy-3-piperidin-4-yl-1,3,4,5-tetrahydro-benzo[d][1,3]diazepin-2-one, 610 mg (1.80 mmol) 6-(3.6-dichloro-pyridazine-4-carbonyl)-3,4-dimethyl-3H-benzoxazol-2-one, 630 mg (4.39 mmol) copper(I) bromide and 430 mL (2.50 mmol) DIPEA in 5 mL DMF were stirred for 2 h at 110° C., then cooled and filtered. The filtrate was combined with 1 mL of a 1N aqueous hydrochloric acid solution and precipitated with 40 mL ice water. The precipitate was suction filtered, washed with water and dried. The solid was stirred with 120 mL DCM/MeOH (11:1), filtered through silica gel and washed with DCM/MeOH. The filtrate was evaporated down. The residue was triturated with diethyl ether, suction filtered and dried. A mixture of isomers was obtained which was further reacted.

Yield: 870 mg (50% of theoretical)
Purity: 60%
ESI-MS: m/z=575 (M-H)⁻
$R_f$(HPLC): 3.70 min (method C)

Intermediate 39

6-(3,5-difluoro-benzoyl)-3,4-dimethyl-3H-benzoxazol-2-one

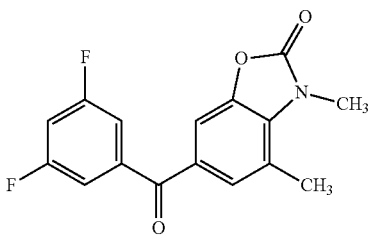 [SMILES: Cc1cc(C(=O)c2cc(F)cc(F)c2)cc2oc(=O)n(C)c12]

Step 1: 3,5-difluoro-benzoic acid chloride

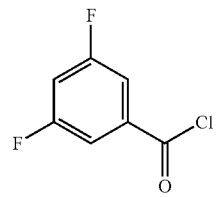 [SMILES: O=C(Cl)c1cc(F)cc(F)c1]

1.63 g (10.00 mmol) 3,5-difluoro-benzoic acid were mixed with 20 mL thionyl chloride and boiled for 2 h. The reaction mixture was evaporated to dryness and coevaporated twice with toluene. The residue was reacted further as the crude product.

Yield: 1.45 g (82% of theoretical)

Step 2: 6-(3,5-difluoro-benzoyl)-4-methyl-3H-benzoxazol-2-one

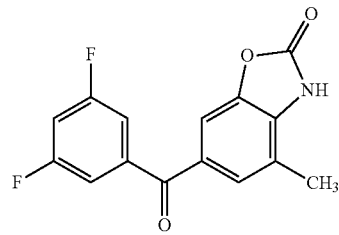 [SMILES: Cc1cc(C(=O)c2cc(F)cc(F)c2)cc2oc(=O)[nH]c12]

1.45 g (8.21 mmol) 3,5-difluorobenzoic acid chloride, 1.22 g (8.21 mmol) 4-methyl-3H-benzoxazol-2-one and 4.40 g (33.0 mmol) aluminium trichloride were heated to 125° C. for 1.5 h with stirring. The mixture was mixed with ice water and the product precipitated as a solid was suction filtered and washed with water. After trituration of the precipitate with MeOH it was suction filtered, washed with MeOH and dried i. vac.

Yield: 2.20 g (93% of theoretical)
ESI-MS: m/z=290 (M+H)⁺
$R_f$(HPLC): 1.61 min (method B)

Step 3: 6-(3,5-difluoro-benzoyl)-3,4-dimethyl-3H-benzoxazol-2-one

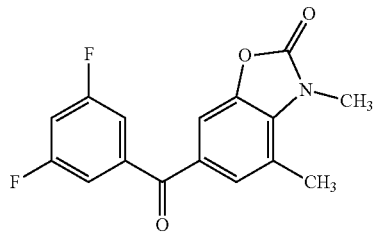 [SMILES: Cc1cc(C(=O)c2cc(F)cc(F)c2)cc2oc(=O)n(C)c12]

0.349 g (8.00 mmol) sodium hydride (55%, suspension in mineral oil) were added at RT to 2.20 g (7.61 mmol) 6-(3,5-difluoro-benzoyl)-4-methyl-3H-benzoxazol-2-one in 10 mL DMF. The reaction mixture was stirred for 30 min at RT. Then 0.634 mL (10.0 mmol) iodomethane were added and the mixture was stirred for 1 h at RT. Then another 0.1 mL iodomethane were added and the mixture was stirred further at RT. After the addition of ice water the mixture was extracted with EtOAc. The organic phase was washed with water, dried on sodium sulphate and evaporated down i. vac. The residue was purified by flash chromatography. The fractions containing the product were combined, evaporated down and dried i. vac.
Yield: 1.00 g (43% of theoretical)
ESI-MS: m/z=304 (M+H)$^+$
$R_t$(HPLC): 1.68 min (method B)

Intermediate 40

6-(6-chloro-pyrimidine-4-carbonyl)-3-methyl-4-pyrazol-1-ylmethyl-3H-benzoxazol-2-one

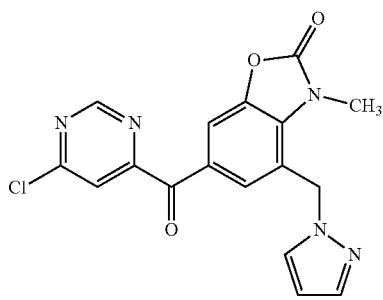 [SMILES: Cn1c(=O)oc2cc(C(=O)c3cc(Cl)ncn3)cc(Cn3cccn3)c21]

Under a nitrogen atmosphere 0.15 g (0.49 mmol) 6-(6-chloropyrimidine-4-carbonyl)-3,4-dimethyl-3H-benzoxazol-2-one, 95 mg (0.53 mmol) N-bromosuccinimide and 5.0 mg (30 mmol) 2,2'-azobis-isobutyronitrile (AIBN) in 15 mL carbon tetrachloride were combined and refluxed for 4 h. The precipitate formed was filtered off and the filtrate was combined with 20 µL isopropanol. After brief stirring 36 mg (0.53 mmol) pyrazole and 0.17 mL (0.99 mmol) DIPEA were added and the mixture was refluxed for 6 h. Then the reaction mixture was filtered through silica gel and washed with DCM/EtOAc (1/1). The filtrate was evaporated down i. vac. and the residue was reacted further as the crude product.
Yield: 210 mg (58% of theoretical)
Purity: 50%
$R_t$(HPLC): 3.35 min (method C)

Intermediate 41

4-(3,4-dimethyl-2-oxo-2,3-dihydro-benzoxazole-6-carbonyl)-2-fluoro-benzonitrile

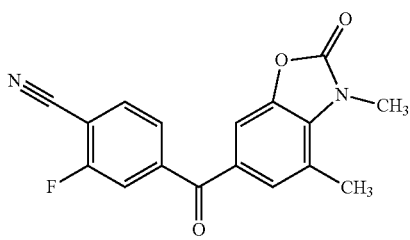 [SMILES: Cc1cc(C(=O)c2ccc(C#N)c(F)c2)cc2oc(=O)n(C)c12]

Step 1: 4-cyano-3-fluoro-benzoic Acid Chloride

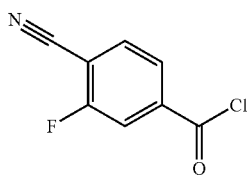 [SMILES: N#Cc1ccc(C(=O)Cl)cc1F]

0.66 g (4.0 mmol) 4-cyano-3-fluoro-benzoic acid were mixed with 10 mL thionyl chloride and boiled for 2 h. The mixture was evaporated to dryness and coevaporated twice with toluene. The residue was reacted further as the crude product.
Yield: 0.73 g (quantitative)

Step 2: 2-fluoro-4-(4-methyl-2-oxo-2,3-dihydro-benzoxazole-6-carbonyl)-benzonitrile

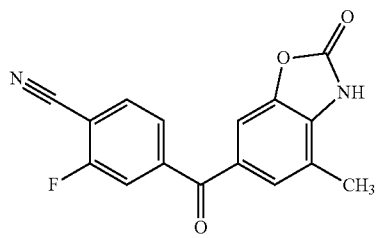 [SMILES: Cc1cc(C(=O)c2ccc(C#N)c(F)c2)cc2oc(=O)[nH]c12]

0.73 g (4.0 mmol) 4-cyano-3-fluoro-benzoic acid chloride, 0.60 g (4.0 mmol) 4-methyl-3H-benzoxazol-2-one and 2.1 g (16 mmol) aluminium trichloride were heated to 125° C. for 1.5 h with stirring. After cooling to RT the mixture was combined with ice water. The precipitate formed was suction filtered, washed with water and dried i. vac.
Yield: 1.2 g (quantitative)
ESI-MS: m/z=295 (M−H)$^−$
$R_t$(HPLC): 1.45 min (method B)

Step 3: 4-(3,4-dimethyl-2-oxo-2,3-dihydro-benzoxazole-6-carbonyl)-2-fluoro-benzonitrile

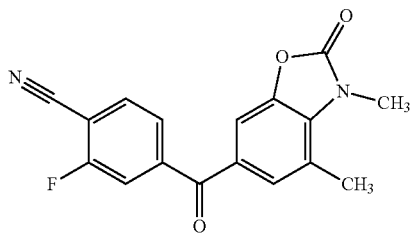 [SMILES: Cc1cc(C(=O)c2ccc(C#N)c(F)c2)cc2oc(=O)n(C)c12]

0.190 g (4.30 mmol) sodium hydride (55%, suspension in mineral oil) were added to 1.15 g (3.88 mmol) 2-fluoro-4-(4-methyl-2-oxo-2,3-dihydro-benzoxazole-6-carbonyl)-benzonitrile in 5.0 mL DMF at RT. The reaction mixture was stirred for 30 min at RT. Then 0.320 mL (5.00 mmol) iodomethane were added and the mixture was stirred for 1 h at RT. Then another 0.1 mL iodomethane were added and stirring was continued at RT. Ice water was added to the reaction mixture and the precipitate formed was suction filtered. The residue was purified by flash chromatography. The fractions containing the product were combined, evaporated down, triturated with diethyl ether, suction filtered and again washed with diethyl ether. The residue was dried i. vac.

Yield: 0.60 g (50% of theoretical)
ESI-MS: m/z=311 (M+H)$^+$
$R_t$(HPLC): 1.54 min (method B)

Intermediate 42

6-(6-chloro-2-methyl-pyrimidine-4-carbonyl)-4-methyl-3H-benzoxazol-2-one

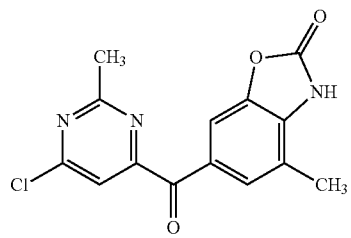 [SMILES: Cc1nc(Cl)cc(C(=O)c2cc(C)c3[nH]c(=O)oc3c2)n1]

Step 1: 6-chloro-2-methyl-pyrimidine-4-carboxylic Acid Chloride

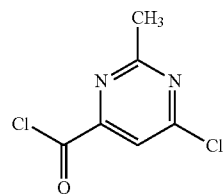

2.00 g (13.0 mmol) 6-hydroxy-2-methylpyrimidine-4-carboxylic acid were refluxed for 2 h with 11.9 mL (130 mmol) phosphorus oxychloride. After cooling to RT, 2.70 g (13.0 mmol) phosphorus-(V)-chloride were added and the mixture was boiled for 2 h. The reaction mixture was cooled to RT, evaporated to dryness i. vac. and coevaporated twice with toluene. The residue was triturated several times with DCM and the excess DCM was decanted off. The combined DCM phases were evaporated down and the residue was reacted further as the crude product.

Yield: 2.48 g (quantitative)

Step 2: 6-(6-chloro-2-methyl-pyrimidine-4-carbonyl)-4-methyl-3H-benzoxazol-2-one

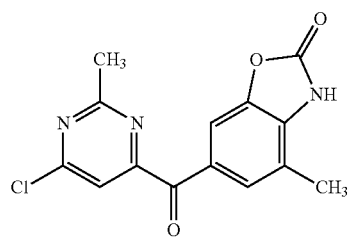 [SMILES: Cc1nc(Cl)cc(C(=O)c2cc(C)c3[nH]c(=O)oc3c2)n1]

2.48 g (13.0 mmol) 6-chloro-2-methyl-pyrimidine-4-carboxylic acid chloride, 1.94 g (13.0 mmol) 4-methyl-3H-benzoxazol-2-one and 6.93 g (52.0 mmol) aluminium trichloride were heated to 125° C. for 1.5 h with stirring. The mixture was combined with ice water and the precipitate formed was suction filtered and washed with water. Then the precipitate was dissolved in MeOH/DCM and filtered through silica gel suction. The filtrate was evaporated down and the residue was purified by flash chromatography. The fractions containing the product were combined, evaporated down and triturated with diethyl ether. The precipitate was suction filtered, washed with diethyl ether and dried i. vac.

Yield: 0.600 g (15% of theoretical)
ESI-MS: m/z=304 (M+H)$^+$
$R_t$(HPLC): 1.42 min (method B)

Intermediate 43

6-(6-chloro-2-methyl-pyrimidine-4-carbonyl)-3,4-dimethyl-3H-benzoxazol-2-one

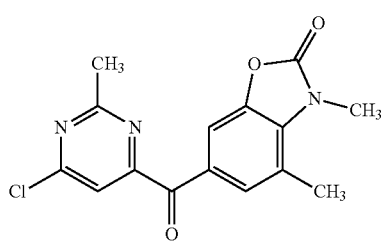 [SMILES: Cc1nc(Cl)cc(C(=O)c2cc(C)c3c(c2)oc(=O)n3C)n1]

59 mg (1.4 mmol) sodium hydride (55%, suspension in mineral oil) were added at RT to 0.37 g (1.2 mmol) 6-(6-chloro-2-methyl-pyrimidine-4-carbonyl)-4-methyl-3H-benzoxazol-2-one in 5.0 mL DMF. The reaction mixture was stirred for 30 min at RT. Then 0.10 mL (1.60 mmol) iodomethane were added and the mixture was stirred for 1 h at RT. Then another 0.10 mL (1.60 mmol) iodomethane were added and the mixture was stirred overnight at RT. The reaction mixture was diluted with ice water and the precipitate formed was suction filtered. The residue was washed with water and dried i. vac.

Yield: 0.37 g (96% of theoretical)
ESI-MS: m/z=318 (M+H)$^+$
$R_f$(HPLC): 1.53 min (method B)

Intermediate 44

6-(2-chloro-5-methyl-pyridine-4-carbonyl)-3,4-dimethyl-3H-benzoxazol-2-one

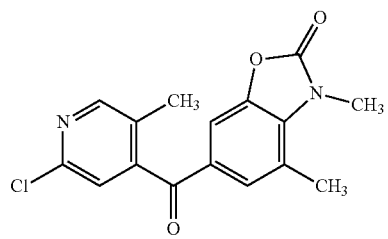 [SMILES: Cc1cnc(Cl)cc1C(=O)c1cc(C)c2c(c1)oc(=O)n2C]

Step 1: 6-(2-chloro-5-methyl-pyridine-4-carbonyl)-4-methyl-3H-benzoxazol-2-one

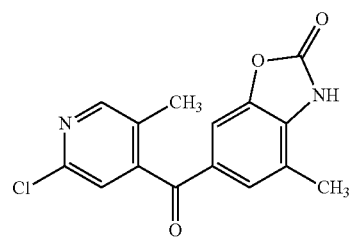 [SMILES: Cc1cnc(Cl)cc1C(=O)c1cc(C)c2[nH]c(=O)oc2c1]

1.53 g (10.0 mmol) 3-methyl-1-oxy-isonicotinic acid were stirred with 9.32 mL (100 mmol) phosphorus oxychloride and boiled for 4 h. The reaction mixture was evaporated to dryness i. vac. and coevaporated twice with toluene. The crude product thus obtained (which was present in admixture with 2-chloro-3-methyl-isonicotinic acid chloride) was combined with 1.49 g (10.0 mmol) 4-methyl-3H-benzoxazol-2-one and 5.33 g (40.0 mmol) aluminium trichloride and heated to 125° C. for 1.5 h with stirring. Then the mixture was mixed with ice water and the precipitated grease was separated from the solvent by decanting. The residue was triturated with MeOH. The precipitate formed was suction filtered, washed with MeOH and diethyl ether and dried i. vac. The product thus obtained, which was present in admixture with 6-(2-chloro-3-methyl-pyridine-4-carbonyl)-4-methyl-3H-benzoxazol-2-one, was reacted further without further purification.

Yield: 400 mg (~13%)
ESI-MS: m/z=303 (M+H)$^+$
$R_f$(HPLC): 1.40 min (method B)

Step 2: 6-(2-chloro-5-methyl-pyridine-4-carbonyl)-3,4-dimethyl-3H-benzoxazol-2-one 0.10 g (2.2 mmol) sodium hydride (55%, suspension in mineral oil) were added to 0.61 g (2.0 mmol) 6-(2-chloro-5-methyl-pyridine-4-carbonyl)-4-methyl-3H-benzoxazol-2-one in admixture with 6-(2-chloro-3-methyl-pyridine-4-carbonyl)-4-methyl-3H-benzoxazol-2-one in 5 mL DMF at RT. The reaction mixture was stirred for 30 min at RT. Then 0.17 mL (2.6 mmol) iodomethane were added and the mixture was stirred for 1 h at RT. Then a further 0.1 mL iodomethane were added and the mixture was stirred further at RT. Ice water was added to the reaction mixture and the precipitate formed was suction filtered. The residue was purified by flash chromatography. The fractions containing the product were combined, evaporated down, triturated with diethyl ether, suction filtered and dried. The product was obtained in admixture with 6-(2-chloro-3-methyl-pyridine-4-carbonyl)-3,4-dimethyl-3H-benzoxazol-2-one and reacted further as such.

Yield: 0.60 g (94% of theoretical) as mixture
ESI-MS: m/z=311 (M+H)$^+$
$R_f$(HPLC): 1.46 min (method B)

Intermediate 45

3-fluoro-5-(4-methyl-2-oxo-2,3-dihydro-benzoxazole-6-carbonyl)-benzonitrile

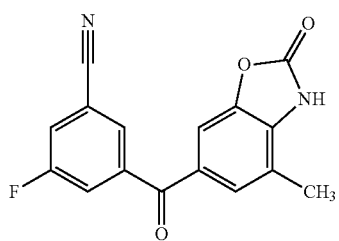 [SMILES: Cc1cc(C(=O)c2cc(F)cc(C#N)c2)cc2oc(=O)[nH]c12]

Step 1: 3-cyano-5-fluoro-benzoic Acid Chloride

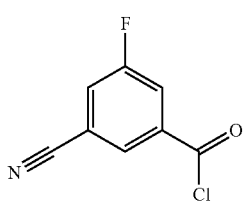 [SMILES: N#Cc1cc(F)cc(C(=O)Cl)c1]

1.65 g (10.0 mmol) 3-cyano-5-fluorobenzoic acid were boiled for 2 h with 7.27 mL (100 mmol) thionyl chloride with stirring. The reaction mixture was evaporated to dryness i. vac. and coevaporated twice with toluene. The residue was reacted further as the crude product.

Yield: 1.84 g (quantitative)

Step 2: 3-fluoro-5-(4-methyl-2-oxo-2,3-dihydro-benzoxazole-6-carbonyl)-benzonitrile

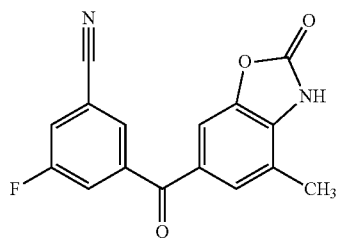 [SMILES: Cc1cc(C(=O)c2cc(F)cc(C#N)c2)cc2oc(=O)[nH]c12]

1.84 g (10.0 mmol) 3-cyano-5-fluoro-benzoic acid chloride, 1.49 g (10.0 mmol) 4-methyl-3H-benzoxazol-2-one and 5.33 g (40.0 mmol) aluminium trichloride were heated to 125° C. for 1.5 h with stirring. Then the mixture was mixed with ice water. The precipitate formed was suction filtered, washed with water and dried i. vac.

Yield: 1.75 g (59% of theoretical)
ESI-MS: m/z=295 (M–H)⁻
R$_t$(HPLC): 1.33 min (method B)

Intermediate 46

9-fluoro-3-piperidin-4-yl-1,3,4,5-tetrahydro-benzo[d][1,3]diazepin-2-one

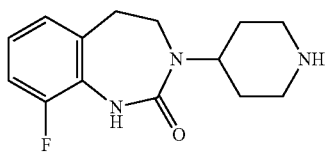 [SMILES: O=C1Nc2c(F)cccc2CCN1C1CCNCC1]

Step 1: dimethyl 2-(3-fluoro-2-nitro-phenyl)-malonate

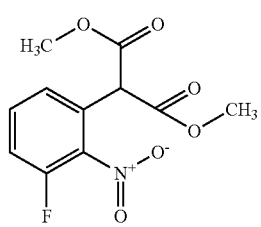 [SMILES: COC(=O)C(C(=O)OC)c1cccc(F)c1[N+](=O)[O-]]

5.40 g (38.3 mmol) potassium carbonate and 4.50 mL (38.0 mmol) dimethylmalonate were added successively to 6.00 g (37.7 mmol) 2,6-difluoronitrobenzene in 60 mL DMF and the mixture was stirred overnight at 65° C. Then the reaction mixture was cooled to RT and slowly poured onto 75 mL of 1N aqueous hydrochloric acid solution. The aqueous phase was extracted several times with EtOAc. The combined organic phases were washed with water and saturated sodium chloride solution, dried on magnesium sulphate, filtered and evaporated down i. vac. The residue was stirred with n-hexane, suction filtered and dried.

Yield: 2.18 g (21% of theoretical)
ESI-MS: m/z=272 (M+H)⁺
R$_f$: 0.32 (silica gel; PE/EtOAc=2/1)

Step 2: (3-fluoro-2-nitro-phenyl)-acetic Acid

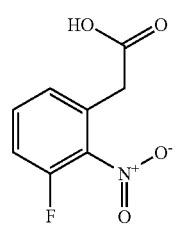 [SMILES: O=C(O)Cc1cccc(F)c1[N+](=O)[O-]]

28.0 g (103 mmol) dimethyl 2-(3-fluoro-2-nitro-phenyl)-malonate were added to 120 mL water and 120 mL conc. hydrochloric acid and refluxed for 5 h. The mixture was cooled to RT and extracted several times with EtOAc. The combined organic phases were dried on magnesium sulphate, filtered and evaporated down i. vac. The residue was triturated with PE/EtOAc=3/1 and suction filtered.

Yield: 17.3 g (84% of theoretical)
ESI-MS: m/z=217 (M+NH₄)⁺
R$_t$(HPLC): 1.13 min (method B)

Step 3: N-(1-benzyl-piperidin-4-yl)-2-(3-fluoro-2-nitro-phenyl)-acetamide

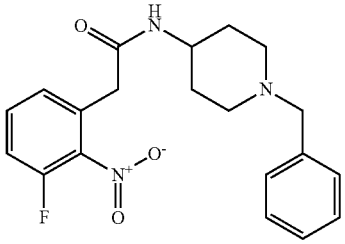 [SMILES: O=C(Cc1cccc(F)c1[N+](=O)[O-])NC1CCN(Cc2ccccc2)CC1]

17.0 g (102 mmol) CDI were added at RT to 18.3 g (91.9 mmol) (3-fluoro-2-nitro-phenyl)-acetic acid in 500 mL THF and stirred for 30 min. Then 20.0 mL (95.8 mmol) 4-amino-1-benzylpiperidine were added and the mixture was stirred for a further 2 h. The reaction mixture was diluted with EtOAc and the organic phase was washed with water and saturated sodium chloride solution. The organic phase was dried on magnesium sulphate, filtered and evaporated down i. vac. The residue was triturated with DIPE and suction filtered.

Yield: 33.0 g (97% of theoretical)
ESI-MS: m/z=372 (M+H)$^+$
$R_t$(HPLC): 1.29 min (method B)

Step 4: (1-benzyl-piperidin-4-yl)-[2-(3-fluoro-2-nitro-phenyl)-ethyl]-amine

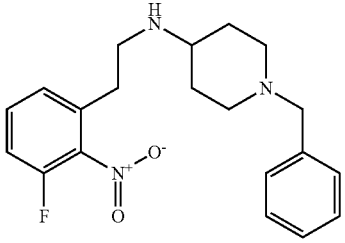 [SMILES: O=[N+]([O-])c1c(F)cccc1CCNC1CCN(Cc2ccccc2)CC1]

23.4 mL (183 mmol) chlorotrimethylsilane were slowly added dropwise, with stirring, to 18.9 g (50.9 mmol) of N-(1-benzyl-piperidin-4-yl)-2-(3-fluoro-2-nitro-phenyl)-acetamide in 500 mL of THF. The mixture was stirred for 1 h at RT. Then 2.70 g (124 mmol) lithium borohydride were added batchwise and the mixture was stirred for 1 h at RT. Then the mixture was refluxed for 5 h and cooled to RT overnight. 16 mL MeOH, 40 mL water and mL conc. hydrochloric acid were added dropwise with stirring and after they had all been added the reaction mixture was refluxed for 3 h. After cooling to RT the organic phase was separated off and the aqueous phase was extracted several times with EtOAc. The combined organic phases were washed with saturated sodium chloride solution, dried on magnesium sulphate, filtered and evaporated down i. vac. The residue was purified by flash chromatography. The fractions containing the product were combined and evaporated down. (Product in the form of a mixture!)

Yield: 14.4 g (79% of theoretical)
ESI-MS: m/z=358 (M+H)$^+$
$R_f$: 0.39 (silica gel; DCM/Cyc/MeOH/NH$_4$OH=70/15/15/2)

Step 5: [2-(2-amino-3-fluoro-phenyl)-ethyl]-(1-benzyl-piperidin-4-yl)-amine

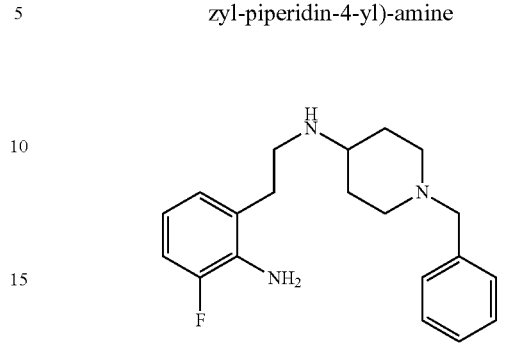

14.4 g (40.3 mmol) (1-benzyl-piperidin-4-yl)-[2-(3-fluoro-2-nitro-phenyl)-ethyl]-amine in 100 mL MeOH were stirred with 2.00 g rhodium charcoal (10%) and shaken at RT under a hydrogen atmosphere (3 bar). The catalyst was filtered off and the solvent was eliminated i. vac. The residue was further reacted immediately as the crude product.

Yield: 13.1 g (99% of theoretical)
$R_t$(HPLC): 0.64 min (method B)

Step 6: 3-(1-benzyl-piperidin-4-yl)-9-fluoro-1,3,4,5-tetrahydro-benzo[d][1,3]diazepin-2-one

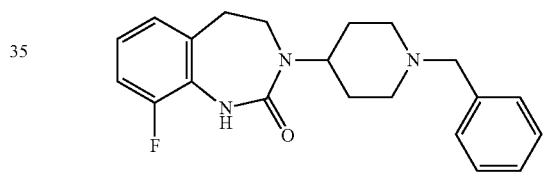

11.0 g (65.8 mmol) CDI were added to 13.1 g (40.0 mmol) [2-(2-amino-3-fluoro-phenyl)-ethyl]-(1-benzyl-piperidin-4-yl)-amine in 120 mL DMF. The mixture was heated to 100° C. and stirred for 1 h. After the reaction mixture had cooled to RT it was poured onto 300 mL ice water. The aqueous phase was extracted several times with DCM, the organic phases were combined, dried on magnesium sulphate, filtered and evaporated down i. vac. The residue was purified by flash chromatography. The fractions containing the product were combined and evaporated down.

Yield: 13.7 g (97% of theoretical)
ESI-MS: m/z=354 (M+H)$^+$
$R_t$(HPLC): 1.00 min (method B)

Step 7: 9-fluoro-3-piperidin-4-yl-1,3,4,5-tetrahydro-benzo[d][1,3]diazepin-2-one

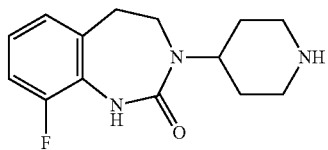 [SMILES: O=C1Nc2c(F)cccc2CCN1C1CCNCC1]

13.7 g (38.8 mmol) 3-(1-benzyl-piperidin-4-yl)-9-fluoro-1,3,4,5-tetrahydro-benzo[d][1,3]diazepin-2-one in 100 mL MeOH were shaken with 2.00 g palladium on charcoal (Pd/C 10%) under a hydrogen atmosphere (3 bar) at RT. The catalyst was filtered off and the solvent was evaporated down. The residue was purified by flash chromatography. The fractions containing the product were combined and evaporated down. The residue was stirred with DIPE/EtOAc, suction filtered and dried.
Yield: 3.10 g (30% of theoretical)
ESI-MS: m/z=264 (M+H)$^+$
R$_t$(HPLC): 2.43 min (method B)

Intermediate 47

6-(2,6-dichloro-pyrimidine-4-carbonyl)-4-methyl-3H-benzoxazol-2-one

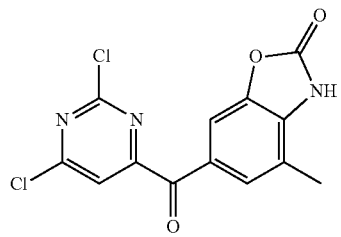 [SMILES: Cc1cc(C(=O)c2cc(Cl)nc(Cl)n2)cc2oc(=O)[nH]c12]

Step 1: 2,6-dihydroxy-pyrimidine-4-carboxylic acid

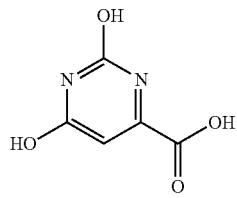 [SMILES: O=C(O)c1cc(O)nc(O)n1]

23.00 g (127.74 mmol) orotic acid lithium salt monohydrate in 400 mL DMF were heated to 70° C. and at this temperature hydrochloric acid was added batchwise within 2 h. The reaction mixture was stirred for a further hour at 70° C. and then evaporated down in vacuo. The residue was stirred with water, suction filtered and dried at 50° C. in the CAD.
Yield: 21.40 g (quantitative)
ESI-MS: m/z=155 (M−H)$^−$ Step 2: 2,6-dichloro-pyrimidine-4-carboxylic Acid Chloride

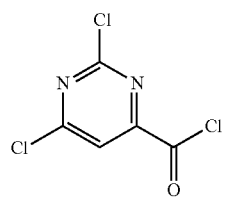 [SMILES: O=C(Cl)c1cc(Cl)nc(Cl)n1]

20 g (0.13 mol) 2,6-dihydroxy-pyrimidine-4-carboxylic acid were refluxed together with 40 mL phosphorus oxychloride. After cooling to RT 60 g (0.29 mol) phosphorus-(V)-chloride were added and refluxing was continued for a further 3 h. The product was obtained by fractional distillation.
Yield: 6.00 g (22% of theoretical)

Step 3: 6-(2,6-dichloro-pyrimidine-4-carbonyl)-4-methyl-3H-benzoxazol-2-one

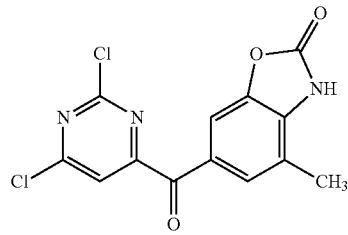 [SMILES: Cc1cc(C(=O)c2cc(Cl)nc(Cl)n2)cc2oc(=O)[nH]c12]

2.75 g (13.0 mmol) 2,6-dichloro-pyrimidine-4-carboxylic acid chloride, 1.94 g (13.0 mmol) 4-methyl-3H-benzoxazol-2-one and 6.93 g (52.0 mmol) aluminium trichloride were heated to 125° C. for 1.5 h with stirring. The mixture combined with ice water and the product precipitated as a solid was suction filtered, washed with water and dried i. vac.
Yield: 3.70 g (88% of theoretical)
ESI-MS: m/z=322 (M−H)$^−$
R$_t$(HPLC): 1.41 min (method B)

Intermediate 48

3-(3,4-dimethyl-2-oxo-2,3-dihydro-benzoxazole-6-carbonyl)-5-fluoro-benzonitrile

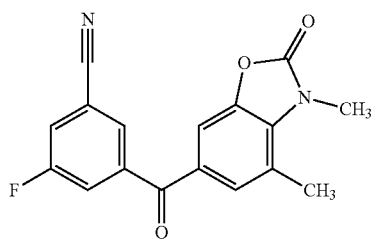 [SMILES: Cc1cc(C(=O)c2cc(F)cc(C#N)c2)cc2oc(=O)n(C)c12]

0.161 g (3.70 mmol) sodium hydride (55%, suspension in mineral oil) were added to 1.00 g (3.38 mmol) 3-fluoro-5-(4-methyl-2-oxo-2,3-dihydro-benzoxazole-6-carbonyl)-benzonitrile in 5 mL DMF at RT and stirred for 30 min at RT. Then 0.317 mL (5.00 mmol) iodomethane were added and the mixture was stirred for 1 h at RT. Then a further 0.1 mL iodomethane were added and stirring was continued at RT. After dilution with ice water the aqueous phase was extracted with EtOAc. The organic phase was washed with water, dried on sodium sulphate, filtered and evaporated down i. vac. The residue was purified by flash chromatography. The fractions containing the product were combined, evaporated down and dried i. vac.
Yield: 0.960 g (92% of theoretical)
ESI-MS: m/z=311 (M+H)$^+$
R$_t$(HPLC): 1.47 min (method B)

Intermediate 49

5-(6-chloro-pyrimidine-4-carbonyl)-7-methyl-1,3-dihydro-indol-2-one

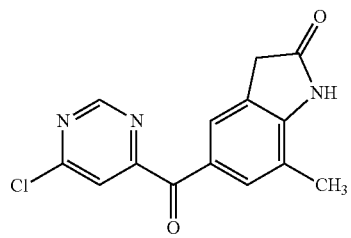 [SMILES: Cc1cc(C(=O)c2cc(Cl)ncn2)cc2c1NC(=O)C2]

Step 1: 7-methyl-1,3-dihydro-indol-2-one

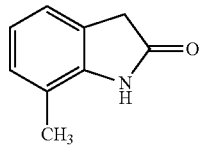

5.00 g (31.0 mmol) 7-methyl-1H-indol-2,3-dione in 18.1 mL (372 mmol) hydrazine hydrate were heated to 110° C. for 3 h. Then the reaction mixture was cooled, the precipitate formed was suction filtered and washed with water. The precipitate was suspended in water, acidified with conc. hydrochloric acid and stirred for 10 min. Then the reaction mixture was stirred for a further 30 min in the ice bath, the precipitate was suction filtered, washed with water and dried.
Yield: 1.60 g (35% of theoretical)
ESI-MS: m/z=148 (M+H)$^+$
$R_t$(HPLC): 2.72 min (method C)

Step 2: 5-(6-chloro-pyrimidine-4-carbonyl)-7-methyl-1,3-dihydro-indol-2-one

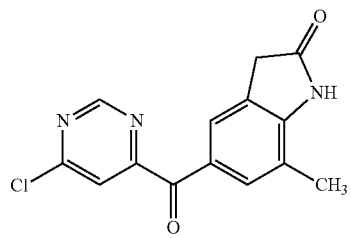 [SMILES: Cc1cc(C(=O)c2cc(Cl)ncn2)cc2c1NC(=O)C2]

1.92 g (10.9 mmol) 6-chloropyrimidine-4-carboxylic acid chloride, 1.60 g (10.9 mmol) 7-methyl-1,3-dihydro-indol-2-one and 7.33 g (55.0 mmol) aluminium trichloride were heated to 130° C. for 3 h with stirring. The mixture was combined first with ice water and then with EtOAc. The precipitate formed as black flakes was suction filtered and the phases were separated. The aqueous phase was extracted several times with EtOAc. The combined organic phases were dried on sodium sulphate, filtered and evaporated down i. vac.
Yield: 250 mg (8% of theoretical)
ESI-MS: m/z=288/90 (Cl) (M+H)$^+$
$R_t$(HPLC): 1.25 min (method B)

Intermediate 50

3-[6'-benzyloxy-4'-(3,4-dimethyl-2-oxo-2,3-dihydro-benzoxazole-6-carbonyl)-3,4,5,6-tetrahydro-2H-[1,2']bipyridinyl-4-yl]-7-methoxy-1,3,4,5-tetrahydro-benzo[d][1,3]diazepin-2-one

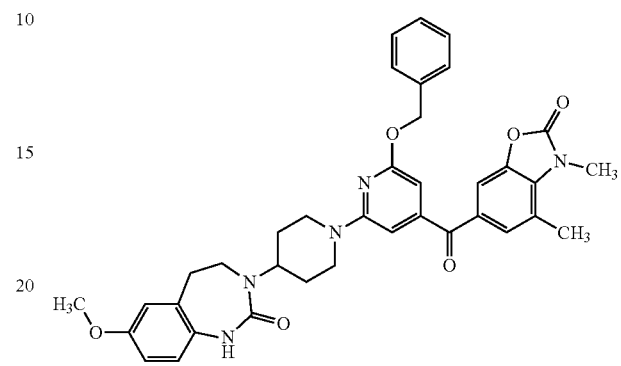

991 mg (3.60 mmol) 7-methoxy-3-piperidin-4-yl-1,3,4,5-tetrahydro-1,3-benzodiazepin-2-one and 500 mg (1.22 mmol) 6-(2-benzyloxy-6-chloro-pyridine-4-carbonyl)-3,4-dimethyl-3H-benzoxazol-2-one were combined in 10 mL NMP and stirred overnight at 120° C. The reaction mixture was purified by preparative HPLC-MS. The fractions containing the product were combined and evaporated down.
Yield: 130 mg (6% of theoretical)
ESI-MS: m/z=648 (M+H)$^+$
$R_t$(HPLC): 1.80 min (method B)

Intermediate 51

(6-chloro-pyrimidin-4-yl)-(1,7-dimethyl-1H-indazol-5-yl)-methanone

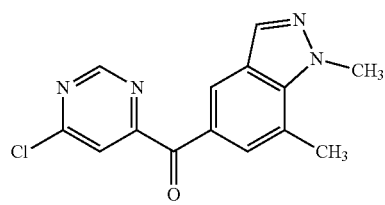 [SMILES: Cc1cc(C(=O)c2cc(Cl)ncn2)cc2cnn(C)c12]

Step 1: 5-bromo-1,7-dimethyl-1H-indazole

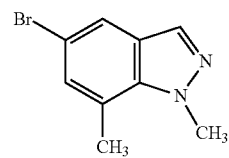

2.11 g (10.0 mmol) 5-bromo-7-methyl-1H-indazole and 1.20 g (10.7 mmol) potassium-tert-butoxide in 50 mL THF were stirred overnight with 0.700 mL (11.2 mmol) iodomethane at RT. Then the precipitate was filtered off and the filtrate was evaporated down i. vac. The residue was purified by flash chromatography.

Yield: 1.92 g (43% of theoretical)
ESI-MS: m/z=225/27 (M+H)$^+$
$R_t$(HPLC): 1.13 min (method E)

Step 2: (6-chloro-pyrimidin-4-yl)-(1,7-dimethyl-1H-indazol-5-yl)-methanone

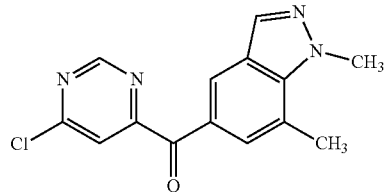 [SMILES: Cc1cc(C(=O)c2cc(Cl)ncn2)cc2cnn(C)c12]

Under an argon atmosphere 0.450 g (2.00 mmol) 5-bromo-1,7-dimethyl-1H-indazole in 25 mL THF were cooled to −75° C., combined with 1.40 mL (2.24 mmol) of a 1.6 molar n-butyllithium solution and stirred for 1 h at −75° C. Then 0.480 g (2.14 mmol) 6-chloro-pyrimidine-4-carboxylic acid methoxy-methyl-amide were added dropwise. The mixture was brought to 0° C. and stirred for a further hour. Then saturated sodium hydrogen carbonate solution was stirred in, the mixture was extracted with EtOAc, the organic phase was dried and evaporated down i. vac. The residue was triturated with DIPE, suction filtered and dried. The precipitate was purified by flash chromatography (Alox).

Yield: 100 mg (14% of theoretical)
$R_t$(HPLC): 1.46 min (method B)

Intermediate 52

(6-iodo-pyrimidin-4-yl)-(8-methyl-2,3-dihydro-benzo[1,4]dioxin-6-yl)-methanone

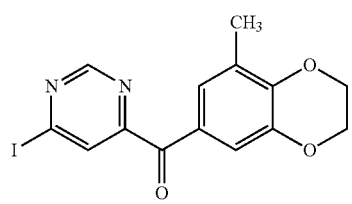 [SMILES: Cc1cc(C(=O)c2cc(I)ncn2)cc2c1OCCO2]

0.131 g (3.00 mmol) sodium hydride (55%, suspension in mineral oil) were added to 0.677 g (2.00 mmol) 4,6-diiodopyrimidine, 0.535 g (3.00 mmol) 8-methyl-2,3-dihydro-benzo[1,4]dioxin-6-carbaldehyde (US2005/256099) and 0.133 g (1.00 mmol) 1,3-dimethylimidazolium chloride in 10 mL THF and the mixture was refluxed for 4 h. Then the reaction mixture was mixed with ice water and extracted with EtOAc. The organic phase was dried on sodium sulphate, evaporated down i. vac. and the residue was purified by preparative HPLC-MS. The fractions containing the product were combined and the organic solvent was evaporated down i. vac. The residue was made alkaline with 1N aqueous sodium hydroxide solution and the grease precipitated was extracted with EtOAc. The organic phase was dried on sodium sulphate, filtered, evaporated down and dried i. vac.

Yield: 200 mg (26% of theoretical)
ESI-MS: m/z=383 (M+H)$^+$
$R_t$(HPLC): 4.19 min (method B)

Intermediate 53

(6-chloro-pyrimidin-4-yl)-(7-methyl-2,3-dihydro-benzofuran-5-yl)-methanone

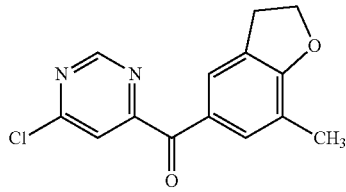 [SMILES: Cc1cc(C(=O)c2cc(Cl)ncn2)cc2c1OCC2]

Step 1: 7-methyl-2,3-dihydro-benzofuran-3-ol

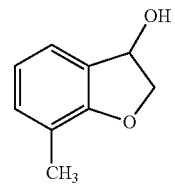

Under a nitrogen atmosphere 0.945 g (7.35 mmol) trimethylsulphoxonium chloride were placed in 20 mL THF, and 0.300 g (7.50 mmol) sodium hydride (55%, suspension in mineral oil) were added batchwise. The reaction mixture was refluxed for 2 h. Then 1.00 g (7.35 mmol) 2-hydroxy-3-methylbenzaldehyde in 20 mL THF were added dropwise to the reaction mixture and it was refluxed overnight. Then PE was added and the suspension obtained was filtered. The filtrate was evaporated down i. vac. and purified by flash chromatography. The fractions containing the product were combined and evaporated down.

Yield: 0.615 g (56% of theoretical)
ESI-MS: m/z=133 (M−H$_2$O+H)$^+$
$R_t$(HPLC): 1.09 min (method B)

Step 2: 7-methyl-2,3-dihydro-benzofuran

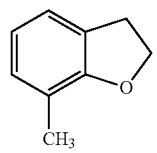

Under a nitrogen atmosphere 0.610 g (4.06 mmol) 7-methyl-2,3-dihydro-benzofuran-3-ol in 5 mL acetic acid were refluxed for 2 h with 770 μL (8.16 mmol) acetic anhydride. After cooling to RT, 60 mg palladium on charcoal (Pd/C 10%) were added and the mixture was hydrogenated for 3.5 h under a hydrogen atmosphere (3 bar). The catalyst was filtered off and the solvent was evaporated down.

Yield: 0.350 g (64% of theoretical)
ESI-MS: m/z=134 (M+)

Step 3: (6-chloro-pyrimidin-4-yl)-(7-methyl-2,3-dihydro-benzofuran-5-yl)-methanone

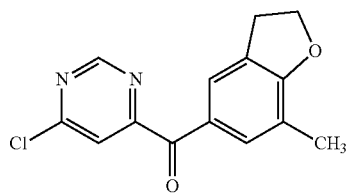 [SMILES: Cc1cc(C(=O)c2cc(Cl)ncn2)cc2c1OCC2]

0.396 g (2.24 mmol) 6-chloropyrimidine-4-carboxylic acid chloride and 0.328 g (2.46 mmol) aluminium trichloride in 10 mL DCM were stirred for 20 min at RT. Then 0.300 g (2.24 mmol) 7-methyl-2,3-dihydro-benzofuran in DCM were added dropwise to the reaction mixture and this was stirred for 1.5 h at RT. After the addition of water and DCM to the reaction mixture the phases were separated and the aqueous phase was extracted with DCM. The combined organic phases were washed with saturated aqueous sodium hydrogen carbonate solution, dried on sodium sulphate, filtered and evaporated down i. vac.

Yield: 0.550 g (62% of theoretical)
Purity: 70%
ESI-MS: m/z=275/277 (Cl) (M+H)+
R$_f$(HPLC): 1.54 min (method B)

Intermediate 54

(6-chloro-pyrimidin-4-yl)-(1,3,3,7-tetramethyl-2,3-dihydro-1H-indol-5-yl)-methanone

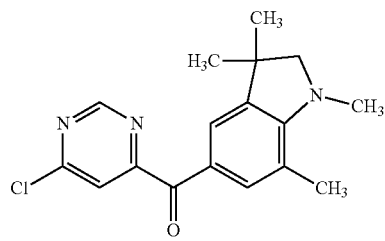 [SMILES: Cc1cc(C(=O)c2cc(Cl)ncn2)cc2c1N(C)CC2(C)C]

Step 1: 1,3,3,7-tetramethyl-1,3-dihydro-indol-2-one

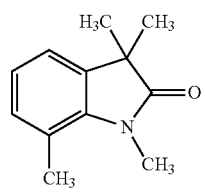

2.00 g (50.0 mmol) sodium hydride (55%, suspension in mineral oil) were added at 0° C. to 2.34 g (3.58 mmol) 7-methyl-1,3-dihydro-indol-2-one in 20 mL DMF and the mixture was stirred for 30 min. Then 3.00 mL (48.2 mmol) iodomethane were added and the mixture was stirred for 2 h at RT. Ice water was added to the reaction mixture, then it was extracted with DCM and aqueous sodium hydrogen carbonate solution. The organic phase was dried on sodium sulphate, filtered and evaporated down i. vac. The residue was purified by preparative HPLC-MS. The fractions containing the product were combined and freeze-dried.

Yield: 1.300 g (43% of theoretical)
Purity: 90%
ESI-MS: m/z=190 (M+H)+
R$_f$(HPLC): 1.41 min (method B)

Step 2: 1,3,3,7-tetramethyl-2,3-dihydro-1H-indole

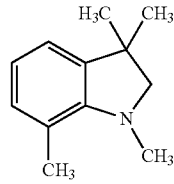

Under an argon atmosphere 5.71 mL of a 1 molar lithium aluminium hydride solution in THF were added dropwise to 600 mg (2.85 mmol) 1,3,3,7-tetramethyl-1,3-dihydro-indol-2-one in 20 mL THF. The reaction mixture was stirred for 2.5 h at 60° C. and then cooled to RT. While cooling with the ice bath, saturated, aqueous sodium sulphate solution was slowly added dropwise and the resulting suspension was filtered through Celite. The filtrate was combined with EtOAc and saturated sodium chloride solution. The organic phase was dried on sodium sulphate, filtered and the filtrate was evaporated down.

Yield: 520 mg (99% of theoretical)
Purity: 95%
ESI-MS: m/z=176 (M+H)+

Step 3: (6-chloro-pyrimidin-4-yl)-(1,3,3,7-tetramethyl-2,3-dihydro-1H-indol-5-yl)-methanone

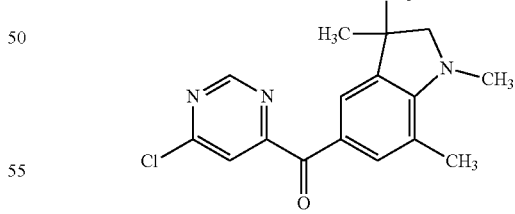

Under an argon atmosphere 0.473 g (2.67 mmol) 6-chloropyrimidine-4-carboxylic acid chloride and 0.427 g (3.20 mmol) aluminium trichloride were stirred in 20 mL DCM for 30 min. Then 0.520 g (2.67 mmol) 1,3,3,7-tetramethyl-2,3-dihydro-1H-indole in DCM were added dropwise to the reaction mixture and it was stirred for 45 min at RT, then for 45 min at 40° C. Next, the reaction mixture was decomposed with ice water/sodium hydroxide solution, extracted with DCM and the organic phase was evaporated down i. vac. The residue was taken up in MeOH and purified by preparative HPLC-MS. The fractions containing the product were combined and freeze-dried.

Yield: 170 mg (20% of theoretical)
ESI-MS: m/z=316 (M+H)+
$R_t$(HPLC): 1.70 min (method B)

Intermediate 55

Tert-butyl[4'-(3,4-dimethyl-2-oxo-2,3-dihydro-benzoxazole-6-carbonyl)-4-(2-oxo-2,3-dihydro-imidazo[4,5-b]pyridin-1-yl)-3,4,5,6-tetrahydro-2H-[1,2']bipyridinyl-6'-yl]-methyl-carbamate

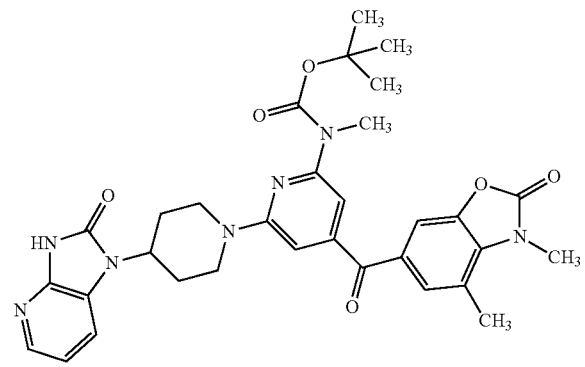 [SMILES: Cc1cc(C(=O)c2cc(N3CCC(n4c(=O)[nH]c5ncccc54)CC3)nc(N(C)C(=O)OC(C)(C)C)c2)cc2oc(=O)n(C)c12]

Under an argon atmosphere 13 mg (0.96 mmol) tert-butyl methyl-carbamate, 11 mg (0.019 mmol) Xantphos, 8.8 mg (0.010 mmol) $Pd_2 dba_3$ and 47 mg (0.15 mmol) caesium carbonate were added to 50 mg (0.10 mmol) 1-[6'-chloro-4'-(3,4-dimethyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one in 1.00 mL dioxane and the mixture was refluxed for 15 h with stirring. The reaction mixture was evaporated down i. vac. and the residue obtained was used in the next step without further purification.

Yield: 59 mg (quantitative)
$R_t$(HPLC): 1.70 min (method B)

Intermediate 56

Tert-butyl[4'-(3,4-dimethyl-2-oxo-2,3-dihydro-benzoxazole-6-carbonyl)-4-(7-methoxy-2-oxo-1,2,4,5-tetrahydro-benzo[d][1,3]diazepin-3-yl)-3,4,5,6-tetrahydro-2H-[1,2']bipyridinyl-6'-yl]-carbamate

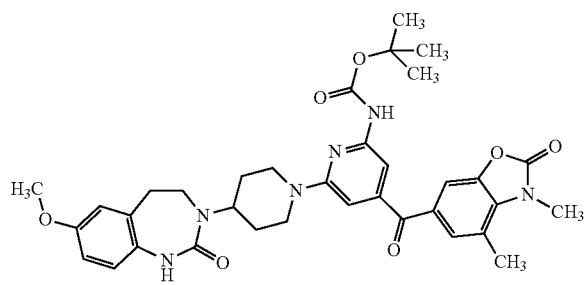

Under an argon atmosphere 31 mg (0.26 mmol) tert-butyl carbamate, 10 mg (0.017 mmol) Xantphos, 8.0 mg (0.009 mmol) $Pd_2 dba_3$ and 42 mg (0.13 mmol) caesium carbonate were added to 50 mg (0.10 mmol) 3-[6'-chloro-4'-(3,4-dimethyl-2-oxo-2,3-dihydro-benzoxazole-carbonyl)-3,4,5,6-tetrahydro-2H-[1,2']bipyridinyl-4-yl]-7-methoxy-1,3,4,5-tetrahydro-benzo[d][1,3]diazepin-2-one in 1.0 mL dioxane and the mixture was refluxed for 15 h with stirring. The reaction mixture was evaporated down i. vac. and the residue obtained was used in the next step without further purification.

Yield: 57 mg (quantitative)
$R_t$(HPLC): 1.72 min (method B)

Intermediate 57

(6-chloro-pyrimidin-4-yl)-phenyl-methanone

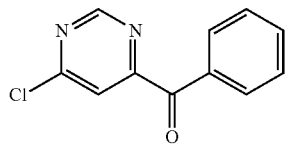 [SMILES: O=C(c1ccccc1)c1cc(Cl)ncn1]

250 mg (1.68 mmol) 4,6-dichloropyrimidine, 258 mg (2.52 mmol) benzaldehyde and 152 mg (0.56 mmol) 1,3-dimethyl-3H-benzimidazol-1-ium-iodide (Chem. Pharm. Bull. 1990, 1147-52) in 3.0 mL THF were stirred at RT. Then 121 mg (2.52 mmol) 50% sodium hydride (suspension in mineral oil) was added and the reaction mixture was stirred for 30 min at RT and then refluxed. The reaction mixture was evaporated down i. vac., the residue was mixed with ice water and the product was extracted with DCM. The organic phases were combined, dried and filtered through silica gel. The filtrate was evaporated down i. vac. and the residue reacted further as the crude product.

Yield: 300 mg (39% of theoretical)
Purity: 48%
ESI-MS: m/z=219/221 (Cl) (M+H)+
$R_f$: 0.5 (silica gel; cyclohexane/EtOAc 5/1)

Intermediate 58

6-[4-(7-methoxy-2-oxo-1,2,4,5-tetrahydro-benzo[d][1,3]diazepin-3-yl)-piperidin-1-yl]-pyrimidine-4-carboxylic acidmethoxy-methyl-amide

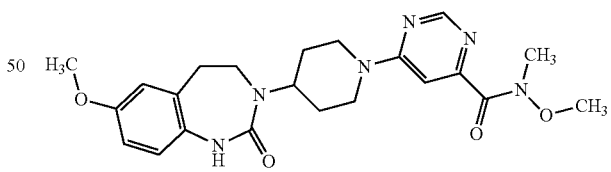

0.20 g (0.99 mmol) 6-chloro-pyrimidine-4-carboxylic acidmethoxy-methyl-amide, 0.28 g 7-methoxy-3-piperidin-4-yl-1,3,4,5-tetrahydro-1,3-benzodiazepin-2-one and 0.20 mL (1.16 mmol) DIPEA in 1.5 mL THF were heated to 120° C. in the microwave for 30 min. The mixture was diluted with water and extracted with DCM. The combined organic phases were dried on sodium sulphate, filtered and evaporated down i. vac. The residue was triturated with diethyl ether, suction filtered and dried.

Yield: 290 mg (66% of theoretical)
ESI-MS: m/z=441 (M+H)+
$R_t$(HPLC): 1.06 min (method B)

Intermediate 59

5-(6-chloro-pyrimidine-4-carbonyl)-1,3-dimethyl-1,3-dihydro-benzimidazol-2-one

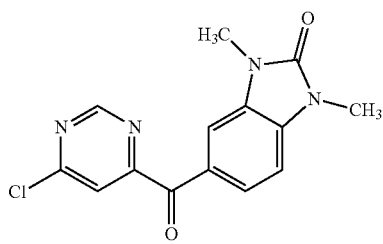 [SMILES: Cn1c(=O)n(C)c2cc(C(=O)c3cc(Cl)ncn3)ccc21]

Step 1: 5-(6-chloro-pyrimidine-4-carbonyl)-1,3-dihydro-benzimidazol-2-one

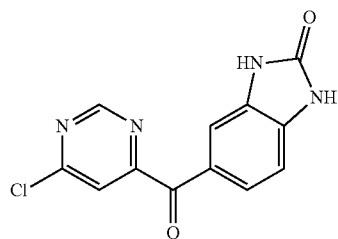 [SMILES: O=C(c1ccc2[nH]c(=O)[nH]c2c1)c1cc(Cl)ncn1]

3.00 g (17.0 mmol) 6-chloro-pyrimidine-4-carboxylic acid chloride, 11.1 g (83.2 mmol) aluminium trichloride and 2.40 g (17.4 mmol) benzimidazole were stirred for 3 h at 130° C. Then the reaction mixture was combined with DCM, water and 15% (w/v) aqueous potassium carbonate solution and the phases were separated. The aqueous phase was extracted several times with DCM. The combined organic phases were combined, dried on magnesium sulphate, filtered and evaporated down i. vac. The residue was triturated with DIPE and isopropanol, suction filtered and dried i. vac.

Yield: 570 mg (12% of theoretical)
ESI-MS: m/z=273 (M−H)⁻
R$_f$: 0.61 (silica gel; DCM/Cyc/MeOH/NH$_4$OH=70/15/15/2)

Step 2: 5-(6-chloro-pyrimidine-4-carbonyl)-1,3-dimethyl-1,3-dihydro-benzimidazol-2-one

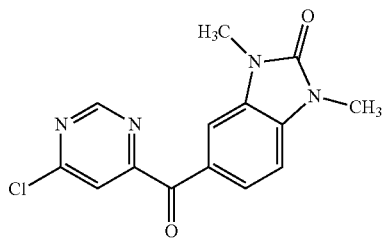 [SMILES: Cn1c(=O)n(C)c2cc(C(=O)c3cc(Cl)ncn3)ccc21]

570 mg (2.08 mmol) 5-(6-chloro-pyrimidine-4-carbonyl)-1,3-dihydro-benzimidazol-2-one in 10.0 mL DMF were combined at 0° C. with 190 mg (4.35 mmol) sodium hydride (55%, suspension in mineral oil). After 1 h stirring at 0° C., 0.300 mL (4.73 mmol) iodomethane were added. The reaction was allowed to come up to RT and stirred overnight. Then iodomethane was added again and the mixture was stirred for a further 2 h at RT. Then the reaction mixture was added to water and stirred for 30 min. The precipitate formed was suction filtered and dried i. vac.

Yield: 400 mg (64% of theoretical)
ESI-MS: m/z=303/305 (Cl) (M+H)⁺
R$_f$: 0.84 (silica gel; DCM/Cyc/MeOH/NH$_4$OH=70/15/15/2)

Preparation of the End Compounds

Example 1

1-{1-[6-(4-methyl-2-oxo-2,3-dihydrobenzoxazole-6-carbonyl)-pyrimidin-4-yl]-piperidin-4-yl}-1,3-dihydro-imidazo[4,5-b]pyridin-2-one

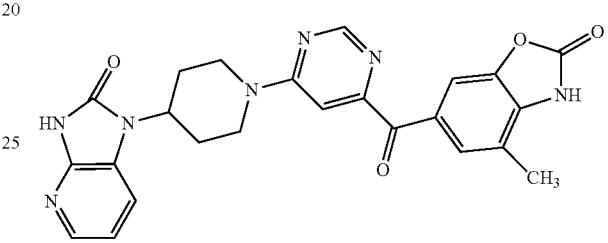

64 mg (0.22 mmol) 1-piperidin-4-yl-1,3-dihydroimidazo[4,5-b]pyridin-2-one-dihydrochloride, 64 mg (0.221 mmol) 6-(6-chloropyrimidine-4-carbonyl)-4-methyl-3H-benzoxazol-2-one and 0.174 mL (1.00 mmol) DIPEA were stirred overnight in 2.0 mL DMF at RT. The mixture was purified by preparative HPLC-MS. The fractions containing the product were combined, the organic solvent was eliminated i. vac. and the aqueous phase remaining was neutralised with 4N aqueous NaOH solution. The precipitate was suction filtered, washed with water and dried in the CAD.

Yield: 56 mg (54% of theoretical)
ESI-MS: m/z=472 (M+H)⁺
R$_t$(HPLC): 2.37 min (method C)

Example 2

7-methoxy-3-{1-[6-(4-methyl-2-oxo-2,3-dihydrobenzoxazole-6-carbonyl)-pyrimidin-4-yl]-piperidin-4-yl}-1,3,4,5-tetrahydro-1,3-benzodiazepin-2-one

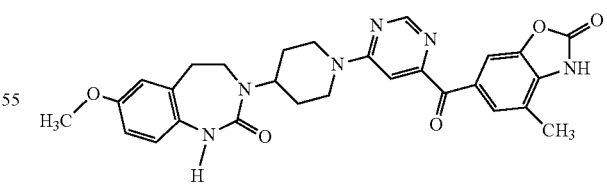

275 mg (1.00 mmol) 7-methoxy-3-piperidin-4-yl-1,3,4,5-tetrahydro-1,3-benzodiazepin-2-one, 289 mg (1.00 mmol) 6-(6-chloropyrimidine-4-carbonyl)-4-methyl-3H-benzoxazol-2-one and 0.348 mL (2.00 mmol) DIPEA were stirred overnight in 10 mL DMF at RT. The mixture was purified by preparative HPLC-MS. The fractions containing the product were combined, the organic solvent was eliminated i. vac. and the aqueous phase remaining was neutralised with 4N aque-

Example 3

4-methyl-6-{6-[4-(5-oxo-3-phenyl-4,5-dihydro-1,2,4-triazol-1-yl)-piperidin-1-yl]-pyrimidine-4-carbonyl}-3H-benzoxazol-2-one

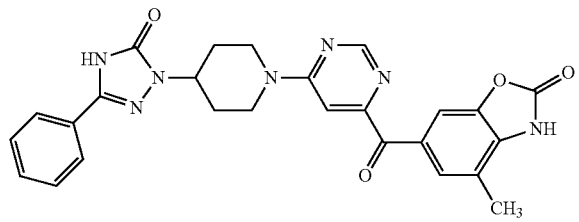 [SMILES: Cc1cc(C(=O)c2cc(N3CCC(n4nc(-c5ccccc5)[nH]c4=O)CC3)ncn2)cc2oc(=O)[nH]c12]

378 mg (1.00 mmol) 5-phenyl-2-piperidin-4-yl-2,4-dihydro-1,2,4-triazol-3-one, 289 mg (1.00 mmol) 6-(6-chloropyrimidine-4-carbonyl)-4-methyl-3H-benzoxazol-2-one and 0.348 mL (2.0 mmol) DIPEA were stirred overnight in 10 mL DMF at RT. The mixture was purified by preparative HPLC-MS. The fractions containing the product were combined, the organic solvent was eliminated i. vac. and the aqueous phase remaining was neutralised with a 4N aqueous NaOH solution. The precipitate was suction filtered, washed with water and dried in the CAD.

Yield: 280 mg (56% of theoretical)
ESI-MS: m/z=498 (M+H)⁺
R$_f$(HPLC)=2.72 min (method C)

Example 4

3-{1-[6-(4-methyl-2-oxo-2,3-dihydro-benzoxazole-6-carbonyl)-pyrimidin-4-yl]-piperidin-4-yl}-1,3-dihydroimidazo[4,5-c]quinolin-2-one

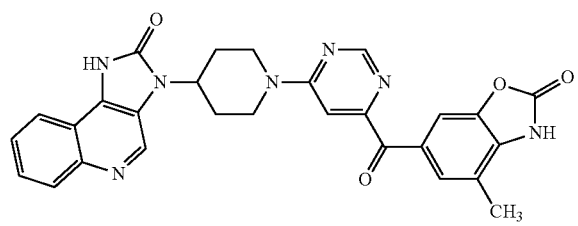 [SMILES: Cc1cc(C(=O)c2cc(N3CCC(n4c(=O)[nH]c5c6ccccc6ncc54)CC3)ncn2)cc2oc(=O)[nH]c12]

134 mg (0.500 mmol) 3-piperidin-4-yl-1,3-dihydroimidazo[4,5-c]quinolin-2-one, 145 mg (0.500 mmol) 6-(6-chloropyrimidine-4-carbonyl)-4-methyl-3H-benzoxazol-2-one and 0.174 mL (1.00 mmol) DIPEA were stirred overnight in 5 mL DMF at RT. The mixture was purified by preparative HPLC-MS. The fractions containing the product were combined, the organic solvent was eliminated i. vac. and the aqueous phase remaining was neutralised with a 4N aqueous NaOH solution. The precipitate was suction filtered, washed with water and dried in the CAD.

Yield: 100 mg (38% of theoretical)
ESI-MS: m/z=522 (M+H)⁺
R$_f$(HPLC)=1.99 min (method C)

Example 5

1-{1-[6-(3,4-dimethyl-2-oxo-2,3-dihydro-benzoxazole-6-carbonyl)-pyrimidin-4-yl]-piperidin-4-yl}-1,3-dihydro-imidazo[4,5-b]pyridin-2-one

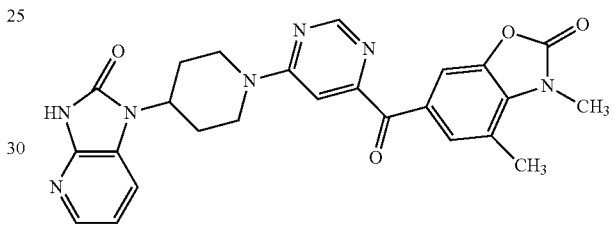

72.8 mg (0.25 mmol) 1-piperidin-4-yl-1,3-dihydroimidazo[4,5-b]pyridin-2-one-dihydrochloride, 75 mg (0.25 mmol) 6-(6-chloropyrimidine-4-carbonyl)-3,4-dimethyl-3H-benzoxazol-2-one and 0.22 mL (1.25 mmol) DIPEA were stirred in 2 mL DMF for 2 h at RT. The mixture was purified by preparative HPLC-MS. The fractions containing the product were combined, the organic solvent was eliminated i. vac. and the aqueous phase remaining was neutralised with a 4N aqueous NaOH solution. The precipitate was suction filtered, washed with water and dried in the CAD.

Yield: 71 mg (59% of theoretical)
ESI-MS: m/z=486 (M+H)⁺
R$_f$(HPLC) 2.67 min (method C)

Example 6

3-{1-[6-(3,4-dimethyl-2-oxo-2,3-dihydro-benzoxazole-6-carbonyl)-pyrimidin-4-yl]-piperidin-4-yl}-7-methoxy-1,3,4,5-tetrahydro-1,3-benzodiazepin-2-one

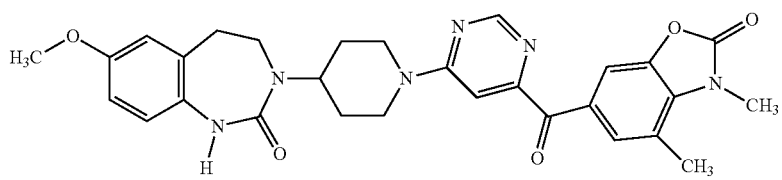

63.3 mg (0.23 mmol) 7-methoxy-3-piperidin-4-yl-1,3,4,5-tetrahydro-1,3-benzodiazepin-2-one, 70 mg (0.23 mmol) 6-(6-chloropyrimidine-4-carbonyl)-3,4-dimethyl-3H-benzoxazol-2-one and 0.08 mL (0.46 mmol) DIPEA were stirred in 2 mL of DMF for 2 h at RT. The mixture was diluted with methanol. The precipitate was suction filtered, washed with methanol and diethyl ether and dried in the CAD.

Yield: 85 mg (68% of theoretical)
ESI-MS: m/z=543 (M+H)$^+$
$R_t$(HPLC) 3.2 min (method C)

Example 7

1-{1-[6-(3,4-dimethyl-benzoyl)-pyrimidin-4-yl]-piperidin-4-yl}-1,3-dihydro-imidazo[4,5-b]-pyridin-2-one

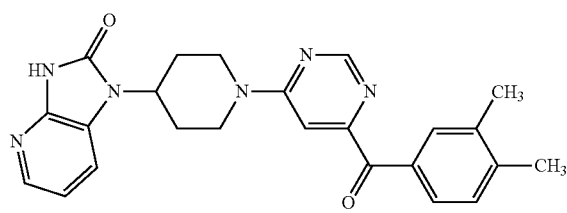 [SMILES: Cc1ccc(C(=O)c2cc(N3CCC(n4c(=O)[nH]c5ncccc54)CC3)ncn2)cc1C]

150 mg (0.515 mmol) 1-piperidin-4-yl-1,3-dihydroimidazo[4,5-b]pyridin-2-one-dihydrochloride, 150 mg (0.527 mmol) (6-chloro-pyrimidin-4-yl)-(3,4-dimethyl-phenyl)-methanone and 0.300 mL (1.74 mmol) DIPEA were stirred overnight in 5.0 mL DMF at RT. The reaction mixture was evaporated down i. vac., the residue was mixed with water and stirred for 10 min. The precipitate was suction filtered and purified by preparative HPLC-MS. The fractions containing the product were combined and freeze-dried.

Yield: 125 mg (57% of theoretical)
ESI-MS: m/z=429 (M+H)$^+$
$R_f$: 0.52 (silica gel, DCM/Cyc/MeOH/NH$_4$OH=70/15/15/2)

Example 8

1-{1-[6-(3,4-diethyl-benzoyl)-pyrimidin-4-yl]-piperidin-4-yl}-1,3-dihydro-imidazo[4,5-b]-pyridin-2-one

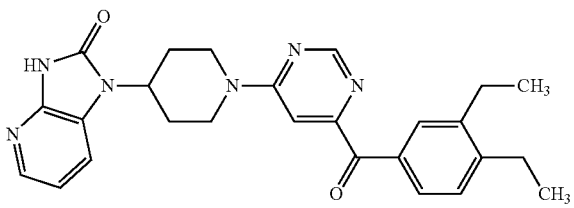 [SMILES: CCc1ccc(C(=O)c2cc(N3CCC(n4c(=O)[nH]c5ncccc54)CC3)ncn2)cc1CC]

150 mg (0.515 mmol) 1-piperidin-4-yl-1,3-dihydroimidazo[4,5-b]pyridin-2-one-dihydrochloride, 150 mg (0.546 mmol) (6-chloro-pyrimidin-4-yl)-(3,4-diethyl-phenyl)-methanone and 0.300 mL (1.74 mmol) DIPEA were stirred overnight in 5.0 mL DMF at RT. The reaction mixture was evaporated down i. vac., the residue was mixed with water and stirred for another 10 min. The precipitate was suction filtered and purified by preparative HPLC-MS. The fractions containing the product were combined and freeze-dried.

Yield: 125 mg (53% of theoretical)
ESI-MS: m/z=457 (M+H)$^+$
$R_f$: 0.53 (silica gel, DCM/Cyc/MeOH/NH$_4$OH=70/15/15/2)

Example 9

3-[1-(6-benzoyl-pyrimidin-4-yl)-piperidin-4-yl]-7-methoxy-1,3,4,5-tetrahydro-benzo[d]-[1,3]diazepin-2-one

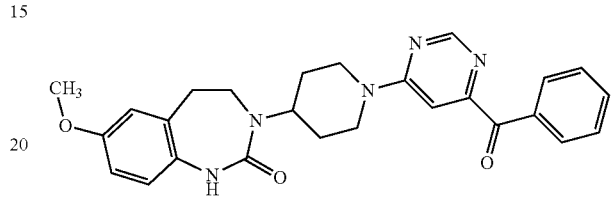

Under a nitrogen atmosphere 100 mg (0.227 mmol) 6-[4-(7-methoxy-2-oxo-1,2,4,5-tetrahydro-benzo[d][1,3]diazepin-3-yl)-piperidin-1-yl]-pyrimidine-4-carboxylic acid-methoxy-methyl-amide were cooled to −10° C. in 5.00 mL THF and combined with 0.400 mL (0.400 mmol) phenylmagnesium bromide solution (1M in THF). The mixture was stirred for 1 h at −10° C. and then heated to 0° C. Then 0.200 mL (0.200 mmol) phenylmagnesium bromide solution (1M in THF) were added, the mixture was stirred for 1 h and then heated to RT. The reaction mixture was combined with a saturated ammonium chloride solution and extracted with EtOAc. The combined organic phases were dried and evaporated down i. vac. The residue was purified by preparative HPLC-MS. The fractions containing the product were combined and evaporated down by half. The precipitate formed was suction filtered and dried.

Yield: 19 mg (18% of theoretical)
ESI-MS: m/z=548 (M+H)$^+$
$R_t$(HPLC): 3.24 min (method C)

Example 10

1-{1-[6-(3,4-dichloro-benzoyl)-pyrimidin-4-yl]-piperidin-4-yl}-1,3-dihydro-imidazo[4,5-b]-pyridin-2-one

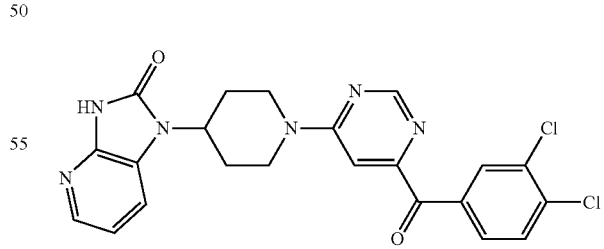

150 mg (0.515 mmol) 1-piperidin-4-yl-1,3-dihydroimidazo[4,5-b]pyridin-2-one-dihydrochloride, 150 mg (0.522 mmol) (6-chloro-pyrimidin-4-yl)-(3,4-dichloro-phenyl)-methanone and 0.300 mL (1.74 mmol) DIPEA were stirred overnight in 5.0 mL DMF at RT. The reaction mixture was evaporated down i. vac., the residue was mixed with water and stirred for another 10 min. Then the precipitate was suction

Example 11

3-[4'-(3,4-dimethyl-2-oxo-2,3-dihydro-benzoxazole-6-carbonyl)-6'-oxo-3,4,5,6.1'.6'-hexa-hydro-2H-[1,2']bipyridinyl-4-yl]-7-methoxy-1,3,4,5-tetrahydro-benzo[d][1,3]diazepin-2-one

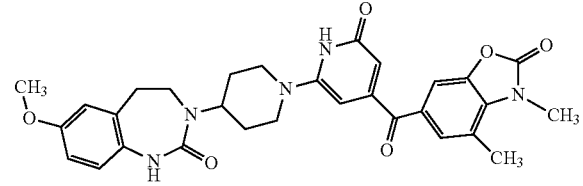

30 mg palladium on charcoal (Pd/C 10%), 30 mL THF and 30 mL DCM were added to 0.13 g (0.20 mmol) 3-[6'-benzyloxy-4'-(3,4-dimethyl-2-oxo-2,3-dihydro-benzoxazole-6-carbonyl)-3,4,5,6-tetrahydro-2H-[1,2']bipyridinyl-4-yl]-7-methoxy-1,3,4,5-tetrahydro-benzo[d][1,3]diazepin-2-one in 20 mL MeOH and the mixture was hydrogenated for 1.5 h under a hydrogen atmosphere. After filtration of the reaction mixture the solvent was evaporated down i. vac. The residue was purified by preparative HPLC-MS. The fractions containing the product were combined and freeze-dried.
Yield: 3 mg (3% of theoretical)
ESI-MS: m/z=558 (M+H)$^+$
$R_t$(HPLC): 1.35 min (method B)

Example 12

7-methoxy-3-{1-[5-(4-methyl-2-oxo-2,3-dihydro-benzoxazole-6-carbonyl)-pyridazin-3-yl]-piperidin-4-yl}-1,3,4,5-tetrahydro-benzo[d][1,3]diazepin-2-one

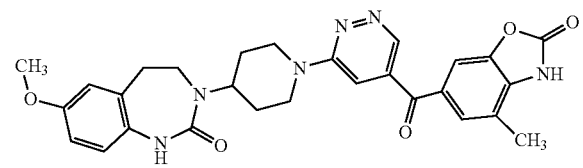 [SMILES: COc1ccc2c(c1)CCN(C1CCN(c3cc(C(=O)c4cc(C)c5[nH]c(=O)oc5c4)cnn3)CC1)C(=O)N2]

0.13 g (0.049 mmol) 3-(1-{5-[hydroxy-(4-methyl-2-oxo-2,3-dihydro-benzoxazol-6-yl)-methyl]-pyridazin-3-yl}-piperidin-4-yl)-7-methoxy-1,3,4,5-tetrahydro-benzo[d][1,3]diazepin-2-one and 1.0 g (12 mmol) manganese(IV)-oxide in 100 mL DCM were stirred overnight at RT. Then 500 mg manganese(IV)-oxide were added and the mixture was stirred for a further 20 h. Then the reaction mixture was combined with 10 mL MeOH, filtered off and evaporated down. The residue was purified by preparative HPLC-MS. The fractions containing the product were combined and freeze-dried.
Yield: 5 mg (17% of theoretical)
ESI-MS: m/z=529 (M+H)$^+$
$R_t$(HPLC): 1.23 min (method G)

filtered and purified by preparative HPLC-MS. The fractions containing the product were combined and freeze-dried.
Yield: 125 mg (52% of theoretical)
ESI-MS: m/z=469/471/473 (2 Cl) (M+H)$^+$
$R_f$: 0.67 (silica gel, DCM/Cyc/MeOH/NH$_4$OH=70/15/15/2)

Example 13

7-methoxy-3-{1-[2-methyl-6-(4-methyl-2-oxo-2,3-dihydro-benzoxazole-6-carbonyl)-pyrimidin-4-yl]-piperidin-4-yl}-1,3,4,5-tetrahydro-benzo[d][1,3]diazepin-2-one

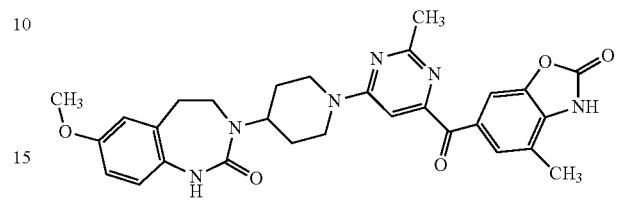

83 mg (0.30 mmol) 7-methoxy-3-piperidin-4-yl-1,3,4,5-tetrahydro-1,3-benzodiazepin-2-one, 91 mg (0.30 mmol) 6-(6-chloro-2-methyl-pyrimidine-4-carbonyl)-4-methyl-3H-benzoxazol-2-one and 0.11 mL (0.60 mmol) DIPEA were stirred together in 3 mL DMF overnight at RT. Then the reaction mixture was purified by preparative HPLC-MS. The fractions containing the product were combined and the organic solvent was evaporated down. The residue was neutralised with 4N aqueous sodium hydroxide solution, the precipitate formed was suction filtered, washed with water and dried i. vac.
Yield: 115 mg (71% of theoretical)
ESI-MS: m/z=543 (M+H)$^+$
$R_t$(HPLC): 1.33 min (method B)

Example 14

3-[5'-(3,4-dimethyl-2-oxo-2,3-dihydro-benzoxazole-6-carbonyl)-1'-oxy-3,4,5,6-tetrahydro-2H-[1.3']bipyridinyl-4-yl]-7-methoxy-1,3,4,5-tetrahydro-benzo[d][1,3]diazepin-2-one

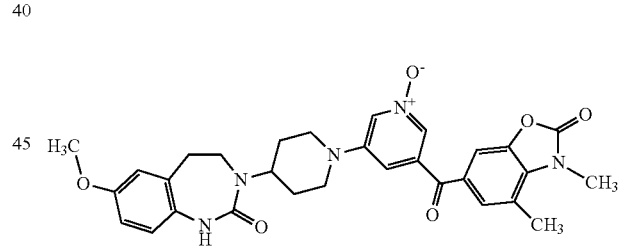

Under an argon atmosphere 275 mg (1.00 mmol) 7-methoxy-3-piperidin-4-yl-1,3,4,5-tetrahydro-benzo[d][1,3]diazepin-2-one, 363 mg (1.00 mmol) 6-(5-bromo-1-oxy-pyridin-3-carbonyl)-3,4-dimethyl-3H-benzoxazol-2-one and 489 mg (1.50 mmol) caesium carbonate were combined in 16 mL dioxane, then mixed with 63 mg (0.10 mmol) BINAP and 23 mg (0.10 mmol) palladium(II)acetate and stirred for 6 h at 120° C. The mixture was evaporated down i. vac. and the residue was purified by preparative HPLC-MS. The fractions containing the product were combined and the acetonitrile was eliminated i. vac. The aqueous residue was made basic with 1N aqueous sodium hydroxide solution, the precipitate formed was suction filtered and washed with water and dried i. vac.
Yield: 35 mg (6% of theoretical)
ESI-MS: m/z=558 (M+H)$^+$
$R_t$(HPLC): 1.38 min (method B)

Example 15

4'-(3,4-dimethyl-2-oxo-2,3-dihydro-benzoxazole-6-carbonyl)-4-(2-oxo-2,3-dihydro-imidazo[4,5-b]pyridin-1-yl)-3,4,5,6-tetrahydro-2H,1'H-[1,2']bipyridinyl-6'-one

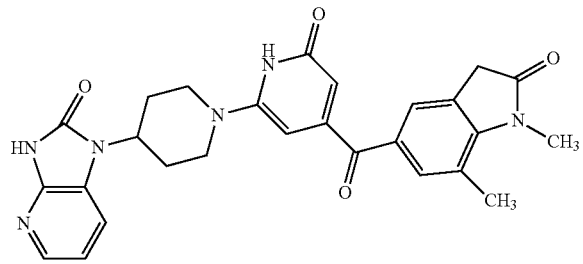 [SMILES: Cc1cc(C(=O)c2cc(N3CCC(n4c(=O)[nH]c5ncccc54)CC3)[nH]c(=O)c2)cc2c1N(C)C(=O)C2]

20 mg (0.034 mmol) 1-[6'-benzyloxy-4'-(3,4-dimethyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one in 0.10 g (0.87 mmol) pyridine hydrochloride were kept in a melt for 4 min. After cooling the mixture was purified by preparative HPLC-MS. The fractions containing the product were combined and freeze-dried.

Yield: 11 mg (65% of theoretical)

ESI-MS: m/z=501 (M+H)$^+$ $R_t$(HPLC): 1.17 min (method B)

Example 16

3-{1-[2-chloro-6-(4-methyl-2-oxo-2,3-dihydro-benzoxazole-6-carbonyl)-pyrimidin-4-yl]-piperidin-4-yl}-7-methoxy-1,3,4,5-tetrahydro-benzo[d][1,3]diazepin-2-one

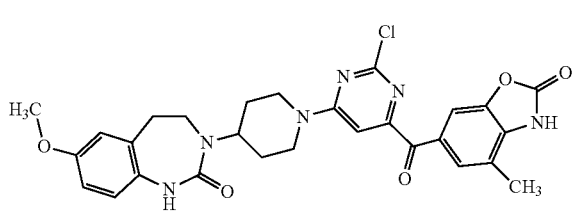 [SMILES: COc1ccc2c(c1)CCN(C1CCN(c3cc(C(=O)c4cc(C)c5[nH]c(=O)oc5c4)nc(Cl)n3)CC1)C(=O)N2]

275 mg (1.00 mmol) 7-methoxy-3-piperidin-4-yl-1,3,4,5-tetrahydro-1,3-benzodiazepin-2-one, 324 mg (1.00 mmol) 6-(2,6-dichloro-pyrimidine-4-carbonyl)-4-methyl-3H-benzoxazol-2-one and 0.348 mL (2.00 mmol) DIPEA in 5.00 mL DMF were stirred overnight at RT. Then the mixture was purified by preparative HPLC-MS. The fractions containing the product were combined and the organic solvent was evaporated down i. vac. The residue was neutralised with 4N aqueous sodium hydroxide solution and the precipitate formed was suction filtered, washed with water and dried.

Yield: 180 mg (32% of theoretical)

ESI-MS: m/z=563 (M+H)$^+$ $R_t$(HPLC): 1.15 min (method B)

Example 17

7-methoxy-3-{1-[6-methoxy-5-(4-methyl-2-oxo-2,3-dihydro-benzoxazole-6-carbonyl)-pyridazin-3-yl]-piperidin-4-yl}-1,3,4,5-tetrahydro-benzo[d][1,3]diazepin-2-one

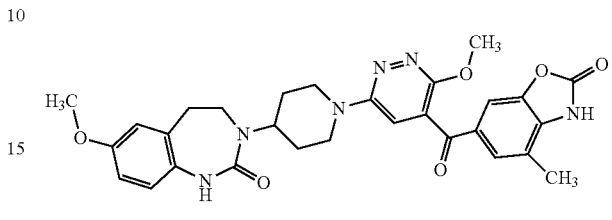

0.13 g (0.11 mmol) (purity 50%) 3-{1-[6-chloro-5-(4-methyl-2-oxo-2,3-dihydro-benzoxazole-6-carbonyl)-pyridazin-3-yl]-piperidin-4-yl}-7-methoxy-1,3,4,5-tetrahydro-benzo[d][1,3]-diazepin-2-one and 0.050 mL (0.29 mmol) DIPEA were heated with 1 mL MeOH in a microwave container for 2 h at 125° C. Then potassium-tert-butoxide was added and the mixture was stirred for 48 h at RT. Next, the reaction mixture was heated for a further 6 h and then it was neutralised with acetic acid and purified by preparative HPLC-MS.

Yield: 13 mg (20% of theoretical)

$R_t$(HPLC): 2.14 min (method H)

Example 18

3-{1-[6-(3,4-dimethyl-2-oxo-2,3-dihydro-benzoxazole-6-carbonyl)-2-methyl-pyrimidin-4-yl]-piperidin-4-yl}-7-methoxy-1,3,4,5-tetrahydro-benzo[d][1,3]diazepin-2-one

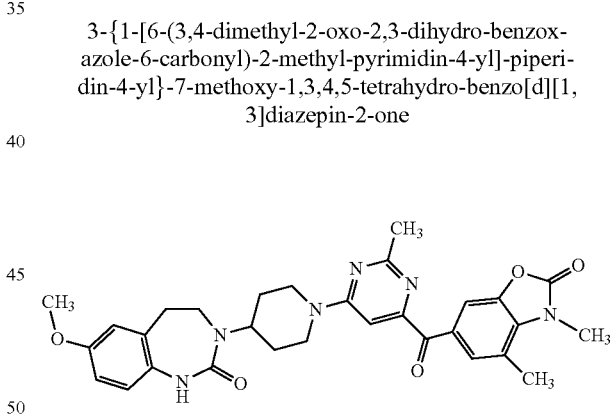

83 mg (0.30 mmol) 7-methoxy-3-piperidin-4-yl-1,3,4,5-tetrahydro-1,3-benzodiazepin-2-one, 95 mg (0.30 mmol) 6-(6-chloro-2-methyl-pyrimidine-4-carbonyl)-3,4-dimethyl-3H-benzoxazol-2-one and 0.11 mL (0.60 mmol) DIPEA were stirred overnight in 3 mL DMF at RT. Then the reaction mixture was purified by preparative HPLC-MS. The fractions containing the product were combined and the organic solvent was evaporated down i. vac. The residue was neutralised with 4N aqueous sodium hydroxide solution, the precipitate formed was suction filtered, washed with water and dried i. vac.

Yield: 115 mg (71% of theoretical)

ESI-MS: m/z=543 (M+H)$^+$ $R_t$(HPLC): 1.33 min (method B)

Example 19

3-[4'-(3,4-dimethyl-2-oxo-2,3-dihydro-benzoxazole-6-carbonyl)-3,4,5,6-tetrahydro-2H-[1,2']bipyridinyl-4-yl]-7-methoxy-1,3,4,5-tetrahydro-benzo[d][1,3]diazepin-2-one

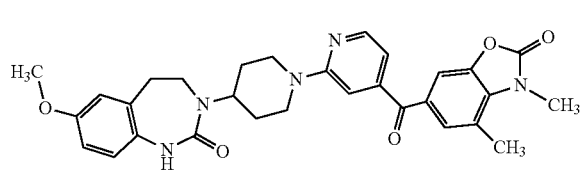

350 mg (1.27 mmol) 7-methoxy-3-piperidin-4-yl-1,3,4,5-tetrahydro-1,3-benzodiazepin-2-one and 180 mg (0.600 mmol) 6-(2-chloro-pyridine-4-carbonyl)-3,4-dimethyl-3H-benzoxazol-2-one were stirred overnight in 3 mL NMP at 120° C. The reaction mixture was diluted with MeOH and purified by preparative HPLC-MS. The fractions containing the product were combined and freeze-dried.

Yield: 60 mg (19% of theoretical)

ESI-MS: m/z=542 (M+H)$^+$ $R_t$(HPLC): 4.24 min (method L)

Example 20

3-{1-[6-(3,4-dimethyl-2-oxo-2,3-dihydro-benzoxazole-6-carbonyl)-pyrimidin-4-yl]-3-fluoro-piperidin-4-yl}-7-methoxy-1,3,4,5-tetrahydro-benzo[d][1,3]diazepin-2-one

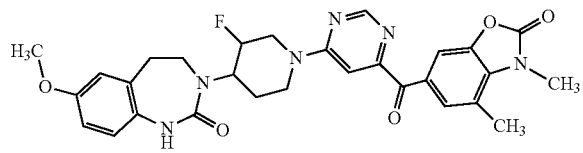

60 mg (0.21 mmol) 3-(3-fluoro-piperidin-4-yl)-7-methoxy-1,3,4,5-tetrahydro-benzo[d]-[1,3]diazepin-2-one, 60 mg (0.20 mmol) 6-(6-chloro-pyrimidine-4-carbonyl)-3,4-dimethyl-3H-benzoxazol-2-one and 0.040 mL (0.30 mmol) TEA were stirred overnight in 1 mL DMF at RT. The reaction mixture was combined with 2 mL MeOH and the precipitate formed was suction filtered, washed with MeOH and diethyl ether and dried.

Yield: 77 mg (70% of theoretical)

ESI-MS: m/z=561 (M+H)$^+$ $R_t$(HPLC): 3.40 min (method C)

Example 21

1-{1-[2-methyl-6-(4-methyl-2-oxo-2,3-dihydro-benzoxazole-6-carbonyl)-pyrimidin-4-yl]-piperidin-4-yl}-1,3-dihydro-imidazo[4,5-b]pyridin-2-one

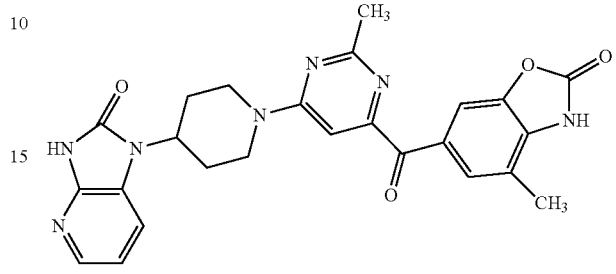

65 mg (0.30 mmol) 1-piperidin-4-yl-1,3-dihydroimidazo[4,5-b]pyridin-2-one, 91 mg (0.30 mmol) 6-(6-chloro-2-methyl-pyrimidine-4-carbonyl)-4-methyl-3H-benzoxazol-2-one and 0.11 mL (0.60 mmol) DIPEA were stirred overnight in 3 mL DMF at RT. Then the reaction mixture was purified by preparative HPLC-MS. The fractions containing the product were combined and the organic solvent evaporated down. The residue was neutralised with 4N aqueous sodium hydroxide solution, the precipitate formed was suction filtered, washed with water and dried.

Yield: 90 mg (62% of theoretical)

ESI-MS: m/z=486 (M+H)$^+$ $R_t$(HPLC): 1.17 min (method B)

Example 22

7-methoxy-3-[4'-(4-methyl-2-oxo-2,3-dihydro-benzoxazole-6-carbonyl)-3,4,5,6-tetrahydro-2H-[1,2']bipyridinyl-4-yl]-1,3,4,5-tetrahydro-benzo[d][1,3]diazepin-2-one

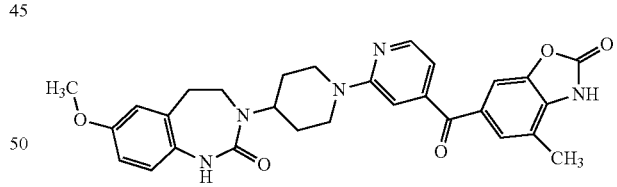

Under a nitrogen atmosphere 0.21 g (0.80 mmol) 7-methoxy-3-piperidin-4-yl-1,3,4,5-tetrahydro-benzo[d][1,3]diazepin-2-one, 0.38 g (1.2 mmol) caesium carbonate, 50 mg (0.10 mmol) BINAP and 25 mg (0.10 mmol) palladium(II) acetate were stirred in 20 mL xylene for 10 min at RT. 0.25 g (0.80 mmol) 6-(2-bromo-pyridine-4-carbonyl)-4-methyl-3H-benzoxazol-2-one were added and the mixture was stirred overnight at 120° C. The mixture was evaporated down, the residue was mixed with 15 mL DMF and 25 mg (0.11 mmol) palladium(II)acetate and 50 mg (0.10 mmol) BINAP were added. The reaction mixture was stirred for 48 h at 120° C. After cooling the solid was filtered off and the filtrate was evaporated down i. vac. The residue was triturated with EtOAc, suction filtered and dissolved in DMF. The product

Example 23

1-{1-[6-(3,4-dimethyl-2-oxo-2,3-dihydro-benzox-azole-6-carbonyl)-2-methyl-pyrimidin-4-yl]-piperidin-4-yl}-1,3-dihydro-imidazo[4,5-b]pyridin-2-one

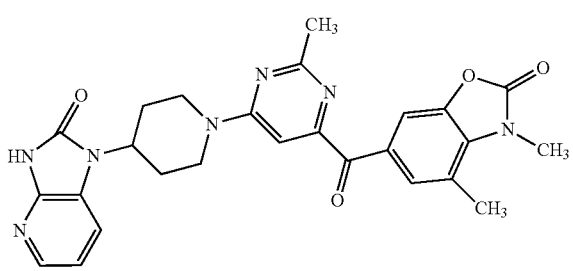 [SMILES: Cc1nc(C(=O)c2cc(C)c3c(c2)oc(=O)n3C)cc(N2CCC(n3c(=O)[nH]c4ncccc43)CC2)n1]

65 mg (0.30 mmol) 1-piperidin-4-yl-1,3-dihydroimidazo[4,5-b]pyridin-2-one, 95 mg (0.30 mmol) 6-(6-chloro-2-methyl-pyrimidine-4-carbonyl)-3,4-dimethyl-3H-benzoxazol-2-one and 0.11 mL (0.60 mmol) DIPEA were stirred overnight in 3 mL DMF at RT. Then the reaction mixture was purified by preparative HPLC-MS. The fractions containing the product were combined and the organic solvent was evaporated down i. vac. The residue was neutralised with 4N aqueous sodium hydroxide solution, the precipitate formed was suction filtered, washed with water and dried.

Yield: 80 mg (53% of theoretical)
ESI-MS: m/z=500 (M+H)$^+$
$R_f$(HPLC): 1.24 min (method B)

Example 24

1-[4'-(3,4-dimethyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one

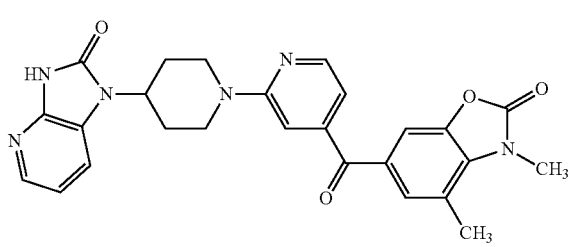 [SMILES: Cc1cc(C(=O)c2ccnc(N3CCC(n4c(=O)[nH]c5ncccc54)CC3)c2)cc2oc(=O)n(C)c12]

0.40 g (1.8 mmol) 1-piperidin-4-yl-1,3-dihydroimidazo[4,5-b]pyridin-2-one and 0.18 g (0.60 mmol) 6-(2-chloro-pyridine-4-carbonyl)-3,4-dimethyl-3H-benzoxazol-2-one were stirred overnight in 3 mL NMP at 120° C. The reaction mixture was diluted with MeOH and purified by preparative HPLC-MS. The fractions containing the product were combined and freeze-dried.

Yield: 65 mg (23% of theoretical)
ESI-MS: m/z=485 (M+H)$^+$
$R_f$(HPLC): 1.23 min (method B)

was purified by preparative HPLC-MS. The fractions containing the product were combined and freeze-dried.
Yield: 10 mg (3% of theoretical)
ESI-MS: m/z=528 (M+H)$^+$
$R_f$: 0.57 (silica gel, DCM/Cyc/MeOH/NH$_4$OH=70/15/15/2)

Example 25

3-{1-[6-chloro-5-(4-methyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one

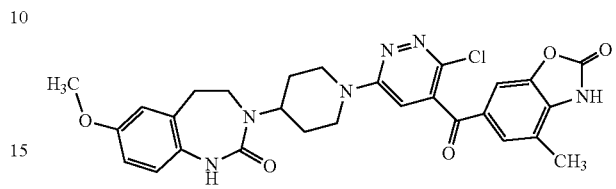

360 mg (1.31 mmol) 7-methoxy-3-piperidin-4-yl-1,3,4,5-tetrahydro-1,3-benzodiazepin-2-one, 480 mg (1.19 mmol) 6-(3,6-dichloro-pyridazine-4-carbonyl)-4-methyl-3H-benzoxazol-2-one and 0.300 mL (1.74 mmol) DIPEA were stirred in 3 mL DMF for 4 h at 100° C. Then the reaction mixture was cooled, combined with 0.5 mL formic acid and 15 mL water, the precipitate formed was suction filtered and dried. This was purified by preparative HPLC-MS. The fractions containing the product were combined and freeze-dried.

Yield: 10 mg (2% of theoretical)
ESI-MS: m/z=563 (M+H)$^+$
$R_f$(HPLC): 1.31 min (method G)

Example 26

3-[4-(7-methoxy-2-oxo-1,2,4,5-tetrahydro-benzo[d][1,3]diazepin-3-yl)-piperidin-1-yl]-5-(4-methyl-2-oxo-2,3-dihydro-benzoxazole-6-carbonyl)-benzonitrile

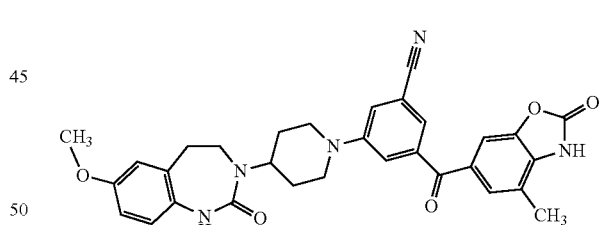

0.22 g (0.80 mmol) 7-methoxy-3-piperidin-4-yl-1,3,4,5-tetrahydro-1,3-benzodiazepin-2-one and 0.12 g (0.40 mmol) 3-fluoro-5-(4-methyl-2-oxo-2,3-dihydro-benzoxazole-6-carbonyl)-benzonitrile were heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried.

Yield: 30 mg (14% of theoretical)
ESI-MS: m/z=552 (M+H)$^+$
$R_f$(HPLC): 1.48 min (method B)

Example 27

1-[1-(6-benzoyl-pyrimidin-4-yl)-piperidin-4-yl]-1,3-dihydro-imidazo[4,5-b]pyridin-2-one

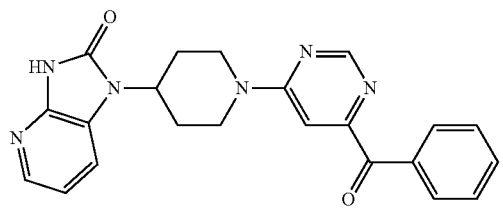 [SMILES: O=C(c1ccccc1)c1cc(N2CCC(n3c(=O)[nH]c4ncccc43)CC2)ncn1]

0.20 g (0.67 mmol) 1-piperidin-4-yl-1,3-dihydroimidazo[4,5-b]pyridin-2-one, 0.15 g (0.33 mmol) (6-chloro-pyrimidin-4-yl)-phenyl-methanone and 0.20 mL (1.1 mmol) DIPEA in 3 mL DMF were heated to 80° C. for 1 h. Then the reaction mixture was purified by preparative HPLC-MS. The fractions containing the product were combined and freeze-dried.

Yield: 87 mg (66% of theoretical)
ESI-MS: m/z=401 (M+H)$^+$
R$_t$(HPLC): 1.59 min (method M)

Example 28

3-{1-[6-(3,4-dimethyl-2-oxo-2,3-dihydro-benzoxazole-6-carbonyl)-pyrimidin-4-yl]-piperidin-4-yl}-1,3,4,5-tetrahydro-benzo[d][1,3]diazepin-2-one

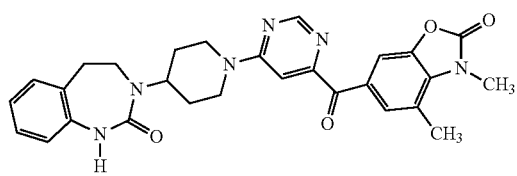 [SMILES: Cc1cc(C(=O)c2cc(N3CCC(N4CCc5ccccc5NC4=O)CC3)ncn2)cc2oc(=O)n(C)c12]

98 mg (0.40 mmol) 3-piperidin-4-yl-1,3,4,5-tetrahydro-1,3-benzodiazepin-2-one, 0.12 g (0.40 mmol) 6-(6-chloropyrimidine-4-carbonyl)-3,4-dimethyl-3H-benzoxazol-2-one and 0.14 mL (0.80 mmol) DIPEA were stirred in 3 mL DMF for 2 h at RT. The mixture was diluted with methanol, and the precipitate formed was suction filtered, washed with MeOH and diethyl ether and dried.

Yield: 185 mg (90% of theoretical)
ESI-MS: m/z=513 (M+H)$^+$
R$_t$(HPLC): 1.36 min (method B)

Example 29

7-methoxy-3-{1-[5-(4-methyl-2-oxo-2,3-dihydro-benzoxazole-6-carbonyl)-6-oxo-5,6-dihydro-pyridazin-3-yl]-piperidin-4-yl}-1,3,4,5-tetrahydro-benzo[d][1,3]diazepin-2-one

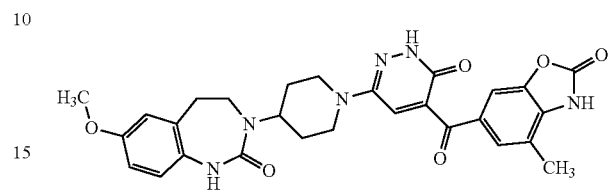

0.10 g (1.0 mmol) potassium acetate were added to 0.13 g (0.20 mmol) 3-{1-[6-chloro-5-(4-methyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one (mixture) in 3 mL acetic acid and the mixture was boiled under a nitrogen atmosphere for 7 h. Then the reaction mixture was evaporated down and the residue was triturated with water, suction filtered and dried. The residue was purified by preparative HPLC-MS. The fractions containing the product were combined and freeze-dried.

Yield: 1.5 mg (1% of theoretical)
ESI-MS: m/z=545 (M+H)$^+$
R$_t$(HPLC): 4.22 min (method I)

Example 30

3-{1-[5-(3,4-dimethyl-2-oxo-2,3-dihydro-benzoxazole-6-carbonyl)-6-oxo-1,6-dihydro-pyridazin-3-yl]-piperidin-4-yl}-7-methoxy-1,3,4,5-tetrahydro-benzo[d][1,3]diazepin-2-one

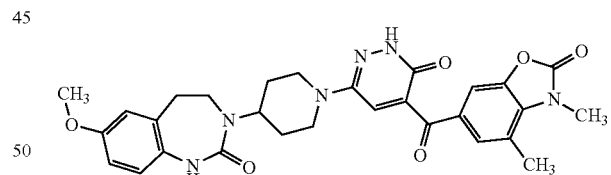

0.10 g (1.02 mmol) potassium acetate were added to 0.13 g (0.20 mmol) 3-{1-[6-chloro-5-(3,4-dimethyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one (mixture) in 2 mL acetic acid and the mixture was boiled for 16 h under a nitrogen atmosphere. Then the reaction mixture was purified by preparative HPLC-MS. The fractions containing the product were combined and freeze-dried.

Yield: 1.6 mg (13% of theoretical)
Purity: 90%
ESI-MS: m/z=559 (M+H)$^+$
R$_t$(HPLC): 1.52 min (method K)

Example 31

7-chloro-3-{1-[6-(3,4-dimethyl-2-oxo-2,3-dihydro-benzoxazole-6-carbonyl)-pyrimidin-4-yl]-piperidin-4-yl}-1,3,4,5-tetrahydro-benzo[d][1,3]diazepin-2-one

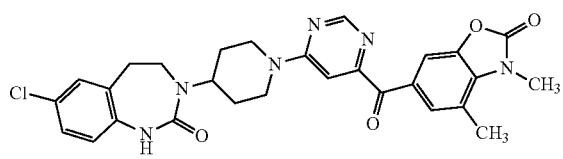 [SMILES: Cc1cc(C(=O)c2cc(N3CCC(N4CCc5cc(Cl)ccc5NC4=O)CC3)ncn2)cc2oc(=O)n(C)c12]

56 mg (0.20 mmol) 7-chloro-3-piperidin-4-yl-1,3,4,5-tetrahydro-benzo[d][1,3]diazepin-2-one, 61 mg (0.20 mmol) 6-(6-chloropyrimidine-4-carbonyl)-3,4-dimethyl-3H-benzoxazol-2-one and 0.070 mL (0.40 mmol) DIPEA were stirred overnight in 1.5 mL DMF at RT. The mixture was diluted with 1.5 mL MeOH, suction filtered, washed with DIPE and dried.

Yield: 87 mg (80% of theoretical)
ESI-MS: m/z=547/549 (M+H)$^+$
R$_t$(HPLC): 3.6 min (method C)

Example 32

3-{1-[6-(3,4-dimethyl-2-oxo-2,3-dihydro-benzoxazole-6-carbonyl)-pyrimidin-4-yl]-piperidin-4-yl}-1,3-dihydro-imidazo[4,5-c]quinolin-2-one

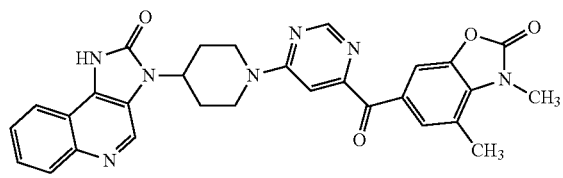 [SMILES: Cc1cc(C(=O)c2cc(N3CCC(n4c(=O)[nH]c5c6ccccc6ncc54)CC3)ncn2)cc2oc(=O)n(C)c12]

0.11 g (0.40 mmol) 3-piperidin-4-yl-1,3-dihydroimidazo[4,5-c]quinolin-2-one, 0.12 g (0.40 mmol) 6-(6-chloropyrimidine-4-carbonyl)-3,4-dimethyl-3H-benzoxazol-2-one and 0.14 mL (0.80 mmol) DIPEA were stirred overnight in 3 mL DMF at RT. The mixture was purified by preparative HPLC-MS. The fractions containing the product were combined, the organic solvent was eliminated i. vac. and the aqueous phase remaining was neutralised with 4M aqueous NaOH solution. The precipitate was suction filtered, washed with water and dried i. vac.

Yield: 150 mg (70% of theoretical)
ESI-MS: m/z=536 (M+H)$^+$
R$_t$(HPLC): 1.0 min (method B)

Example 33

3-[6'-chloro-4'-(3,4-dimethyl-2-oxo-2,3-dihydro-benzoxazole-6-carbonyl)-3,4,5,6-tetrahydro-2H-[1,2']bipyridinyl-4-yl]-7-methoxy-1,3,4,5-tetrahydro-benzo[d][1,3]diazepin-2-one

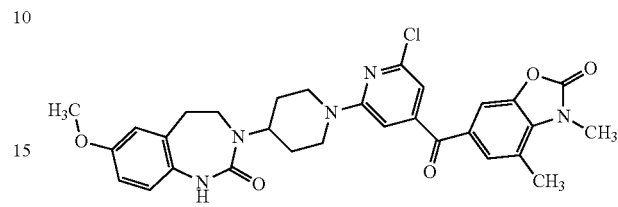

0.41 g (1.5 mmol) 7-methoxy-3-piperidin-4-yl-1,3,4,5-tetrahydro-benzo[d][1,3]diazepin-2-one and 0.20 g (0.49 mmol) 6-(2,6-dichloro-pyridine-4-carbonyl)-3,4-dimethyl-3H-benzoxazol-2-one were stirred in 3 mL NMP for 3 h at 120° C. The reaction mixture was purified by preparative HPLC. The fractions containing the product were combined and freeze-dried.

Yield: 150 mg (53% of theoretical)
ESI-MS: m/z=576/78 (Cl) (M+H)$^+$
R$_t$(HPLC): 1.67 min (method B)

Example 34

3-{1-[6-chloro-5-(3,4-dimethyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one

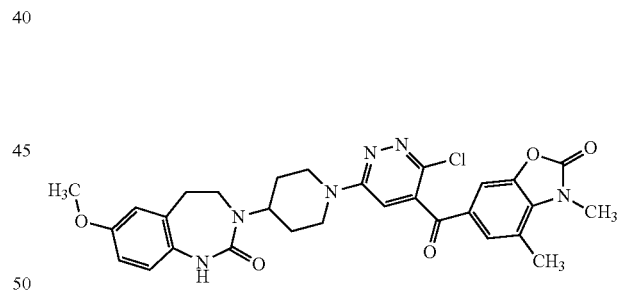

0.10 g (1.0 mmol) potassium acetate were added to 0.13 g (0.20 mmol) 3-{1-[6-chloro-5-(3,4-dimethyl-2-oxo-2,3-dihydro-benzoxazole-6-carbonyl)-pyridazin-3-yl]-piperidin-4-yl}-7-methoxy-1,3,4,5-tetrahydro-benzo[d][1,3]diazepin-2-one (mixture) in 2 mL acetic acid and boiled for 16 h under a nitrogen atmosphere. Then the reaction mixture was purified by preparative HPLC-MS. The fractions containing the product were combined and freeze-dried.

Yield: 5 mg (4% of theoretical)
Purity: 90%
ESI-MS: m/z=577 (M+H)$^+$
R$_t$(HPLC): 3.67 min (method C)

Example 35

1-[4'-(4-methyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one

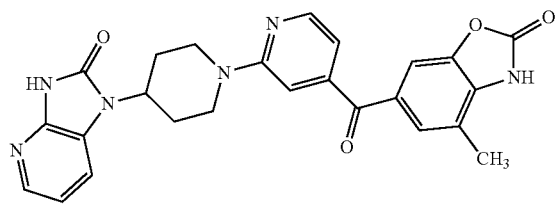 [SMILES: Cc1cc(C(=O)c2ccnc(N3CCC(n4c(=O)[nH]c5ncccc54)CC3)c2)cc2oc(=O)[nH]c12]

0.20 g (0.70 mmol) 1-piperidin-4-yl-1,3-dihydroimidazo[4,5-b]pyridin-2-one-dihydrochloride, 0.20 g (0.70 mmol) 6-(6-chloropyrimidine-4-carbonyl)-4-methyl-3H-benzoxazol-2-one and 0.30 g (2.2 mmol) potassium carbonate were stirred in 3.0 mL NMP overnight at 130° C. The reaction mixture was filtered, the filtrate was diluted with a little water and then purified by preparative HPLC-MS. The fractions containing the product were combined and freeze-dried.

Yield: 40 mg (12% of theoretical)

ESI-MS: m/z=471 (M+H)$^+$ $R_f$: 0.62 (silica gel, DCM/Cyc/MeOH/NH$_4$OH=70/15/15/2)

Example 36

3-(3,4-dimethyl-2-oxo-2,3-dihydro-benzoxazole-6-carbonyl)-5-[4-(7-methoxy-2-oxo-1,2,4,5-tetrahydro-benzo[d][1,3]diazepin-3-yl)-piperidin-1-yl]-benzonitrile

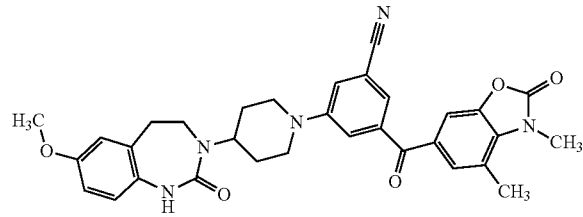

0.22 g (0.80 mmol) 7-methoxy-3-piperidin-4-yl-1,3,4,5-tetrahydro-1,3-benzodiazepin-2-one and 0.12 g (0.40 mmol) 3-(3,4-dimethyl-2-oxo-2,3-dihydro-benzoxazole-6-carbonyl)-5-fluoro-benzonitrile were combined and heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried i. vac.

Yield: 25 mg (11% of theoretical)

ESI-MS: m/z=566 (M+H)$^+$ $R_t$(HPLC): 1.56 min (method B)

Example 37

4-methyl-6-[4-(2-oxo-2,3-dihydro-benzimidazole-1-yl)-3,4,5,6-tetrahydro-2H-[1.4']bipyridinyl-2'-carbonyl]-3H-benzoxazol-2-one

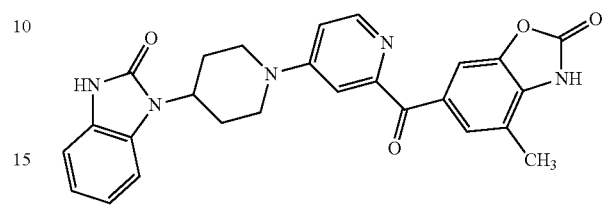

0.20 g (0.90 mmol) 1-piperidin-4-yl-1,3-dihydro-benzimidazol-2-one, 0.25 g (0.90 mmol) 6-(4-chloro-pyridin-2-carbonyl)-4-methyl-3H-benzoxazol-2-one and 0.13 g (0.90 mmol) potassium carbonate were stirred in 3 mL NMP overnight at 130° C. The solid was filtered off, the filtrate was diluted with DMF and purified by preparative HPLC-MS. The fractions containing the product were combined and freeze-dried.

Yield: 20 mg (5% of theoretical)

ESI-MS: m/z=471 (M+H)$^+$ $R_f$: 0.51 (silica gel, DCM/Cyc/MeOH/NH$_4$OH=70/15/15/2)

Example 38

3-[4'-(3,4-dimethyl-2-oxo-2,3-dihydro-benzoxazole-6-carbonyl)-5'-methyl-3,4,5,6-tetrahydro-2H-[1,2']bipyridinyl-4-yl]-7-methoxy-1,3,4,5-tetrahydro-benzo[d][1,3]diazepin-2-one

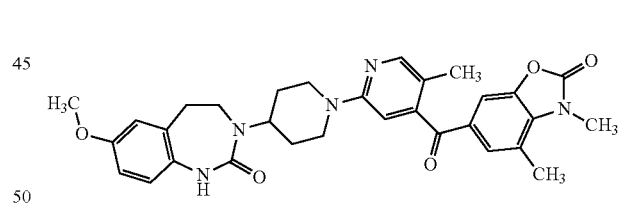

0.33 g (1.2 mmol) 7-methoxy-3-piperidin-4-yl-1,3,4,5-tetrahydro-1,3-benzodiazepin-2-one and 0.13 g (0.40 mmol) 6-(2-chloro-5-methyl-pyridine-4-carbonyl)-3,4-dimethyl-3H-benzoxazol-2-one (mixture) were combined and heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried i. vac.

Yield: 40 mg (18% of theoretical)

ESI-MS: m/z=556 (M+H)$^+$ $R_t$(HPLC): 1.51 min (method B)

Example 39

3-{1-[3-(3,4-dimethyl-2-oxo-2,3-dihydro-benzoxazole-6-carbonyl)-5-fluoro-phenyl]-piperidin-4-yl}-7-methoxy-1,3,4,5-tetrahydro-benzo[d][1,3]diazepin-2-one

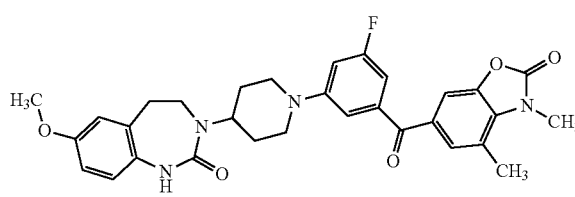

440 mg (1.60 mmol) 7-methoxy-3-piperidin-4-yl-1,3,4,5-tetrahydro-1,3-benzodiazepin-2-one and 121 mg (0.40 mmol) 6-(3,5-difluoro-benzoyl)-3,4-dimethyl-3H-benzoxazol-2-one were combined and heated to 300° C. for approx. 10 min using the hot gun. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried i. vac.

Yield: 50 mg (22% of theoretical)

ESI-MS: m/z=559 (M+H)+

$R_t$(HPLC): 1.77 min (method B)

Example 40

1-[6'-chloro-4'-(3,4-dimethyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one

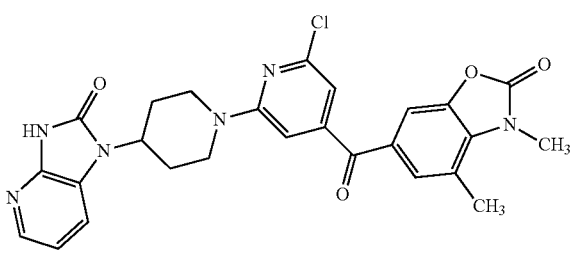 [SMILES: Cc1cc(C(=O)c2cc(Cl)nc(N3CCC(n4c(=O)[nH]c5ncccc54)CC3)c2)cc2oc(=O)n(C)c12]

0.33 g (1.5 mmol) 1-piperidin-4-yl-1,3-dihydroimidazo[4,5-b]pyridin-2-one and 0.20 g (0.49 mmol) 6-(2,6-dichloro-pyridine-4-carbonyl)-3,4-dimethyl-3H-benzoxazol-2-one were stirred in 3 mL NMP for 3 h at 120° C. The reaction mixture was purified by preparative HPLC. The fractions containing the product were combined and freeze-dried.

Yield: 160 mg (63% of theoretical)

ESI-MS: m/z=519/21 (Cl) (M+H)+

$R_t$(HPLC): 1.54 min (method B)

Example 41

7-methoxy-3-{1-[6-(7-methyl-1H-indazole-5-carbonyl)-pyrimidin-4-yl]-piperidin-4-yl}-1,3,4,5-tetrahydro-benzo[d][1,3]diazepin-2-one

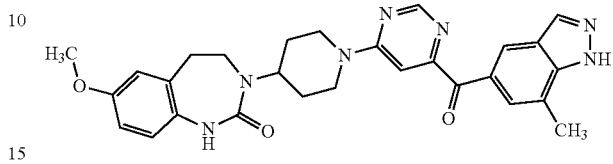

65 mg (0.10 mmol) 7-methoxy-3-(1-{6-[7-methyl-1-(2-trimethylsilanyl-ethoxymethyl)-1H-indazole-5-carbonyl]-pyrimidin-4-yl}-piperidin-4-yl)-1,3,4,5-tetrahydro-benzo[d][1,3]diazepin-2-one in 0.4 mL MeOH and 0.6 mL (2.4 mmol) of a 4 molar HCl solution in dioxane was stirred overnight at RT. The mixture was neutralised with 0.4 mL of a 6 molar methanolic ammonia solution, mixed with some water and purified by preparative HPLC-MS. The fractions containing the product were combined and freeze-dried.

Yield: 16 mg (28% of theoretical)

Purity: 90%

ESI-MS: m/z=512 (M+H)+

$R_t$(HPLC): 2.76 min (method C)

Example 42

3-{1-[6-(3,4-dimethyl-2-oxo-2,3-dihydro-benzoxazole-6-carbonyl)-pyrimidin-4-yl]-3-methyl-piperidin-4-yl}-7-methoxy-1,3,4,5-tetrahydro-benzo[d][1,3]diazepin-2-one

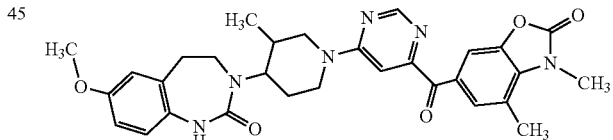

60 mg (0.21 mmol) 7-methoxy-3-(3-methyl-piperidin-4-yl)-1,3,4,5-tetrahydro-benzo[d]-[1,3]diazepin-2-one, 60 mg (0.20 mmol) 6-(6-chloro-pyrimidine-4-carbonyl)-3,4-dimethyl-3H-benzoxazol-2-one and 0.040 mL (0.29 mmol) TEA were stirred overnight in 1 mL DMF at RT. Then the reaction mixture was combined with 2 mL MeOH, the precipitate formed was suction filtered, washed with MeOH and diethyl ether and dried.

Yield: 80 mg (66% of theoretical)

ESI-MS: m/z=557 (M+H)+

$R_t$(HPLC): 1.41 min (method C)

Example 43

4-(3,4-dimethyl-2-oxo-2,3-dihydro-benzoxazole-6-carbonyl)-2-[4-(7-methoxy-2-oxo-1,2,4,5-tetrahydro-benzo[d][1,3]diazepin-3-yl)-piperidin-1-yl]-benzonitrile

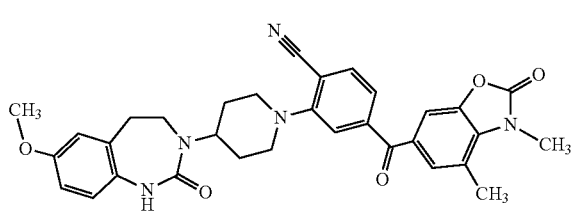

440 mg (1.60 mmol) 7-methoxy-3-piperidin-4-yl-1,3,4,5-tetrahydro-1,3-benzodiazepin-2-one and 124 mg (0.400 mmol) 4-(3,4-dimethyl-2-oxo-2,3-dihydro-benzoxazole-6-carbonyl)-2-fluoro-benzonitrile were combined and heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried.

Yield: 125 mg (55% of theoretical)
ESI-MS: m/z=566 (M+H)+
$R_t$(HPLC): 1.65 min (method B)

Example 44

7-methoxy-3-{1-[6-(4-methyl-2-oxo-2,3-dihydro-benzothiazole-6-carbonyl)-pyrimidin-4-yl]-piperidin-4-yl}-1,3,4,5-tetrahydro-benzo[d][1,3]diazepin-2-one

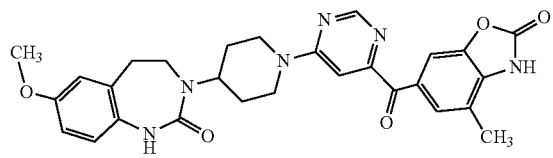 [SMILES: COc1ccc2c(c1)CCN(C1CCN(c3cc(C(=O)c4cc(C)c5[nH]c(=O)oc5c4)ncn3)CC1)C(=O)N2]

63 mg (0.23 mmol) 7-methoxy-3-piperidin-4-yl-1,3,4,5-tetrahydro-benzo[d][1,3]diazepin-2-one, 71 mg (0.23 mmol) 6-(6-chloro-pyrimidine-4-carbonyl)-4-methyl-3H-benzothiazol-2-one and 0.047 mL (0.27 mmol) DIPEA were combined in 2 mL DMF and shaken overnight at RT. The reaction mixture was taken up in acetonitrile/water and purified by preparative HPLC. The fractions containing the product were combined and freeze-dried.

Yield: 25 mg (20% of theoretical)
ESI-MS: m/z=545 (M+H)+
$R_t$(HPLC): 3.48 min (method C)

Example 45

3-{1-[3-(3,4-dimethyl-2-oxo-2,3-dihydro-benzoxazole-6-carbonyl)-phenyl]-piperidin-4-yl}-7-methoxy-1,3,4,5-tetrahydro-benzo[d][1,3]diazepin-2-one

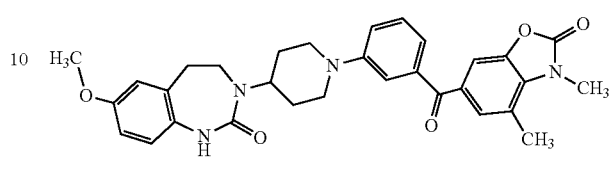

Under an argon atmosphere 330 mg (1.20 mmol) 7-methoxy-3-piperidin-4-yl-1,3,4,5-tetrahydro-benzo[d][1,3]diazepin-2-one, 350 mg (1.01 mmol) 6-(3-bromo-benzoyl)-3,4-dimethyl-3H-benzoxazol-2-one and 586 mg (1.80 mmol) caesium carbonate were stirred in 10 mL xylene, then combined with 56 mg (0.090 mmol) BINAP and 20 mg (0.089 mmol) palladium(II)acetate and stirred for 48 h at 100° C. The mixture was evaporated down i. vac., the residue was dissolved in DMF/MeOH and purified by preparative HPLC-MS. The fractions containing the product were combined and the acetonitrile was evaporated down. The aqueous residue was made basic with 1N aqueous sodium hydroxide solution, the precipitate formed was suction filtered and washed with water and dried. The product was again purified by preparative HPLC-MS. The fractions containing the product were combined and freeze-dried.

Yield: 7 mg (1% of theoretical)
ESI-MS: m/z=541 (M+H)+
$R_t$(HPLC): 1.58 min (method B)

Example 46

4-(3,4-dimethyl-2-oxo-2,3-dihydro-benzoxazole-6-carbonyl)-2-[4-(2-oxo-2,3-dihydro-imidazo[4,5-b]pyridin-1-yl)-piperidin-1-yl]-benzonitrile

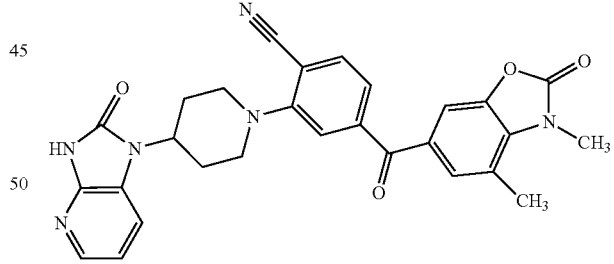

0.26 g (1.2 mmol) 1-piperidin-4-yl-1,3-dihydroimidazo[4,5-b]pyridin-2-one and 93 mg (0.30 mmol) 4-(3,4-dimethyl-2-oxo-2,3-dihydro-benzoxazole-6-carbonyl)-2-fluoro-benzonitrile were combined and heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried.

Yield: 7 mg (5% of theoretical)
ESI-MS: m/z=509 (M+H)+
$R_t$(HPLC): 1.50 min (method B)

Example 47

1-[4'-(3,4-dimethyl-2-oxo-2,3-dihydro-benzoxazole-6-carbonyl)-6'-methoxy-3,4,5,6-tetrahydro-2H-[1,2']bipyridinyl-4-yl]-1,3-dihydro-imidazo[4,5-b]pyridin-2-one

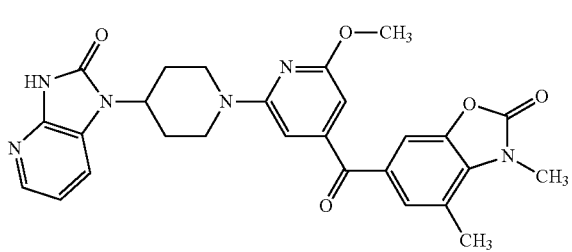 [SMILES: COc1cc(C(=O)c2cc(C)c3c(c2)oc(=O)n3C)cc(N2CCC(n3c(=O)[nH]c4ncccc43)CC2)n1]

785 mg (3.60 mmol) 1-piperidin-4-yl-1,3-dihydroimidazo[4,5-b]pyridin-2-one and 420 mg (1.26 mmol) 6-(2-chloro-6-methoxy-pyridine-4-carbonyl)-3,4-dimethyl-3H-benzoxazol-2-one were combined in 3 mL NMP and stirred for 12 h at 120° C. The mixture was purified by preparative HPLC-MS. The fractions containing the product were combined and the acetonitrile was eliminated i. vac. The residue was diluted with water, the precipitated solid was suction filtered, washed with water and dried.

Yield: 180 mg (10% of theoretical)
ESI-MS: m/z=515 (M+H)$^+$
R$_t$(HPLC): 1.60 min (method B)

Example 48

3-[4'-(3,4-dimethyl-2-oxo-2,3-dihydro-benzoxazole-6-carbonyl)-6'-methoxy-3,4,5,6-tetrahydro-2H-[1,2']bipyridinyl-4-yl]-7-methoxy-1,3,4,5-tetrahydro-benzo[d][1,3]diazepin-2-one

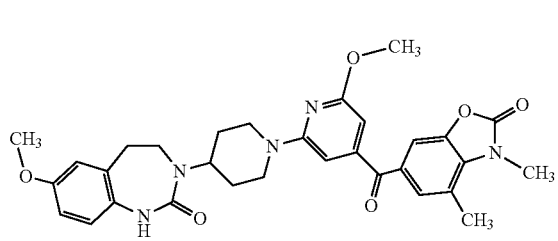

991 mg (3.60 mmol) 7-methoxy-3-piperidin-4-yl-1,3,4,5-tetrahydro-benzo[d][1,3]diazepin-2-one and 420 mg (1.26 mmol) 6-(2-chloro-6-methoxy-pyridine-4-carbonyl)-3,4-dimethyl-3H-benzoxazol-2-one were combined in 3 mL NMP and stirred for 12 h at 120° C. The mixture was purified by preparative HPLC-MS. The fractions containing the product were combined and the acetonitrile was eliminated i. vac. The residue was diluted with water, the precipitated solid was suction filtered, washed with water and dried.

Yield: 290 mg (14% of theoretical)
ESI-MS: m/z=572 (M+H)$^+$
R$_t$(HPLC): 1.70 min (method B)

Example 49

3-{1-[6-(3,4-dimethyl-2-oxo-2,3-dihydro-benzoxazole-6-carbonyl)-pyrimidin-4-yl]-piperidin-4-yl}-1H-quinolin-2-one

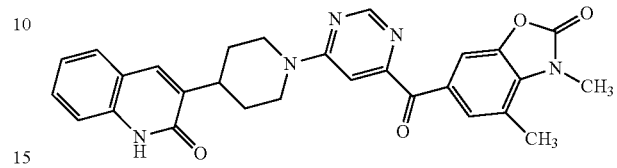

60 mg (0.26 mmol) 3-piperidin-4-yl-1H-quinolin-2-one, 80 mg (0.26 mmol) 6-(6-chloropyrimidine-4-carbonyl)-3,4-dimethyl-3H-benzoxazol-2-one and 0.15 mL (0.86 mmol) DIPEA were combined in 3 mL DMF and stirred overnight at RT. The reaction mixture was added to water and the precipitate formed was suction filtered, washed with MeOH and dried.

Yield: 110 mg (80% of theoretical)
ESI-MS: m/z=496 (M+H)$^+$
R$_t$(HPLC): 1.34 min (method B)

Example 50

3,4-dimethyl-6-{6-[4-(5-oxo-3-phenyl-4,5-dihydro-[1,2,4]triazol-1-yl)-piperidin-1-yl]-pyrimidine-4-carbonyl}-3H-benzoxazol-2-one

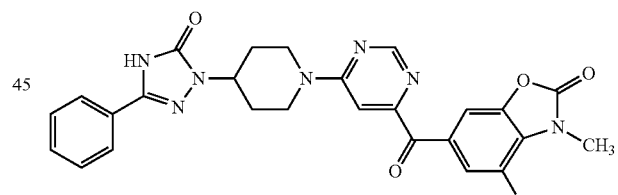

98 mg (0.40 mmol) 5-phenyl-2-piperidin-4-yl-2,4-dihydro-[1,2,4]triazol-3-one, 0.12 g (0.40 mmol) 6-(6-chloro-pyrimidine-4-carbonyl)-3,4-dimethyl-3H-benzoxazol-2-one and 0.14 mL (0.80 mmol) DIPEA were combined in 3 mL DMF and stirred for 48 h at RT. The mixture was diluted with MeOH, suction filtered, washed with MeOH and diethyl ether and dried.

Yield: 158 mg (77% of theoretical)
ESI-MS: m/z=512 (M+H)$^+$
R$_t$(HPLC): 1.27 min (method A)

Example 51

7-methoxy-3-{1-[6-(7-methyl-2-oxo-2,3-dihydro-1H-indol-5-carbonyl)-pyrimidin-4-yl]-piperidin-4-yl}-1,3,4,5-tetrahydro-benzo[d][1,3]diazepin-2-one

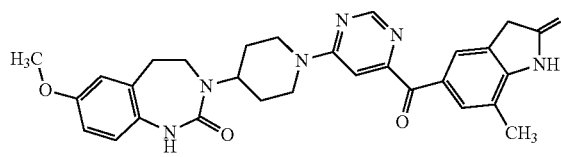

0.12 g (0.42 mmol) 7-methoxy-3-piperidin-4-yl-1,3,4,5-tetrahydro-1,3-benzodiazepin-2-one, 0.12 g (0.42 mmol) 5-(6-chloro-pyrimidine-4-carbonyl)-7-methyl-1,3-dihydro-indol-2-one and 0.08 mL (0.46 mmol) DIPEA were combined in 2 mL DMF and shaken overnight at RT. Then the reaction mixture was taken up in acetonitrile/water and purified by preparative HPLC-MS. The fractions containing the product were combined and freeze-dried.

Yield: 30 mg (14% of theoretical)
ESI-MS: m/z=527 (M+H)$^+$
$R_t$(HPLC): 1.18 min (method B)

Example 52

1-[4'-(3,4-dimethyl-2-oxo-2,3-dihydro-benzoxazole-6-carbonyl)-5'-methyl-3,4,5,6-tetrahydro-2H-[1,2']bipyridinyl-4-yl]-1,3-dihydro-imidazo[4,5-b]pyridin-2-one

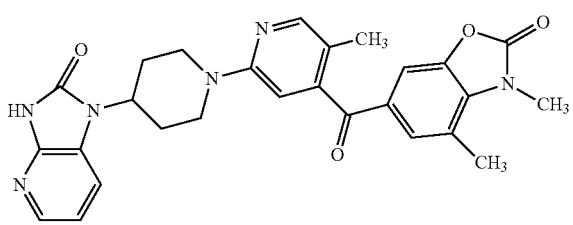 [SMILES: Cc1cnc(N2CCC(n3c(=O)[nH]c4ncccc43)CC2)cc1C(=O)c1cc(C)c2c(c1)oc(=O)n2C]

0.26 g (1.2 mmol) 1-piperidin-4-yl-1,3-dihydroimidazo[4,5-b]pyridin-2-one and 0.13 g (0.40 mmol) 6-(2-chloro-5-methyl-pyridine-4-carbonyl)-3,4-dimethyl-3H-benzoxazol-2-one (mixture) were combined and heated to 250° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried.

Yield: 52 mg (26% of theoretical)
ESI-MS: m/z=499 (M+H)$^+$
$R_t$(HPLC): 1.34 min (method B)

Example 53

3-{1-[6-(3,4-dimethyl-2-oxo-2,3-dihydro-benzoxazole-6-carbonyl)-pyrimidin-4-yl]-piperidin-4-yl}-6-methoxy-1H-quinolin-2-one

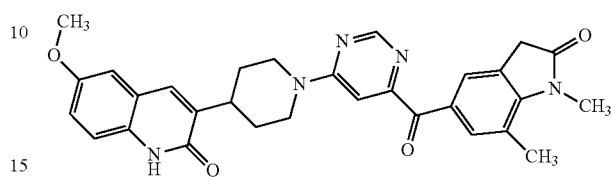

30 mg (0.087 mmol) 6-methoxy-3-piperidin-4-yl-1H-quinoline-2-one, 30 mg (0.10 mmol) 6-(6-chloro-pyrimidine-4-carbonyl)-3,4-dimethyl-3H-benzoxazol-2-one and 50 µl (0.36 mmol) TEA were combined in 3 mL DMF and stirred overnight at RT. Then the reaction mixture was added to water, the precipitate formed was suction filtered and washed with MeOH. Next, the precipitate was boiled in DMF/MeOH and the precipitate was suction filtered.

Yield: 12 mg (24% of theoretical)
ESI-MS: m/z=526 (M+H)$^+$
$R_t$(HPLC): 1.33 min (method B)

Example 54

3-{1-[6-(4-hydroxy-3,5-dimethyl-benzoyl)-pyrimidin-4-yl]-piperidin-4-yl}-7-methoxy-1,3,4,5-tetrahydro-benzo[d][1,3]diazepin-2-one

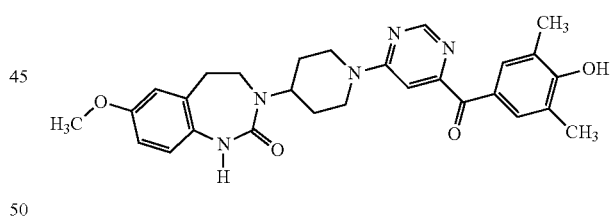

70 mg (0.10 mmol) 3-{1-[6-(4-benzyloxy-3,5-dimethyl-benzoyl)-pyrimidin-4-yl]-piperidin-4-yl}-7-methoxy-1,3,4,5-tetrahydro-benzo[d][1,3]diazepin-2-one and 20 mg palladium on charcoal (Pd/C 10%) in 10 mL MeOH were hydrogenated for 30 min at RT in a hydrogen atmosphere of 10 psi. After filtration of the reaction mixture the solvent was eliminated i. vac. and the residue was purified by preparative HPLC-MS. The fractions containing the product were combined and freeze-dried.

Yield: 11 mg (21% of theoretical)
ESI-MS: m/z=502 (M+H)$^+$
$R_t$(HPLC): 3.0 min (method C)

Example 55

1-{1-[6-(4-methyl-2-oxo-2,3-dihydro-benzothiazole-6-carbonyl)-pyrimidin-4-yl]-piperidin-4-yl}-1,3-dihydro-imidazo[4,5-b]pyridin-2-one

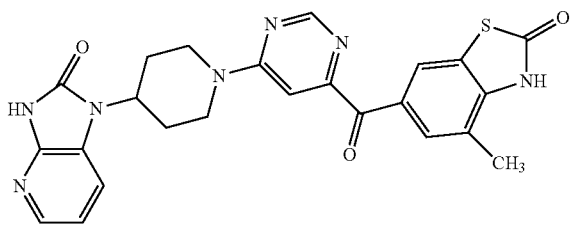 [SMILES: Cc1cc(C(=O)c2cc(N3CCC(n4c(=O)[nH]c5ncccc54)CC3)ncn2)cc2sc(=O)[nH]c12]

50 mg (0.23 mmol) 1-piperidin-4-yl-1,3-dihydroimidazo[4,5-b]pyridin-2-one, 70.6 mg (0.23 mmol) 6-(6-chloro-pyrimidine-4-carbonyl)-4-methyl-3H-benzothiazol-2-one and 0.05 mL (0.27 mmol) DIPEA were combined in 2 mL DMF and shaken overnight at RT. The reaction mixture was taken up in acetonitrile/water and purified by preparative HPLC. The fractions containing the product were combined and freeze-dried.

Yield: 12 mg (11% of theoretical)
ESI-MS: m/z=488 (M+H)+
$R_f$(HPLC): 2.80 min (method C)

Example 56

1-{1-[6-(4-hydroxy-3,5-dimethyl-benzoyl)-pyrimidin-4-yl]-piperidin-4-yl}-1,3-dihydro-imidazo[4,5-b]pyridin-2-one

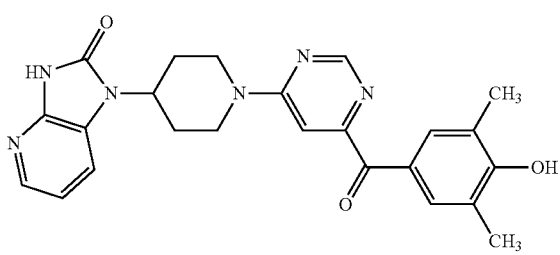 [SMILES: Cc1cc(C(=O)c2cc(N3CCC(n4c(=O)[nH]c5ncccc54)CC3)ncn2)cc(C)c1O]

50 mg palladium/charcoal (10%) were added to 390 mg (0.7 mmol) 1-{1-[6-(4-benzyloxy-3,5-dimethyl-benzoyl)-pyrimidin-4-yl]-piperidin-4-yl}-1,3-dihydro-imidazo[4,5-b]pyridin-2-one in 50 mL MeOH and the mixture was hydrogenated for 40 min in a 5 psi hydrogen atmosphere at RT. The catalyst was removed by suction filtering and the filtrate was evaporated down. The residue was triturated with some MeOH, suction filtered and washed with diethyl ether. The suction filtered catalyst was decocted with 120 mL MeOH for 1 h, filtered hot and the filtrate was evaporated down. The residue was triturated with a little MeOH, suction filtered and dried. The two batches of solid were combined and purified by preparative HPLC-MS. The fractions containing the product were combined and freeze-dried.

Yield: 30 mg (10% of theoretical)
ESI-MS: m/z=445 (M+H)+
$R_f$(HPLC): 2.48 min (method C)

Example 57

3-{1-[6-(1,7-dimethyl-1H-indazole-5-carbonyl)-pyrimidin-4-yl]-piperidin-4-yl}-7-methoxy-1,3,4,5-tetrahydro-benzo[d][1,3]diazepin-2-one

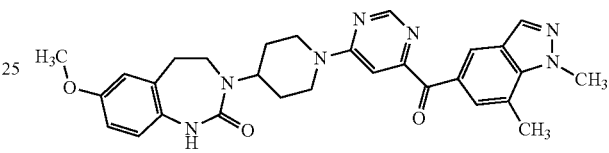

33 mg (0.12 mmol) 7-methoxy-3-piperidin-4-yl-1,3,4,5-tetrahydro-1,3-benzodiazepin-2-one, 45 mg (0.13 mmol) (6-chloro-pyrimidin-4-yl)-(1,7-dimethyl-1H-indazol-5-yl)-methanone and 25 μL (0.18 mmol) TEA were combined in 1 mL DMF and stirred overnight at RT. The reaction mixture was purified by preparative HPLC. The fractions containing the product were combined and evaporated down to approx. 10 mL. This residue was neutralised with saturated sodium hydrogen carbonate solution, the precipitate formed was suction filtered and dried.

Yield: 30 mg (48% of theoretical)
ESI-MS: m/z=526 (M+H)+
$R_f$(HPLC): 3.11 min (method C)

Example 58

3-{1-[6-(3-ethyl-4-methyl-2-oxo-2,3-dihydro-benzoxazole-6-carbonyl)-pyrimidin-4-yl]-piperidin-4-yl}-7-methoxy-1,3,4,5-tetrahydro-benzo[d][1,3]diazepin-2-one

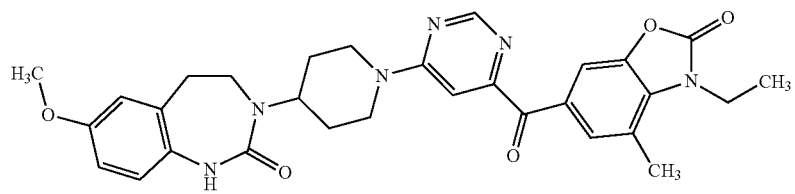 [SMILES: CCn1c(=O)oc2cc(C(=O)c3cc(N4CCC(N5CCc6cc(OC)ccc6NC5=O)CC4)ncn3)cc(C)c21]

44 mg (0.20 mmol) 7-methoxy-3-piperidin-4-yl-1,3,4,5-tetrahydro-benzo[d][1,3]diazepin-2-one, 50 mg (0.20 mmol) 6-(6-chloro-pyrimidine-4-carbonyl)-3-ethyl-4-methyl-3H-benzoxazol-2-one and 56 μL (0.30 mmol) DIPEA were combined in 2 mL DMF and stirred overnight at RT. The reaction mixture was purified by preparative HPLC. The fractions containing the product were combined, the organic solvent was evaporated down and the residue was neutralised with 1N aqueous sodium hydroxide solution. The precipitate formed was suction filtered, washed with water and dried.

Yield: 43 mg (48% of theoretical)
ESI-MS: m/z=557 (M+H)$^+$
$R_f$(HPLC): 3.41 min (method C)

Example 59

7-methoxy-3-{1-[6-(3-methyl-2-oxo-2,3-dihydro-benzoxazole-6-carbonyl)-pyrimidin-4-yl]-piperidin-4-yl}-1,3,4,5-tetrahydro-benzo[d][1,3]diazepin-2-one

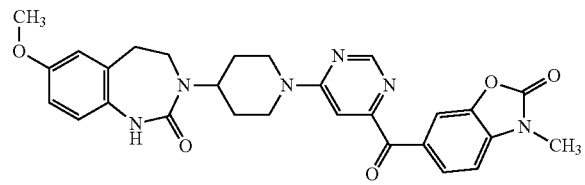 [SMILES: COc1ccc2c(c1)CCN(C1CCN(c3cc(C(=O)c4ccc5c(c4)oc(=O)n5C)ncn3)CC1)C(=O)N2]

99 mg (0.40 mmol) 7-methoxy-3-piperidin-4-yl-1,3,4,5-tetrahydro-1,3-benzodiazepin-2-one, 0.10 g (0.40 mmol) 6-(6-chloro-pyrimidine-4-carbonyl)-3-methyl-3H-benzoxazol-2-one and 0.070 mL (0.40 mmol) DIPEA were combined in 2 mL DMF and shaken overnight at RT. The mixture was diluted with acetonitrile/water and purified by preparative HPLC-MS. The fractions containing the product were combined and freeze-dried.

Yield: 140 mg (74% of theoretical)
ESI-MS: m/z=529 (M+H)$^+$
$R_f$(HPLC): 1.27 min (method B)

Example 60

7-methoxy-3-{1-[6-(2-oxo-2,3-dihydro-benzoxazole-6-carbonyl)-pyrimidin-4-yl]-piperidin-4-yl}-1,3,4,5-tetrahydro-benzo[d][1,3]diazepin-2-one

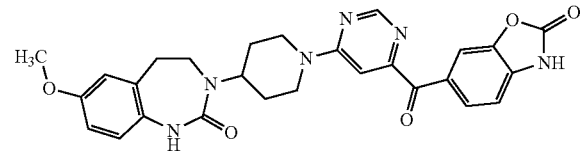 [SMILES: COc1ccc2c(c1)CCN(C1CCN(c3cc(C(=O)c4ccc5[nH]c(=O)oc5c4)ncn3)CC1)C(=O)N2]

99 mg (0.40 mmol) 7-methoxy-3-piperidin-4-yl-1,3,4,5-tetrahydro-1,3-benzodiazepin-2-one, 0.10 g (0.40 mmol) 6-(6-chloro-pyrimidine-4-carbonyl)-3H-benzoxazol-2-one and 0.07 mL (0.40 mmol) DIPEA were combined in 2 mL DMF and shaken overnight at RT. The mixture was diluted with acetonitrile/water and purified by preparative HPLC-MS. The fractions containing the product were combined and freeze-dried.

Yield: 105 mg (57% of theoretical)
ESI-MS: m/z=513 (M−H)$^−$
$R_f$(HPLC): 1.18 min (method B)

Example 61

1-{1-[6-(7-methyl-2-oxo-2,3-dihydro-1H-indol-5-carbonyl)-pyrimidin-4-yl]-piperidin-4-yl}-1,3-dihydro-imidazo[4,5-b]pyridin-2-one

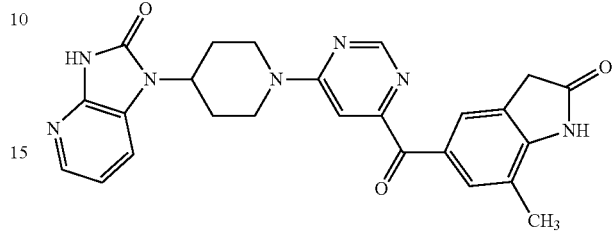

91 mg (0.42 mmol) 1-piperidin-4-yl-1,3-dihydroimidazo[4,5-b]pyridin-2-one, 120 mg (0.42 mmol) 5-(6-chloro-pyrimidine-4-carbonyl)-7-methyl-1,3-dihydro-indol-2-one and 0.080 mL (0.46 mmol) DIPEA were combined in 2 mL DMF and shaken overnight at RT. Then the reaction mixture was in taken up acetonitrile/water and purified by preparative HPLC-MS. The fractions containing the product were combined and freeze-dried.

Yield: 33 mg (17% of theoretical)
ESI-MS: m/z=468 (M−H)$^−$
$R_f$(HPLC): 1.07 min (method B)

Example 62

1-{1-[6-(3,4,5-trimethyl-benzoyl)-pyrimidin-4-yl]-piperidin-4-yl}-1,3-dihydro-imidazo[4,5-b]-pyridin-2-one

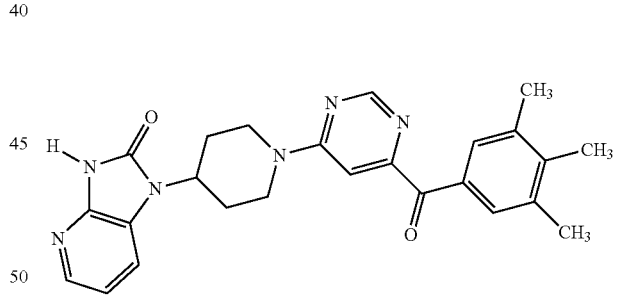

0.20 g (0.70 mmol) 1-piperidin-4-yl-1,3-dihydroimidazo[4,5-b]pyridin-2-one-dihydrochloride, 0.18 g (0.70 mmol) (6-chloro-pyrimidin-4-yl)-(3,4,5-trimethyl-phenyl)-methanone and 0.40 mL (2.3 mmol) DIPEA were combined in 10 mL DMF and stirred overnight at RT. The reaction mixture was evaporated down i. vac., the residue was mixed with water and stirred for another 10 min. The precipitate was suction filtered and purified by preparative HPLC-MS. The fractions containing the product were combined and freeze-dried.

Yield: 30 mg (10% of theoretical)
ESI-MS: m/z=443 (M+H)$^+$
$R_f$: 0.66 (silica gel, DCM/Cyc/MeOH/NH$_4$OH=70/15/15/2)

Example 63

1-[6'-benzyloxy-4'-(3,4-dimethyl-2-oxo-2,3-dihydro-benzoxazole-6-carbonyl)-3,4,5,6-tetrahydro-2H-[1,2']bipyridinyl-4-yl]-1,3-dihydro-imidazo[4,5-b]pyridin-2-one

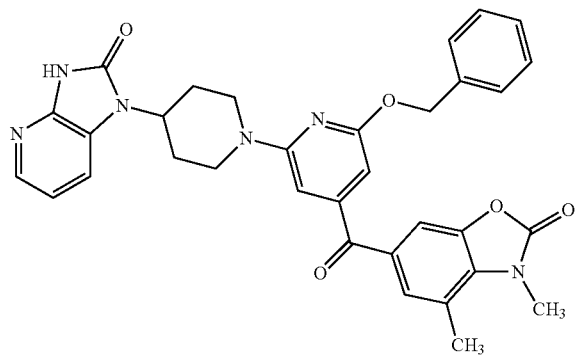 [SMILES: Cc1cc(C(=O)c2cc(OCc3ccccc3)nc(N3CCC(n4c(=O)[nH]c5ncccc54)CC3)c2)cc2oc(=O)n(C)c12]

785 mg (3.60 mmol) 1-piperidin-4-yl-1,3-dihydroimidazo[4,5-b]pyridin-2-one and 500 mg (1.22 mmol) 6-(2-benzyloxy-6-chloro-pyridine-4-carbonyl)-3,4-dimethyl-3H-benzoxazol-2-one (mixture) were combined in 5 mL NMP and stirred overnight at 120° C. The reaction mixture was purified by preparative HPLC. The fractions containing the product were combined and evaporated down. The residue was triturated with DIPE, suction filtered, washed with DIPE and dried.

Yield: 300 mg (14% of theoretical)

ESI-MS: m/z=591 (M+H)$^+$

R$_t$(HPLC): 1.70 min (method B)

Example 64

7-methoxy-3-{1-[6-(3-methyl-2-oxo-4-pyrazol-1-ylmethyl-2,3-dihydro-benzoxazole-6-carbonyl)-pyrimidin-4-yl]-piperidin-4-yl}-1,3,4,5-tetrahydro-benzo[d][1,3]diazepin-2-one

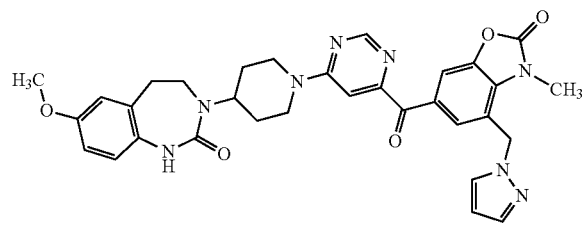

140 mg (0.508 mmol) 7-methoxy-3-piperidin-4-yl-1,3,4,5-tetrahydro-1,3-benzodiazepin-2-one, 210 mg (0.284 mmol) 6-(6-chloro-pyrimidine-4-carbonyl)-3-methyl-4-pyrazol-1-ylmethyl-3H-benzoxazol-2-one and 0.100 mL (0.581 mmol) DIPEA were combined in 1.0 mL DMF and stirred for 48 h at RT. Then the reaction mixture was purified several times by preparative HPLC-MS. The fractions containing the product were combined and freeze-dried.

Yield: 12 mg (6% of theoretical)

ESI-MS: m/z=609 (M+H)$^+$

R$_t$(HPLC): 4.33 min (method D)

Example 65

1-{1-[6-(1,7-dimethyl-1H-indazole-5-carbonyl)-pyrimidin-4-yl]-piperidin-4-yl}-1,3-dihydro-imidazo[4,5-b]pyridin-2-one

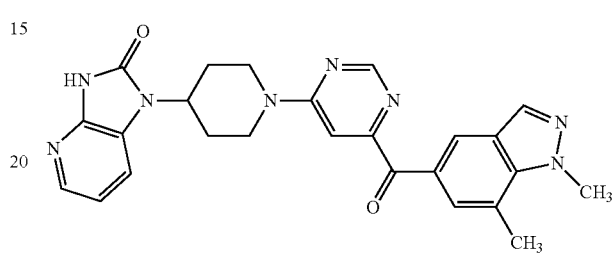

25 mg (0.12 mmol) 1-piperidin-4-yl-1,3-dihydroimidazo[4,5-b]pyridin-2-one, 35 mg (0.10 mmol) (6-chloro-pyrimidin-4-yl)-(1,7-dimethyl-1H-indazol-5-yl)-methanone and 25 μL (0.18 mmol) TEA were combined in 1 mL DMF and stirred overnight at RT. The reaction mixture was purified by preparative HPLC. The fractions containing the product were combined and evaporated down to approx. 5 mL. This residue was neutralised with saturated sodium hydrogen carbonate solution, the precipitate formed was suction filtered and dried.

Yield: 20 mg (44% of theoretical)

ESI-MS: m/z=469 (M+H)$^+$

R$_t$(HPLC): 2.63 min (method C)

Example 66

7-methoxy-3-{1-[6-(7-methyl-2,3-dihydro-benzofuran-5-carbonyl)-pyrimidin-4-yl]-piperidin-4-yl}-1,3,4,5-tetrahydro-benzo[d][1,3]diazepin-2-one

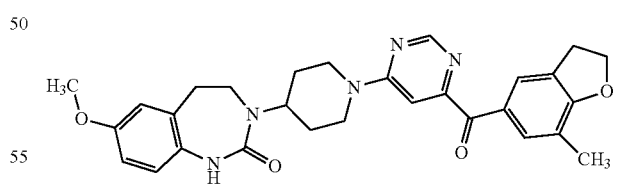

100 mg (0.363 mmol) 7-methoxy-3-piperidin-4-yl-1,3,4,5-tetrahydro-1,3-benzodiazepin-2-one, 90.0 mg (0.229 mmol) (6-chloro-pyrimidin-4-yl)-(7-methyl-2,3-dihydro-benzofuran-5-yl)-methanone and 0.200 mL (1.16 mmol) DIPEA were combined in 1.5 mL DMF and stirred for 48 h at RT. Then the reaction mixture was combined with a few drops of hydrochloric acid and purified by preparative HPLC-MS. The fractions containing the product were combined and freeze-dried.

Yield: 75 mg (64% of theoretical)
ESI-MS: m/z=514 (M+H)$^+$
R$_f$(HPLC): 1.3 min (method B)

Example 67

1-{1-[6-(3-ethyl-4-methyl-2-oxo-2,3-dihydro-benzoxazole-6-carbonyl)-pyrimidin-4-yl]-piperidin-4-yl}-1,3-dihydro-imidazo[4,5-b]pyridin-2-one

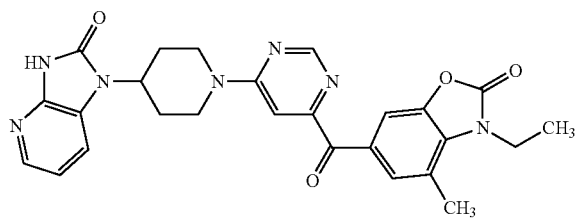 [SMILES: CCn1c(=O)oc2cc(C(=O)c3cc(N4CCC(n5c(=O)[nH]c6ncccc65)CC4)ncn3)cc(C)c21]

47 mg (0.20 mmol) 1-piperidin-4-yl-1,3-dihydroimidazo[4,5-b]pyridin-2-one-dihydrochloride, 50 mg (0.20 mmol) 6-(6-chloro-pyrimidine-4-carbonyl)-3-ethyl-4-methyl-3H-benzoxazol-2-one and 0.11 mL (0.64 mmol) DIPEA were combined in 2.0 mL DMF and stirred overnight at RT. The reaction mixture was purified by preparative HPLC. The fractions containing the product were combined, the organic solvent was evaporated down and the residue was neutralised with 1N aqueous sodium hydroxide solution. The precipitate formed was suction filtered, washed with water and dried.

Yield: 47 mg (59% of theoretical)
ESI-MS: m/z=500 (M+H)$^+$
R$_f$(HPLC): 2.89 min (method C)

Example 68

7-methoxy-3-{1-[6-(1,3,3,7-tetramethyl-2,3-dihydro-1H-indol-5-carbonyl)-pyrimidin-4-yl]-piperidin-4-yl}-1,3,4,5-tetrahydro-benzo[d][1,3]diazepin-2-one

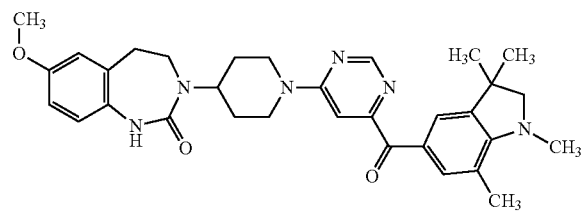 [SMILES: COc1ccc2c(c1)CCN(C1CCN(c3cc(C(=O)c4cc(C)c5c(c4)C(C)(C)CN5C)ncn3)CC1)C(=O)N2]

48 mg (0.17 mmol) 7-methoxy-3-piperidin-4-yl-1,3,4,5-tetrahydro-1,3-benzodiazepin-2-one, 55 mg (0.17 mmol) (6-chloro-pyrimidin-4-yl)-(1,3,3,7-tetramethyl-2,3-dihydro-1H-indol-5-yl)-methanone and 0.050 mL (0.29 mmol) DIPEA were combined in 2 mL DMF and stirred overnight at 40° C. Then the reaction mixture was purified by preparative HPLC-MS. The fractions containing the product were combined and freeze-dried.

Yield: 50 mg (52% of theoretical)
ESI-MS: m/z=555 (M+H)$^+$
R$_f$(HPLC): 1.39 min (method B)

Example 69

3-{1-[6-(3,4-dimethyl-2-oxo-2,3-dihydro-benzoxazole-6-carbonyl)-pyrimidin-4-yl]-piperidin-4-yl}-9-fluoro-1,3,4,5-tetrahydro-benzo[d][1,3]diazepin-2-one

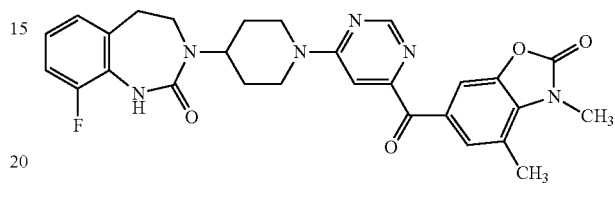

61 mg (0.23 mmol) 9-fluoro-3-piperidin-4-yl-1,3,4,5-tetrahydro-benzo[d][1,3]diazepin-2-one, 70 mg (0.23 mmol) 6-(6-chloropyrimidine-4-carbonyl)-3,4-dimethyl-3H-benzoxazol-2-one and 0.080 mL (0.46 mmol) DIPEA were combined in 2 mL DMF and stirred for 2 h at RT. Then the reaction mixture was diluted with MeOH, the precipitate formed was suction filtered, washed with MeOH and diethyl ether and dried.

Yield: 78 mg (64% of theoretical)
ESI-MS: m/z=531 (M+H)$^+$
R$_f$(HPLC): 1.38 min (method B)

Example 70

3-{1-[5-(3,4-dimethyl-2-oxo-2,3-dihydro-benzoxazole-6-carbonyl)-2-fluoro-phenyl]-piperidin-4-yl}-7-methoxy-1,3,4,5-tetrahydro-benzo[d][1,3]diazepin-2-one

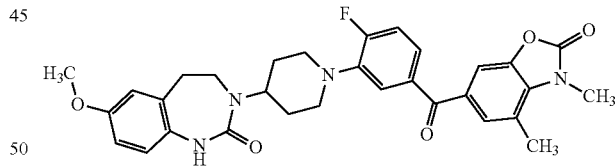

Under an argon atmosphere 330 mg (1.20 mmol) 7-methoxy-3-piperidin-4-yl-1,3,4,5-tetrahydro-benzo[d][1,3]diazepin-2-one, 437 mg (1.20 mmol) 6-(3-bromo-4-fluoro-benzoyl)-3,4-dimethyl-3H-benzoxazol-2-one and 586 mg (1.80 mmol) caesium carbonate were combined in 10 mL dioxane, then mixed with 75 mg (0.12 mmol) BINAP and 27 mg (0.12 mmol) palladium(II)acetate and stirred for 48 h at 100° C. The mixture was evaporated down, the residue was dissolved in DMF/MeOH and purified by preparative HPLC-MS. The fractions containing the product were combined and the acetonitrile was evaporated down. The aqueous residue was made basic with 1N aqueous sodium hydroxide solution, the precipitate formed was suction filtered and washed with water and dried. As the product was still contaminated, it was then purified again by preparative HPLC-MS.

Yield: 40 mg (6% of theoretical)
ESI-MS: m/z=559 (M+H)+
$R_f$(HPLC): 4.21 min (method C)

Example 71

1-{1-[6-(7-methyl-2,3-dihydro-benzofuran-5-carbonyl)-pyrimidin-4-yl]-piperidin-4-yl}-1,3-di-hydro-imidazo[4,5-b]pyridin-2-one-formate

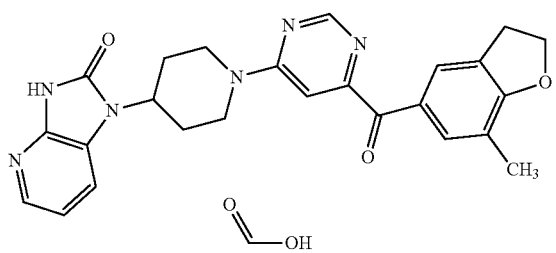 [SMILES: Cc1cc(C(=O)c2cc(N3CCC(n4c(=O)[nH]c5ncccc54)CC3)ncn2)cc2c1OCC2 ; O=CO]

0.11 g (0.36 mmol) 1-piperidin-4-yl-1,3-dihydroimidazo[4,5-b]pyridin-2-one-dihydrochloride, 90 mg (0.23 mmol) (6-chloro-pyrimidin-4-yl)-(7-methyl-2,3-dihydro-benzofuran-5-yl)-methanone and 0.20 mL (1.16 mmol) DIPEA were combined in 1.5 mL DMF and stirred for 48 h at RT. Then the reaction mixture was mixed with a few drops of hydrochloric acid and purified by preparative HPLC-MS. The fractions containing the product were combined and freeze-dried.

Yield: 60 mg (52% of theoretical)
ESI-MS: m/z=457 (M+H)+
$R_f$(HPLC): 1.18 min (method B)

Example 72

1-{1-[6-(2-oxo-2,3-dihydro-benzoxazole-6-carbonyl)-pyrimidin-4-yl]-piperidin-4-yl}-1,3-di-hydro-imidazo[4,5-b]pyridin-2-one

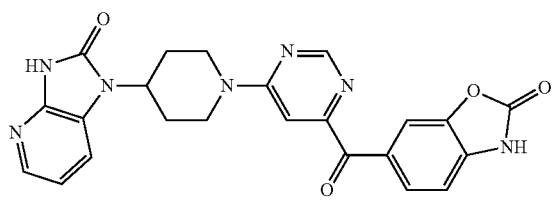 [SMILES: O=C(c1ccc2[nH]c(=O)oc2c1)c1cc(N2CCC(n3c(=O)[nH]c4ncccc43)CC2)ncn1]

78 mg (0.40 mmol) 1-piperidin-4-yl-1,3-dihydro-imidazo[4,5-b]pyridin-2-one, 0.10 g (0.40 mmol) 6-(6-chloro-pyrimidine-4-carbonyl)-3H-benzoxazol-2-one and 0.070 mL (0.40 mmol) DIPEA were combined in 2 mL DMF and shaken overnight at RT. The mixture was diluted with acetonitrile/water and purified by preparative HPLC-MS. The fractions containing the product were combined and freeze-dried.

Yield: 98 mg (60% of theoretical)
ESI-MS: m/z=456 (M−H)−
$R_f$(HPLC): 1.02 min (method B)

Example 73

7-methoxy-3-{1-[6-(8-methyl-2,3-dihydro-benzo[1,4]dioxin-6-carbonyl)-pyrimidin-4-yl]-piperidin-4-yl}-1,3,4,5-tetrahydro-benzo[d][1,3]diazepin-2-one

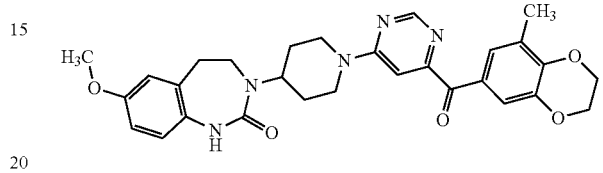

61 mg (0.22 mmol) 7-methoxy-3-piperidin-4-yl-1,3,4,5-tetrahydro-1,3-benzodiazepin-2-one, 84 mg (0.22 mmol) (6-iodo-pyrimidin-4-yl)-(8-methyl-2,3-dihydro-benzo[1,4]dioxin-6-yl)-methanone and 0.08 mL (0.44 mmol) DIPEA were combined in 2.5 mL DMF and stirred overnight at RT. Then the reaction mixture was purified by preparative HPLC-MS. The fractions containing the product were combined and the organic solvent was evaporated down. The residue was combined with 1N aqueous sodium hydroxide solution, the precipitate formed was suction filtered, washed with water and dried.

Yield: 65 mg (56% of theoretical)
ESI-MS: m/z=530 (M+H)+
$R_f$(HPLC): 3.38 min (method B)

Example 74

1-{1-[6-(8-methyl-2,3-dihydro-benzo[1,4]dioxin-6-carbonyl)-pyrimidin-4-yl]-piperidin-4-yl}-1,3-dihydro-imidazo[4,5-b]pyridin-2-one

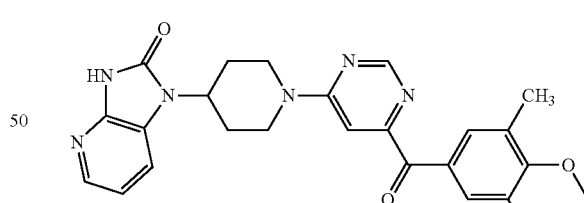

64 mg (0.22 mmol) 1-piperidin-4-yl-1,3-dihydroimidazo[4,5-b]pyridin-2-one-dihydrochloride, 84 mg (0.22 mmol) (6-iodo-pyrimidin-4-yl)-(8-methyl-2,3-dihydro-benzo[1,4]dioxin-6-yl)-methanone and 0.15 mL (0.88 mmol) DIPEA were combined in 2.5 mL DMF and stirred overnight at RT. Then the reaction mixture was purified by preparative HPLC-MS. The fractions containing the product were combined and the organic solvent was evaporated down. The residue was mixed with 1N aqueous sodium hydroxide solution, the precipitate formed was suction filtered, washed with water and dried.

Example 75

1-{1-[6-(3-methyl-2-oxo-2,3-dihydro-benzoxazole-6-carbonyl)-pyrimidin-4-yl]-piperidin-4-yl}-1,3-dihydro-imidazo[4,5-b]pyridin-2-one

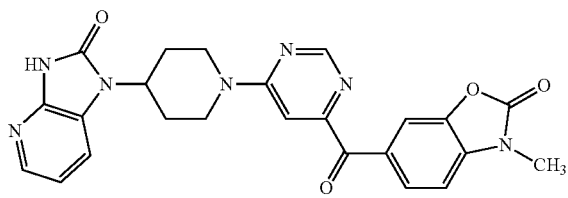 [SMILES: Cn1c(=O)oc2cc(C(=O)c3cc(N4CCC(n5c(=O)[nH]c6ncccc65)CC4)ncn3)ccc21]

78 mg (0.40 mmol) 1-piperidin-4-yl-1,3-dihydro-imidazo[4,5-b]pyridin-2-one, 0.10 g (0.40 mmol) 6-(6-chloro-pyrimidine-4-carbonyl)-3-methyl-3H-benzoxazol-2-one and 0.070 mL (0.40 mmol) DIPEA were combined in 2 mL DMF and shaken overnight at RT. The mixture was diluted with acetonitrile/water and purified by preparative HPLC-MS. The fractions containing the product were combined and freeze-dried.

Yield: 126 mg (74% of theoretical)
ESI-MS: m/z=470 (M−H)⁻
$R_t$(HPLC): 1.1 min (method B)

Example 76

7-methoxy-3-{1-[6-(2-oxo-2,3-dihydro-1H-indol-5-carbonyl)-pyrimidin-4-yl]-piperidin-4-yl}-1,3,4,5-tetrahydro-benzo[d][1,3]diazepin-2-one

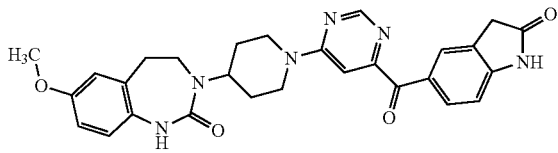 [SMILES: COc1ccc2c(c1)CCN(C1CCN(c3cc(C(=O)c4ccc5c(c4)CC(=O)N5)ncn3)CC1)C(=O)N2]

99 mg (0.40 mmol) 7-methoxy-3-piperidin-4-yl-1,3,4,5-tetrahydro-benzo[d][1,3]diazepin-2-one, 98 mg (0.40 mmol) 5-(6-chloro-pyrimidine-4-carbonyl)-1,3-dihydro-indol-2-one and 0.070 mL (0.40 mmol) DIPEA were combined in 2 mL DMF and shaken overnight at RT. The mixture was diluted with acetonitrile/water and purified by preparative HPLC-MS. The fractions containing the product were combined and freeze-dried.

Yield: 91 mg (49% of theoretical)
ESI-MS: m/z=511 (M−H)⁻
$R_t$(HPLC): 1.1 min (method B)

Example 77

1-{1-[6-(1,3,3,7-tetramethyl-2,3-dihydro-1H-indol-5-carbonyl)-pyrimidin-4-yl]-piperidin-4-yl}-1,3-dihydro-imidazo[4,5-b]pyridin-2-one

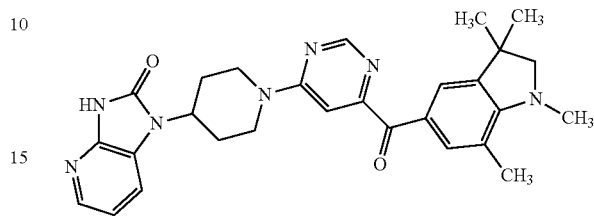

38 mg (0.17 mmol) 1-piperidin-4-yl-1,3-dihydroimidazo[4,5-b]pyridin-2-one, 55 mg (0.17 mmol) (6-chloro-pyrimidin-4-yl)-(1,3,3,7-tetramethyl-2,3-dihydro-1H-indol-5-yl)-methanone and 0.050 mL (0.29 mmol) DIPEA were combined in 2 mL DMF and stirred overnight at 40° C. Then the reaction mixture was purified by preparative HPLC-MS. The fractions containing the product were combined and freeze-dried.

Yield: 60 mg (69% of theoretical)
ESI-MS: m/z=498 (M+H)⁺
$R_t$(HPLC): 1.24 min (method B)

Example 78

3-{1-[6-(3,4-dimethyl-2-oxo-2,3-dihydro-benzoxazole-6-carbonyl)-pyrimidin-4-yl]-2-methyl-piperidin-4-yl}-7-methoxy-1,3,4,5-tetrahydro-benzo[d][1,3]diazepin-2-one

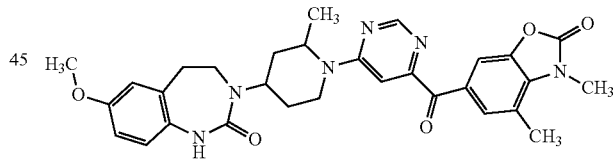

60 mg (0.21 mmol) 7-methoxy-3-(2-methyl-piperidin-4-yl)-1,3,4,5-tetrahydro-benzo[d]-[1,3]diazepin-2-one, 60 mg (0.20 mmol) 6-(6-chloropyrimidine-4-carbonyl)-3,4-dimethyl-3H-benzoxazol-2-one and 0.040 mL (0.29 mmol) TEA were combined in 1 mL DMF and stirred for three days at RT. Then 7-methoxy-3-(2-methyl-piperidin-4-yl)-1,3,4,5-tetrahydrobenzo[d][1,3]diazepin-2-one was added again and the mixture was stirred for 3 h at 80° C. The reaction mixture was purified by preparative HPLC. The fractions containing the product were combined and the solvent was evaporated down by half. The aqueous residue was extracted with DCM, the combined organic phases were dried on sodium sulphate, filtered and the filtrate was evaporated down.

Yield: 9 mg (8% of theoretical)
ESI-MS: m/z=557 (M+H)⁺
$R_t$(HPLC): 3.54 min (method C)

---

Yield: 70 mg (67% of theoretical)
ESI-MS: m/z=473 (M+H)⁺
$R_t$(HPLC): 2.85 min (method B)

Example 79

1-{1-[6-(1,3-dimethyl-2-oxo-2,3-dihydro-1H-benz-imidazole-5-carbonyl)-pyrimidin-4-yl]-piperidin-4-yl}-1,3-dihydro-imidazo[4,5-b]pyridin-2-one

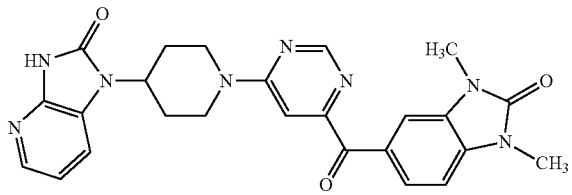 [SMILES: Cn1c(=O)n(C)c2cc(C(=O)c3cc(N4CCC(n5c(=O)[nH]c6ncccc65)CC4)ncn3)ccc21]

75 mg (0.34 mmol) 1-piperidin-4-yl-1,3-dihydroimidazo[4,5-b]pyridin-2-one, 0.10 g (0.33 mmol) 5-(6-chloro-pyrimidine-4-carbonyl)-1,3-dimethyl-1,3-dihydro-benzimidazol-2-one and 0.10 mL (0.58 mmol) DIPEA were combined in 5 mL DMF and stirred overnight at RT. Then the reaction mixture was evaporated down, the residue was mixed with water and stirred for another 10 min. The precipitate formed was suction filtered, dissolved in DMF and purified by preparative HPLC-MS. The fractions containing the product were combined and freeze-dried.

Yield: 75 mg (45% of theoretical)

ESI-MS: m/z=485 (M+H)$^+$ $R_f$: 0.59 (silica gel; DCM/Cyc/MeOH/NH$_4$OH=70/15/15/2)

Example 80

3-{1-[6-(1,3-dimethyl-2-oxo-2,3-dihydro-1H-benz-imidazole-5-carbonyl)-pyrimidin-4-yl]-piperidin-4-yl}-7-methoxy-1,3,4,5-tetrahydro-benzo[d][1,3]diazepin-2-one

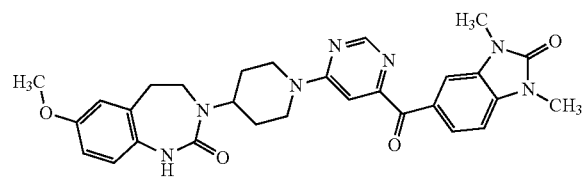

90 mg (0.34 mmol) 7-methoxy-3-piperidin-4-yl-1,3,4,5-tetrahydro-1,3-benzodiazepin-2-one, 0.10 g (0.33 mmol) 5-(6-chloro-pyrimidine-4-carbonyl)-1,3-dimethyl-1,3-dihydro-benzimidazol-2-one and 0.10 mL (0.58 mmol) DIPEA in 5 mL DMF were combined and stirred overnight at RT. Then the reaction mixture was evaporated down, the residue was mixed with water and stirred for another 10 min. The precipitate formed was suction filtered, dissolved in DMF and purified by preparative HPLC-MS. The fractions containing the product were combined and freeze-dried.

Yield: 55 mg (31% of theoretical)

ESI-MS: m/z=542 (M+H)$^+$ $R_f$: 0.64 (silica gel; DCM/Cyc/MeOH/NH$_4$OH=70/15/15/2)

Example 81

3-[6'-amino-4'-(3,4-dimethyl-2-oxo-2,3-dihydro-benzoxazole-6-carbonyl)-3,4,5,6-tetrahydro-2H-[1,2']bipyridinyl-4-yl]-7-methoxy-1,3,4,5-tetrahydro-benzo[d][1,3]diazepin-2-one

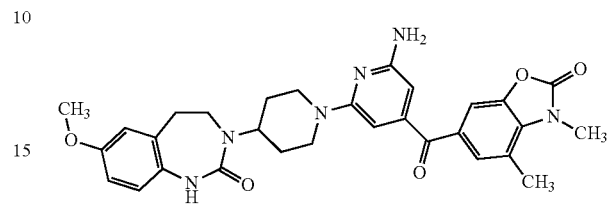

0.50 mL TFA were added to 57 mg (0.10 mmol) tert-butyl [4'-(3,4-dimethyl-2-oxo-2,3-dihydro-benzoxazole-6-carbonyl)-4-(7-methoxy-2-oxo-1,2,4,5-tetrahydro-benzo[d][1,3]diazepin-3-yl)-3,4,5,6-tetrahydro-2H-[1,2']bipyridinyl-6'-yl]-carbamate in 5.00 mL DCM and stirred for 3 h at RT. Then another 0.50 mL TFA were added and the mixture was stirred overnight at RT. Then the reaction mixture was evaporated down, the residue was dissolved in DMF and purified by preparative HPLC-MS. The fractions containing the product were combined and freeze-dried.

Yield: 4 mg (8% of theoretical)

ESI-MS: m/z=557 (M+H)$^+$ $R_t$(HPLC): 1.30 min (method B)

Example 82

3-{1-[6-(3,4-dimethyl-2-oxo-2,3-dihydro-benzoxazole-6-carbonyl)-2-methyl-pyrimidin-4-yl]-3-fluoro-piperidin-4-yl}-7-methoxy-1,3,4,5-tetrahydro-benzo[d][1,3]diazepin-2-one

82 mg (0.28 mmol) 3-(3-fluoro-piperidin-4-yl)-7-methoxy-1,3,4,5-tetrahydro-benzo[d]-[1,3]diazepin-2-one, 85 mg (0.27 mmol) 6-(6-chloro-2-methyl-pyrimidine-4-carbonyl)-3,4-dimethyl-3H-benzoxazol-2-one and 0.10 mL (0.56 mmol) DIPEA were combined in 2 mL DMF and stirred overnight at RT. Then the reaction mixture was purified by preparative HPLC-MS. The fractions containing the product were combined and the organic solvent was evaporated down. The residue was neutralised with 4N aqueous sodium hydroxide solution, the precipitate formed was suction filtered, washed with water and dried.

Yield: 64 mg (40% of theoretical)

ESI-MS: m/z=575 (M+H)$^+$ $R_t$(HPLC): 1.32 min (method B)

Example 83

7-methoxy-3-[5'-methyl-4'-(4-methyl-2-oxo-2,3-dihydro-benzoxazole-6-carbonyl)-3,4,5,6-tetrahydro-2H-[1,2']bipyridinyl-4-yl]-1,3,4,5-tetrahydro-benzo[d][1,3]diazepin-2-one

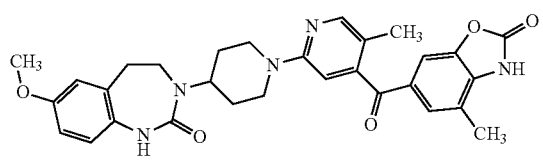 [SMILES: COc1ccc2c(c1)CCN(C1CCN(c3cc(C(=O)c4cc(C)c5[nH]c(=O)oc5c4)c(C)cn3)CC1)C(=O)N2]

688 mg (2.50 mmol) 7-methoxy-3-piperidin-4-yl-1,3,4,5-tetrahydro-1,3-benzodiazepin-2-one and 378 mg (1.25 mmol) 6-(2-chloro-5-methyl-pyridine-4-carbonyl)-4-methyl-3H-benzoxazol-2-one (mixture) were combined and heated to 300° C. for approx. 10 min. Then the mixture was dissolved in DMF and purified by preparative HPLC-MS. The fractions containing the product were combined and the organic solvent was evaporated down. The residue was neutralised with 1N aqueous sodium hydroxide solution, the precipitate formed was suction filtered, washed with water and dried.

Yield: 115 mg (17% of theoretical)
ESI-MS: m/z=542 (M+H)$^+$
$R_t$(HPLC): 1.15 min (method B)

Example 84

1-[4'-(3,4-dimethyl-2-oxo-2,3-dihydro-benzoxazole-6-carbonyl)-6'-methylamino-3,4,5,6-tetrahydro-2H-[1,2']bipyridinyl-4-yl]-1,3-dihydro-imidazo[4,5-b]pyridin-2-one

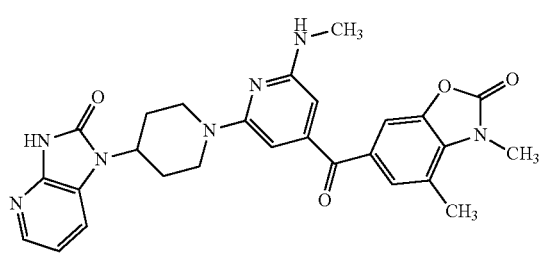 [SMILES: CNc1cc(C(=O)c2cc(C)c3c(c2)oc(=O)n3C)cc(N2CCC(n3c(=O)[nH]c4ncccc43)CC2)n1]

1.00 mL TFA were added to 59 mg (0.096 mmol) tert-butyl [4'-(3,4-dimethyl-2-oxo-2,3-dihydro-benzoxazole-6-carbonyl)-4-(2-oxo-2,3-dihydro-imidazo[4,5-b]pyridin-1-yl)-3,4,5,6-tetrahydro-2H-[1,2']bipyridinyl-6'-yl]-methyl-carbamate in 5.00 mL DCM and the mixture was stirred for 3 h at RT. Then the reaction mixture was evaporated down, the residue was dissolved in DMF and purified by preparative HPLC-MS. The fractions containing the product were combined and freeze-dried.

Yield: 3 mg (6% of theoretical)
ESI-MS: m/z=514 (M+H)$^+$
$R_t$(HPLC): 1.28 min (method B)

Example 85

1-[2'-(4-methyl-2-oxo-2,3-dihydro-benzoxazole-6-carbonyl)-3,4,5,6-tetrahydro-2H-[1,4']bipyridinyl-4-yl]-1,3-dihydro-imidazo[4,5-b]pyridin-2-one

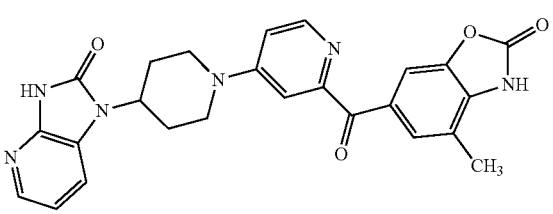 [SMILES: Cc1cc(C(=O)c2cc(N3CCC(n4c(=O)[nH]c5ncccc54)CC3)ccn2)cc2oc(=O)[nH]c12]

32 mg (0.11 mmol) 1-piperidin-4-yl-1,3-dihydroimidazo[4,5-b]pyridin-2-one, 30 mg (0.10 mmol) 6-(4-chloro-pyridin-2-carbonyl)-4-methyl-3H-benzoxazol-2-one and 45 mg (0.33 mmol) potassium carbonate were combined in 1 mL NMP and stirred overnight at 130° C. The reaction mixture was filtered, the filtrate was diluted with 1 mL DMF and purified by preparative HPLC-MS. The fractions containing the product were combined and freeze-dried.

Yield: 10 mg (21% of theoretical)
ESI-MS: m/z=471 (M+H)$^+$
$R_f$: 0.49 (silica gel, DCM/Cyc/MeOH/NH$_4$OH=70/15/15/2)

The following Examples describe the preparation of pharmaceutical formulations that contain as active substance any desired compound of general formula I:

Example I

Capsules for Powder Inhalation Containing 1 mg of Active Ingredient

Composition:
1 capsule for powder inhalation contains:

| | |
|---|---|
| active ingredient | 1.0 mg |
| lactose | 20.0 mg |
| hard gelatine capsules | 50.0 mg |
| | 71.0 mg |

Method of Preparation:

The active ingredient is ground to the particle size required for inhaled substances. The ground active ingredient is homogeneously mixed with the lactose. The mixture is transferred into hard gelatine capsules.

Example II

Inhalable Solution for Respimat® Containing 1 mg of Active Ingredient

Composition:
1 puff contains:

| | |
|---|---|
| active ingredient | 1.0 mg |
| benzalkonium chloride | 0.002 mg |
| disodium edetate | 0.0075 mg |
| purified water ad | 15.0 µl |

Method of Preparation:
The active ingredient and benzalkonium chloride are dissolved in water and transferred into Respimat® cartridges.

Example III

Inhalable Solution for Nebulisers Containing 1 mg of Active Ingredient

Composition:
1 vial contains:

| | |
|---|---|
| active ingredient | 0.1 g |
| sodium chloride | 0.18 g |
| benzalkonium chloride | 0.002 g |
| purified water ad | 20.0 ml |

Method of Preparation:
The active ingredient, sodium chloride and benzalkonium chloride are dissolved in water.

Example IV

Propellant Gas-Operated Metered Dose Aerosol Containing 1 mg of Active Ingredient

Composition:
1 puff contains:

| | |
|---|---|
| active ingredient | 1.0 mg |
| lecithin | 0.1% |
| propellant gas ad | 50.0 µl |

Method of Preparation:
The micronised active ingredient is homogeneously suspended in the mixture of lecithin and propellant gas. The suspension is transferred into a pressurised container with a metering valve.

Example V

Nasal Spray Containing 1 mg of Active Ingredient

Composition:

| | |
|---|---|
| active ingredient | 1.0 mg |
| sodium chloride | 0.9 mg |
| benzalkonium chloride | 0.025 mg |
| disodium edetate | 0.05 mg |
| purified water ad | 0.1 ml |

Method of Preparation:
The active ingredient and the excipients are dissolved in water and transferred into a suitable container.

Example VI

Injectable Solution Containing 5 mg of Active Substance Per 5 ml

Composition:

| | |
|---|---|
| active substance | 5 mg |
| glucose | 250 mg |
| human serum albumin | 10 mg |
| glycofurol | 250 mg |
| water for injections ad | 5 ml |

Preparation:
Glycofurol and glucose are dissolved in water for injections (Wfl); human serum albumin is added; active ingredient is dissolved with heating; made up to specified volume with Wfl; transferred into ampoules under nitrogen gas.

Example VII

Injectable Solution Containing 100 mg of Active Substance Per 20 ml

Composition:

| | |
|---|---|
| active substance | 100 mg |
| monopotassium dihydrogen phosphate = $KH_2PO_4$ | 12 mg |
| disodium hydrogen phosphate = $Na_2HPO_4 \cdot 2H_2O$ | 2 mg |
| sodium chloride | 180 mg |
| human serum albumin | 50 mg |
| Polysorbate 80 | 20 mg |
| water for injections ad | 10 ml |

Preparation:
Polysorbate 80, sodium chloride, monopotassium dihydrogen phosphate and disodium hydrogen phosphate are dissolved in water for injections (Wfl); human serum albumin is added; active ingredient is dissolved with heating; made up to specified volume with Wfl; transferred into ampoules.

Example VIII

Lyophilisate Containing 10 mg of Active Substance

Composition:

| | |
|---|---|
| Active substance | 10 mg |
| Mannitol | 300 mg |
| human serum albumin | 20 mg |
| water for injections ad | 2 ml |

Preparation:

Mannitol is dissolved in water for injections (Wfl); human serum albumin is added; active ingredient is dissolved with heating; made up to specified volume with Wfl; transferred into vials; freeze-dried.

Solvent for Lyophilisate:

| | |
|---|---|
| Polysorbate 80 = Tween 80 | 20 mg |
| mannitol | 200 mg |
| water for injections ad | 10 ml |

Preparation:

Polysorbate 80 and mannitol are dissolved in water for injections (Wfl); transferred into ampoules.

Example IX

Tablets Containing 20 mg of Active Substance

Composition:

| | |
|---|---|
| active substance | 20 mg |
| lactose | 120 mg |
| corn starch | 40 mg |
| magnesium stearate | 2 mg |
| Povidone K 25 | 18 mg |

Preparation:

Active substance, lactose and corn starch are homogeneously mixed; granulated with an aqueous solution of Povidone; mixed with magnesium stearate; compressed in a tablet press; weight of tablet 200 mg.

Example X

Capsules Containing 20 mg Active Substance

Composition:

| | |
|---|---|
| active substance | 20 mg |
| corn starch | 80 mg |
| highly dispersed silica | 5 mg |
| magnesium stearate | 2.5 mg |

Preparation:

Active substance, corn starch and silica are homogeneously mixed; mixed with magnesium stearate; the mixture is packed into size for 3 hard gelatine capsules in a capsule filling machine.

Example XI

Suppositories Containing 50 mg of Active Substance

Composition:

| | |
|---|---|
| active substance | 50 mg |
| hard fat (Adeps solidus) q.s. Ad | 1700 mg |

Preparation:

Hard fat is melted at about 38° C.; ground active substance is homogeneously dispersed in the molten hard fat; after cooling to about 35° C. it is poured into chilled moulds.

Example XII

Injectable Solution Containing 10 mg of Active Substance per 1 ml

Composition:

| | |
|---|---|
| active substance | 10 mg |
| mannitol | 50 mg |
| human serum albumin | 10 mg |
| water for injections ad | 1 ml |

Preparation:

Mannitol is dissolved in water for injections (Wfl); human serum albumin is added; active ingredient is dissolved with heating; made up to specified volume with Wfl; transferred into ampoules under nitrogen gas.

The invention claimed is:

1. A compound of the formula I,

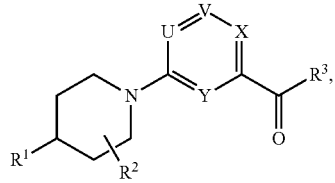

(I)

wherein

R$^1$ denotes a group of the formula II

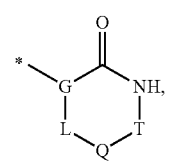

(II)

wherein

G-L denotes N—C(R$^{4.1}$)$_2$—C(R$^{4.1}$)$_2$,

Q-T denotes C(R$^5$)=C(R$^5$), wherein R$^5$ together with the adjacent group R$^5$ and the atoms to which these groups are bound denote a phenyl group, which is substituted independently of one another by 1, 2 or 3 substituents R$^{5.1}$, R$^2$ denotes (a) H, (b) F, —CN, C$_{1-3}$-alkyl, —CO$_2$—R$^{2.1}$ or (c) a C$_{1-3}$-alkyl group wherein each methylene group is substituted by up to two fluorine atoms and each methyl group is substituted by up to three fluorine atoms, R$^{2.1}$ denotes H or C$_{1-6}$-alkyl, R$^3$ denotes a group of the formula

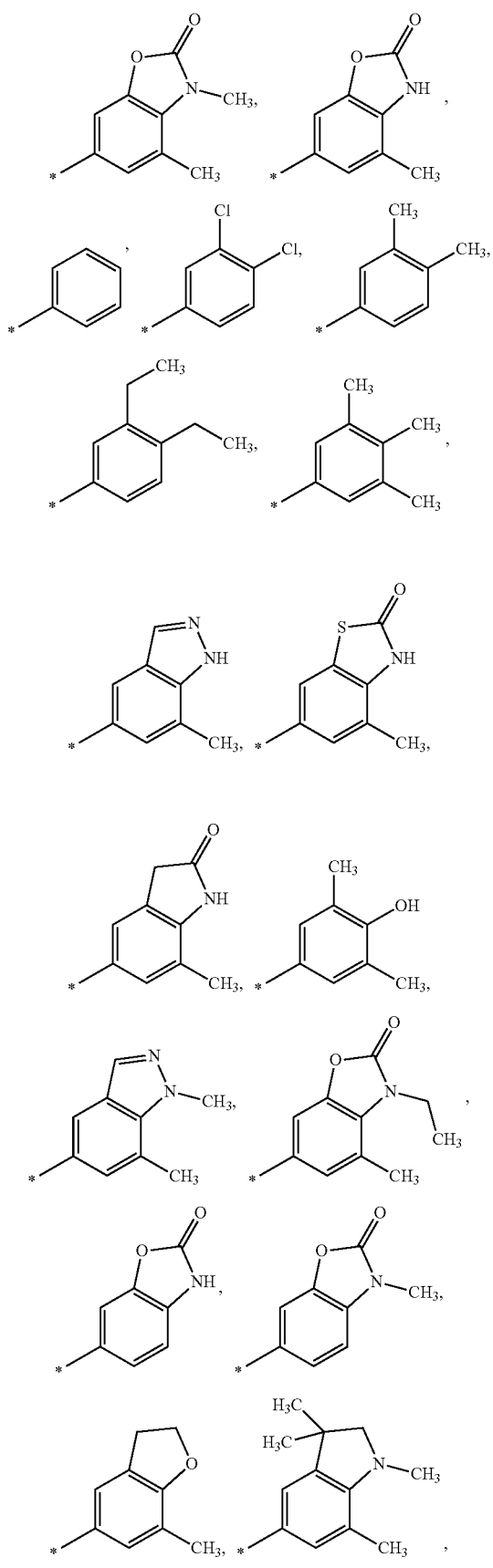

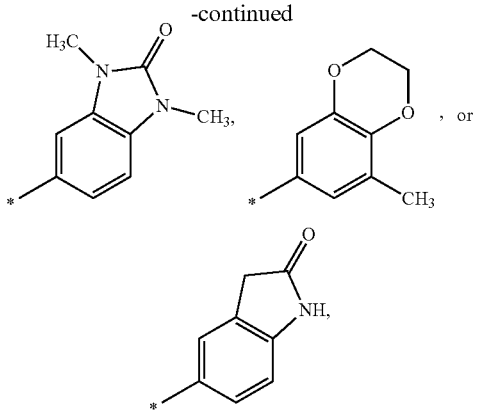

$R^{4.1}$ independently of one another denote
(a) H,
(b) $C_{1-6}$-alkyl, —CN, —OH, —O—$C_{1-3}$-alkyl,
(c) a $C_{1-3}$-alkyl- or $C_{1-3}$-alkyl-O— group wherein each methylene group is substituted by up to two fluorine atoms and each methyl group is substituted by up to three fluorine atoms, $R^{5.1}$ independently of one another denote
(a) H, halogen, $C_{1-6}$-alkyl, $C_{3-6}$-cycloalkyl,
(b) —O—$C_{1-6}$-alkylene-$NR^7R^8$, —O—$R^6$, —O—$(CH_2)_s$—O—$R^6$—$CO_2$—$R^6$, —C(O)—$NR^7R^8$, —O—C(O)—$NR^7R^8$, —$NR^6$—C(O)—$NR^7R^8$, —$NR^7$—C(O)—$R^8$, —$NR^7$—C(O)—O—$R^8$, —$SO_2$—$NR^7R^8$, —$NR^7$—$SO_2$—$R^8$, —$S(O)_m R^7$, —CN, —$NR^7R^8$, —$NR^6$—C(O)—$NR^7R^8$, —O—C(O)—$R^6$,
(c) a $C_{1-3}$-alkyl- or $C_{1-3}$-alkyl-O— group wherein each methylene group is substituted by up to two fluorine atoms and each methyl group is substituted by up to three fluorine atoms,
(d) an aryl group substituted by 1, 2 or 3 substituents $R^6$, wherein the substituents $R^6$ may be identical or different,
(e) a heteroaryl group substituted by 1, 2 or 3 substituents $R^6$, wherein the substituents $R^6$ may be identical or different,
(f) a heterocyclic group substituted by 1, 2 or 3 substituents $R^6$, wherein the substituents $R^6$ may be identical or different, $R^{5.2}$ independently of one another denote
(a) halogen, $C_{1-6}$-alkyl, $C_{3-6}$-cycloalkyl,
(b) —O—$R^6$, —O—$(CH_2)_s$—O—$R^6$—$CO_2R^6$, —C(O)—$NR^7R^8$, —O—(CO)—$NR^7R^8$, —$N(R^6)$—C(O)—$NR^7R^8$, —$N(R^7)$—C(O)—$R^8$, —$N(R^7)$—C(O)—O—$R^8$, —$SO_2$—$NR^7R^8$, —$N(R^7)$—$SO_2$—$R^8$, —$S(O)_m$—$R^7$, —CN, —$NR^7R^8$, —$N(R^6)$—C(O)—$NR^7R^8$, —O—C(O)—$R^6$ or
(c) a $C_{1-3}$-alkyl group wherein each methylene group is substituted by up to two fluorine atoms and each methyl group is substituted by up to three fluorine atoms, $R^6$ denotes
(a) H,
(b) $C_{1-6}$-alkyl, $C_{3-6}$-cycloalkyl, aryl, heteroaryl, benzyl, which may be substituted by a group $R^{6.1}$, or
(c) a $C_{1-3}$-alkyl group wherein each methylene group is substituted by up to two fluorine atoms and each methyl group is substituted by up to three fluorine atoms, $R^{6.1}$ denotes halogen, HO— or $C_{1-6}$-alkyl-O—, $R^7$ denotes
- (a) H,
- (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, $R^8$ denotes
- (a) H,
- (b) $C_{1-6}$-alkyl, $C_{3-6}$-cycloalkyl, aryl, heteroaryl or benzyl, while the groups are unsubstituted or may be substituted by halogen, HO— or $C_{1-6}$-alkyl-O—, or
- (c) a $C_{1-3}$-alkyl group wherein each methylene group is substituted by up to two fluorine atoms and each methyl group is substituted by up to three fluorine atoms, or $R^7$ and $R^8$ together may also form a ring which is selected from among azetidinyl, pyrrolidinyl, piperidinyl, piperazinyl and morpholinyl, wherein the ring may be unsubstituted or substituted by 1, 2 or 3 substituents $R^6$ or fluorine, wherein the substituents $R^6$ are independent of one another, m denotes one of the numbers 0, 1 or 2, U denotes N,N-oxide or C—$R^9$, V denotes N,N-oxide or C—$R^{10}$, X denotes N,N-oxide or $CR^{11}$, Y denotes N or C—$R^{12}$,
while at most three of the previously mentioned groups U, V, X or Y simultaneously denote a nitrogen atom, $R^9$ denotes
- (a) H,
- (b) a $C_{1-6}$-alkyl- or $C_{1-3}$-alkyl-O— group which may each be substituted by a group $R^{9.1}$,
- (c) $R^{9.2}R^{9.3}N$, $R^{9.2}R^{9.3}N—C_{1-3}$-alkylene-,
- (d) halogen, —CN, —OH, —COOH, $C_{1-3}$-alkyl-O—$C_{1-3}$-alkylene, $C_{3-6}$-cycloalkyl, $C_{3-6}$-cycloalkyl-$C_{1-4}$-alkylene-, $C_{1-3}$-alkyl-C(O)—O—$C_{1-3}$-alkylene,
- (e) a $C_{1-3}$-alkyl or $C_{1-3}$-alkyl-O— group wherein each methylene group is substituted by up to two fluorine atoms and each methyl group is substituted by up to three fluorine atoms, $R^{9.1}$ denotes H, OH or —O—$CH_3$, $R^{9.2}$ denotes H or $C_{1-3}$-alkyl, $R^{9.3}$ denotes H or $C_{1-3}$-alkyl, or $R^{9.2}$ and $R^{9.3}$ together with the nitrogen atom to which they are attached denote a 3- to 6-membered heterocyclic group, $R^{10}$ denotes
- (a) H,
- (b) a $C_{1-6}$-alkyl- or $C_{1-3}$-alkyl-O— group which may each be substituted by a group $R^{10.1}$,
- (c) —$NR^{10.2}R^{10.3}$, $NR^{10.2}R^{10.3}$—$C_{1-3}$-alkylene-,
- (d) halogen, —CN, —OH, $C_{1-3}$-alkyl-O—$C_{1-3}$-alkylene, $C_{3-6}$-cycloalkyl, $C_{3-6}$-cycloalkyl-$C_{1-4}$-alkylene, $C_{1-3}$-alkyl-C(O)—O—$C_{1-3}$-alkylene,
- (e) an aryl-$C_{0-3}$-alkylene-O— group,
- (f) a $C_{1-3}$-alkyl or $C_{1-3}$-alkyl-O— group wherein each methylene group is substituted by up to two fluorine atoms and each methyl group is substituted by up to three fluorine atoms, $R^{10.1}$ denotes H, OH or —O—$CH_3$, $R^{10.2}$ denotes H or $C_{1-3}$-alkyl, $R^{10.3}$ denotes H, $C_{1-6}$-alkyl or —$SO_2$—$C_{1-3}$-alkyl, or $R^{10.2}$ and $R^{10.3}$ together with the nitrogen atom to which they are attached denote a 3- to 6-membered heterocyclic group, $R^{11}$ denotes
- (a) H,
- (b) a $C_{1-6}$-alkyl- or $C_{1-3}$-alkyl-O— group which may each be substituted by a group $R^{11.1}$,
- (c) $R^{11.2}R^{11.3}N$, $R^{11.2}R^{11.3}N—C_{1-3}$-alkylene-,
- (d) halogen, —CN, —OH, —COOH, $C_{1-3}$-alkyl-O—$C_{1-3}$-alkylene-, $C_{3-6}$-cycloalkyl, $C_{3-6}$-cycloalkyl-$C_{1-4}$-alkylene-, $C_{1-3}$-alkyl-C(O)—O—$C_{1-3}$-alkylene,
- (e) a $C_{1-3}$-alkyl- or $C_{1-3}$-alkyl-O— group wherein each methylene group is substituted by up to two fluorine atoms and each methyl group is substituted by up to three fluorine atoms, $R^{11.1}$ denotes H, OH or —O—$CH_3$, $R^{11.2}$ denotes H or $C_{1-3}$-alkyl, $R^{11.3}$ denotes H or $C_{1-3}$-alkyl, or $R^{11.2}$ and $R^{11.3}$ together with the nitrogen atom to which they are attached denote a 3- to 6-membered heterocyclic group, and $R^{12}$ denotes H, halogen or $C_{1-3}$-alkyl, or a tautomer or pharmaceutically acceptable salt thereof.

2. A compound of the formula I according to claim 1, wherein $R^3$ denotes a group of the formula

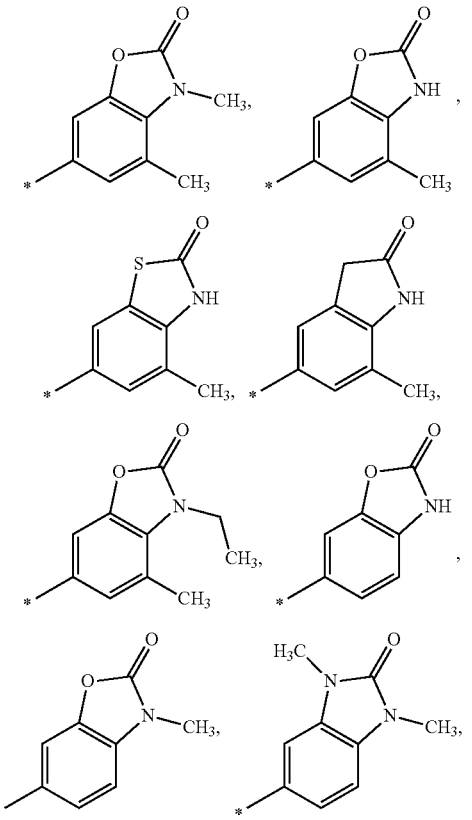

-continued
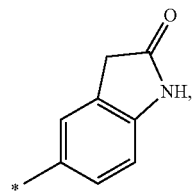
or a tautomer or pharmaceutically acceptable salt thereof.
3. A compound of the formula I according to claim 1, wherein
R¹ denotes a group of the formula
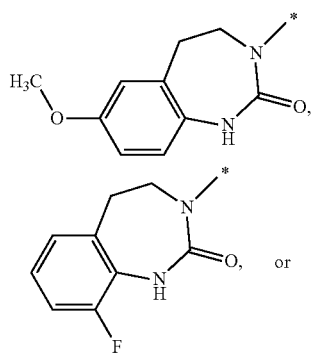
R² denotes H and
R³ denotes a group of the formula
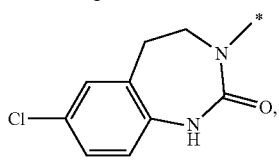
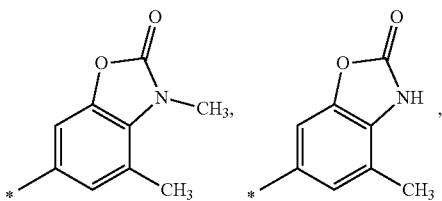
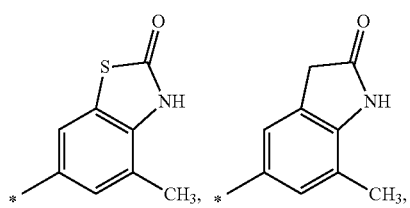
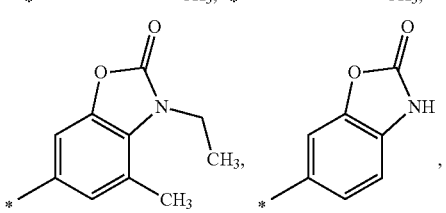
-continued
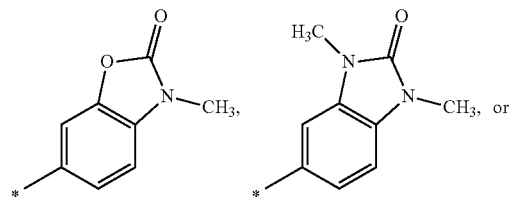
and the ring
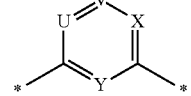
denotes a group of the formula
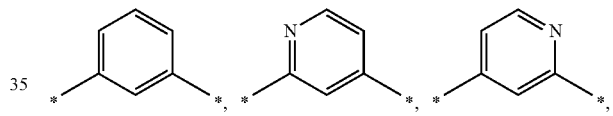
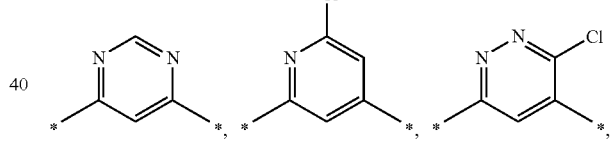
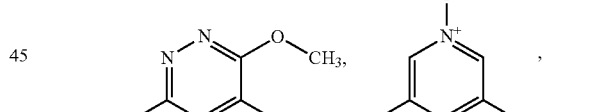
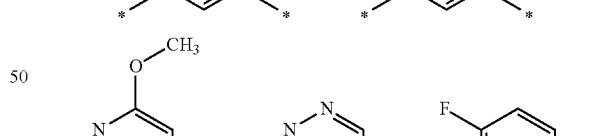
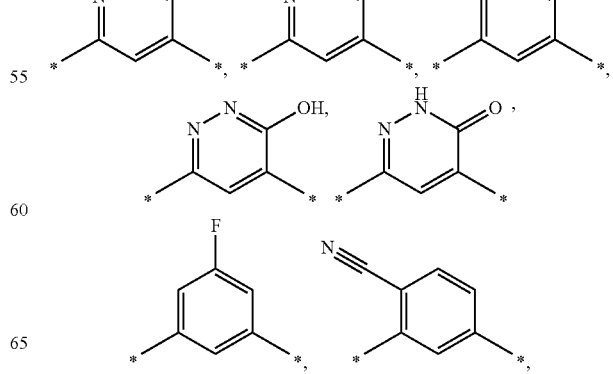

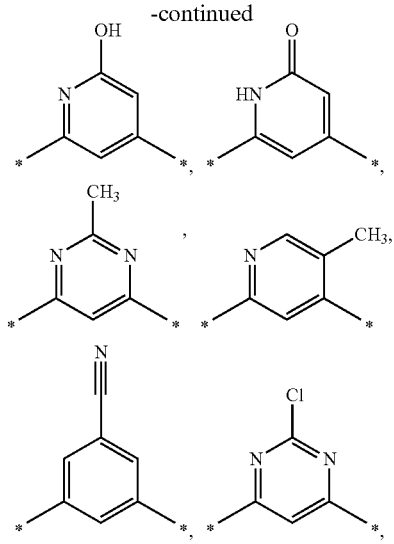
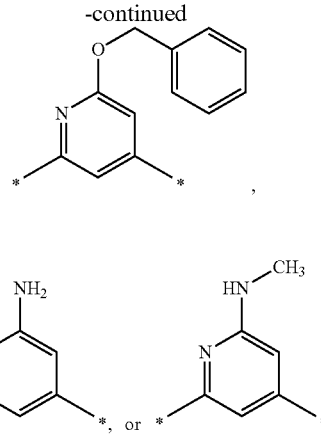
or a tautomer or pharmaceutically acceptable salt thereof.
4. A compound according to claim 1 selected from the group consisting of:
| No. | Structure |
|---|---|
| (2) | 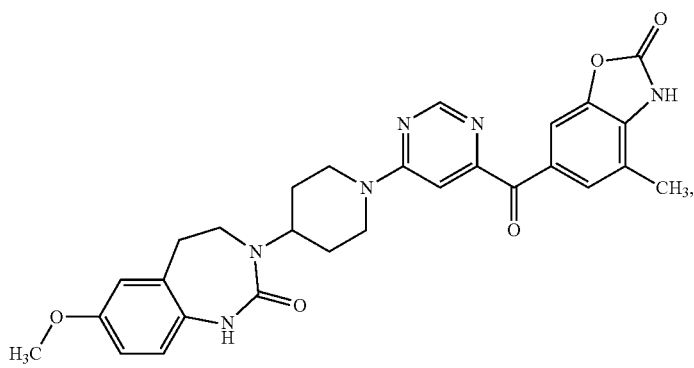 [SMILES: COc1ccc2c(c1)CCN(C1CCN(c3cc(C(=O)c4cc(C)c5[nH]c(=O)oc5c4)ncn3)CC1)C(=O)N2] |
| (9) | 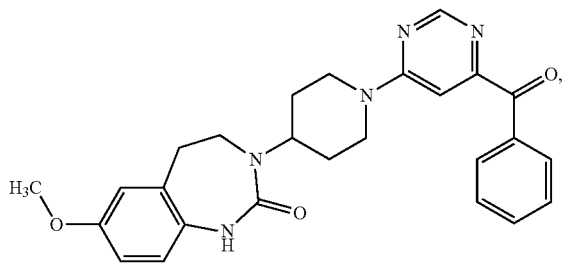 [SMILES: COc1ccc2c(c1)CCN(C1CCN(c3cc(C(=O)c4ccccc4)ncn3)CC1)C(=O)N2] |
| (10) | 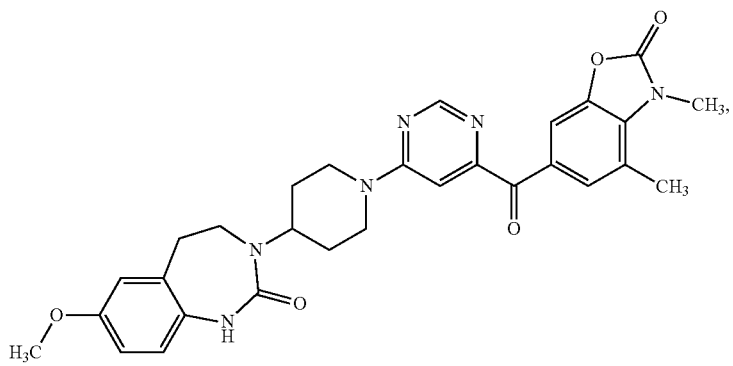 [SMILES: COc1ccc2c(c1)CCN(C1CCN(c3cc(C(=O)c4cc(C)c5c(c4)oc(=O)n5C)ncn3)CC1)C(=O)N2] |

| No. | Structure |
|---|---|
| (11) | 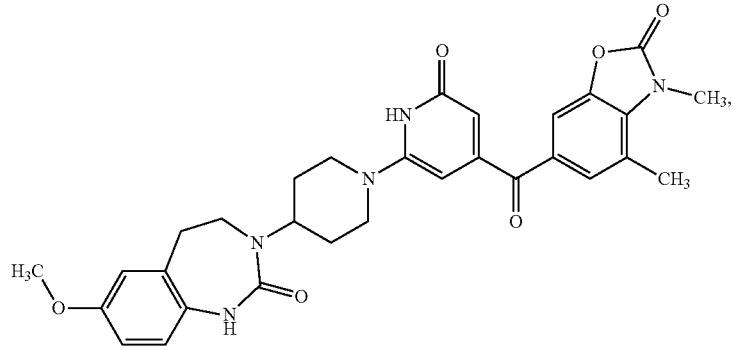 [SMILES: COc1ccc2c(c1)CCN(C1CCN(c3cc(C(=O)c4cc(C)c5c(c4)oc(=O)n5C)cc(=O)[nH]3)CC1)C(=O)N2] |
| (12) | 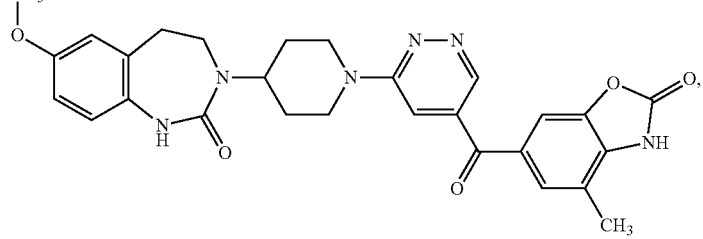 |
| (13) | 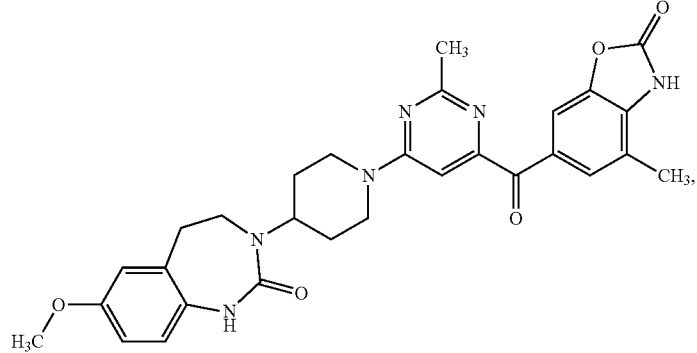 [SMILES: COc1ccc2c(c1)CCN(C1CCN(c3cc(C(=O)c4cc(C)c5[nH]c(=O)oc5c4)nc(C)n3)CC1)C(=O)N2] |
| (14) | 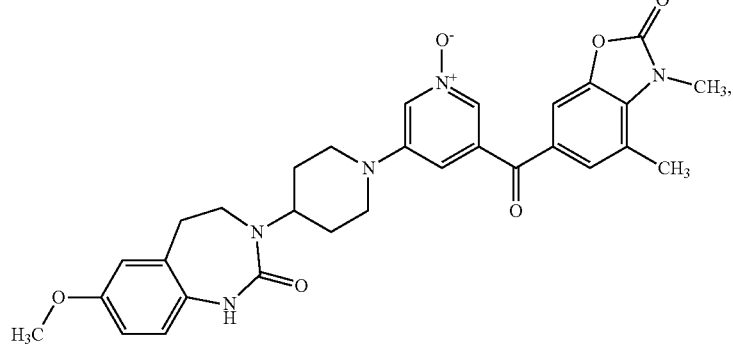 |

| No. | Structure |
|---|---|
| (16) | 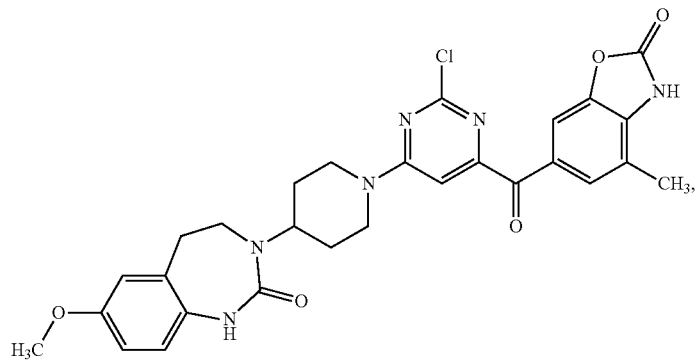 |
| (17) | 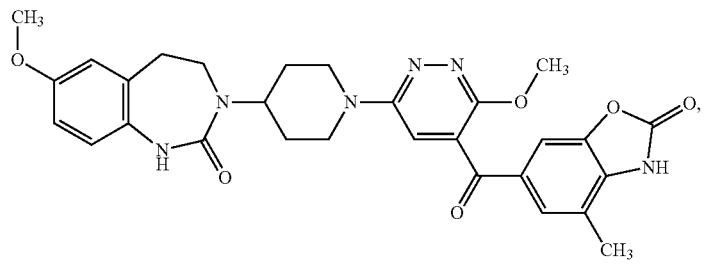 [SMILES: COc1ccc2c(c1)CCN(C1CCN(c3cc(C(=O)c4cc(C)c5[nH]c(=O)oc5c4)c(OC)nn3)CC1)C(=O)N2] |
| (18) | 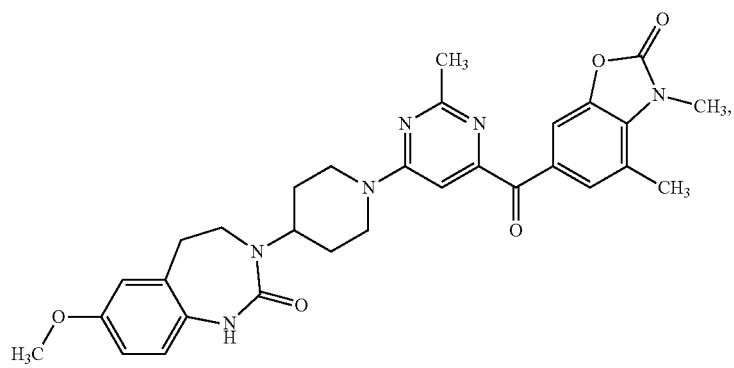 [SMILES: COc1ccc2c(c1)CCN(C1CCN(c3cc(C(=O)c4cc(C)c5c(c4)oc(=O)n5C)nc(C)n3)CC1)C(=O)N2] |
| (19) | 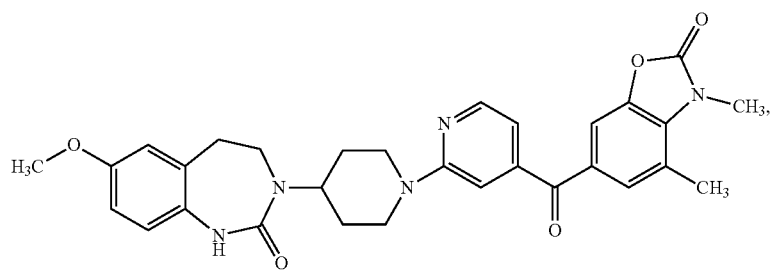 [SMILES: COc1ccc2c(c1)CCN(C1CCN(c3cc(C(=O)c4cc(C)c5c(c4)oc(=O)n5C)ccn3)CC1)C(=O)N2] |
| (20) | 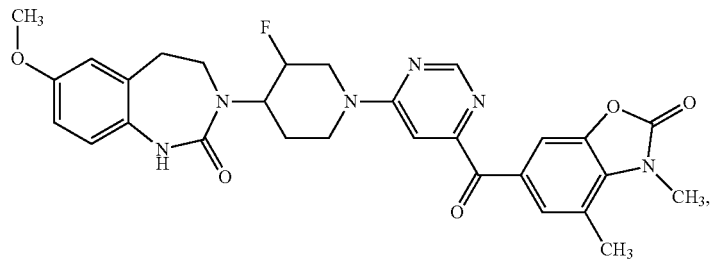 |

| No. | Structure |
|-----|-----------|
| (22) | [Chemical structure: 7-methoxy-benzodiazepinone linked via piperidine to pyridine bearing a (4-methyl-2-oxo-benzoxazol-6-yl)carbonyl group] |
| (25) | [Chemical structure: 7-methoxy-benzodiazepinone linked via piperidine to chloropyridazine bearing a (4-methyl-2-oxo-benzoxazol-6-yl)carbonyl group] |
| (26) | [Chemical structure: 7-methoxy-benzodiazepinone linked via piperidine to cyanobenzene bearing a (4-methyl-2-oxo-benzoxazol-6-yl)carbonyl group] |
| (29) | [Chemical structure: 7-methoxy-benzodiazepinone linked via piperidine to oxo-dihydropyridazine bearing a (4-methyl-2-oxo-benzoxazol-6-yl)carbonyl group] |
| (30) | [Chemical structure: 7-methoxy-benzodiazepinone linked via piperidine to oxo-dihydropyridazine bearing a (3,4-dimethyl-2-oxo-benzoxazol-6-yl)carbonyl group] |

-continued
| No. | Structure |
|---|---|
| (31) | 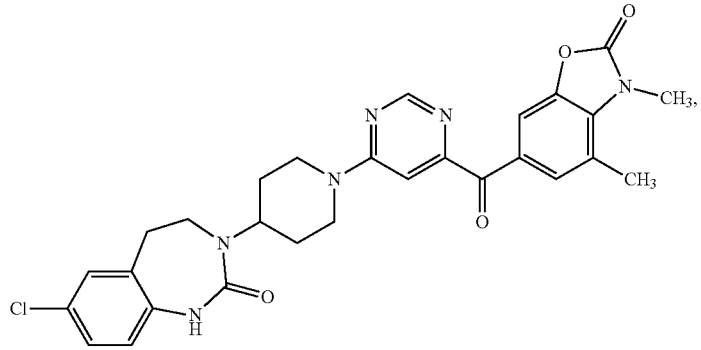 [SMILES: Cc1cc(C(=O)c2cc(N3CCC(N4CCc5cc(Cl)ccc5NC4=O)CC3)ncn2)cc2oc(=O)n(C)c12] |
| (33) | 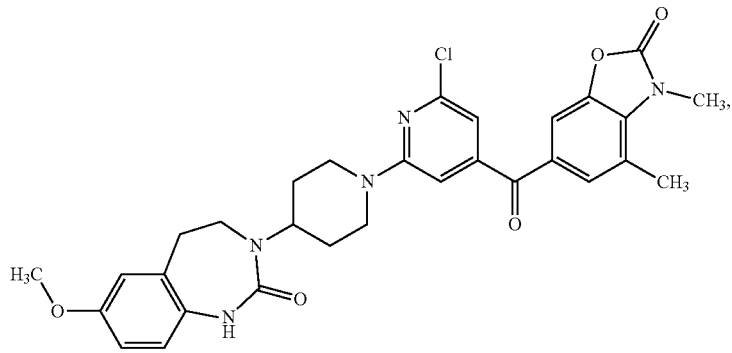 [SMILES: COc1ccc2c(c1)CCN(C1CCN(c3cc(C(=O)c4cc(C)c5c(c4)oc(=O)n5C)cc(Cl)n3)CC1)C(=O)N2] |
| (34) | 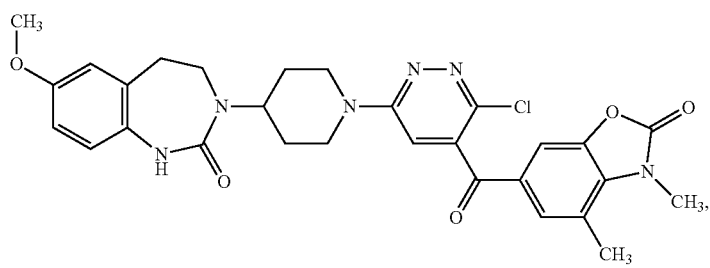 [SMILES: COc1ccc2c(c1)CCN(C1CCN(c3cc(C(=O)c4cc(C)c5c(c4)oc(=O)n5C)c(Cl)nn3)CC1)C(=O)N2] |
| (36) | 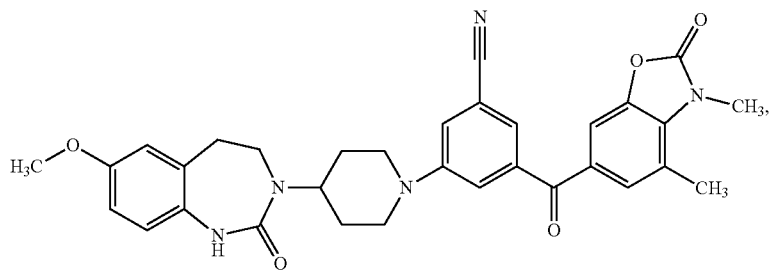 [SMILES: COc1ccc2c(c1)CCN(C1CCN(c3cc(C#N)cc(C(=O)c4cc(C)c5c(c4)oc(=O)n5C)c3)CC1)C(=O)N2] |
| (38) | 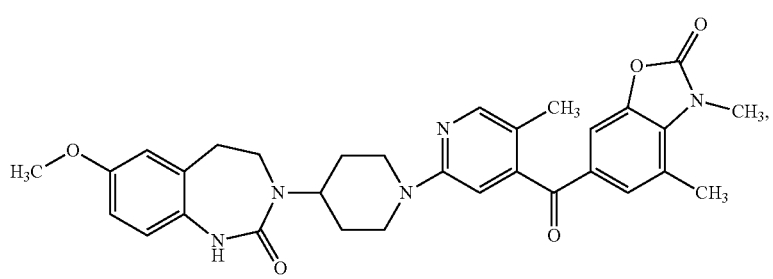 [SMILES: COc1ccc2c(c1)CCN(C1CCN(c3cc(C(=O)c4cc(C)c5c(c4)oc(=O)n5C)c(C)cn3)CC1)C(=O)N2] |

-continued
| No. | Structure |
|---|---|
| (39) | 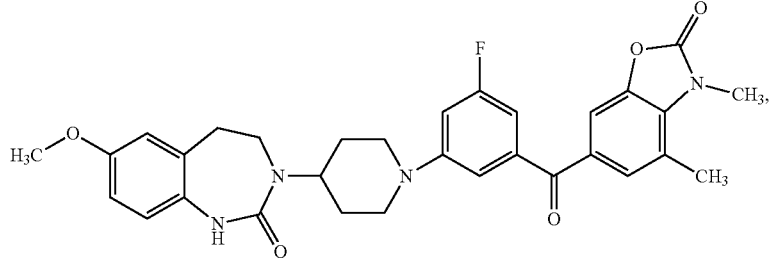 [SMILES: COc1ccc2c(c1)CCN(C1CCN(c3cc(F)cc(C(=O)c4cc(C)c5c(c4)oc(=O)n5C)c3)CC1)C(=O)N2] |
| (41) | 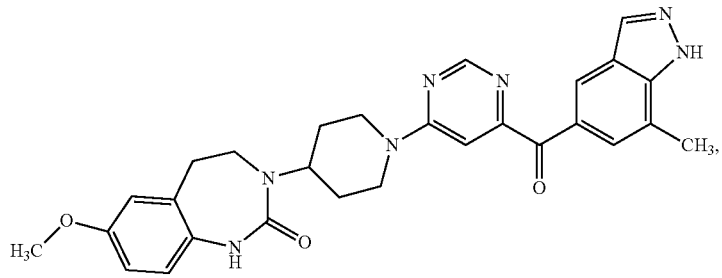 [SMILES: COc1ccc2c(c1)CCN(C1CCN(c3cc(C(=O)c4cc(C)c5[nH]ncc5c4)ncn3)CC1)C(=O)N2] |
| (42) | 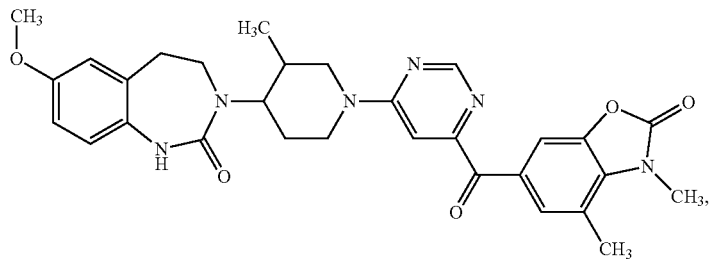 [SMILES: COc1ccc2c(c1)CCN(C1CCN(c3cc(C(=O)c4cc(C)c5c(c4)oc(=O)n5C)ncn3)CC1C)C(=O)N2] |
| (43) | 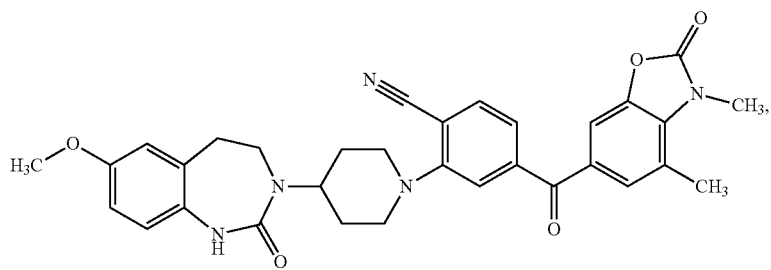 [SMILES: COc1ccc2c(c1)CCN(C1CCN(c3cc(C(=O)c4cc(C)c5c(c4)oc(=O)n5C)ccc3C#N)CC1)C(=O)N2] |
| (44) | 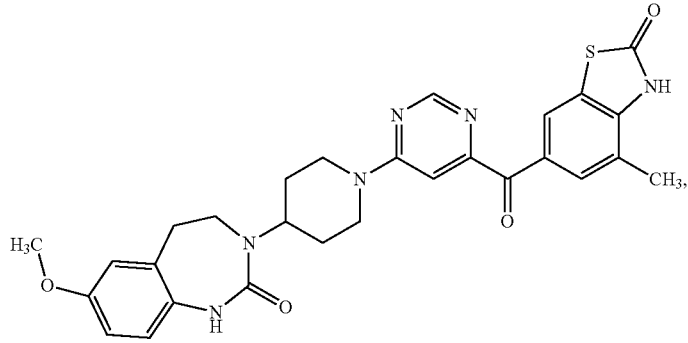 [SMILES: COc1ccc2c(c1)CCN(C1CCN(c3cc(C(=O)c4cc(C)c5[nH]c(=O)sc5c4)ncn3)CC1)C(=O)N2] |

| No. | Structure |
|---|---|
| (45) | 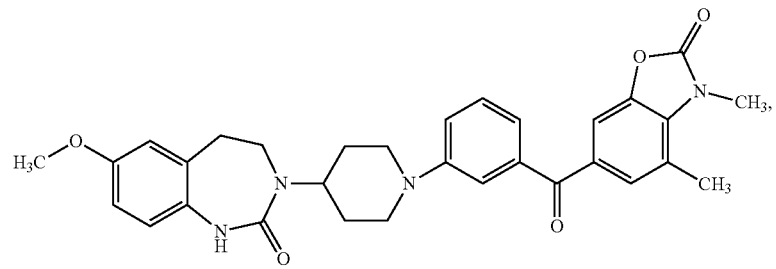 [SMILES: COc1ccc2c(c1)CCN(C1CCN(c3cccc(C(=O)c4cc(C)c5c(c4)oc(=O)n5C)c3)CC1)C(=O)N2] |
| (48) | 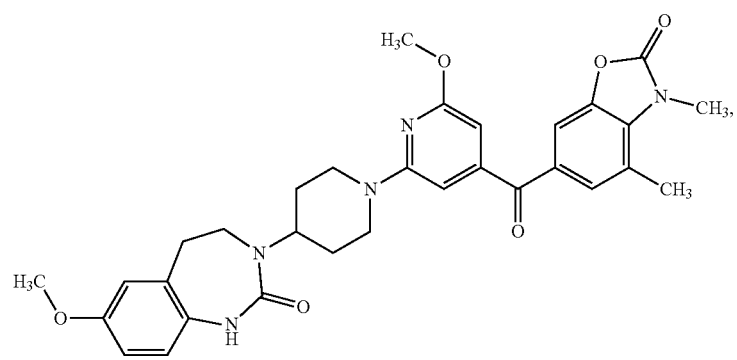 [SMILES: COc1ccc2c(c1)CCN(C1CCN(c3cc(C(=O)c4cc(C)c5c(c4)oc(=O)n5C)cc(OC)n3)CC1)C(=O)N2] |
| (51) | 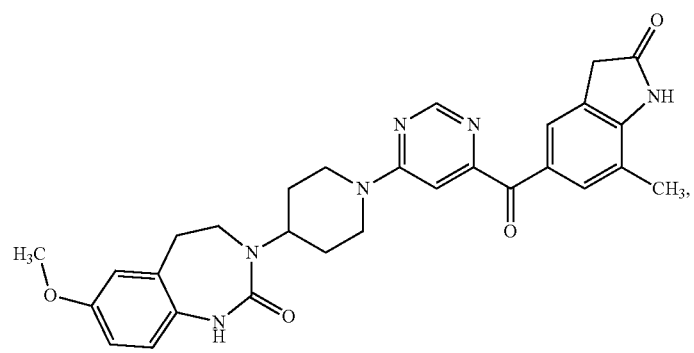 |
| (54) | 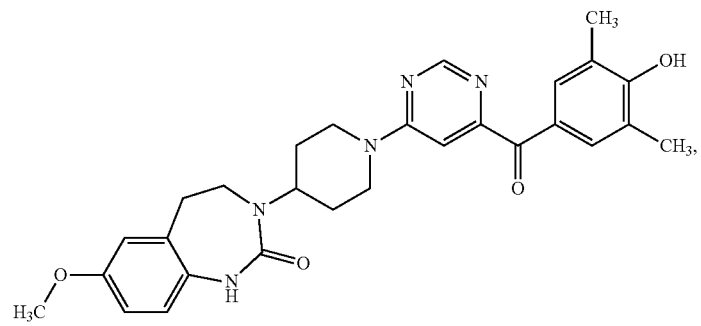 [SMILES: COc1ccc2c(c1)CCN(C1CCN(c3cc(C(=O)c4cc(C)c(O)c(C)c4)ncn3)CC1)C(=O)N2] |

| No. | Structure |
|---|---|
| (57) | 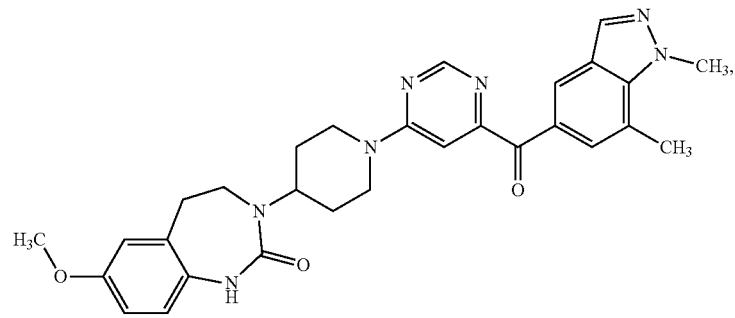 [SMILES: COc1ccc2c(c1)CCN(C1CCN(c3cc(C(=O)c4cc(C)c5c(cnn5C)c4)ncn3)CC1)C(=O)N2] |
| (58) | 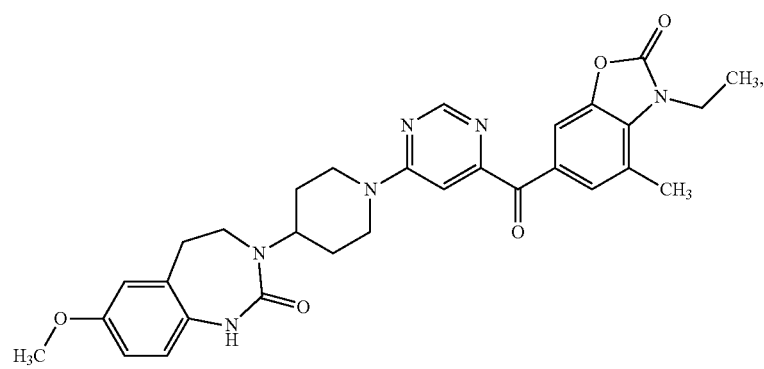 [SMILES: CCn1c(=O)oc2cc(C(=O)c3cc(N4CCC(N5CCc6cc(OC)ccc6NC5=O)CC4)ncn3)cc(C)c21] |
| (59) | 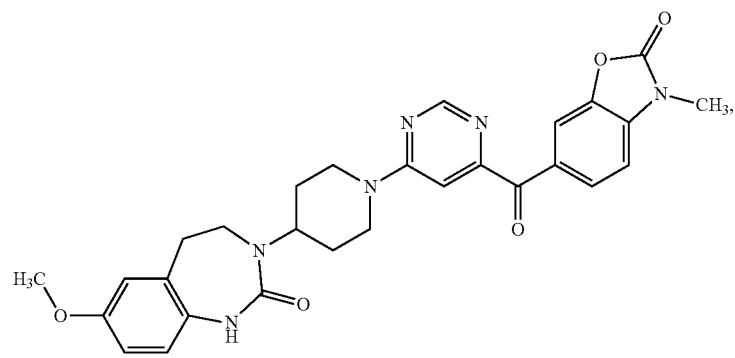 [SMILES: COc1ccc2c(c1)CCN(C1CCN(c3cc(C(=O)c4ccc5c(c4)oc(=O)n5C)ncn3)CC1)C(=O)N2] |
| (60) | 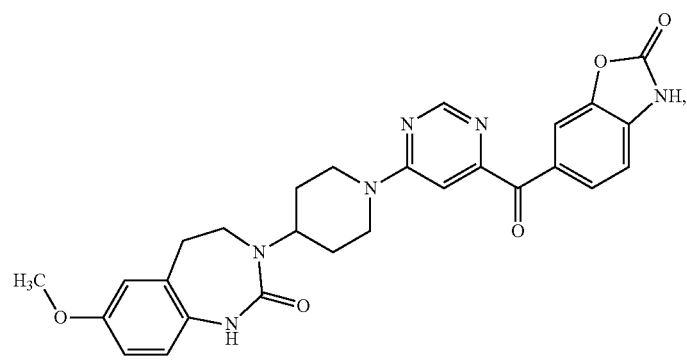 [SMILES: COc1ccc2c(c1)CCN(C1CCN(c3cc(C(=O)c4ccc5[nH]c(=O)oc5c4)ncn3)CC1)C(=O)N2] |

-continued
| No. | Structure |
|---|---|
| (64) | 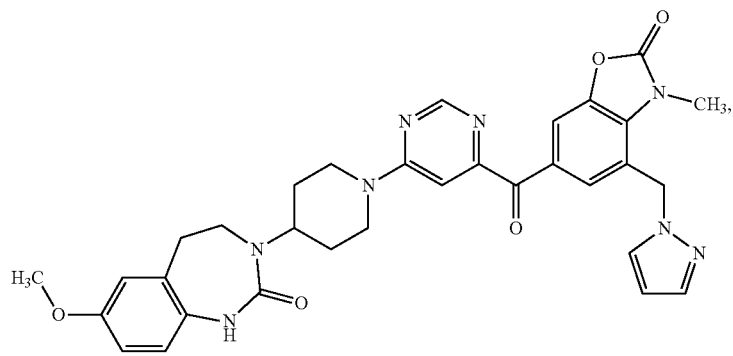 [SMILES: COc1ccc2c(c1)CCN(C1CCN(c3cc(C(=O)c4cc(Cn5cccn5)c5c(c4)oc(=O)n5C)ncn3)CC1)C(=O)N2] |
| (66) | 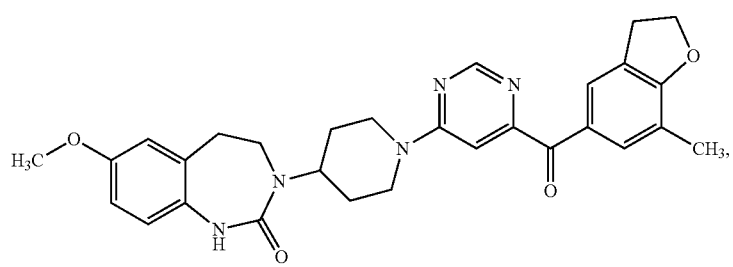 [SMILES: COc1ccc2c(c1)CCN(C1CCN(c3cc(C(=O)c4cc(C)c5c(c4)CCO5)ncn3)CC1)C(=O)N2] |
| (68) | 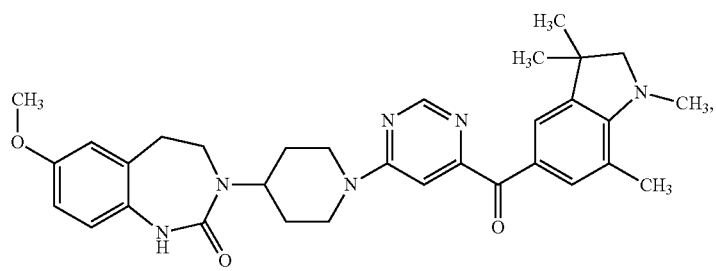 [SMILES: COc1ccc2c(c1)CCN(C1CCN(c3cc(C(=O)c4cc(C)c5c(c4)C(C)(C)CN5C)ncn3)CC1)C(=O)N2] |
| (69) | 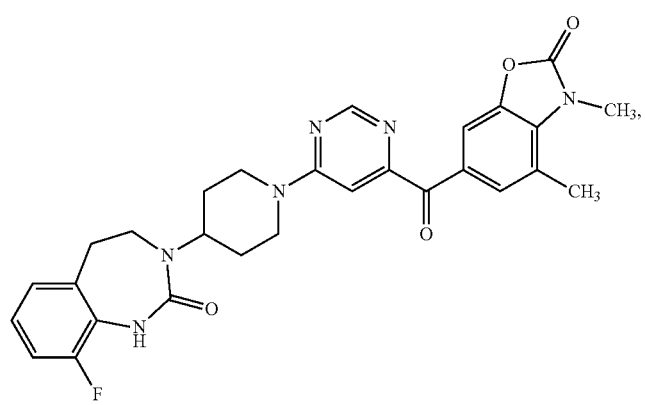 [SMILES: Cc1cc(C(=O)c2cc(N3CCC(N4CCc5cccc(F)c5NC4=O)CC3)ncn2)cc2oc(=O)n(C)c12] |
| (70) | 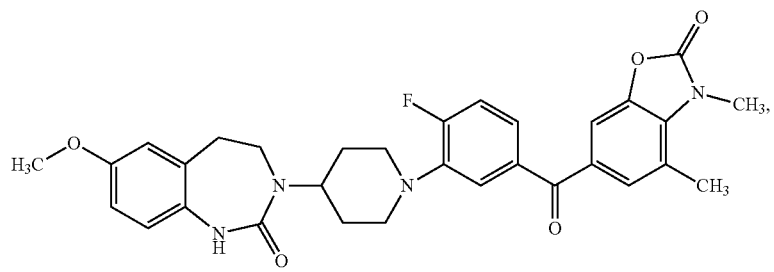 [SMILES: COc1ccc2c(c1)CCN(C1CCN(c3cc(C(=O)c4cc(C)c5c(c4)oc(=O)n5C)ccc3F)CC1)C(=O)N2] |

-continued
| No. | Structure |
|---|---|
| (73) | 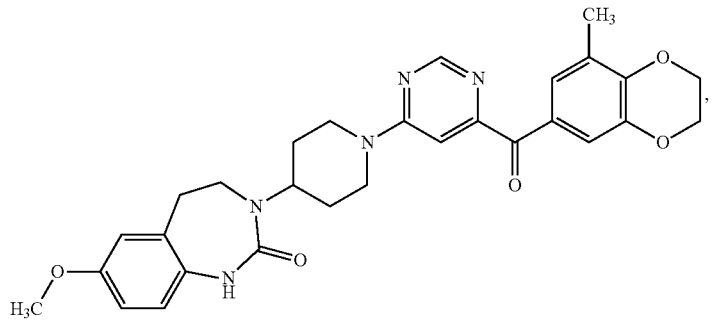 [SMILES: COc1ccc2c(c1)CCN(C1CCN(c3cc(C(=O)c4cc(C)c5c(c4)OCCO5)ncn3)CC1)C(=O)N2] |
| (76) | 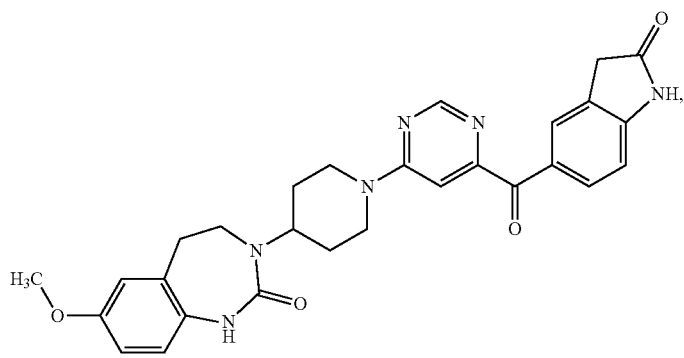 [SMILES: COc1ccc2c(c1)CCN(C1CCN(c3cc(C(=O)c4ccc5c(c4)CC(=O)N5)ncn3)CC1)C(=O)N2] |
| (78) | 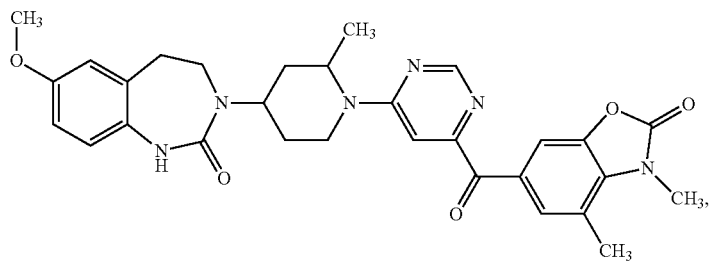 |
| (80) | 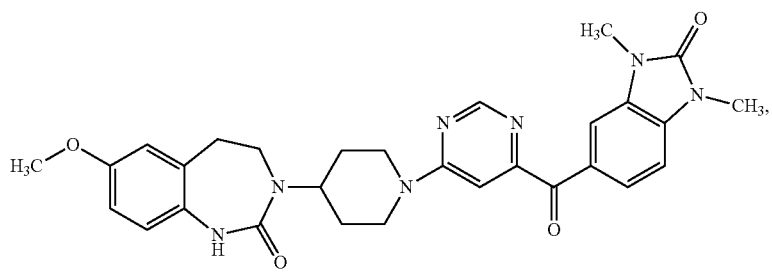 [SMILES: COc1ccc2c(c1)CCN(C1CCN(c3cc(C(=O)c4ccc5c(c4)n(C)c(=O)n5C)ncn3)CC1)C(=O)N2] |
| (81) | 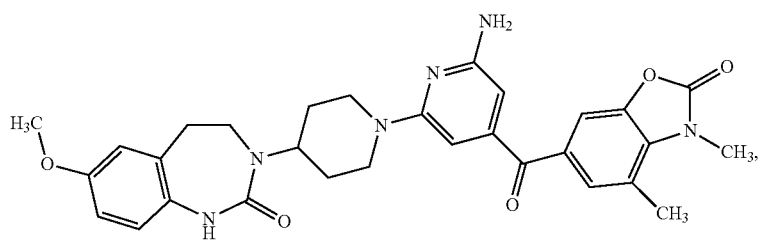 [SMILES: COc1ccc2c(c1)CCN(C1CCN(c3cc(C(=O)c4cc(C)c5c(c4)oc(=O)n5C)cc(N)n3)CC1)C(=O)N2] |

| No. | Structure |
|---|---|
| (82) | 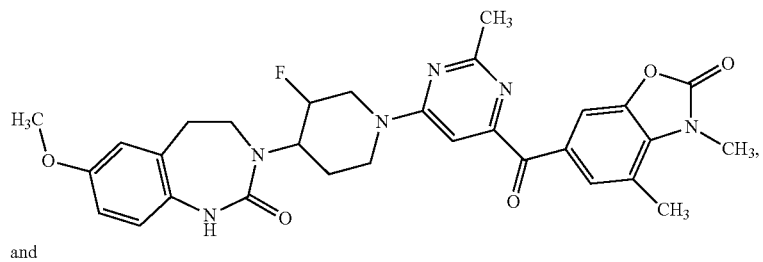 and |
| (83) | 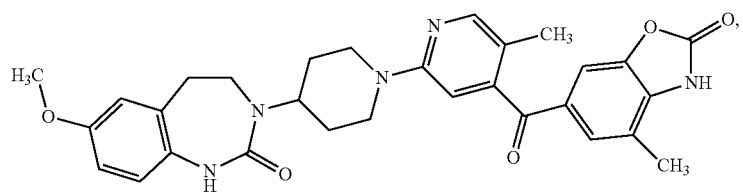 [SMILES: COc1ccc2c(c1)CCN(C1CCN(c3cc(C(=O)c4cc(C)c5[nH]c(=O)oc5c4)c(C)cn3)CC1)C(=O)N2] | or a pharmaceutically acceptable salt thereof.

5. A pharmaceutical composition comprising a compound according to claim 1, or a physiologically acceptable salt thereof, and a carrier or diluent.

6. A method of treating headache, migraine headache or cluster headache which comprises administering to a host suffering from the same a therapeutically effective amount of a compound according to claim 1, or a physiologically acceptable salt thereof.

* * * * *